(12) United States Patent
Pekari et al.

(10) Patent No.: US 7,723,523 B2
(45) Date of Patent: May 25, 2010

(54) TETRAHYDROPYRIDOTHIOPHENES

(75) Inventors: Klaus Pekari, Radolfzell (DE); Thomas Baer, Reichenau (DE); Björn Bartels, Radolfzell (DE); Mathias Schmidt, Constance (DE); Thomas Beckers, Constance (DE)

(73) Assignee: 4SC AG, Planegg Martinsrid (DE)

( * ) Notice: Subject to any disclaimer, the term of this patent is extended or adjusted under 35 U.S.C. 154(b) by 0 days.

(21) Appl. No.: 11/597,142

(22) PCT Filed: May 25, 2005

(86) PCT No.: PCT/EP2005/052384

§ 371 (c)(1),
(2), (4) Date: Nov. 20, 2006

(87) PCT Pub. No.: WO2005/118071

PCT Pub. Date: Dec. 15, 2005

(65) Prior Publication Data

US 2007/0244112 A1   Oct. 18, 2007

(30) Foreign Application Priority Data

May 28, 2004 (EP) .................................. 04102413
Sep. 1, 2004 (EP) .................................. 04104193

(51) Int. Cl.
*C07D 471/02* (2006.01)
(52) U.S. Cl. ..................................................... 546/114
(58) Field of Classification Search .................. 546/114
See application file for complete search history.

(56) References Cited

U.S. PATENT DOCUMENTS

| 3,449,439 A | 6/1969 | Kuhnen et al. |
| 4,963,559 A | 10/1990 | Suzuki |
| 5,422,335 A | 6/1995 | Hagen et al. |
| 6,069,620 A | 5/2000 | Nakamura et al. |
| 2003/0218593 A1 | 11/2003 | Inoue et al. |
| 2003/0232994 A1 | 12/2003 | Lu et al. |
| 2004/0171603 A1 | 9/2004 | Pato et al. |
| 2004/0209943 A1 | 10/2004 | Erickson et al. |
| 2005/0154024 A1 | 7/2005 | Bryans |

FOREIGN PATENT DOCUMENTS

| DE | 272 078 A1 | 9/1989 |
| DE | 40 39 734 A1 | 6/1992 |
| WO | 9427969 A1 | 12/1994 |
| WO | 98/02440 A1 | 1/1998 |
| WO | 99/46267 A1 | 9/1999 |
| WO | 0014090 A1 | 3/2000 |
| WO | 0247762 A1 | 6/2002 |
| WO | 02/092076 A1 | 11/2002 |
| WO | WO 02/092076 | 11/2002 |
| WO | 03084947 A1 | 10/2003 |
| WO | WO 03080607 | 10/2003 |
| WO | WO 03/102153 | 12/2003 |
| WO | 2004/024065 A2 | 3/2004 |
| WO | 2004/024066 A2 | 3/2004 |
| WO | 2004/069149 A2 | 8/2004 |
| WO | 2004065351 A1 | 8/2004 |
| WO | 2004/092156 A1 | 10/2004 |
| WO | WO 2005/023818 | 3/2005 |
| WO | 2005/033102 A2 | 4/2005 |
| WO | WO 2005030770 | 4/2005 |
| WO | 2005/044008 A2 | 5/2005 |
| WO | 2005/060711 A2 | 7/2005 |
| WO | 2005/118592 A1 | 12/2005 |
| WO | 2005/120642 A2 | 12/2005 |
| WO | WO 2005/118071 | 12/2005 |
| WO | 2006014135 A1 | 2/2006 |
| WO | 2006084869 A1 | 8/2006 |
| WO | 2006084904 A1 | 8/2006 |
| WO | 2006125813 A1 | 11/2006 |
| WO | 2006125815 A2 | 11/2006 |
| WO | WO 2008/020045 | 12/2007 |

OTHER PUBLICATIONS

Fujita et. al. Bioorganic & Medicinal Chemistry Letters (2002), 12, 1897-1900.*
Database Chemcats, Chemical Abstracts Service, Columbus, Ohio, US; XP002303659; abstract & "Ambinter Screening Library", Jan. 1, 2004.
Database Chemcats, Chemical Abstracts Service, Columbus, Ohio, US; XP002369767; abstract * "Interchim Intermediates", Jan. 18, 2005.
Database Chemcats, Chemical Abstracts Service, Columbus, Ohio, US; XP002369768; abstract & "Ambinter Stock Screening Collection", Jul. 3, 2005.
Database Chemcats, Chemical Abstracts Service, Columbus, Ohio, US; XP002361378; abstract & "Interchim Intermediates", Jan. 18, 2005.

(Continued)

*Primary Examiner*—D. Margaret Seaman
*Assistant Examiner*—Nizal S Chandrakumar
(74) *Attorney, Agent, or Firm*—Millen, White, Zelano & Branigan, P.C.

(57) ABSTRACT

Compounds of a certain formula (I)

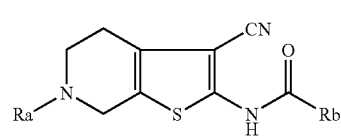

in which Ra and Rb have the meanings indicated in the description, are novel, effective compounds with anti-proliferative and/or apoptosis inducing activity.

25 Claims, 1 Drawing Sheet

OTHER PUBLICATIONS

Database Chemcats, Chemical Abstracts Service, Columbus, Ohio, US; XP002303660; abstract & "TimTec Overseas Stock", Jun. 1, 2004.

Database Chemcats, Chemical Abstracts Service, Columbus, Ohio, US; XP002361377; abstract & "Ambinter Screening Library", Jan. 1, 2004.

Fujita, M. et al., "Synthesis and Bioactivities of Novel Bicyclic Thiophenes and 4,5,6,7-Tetrahydrothieno[2,3-c]pyridines as Inhibitors of Tumor Necrosis Factor-alpha (TNF-alpha) Production," Bioorganic & Medicinal Chemistry Letters, vol. 12, pp. 1897-1900 (2002).

Sensfuss, U. et al., "2-Aminothiophenes from Triacetonamine: A Convenient Way to Novel Sterically Hindered Piperidine Derivatives," Heteroatom Chemistry, vol. 9, No. 6, pp. 529-536 (1998).

Sensfuss, U. et al., "An Unusual Cascade Reaction Yielding Ortho-Peri-Fused Thienopyridopyrimidines," Heterocycles, vol. 55, No. 1, pp. 171-180 (2001).

Ashlmori et al., "Novel 1,4-Dihydropyridine Calcium Antagonists. I. Synthesis and Hypotensive Activity of 4-(Substituted Pyridol)-1,4-dihydropyridine Derivatives," Chem. Pharm. Bull., v.38(9), pp. 2446-2458. 1990.

Srlkrlahna et al., "A simple Strategy for Spirocyclopantannulation of Cyclic Ketones, Formal Total Synthesis of (2)-Acerone." *Tetrahedron Letters*, v.37(10), pp. 1683-1686, 1996.

Uemura at el., "Highly Efficient Enantioselective Synthesis of Optically Active Carboxylic Acids by RU (OCOCH$_3$)$_2$[(S)-H$_5$-BINAP]," *J, Org. Chem*, v.61, pp. 5510-5516, 1996.

Database Chemcats, Columbus, Ohio, U.S., XP 002377744, 2 pages.

Chemical Abstracts, CAS RN 724704-04-5 CAS RN 724704-02-3 XP 002338416, 10 pages.

Database Chemcats, Chemical Abstracts Service, Columbus, Ohio, U.S.; XP002303659; Abstract and "Ambinter Screening Library", Jan. 1, 2004.

Castanedo, G. and Sutherlin, D. "Synthesis of terrasubstituted thiphenos on solid-support using the Gewald reaction," Tetrahedron Letters, vol. 42, pp. 7181-7184 (2001).

Charette, A. Jones, M. Label, H., "Bis(oxazoline)copper(1)-catalyzed enantioselective cyclopropanation of cinnamate esters with diazomethane," Tetrahedron: Asymmetry, vol. 14, pp. 867-872 (2003).

Ezquerre, J., Prieto, L., Avendano, C., Martos, J., And de la Cuesta, E. "Asymmetric Michael Addition Reactions Using Ethyl (S)-4,4-Dimethylpyroglutamate as a Chiral Auxilliary," Tetrahedron Letters, vol. 40, pp. 1575-1678 (1999).

Huang, K., Huang, Z.. "A practical and Controllable Enantioselective Synthesis of 2-Phenyl-cyclopropanecarboxylates via a Camphor-Derived Sulfonium Ylide," Synlett, No. 10, pp. 1621-1823 (2005).

Lipshutz, B. Servesko. J., and Taft, B., "Asymmetric 1,4-Hydrosllylations of alpha, beta-Unsaturated Esters," J. Am. Chem. Soc., vol. 126, pp. 8352-8353 (2004).

Lylo, M., Wilson, P., "Synthesis of a New Chiral Nonracemic C2-Symmetric 2,2'-Blpyridyl Ligand and Its Application in Copper (l)-Catalyzed Enantloselective Cyclopropanation Reactions," Organic Letters, vol. 6, No. 5, pp. 855-857.

Sakuma, S., Sakal, M, Itooks, R., and Mlyaura, N. "Asymmetric Conjugate 1.4-Addition of Arylboronic Acids to alpha, beta-Unsaturated Esters Catalyzed by Rhodium(l)(S)-binap," J. Org. Chem., vol 55, pp. 5951-5955 (2000).

Lindstadt, E. and Nilsson, M., "2-Thienyl as Auxillary Group in Mixed Lithium Diorganocuprates," Acta Chemica Scandinavica, B 40, pp. 466-469 (1986).

Sainsbury, M., Weerasinghe, D., and Doiman, D., Chemistry of 6H-pyridol[4,3-b]carbazoles, Part 9, An Efficient route to 3-[1-(3-Ethylpyridyl)] Indoles and the Synthesis of Some New Eillptlcinos, J.C.S. Perkin l, pp. 587-590.

Tang, W., Wang, W., and Zhang, X., "Phospholana-Oxazoline Ligands for Ir-Catalyzed Asymmetric Hydrogonation," Angew. Chem. Int. Ed., vol. 42, No. 8, pp. 943-946 (2003).

Sep. 3, 2007—SciFinder pp. 1 and 2.

Chemcats, Interchim Intermediates—XP-002361378—"Thleno[2.3-c]pyridine-6(5H)-carboxylic acid, 2-[(3-chlorobenzoyl)amino]-3-cyano-4,7-dlhydroethyl ester" pp. 1-5.

Non-Final Office Action dated Jun. 19, 2006 in related U.S. Appl. No. 11/597,566 filed Nov. 26, 2007, (US-2007-0213360-A1).

Non-Final Office Action dated Oct. 8, 2008 in related U.S. Appl. No. 11/883,596 filed Sep. 17, 2007. (US-2008-0096914-A1).

Non-Final Office Action dated Oct. 8, 2008 in related U.S. Appl. No. 11/628,369 filed Dec. 4, 2006. (US-2007-0259911).

Non-Final Office Action dated Jun. 3, 2009 in related U.S. Appl. No. 12/411,486 filed Mar. 26, 2009.

Non-Final Office Action dated Jun. 4, 2009 in related U.S. Appl. No. 12/390,827 filed Feb. 23, 2009.

* cited by examiner

US 7,723,523 B2

TETRAHYDROPYRIDOTHIOPHENES

This application was filed under 35 U. S. C. 371 as a national stage of PCT/EP2005/052384, filed May 25, 2005.

FIELD OF APPLICATION OF THE INVENTION

The invention relates to tetrahydropyridothiophene derivatives, which can be used in the pharmaceutical industry for the production of pharmaceutical compositions.

The invention further relates to the contribution made to the art by the finding, that said tetrahydropyridothiophene derivatives display cell-cycle dependent, anti-proliferative and apoptosis inducing activity.

The invention also relates to the use of these compounds for the therapy of hyperproliferative diseases, in particular human cancer.

KNOWN TECHNICAL BACKGROUND

Cancer chemotherapy was established with the alkylating agent Cyclophosphamide (Endoxan®), an oxazaphosphorine pro-drug activated preferentially in the tumor. The target of alkylating agents like Cyclophosphamide is DNA and the concept, that cancer cells with uncontrolled proliferation and a high mitotic index are killed preferentially, proved to be very successful. Standard cancer chemotherapeutic drugs finally kill cancer cells upon induction of programmed cell death ("apoptosis") by targeting basic cellular processes and molecules. These basic cellular processes and molecules include RNA/DNA (alkylating and carbamoylating agents, platin analogs and topoisomerase inhibitors), metabolism (drugs of this class are named anti-metabolites and examples are folic acid, purin and pyrimidine antagonist) as well as the mitotic spindle apparatus with αβ-tubulin heterodimers as the essential component (drugs are categorized into stabilizing and destabilizing tubulin inhibitors; examples are Taxol/Paclitaxel®, Docetaxel/Taxotere® and vinca alkaloids).

A subgroup of proapoptotic anticancer agents target cells preferentially in mitosis. In general these agents do not induce apoptosis in non-dividing cells, arrested in the G0, G1 or G2 phase of the cell division cycle. In contrast, dividing cells going through mitosis (M-phase of the cell division cycle), are killed efficiently by induction of apoptosis by this subgroup agents. Therefore, this subgroup or class of anti-cancer agents is described as cell-cycle specific or cell-cycle dependent. Tubulin inhibitors, with Taxol (Paclitaxel®) as a prominent example, belong to this class of cell-cycle specific, apoptosis inducing anti-cancer agents.

PRIOR ART

The international application WO2004/024065 describes, inter alia, tetrahydropyridothiophene derivatives as glucagons antagonists for the treatment of diabetes.

The german document DE4039734 describes, inter alia, N-alkylated tetrahydropyridothiophene derivatives as components of herbicidal agents.

The german document DD272078 describes, inter alia, N-alkylated tetrahydropyridothiophene derivatives with anti-anaphylactic und antihistaminergic properties.

The international application WO98/02440 describes 3-ureido-pyridothiophens which can be used for the treatment of acute and chronic inflammatory processes.

The Ambinter Screening Library discloses certain tetrahydropyridothiophens which differ profoundly from the compounds according to the present invention.

The international application WO2005/033102 describes thiophene-based compounds exhibiting ATP-utilizing enzyme inhibitory activity.

DESCRIPTION OF THE INVENTION

It has now been found that the tetrahydropyridothiophene derivatives, which are described in greater details below, differ from prior art compounds by creative structural alterations and have surprising and particularly advantageous properties.

In more detail, it has been unexpectedly found that tetrahydropyridothiophene derivatives, which are described in greater details below, are potent and highly efficacious inhibitors of cellular (hyper)proliferation and/or cell-cycle specific inducers of apoptosis in cancer cells. Therefore, unanticipatedly, these tetrahydropyridothiophene derivatives can be useful for treating (hyper)proliferative diseases and/or disorders responsive to the induction of apoptosis, in particular cancer. By having a cell-cycle specific mode of action, tetrahydropyridothiophene derivates according to this invention should have a higher therapeutic index compared to standard chemotherapeutic drugs targeting basic cellular processes like DNA replication or interfering with basic cellular molecules like DNA.

Thus, for example, the compounds according to this invention are expected to be useful in targeted cancer therapy.

The invention thus relates in a first aspect (aspect 1) to compounds of formula I

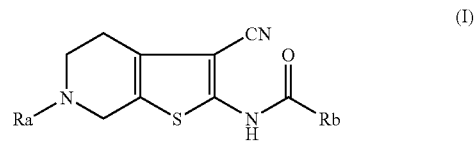

wherein

Ra is —C(O)R1, —C(O)OR2, —C(O)SR2, —C(O)N(R3)R4, —S(O)$_2$R1, or —S(O)$_2$N(R3)R4;

Rb is Q-2-4C-alkenyl, in which either

Q is optionally substituted by Rba and/or Rbb and/or Rbc, and is phenyl or naphthyl, or Q is optionally substituted by Rca and/or Rcb, and is Har, or Q is Cyc;

in which

R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R5;

each R4 is independently selected from the group consisting of: hydrogen, 1-7C-alkyl and 3-7C-cycloalkyl, wherein each of said 1-7C-alkyl and 3-7C-cycloalkyl can be unsubstituted or optionally substituted by at least one substituent independently selected from R5;

R5, Rba, Rbb, Rbc, Rca and Rcb may be the same or different and are independently selected from the group consisting of:

1-7C-alkyl, 3-7C-cycloalkyl, Ar, Har, Het, halogen, trifluoromethyl, nitro, cyano, guanidino, amidino,
—C(O)R6, —C(O)OR7, —C(O)N(R8)R9, —S(O)$_2$R6, —S(O)$_2$N(R8)R9,
—N(R10)C(O)R6, —N(R10)C(O)OR7, —N(R10)C(O)N(R8)R9, —N(R10)S(O)$_2$R6,
—N(R10)S(O)$_2$N(R8)R9,
—OC(O)R6, —OC(O)N(R8)R9,
—OR7, —N(R8)R9 and —SR7, wherein each of said 1-7C-alkyl, 3-7C-cycloalkyl, Ar, Har and Het can be unsubstituted or optionally substituted by at least one substituent independently selected from R11;

R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12;

each R9 is independently selected from the group consisting of: hydrogen, 1-7C-alkyl and 3-7C-cycloalkyl, wherein each of said 1-7C-alkyl and 3-7C-cycloalkyl can be unsubstituted or optionally substituted by at least one substituent independently selected from R12;

each R10 is independently selected from the group consisting of: hydrogen, 1-7C-alkyl and 3-7C-cycloalkyl;

R11 is selected from the group consisting of: R5 as defined above;

each R12 is independently selected from the group consisting of: R5 as defined above;

each Ar is independently selected from phenyl and naphthyl;

each Har is independently any fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, any 3-7C-cycloalkane group as defined herein, any additional heteroaryl ring A as defined herein, or any heterocyclic ring B as defined herein, whereby said Har ring or ring system is attached to the parent molecular group via a substitutable ring carbon or ring nitrogen atom;

each Het is independently any fully saturated or partially unsaturated mono- or fused bicyclic ring or ring system made up of a first constituent being a 3- to 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, any 3-7C-cycloalkane group as defined herein, or any additional heterocyclic ring B as defined herein, whereby said Het ring or ring system is attached to the parent molecular group via a substitutable ring carbon or ring nitrogen atom;

Cyc is optionally substituted by halogen on its benzene ring, and is a group of formula A

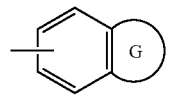

(A)

in which

G is optionally substituted by Rda and/or Rdb, and is a 5- or 6-membered saturated heterocyclic ring comprising one or two heteroatoms independently selected from the group consisting of nitrogen, oxygen and sulfur, in which Rda is 1-4C-alkyl or halogen, Rdb is 1-4C-alkyl or halogen, whereby said Cyc ring system is attached to the parent molecular group via a substitutable benzoring carbon atom;

and the salts, solvates or the solvates of the salts thereof.

The invention further relates in a second aspect (aspect 2), which is an embodiment of aspect 1, to compounds of formula I wherein Ra is —C(O)R1, —C(O)OR2, —C(O)SR2, —C(O)N(R3)R4, —S(O)$_2$R1, or —S(O)$_2$N(R3)R4;

Rb is Q-2-4C-alkenyl, in which either

Q is optionally substituted by Rba and/or Rbb and/or Rbc, and is phenyl or naphthyl, or Q is optionally substituted by Rca and/or Rcb, and is Har, or Q is Cyc;

in which

R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R5;

each R4 is independently selected from the group consisting of: hydrogen, 1-7C-alkyl and 3-7C-cycloalkyl, wherein each of said 1-7C-alkyl and 3-7C-cycloalkyl can be unsubstituted or optionally substituted by at least one substituent independently selected from R5;

R5, Rba, Rbb, Rbc, Rca and Rcb may be the same or different and are independently selected from the group consisting of:

1-7C-alkyl, 3-7C-cycloalkyl, Ar, Har, Het, halogen, trifluoromethyl, nitro, cyano, guanidino, amidino,
—C(O)R6, —C(O)OR7, —C(O)N(R8)R9, —S(O)$_2$R6, —S(O)$_2$N(R8)R9,
—N(R10)C(O)R6, —N(R10)C(O)OR7, —N(R10)C(O)N(R8)R9, —N(R10)S(O)$_2$R6,
—N(R10)S(O)$_2$N(R8)R9,
—OC(O)R6, —OC(O)N(R8)R9,
—OR7, —N(R8)R9 and —SR7, wherein each of said 1-7C-alkyl, 3-7C-cycloalkyl, Ar, Har and Het can be unsubstituted or optionally substituted by at least one substituent independently selected from R11;

R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12;

each R9 is independently selected from the group consisting of: hydrogen, 1-7C-alkyl and 3-7C-cycloalkyl, wherein each of said 1-7C-alkyl and 3-7C-cycloalkyl can be unsubstituted or optionally substituted by at least one substituent independently selected from R12;

each R10 is independently selected from the group consisting of: hydrogen, 1-7C-alkyl and 3-7C-cycloalkyl;

R11 is selected from the group consisting of: R5 as defined above;

each R12 is independently selected from the group consisting of: R5 as defined above;

each Ar is independently selected from phenyl and naphthyl;

each Har is independently any fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, any 3-7C-cycloalkane group as defined herein, any additional heteroaryl ring A as defined herein, or any heterocyclic ring B as defined herein, whereby said Har ring or ring system is attached to the parent molecular group via a substitutable ring carbon or ring nitrogen atom;

each Het is independently any fully saturated or partially unsaturated mono- or fused bicyclic ring or ring system made up of a first constituent being a 3- to 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, any 3-7C-cycloalkane group as defined herein, or any additional heterocyclic ring B as defined herein, whereby said Het ring or ring system is attached to the parent molecular group via a substitutable ring carbon or ring nitrogen atom;

Cyc is a group of formula A

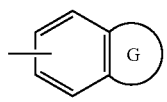

(A)

in which

G is a 5- or 6-membered saturated heterocyclic ring comprising one or two heteroatoms independently selected from the group consisting of nitrogen, oxygen and sulfur, whereby said Cyc ring system is attached to the parent molecular group via a substitutable benzoring carbon atom;

and the salts, solvates or the solvates of the salts thereof.

As used herein, "alkyl" refers to both branched and straight chain saturated aliphatic hydrocarbon groups having the specified numbers of carbon atoms, such as for example:

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, isopropyl, and, in particular, the propyl, ethyl and methyl radicals, in more particular the ethyl and methyl radicals.

1-7C-Alkyl, which is substituted as described herein, refers to one of the abovementioned 1-7C-alkyl radicals, which is substituted as described herein, and may include for example, without being restricted thereto, propyl, ethyl or methyl.

One notable embodiment of herein-mentioned "alkyl" having the specified numbers of carbon atoms refers to the straight-chain radicals thereof. Thus, for example, a notable embodiment of 1-7C-alkyl, 1-6C-alkyl or 1-5C-alkyl as mentioned herein refers to straight-chain 1-5C-alkyl radicals, especially to straight-chain 1-4C-alkyl radicals, such as e.g. the methyl, ethyl, propyl, butyl or pentyl radical.

2-4C-Alkenyl is a straight chain or branched alkenyl radical having 2 to 4 carbon atoms. Examples are the 2-butenyl, 3-butenyl, isopropenyl, 1-propenyl, 2-propenyl(allyl) and, particularly, the ethenyl (vinyl) radical, as well as all possible stereoisomers thereof.

Q-2-4C-alkenyl stands for one of the abovementioned 2-4C-alkenyl radicals substituted by the moiety Q, which has the meanings as given herein. Exemplarily may be preferably mentioned the 2-Q-ethen-1-yl radical [—CH=CH-Q], which stands for an ethenyl radical substituted in 2-position by the moiety Q, particularly the trans isomer thereof. As further example, the 2-Q-(1-methyl)-ethen-1-yl radical [—C(CH$_3$)=CH-Q] may be mentioned.

3-7C-Cycloalkyl stands for cyclopropyl, cyclobutyl, cyclopentyl, cyclohexyl and cycloheptyl, of which cyclopropyl and cyclopentyl are to be emphasized.

3-7C-Cycloalkane stands for cyclopropane, cyclobutane, cyclopentane, cyclohexane and cycloheptane, of which cyclohexane and cyclopentane are to be emphasized.

Halogen within the meaning of the present invention is iodine, or, particularly, bromine, chlorine and fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radical.

1-4C-Alkoxy-2-4C-alkoxy stands for a 2-4C-alkoxy radical which is substituted by one of the abovementioned 1-4C-alkoxy radicals. Examples which may be mentioned are the 2-(methoxy)ethoxy (—O—CH$_2$—CH$_2$—O—CH$_3$) and the 2-(ethoxy)ethoxy radical (—O—CH$_2$—CH$_2$—O—CH$_2$—CH$_3$).

Phenyl-1-4C-alkoxy represents one of the abovementioned 1-4C-alkoxy radicals, which is substituted by a phenyl radical. Examples which may be mentioned are the phenethoxy and the benzyloxy radicals.

1-4C-Alkylcarbonyl represents a radical which, in addition to the carbonyl group, contains one of the abovementioned 1-4C-alkyl radicals. An example which may be mentioned is the acetyl radical.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

1-4C-Alkylcarbonyloxy radicals contain, in addition to the oxygen atom, one of the abovementioned 1-4C-alkylcarbonyl radicals. An example is the acetoxy radical ($CH_3C(O)-O-$).

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

An 1-4C-Alkylcarbonylamino radical is, for example, the propionylamino ($C_3H_7C(O)NH-$) and the acetylamino radical ($CH_3C(O)NH-$).

Phenyl-1-4C-alkyl represents one of the abovementioned 1-4C-alkyl radicals, which is substituted by a phenyl radical. Examples which may be mentioned are the phenethyl and the benzyl radicals.

(1-4C-Alkoxy)-phenyl stands for a phenyl radical which is substituted by one of the abovementioned 1-4C-alkoxy radicals.

Di-(1-4C-alkoxy)-phenyl stands for a phenyl radical which is substituted by two of the abovementioned 1-4C-alkoxy radicals.

Ar stands for naphthyl or, particularly, phenyl.

As completely or predominantly fluorine-substituted 1-4C-alkoxy, for example, the 2,2,3,3,3-penta-fluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1-4C-alkoxy radicals are replaced by fluorine atoms.

Pyridyl-1-4C-alkoxy represents one of the abovementioned 1-4C-alkoxy radicals, which is substituted by a pyridyl radical. Examples which may be mentioned are the 2-pyridyl-ethoxy and the pyridylmethoxy radicals.

Pyridyl includes pyridin-2-yl, pyridin-3-yl and pyridin-4-yl.

As it is known for the skilled person, the terms imidazolo, pyrazolo, piperidino or morpholino stands for imidazol-1-yl, pyrazol-1-yl, piperidin-1-yl or morpholin-4-yl, respectively. Similar terms used herein are to be understood similarly, mutatis mutandis, as defined for these terms.

(1-4C-Alkoxy-2-4C-alkoxy)-2-4C-alkoxy represents 2-4C-alkoxy radicals, which are substituted by one of the abovementioned 1-4C-alkoxy-2-4C-alkoxy radicals. Examples which may be mentioned are the 2-(2-methoxyethoxy)-ethoxy and the 2-(2-ethoxyethoxy)-ethoxy radicals.

Hydroxy-2-4C-alkoxy represents 2-4C-alkoxy radicals, which are substituted by a hydroxyl group. Examples which may be mentioned are the 2-hydroxyethoxy and the 3-hydroxypropoxy radicals.

3-7C-Cycloalkyl-1-4C-alkoxy stands for one of the abovementioned 1-4C-alkoxy radicals substituted by one of the abovementioned 3-7C-cycloalkyl radicals. Examples which may be mentioned are the 3-7C-cycloalkylmethoxy radicals, such as cyclopropylmethoxy, cyclobutylmethoxy, cyclopentylmethoxy, cyclohexylmethoxy or cycloheptylmethoxy, of which cyclopropylmethoxy, cyclobutylmethoxy or cyclopentylmethoxy are in particular to be mentioned.

3-7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are to be emphasized.

Cyano-1-4C-alkoxy represents 1-4C-alkoxy radicals, which are substituted by one cyano radical. Examples which may be mentioned are the cyanomethoxy and the 2-cyanoyethoxy radicals.

The expression (Rba)-phenyl means that the phenyl radical is substituted by Rba, which is attached to any of the positions of the phenyl ring; the expression 2-(Rba)-phenyl means that the phenyl radical is substituted by Rba, which is attached in the 2-position to the phenyl radical (i.e. the ortho position with respect to the binding position in which the phenyl ring is bonded to the parent molecular group); the expression "Rbb-substituted 2-(Rba)-phenyl" means that the phenyl radical is substituted by both Rbb and Rba, whereby the substituent Rba is bonded in the 2-position to the phenyl radical, and the substituent Rbb is bonded in any other position to the phenyl ring; and the expression "2-(Rba)-5-(Rbb)-phenyl" means, that the phenyl radical is substituted by both Rba and Rbb, whereby the substituent Rba is bonded in the 2-position to the phenyl radical, and the substituent Rbb is bonded in the 5-position to the phenyl ring; In this connection, further similar expressions mentioned herein indicating in short form the positions in which substituents are bonded to a ring radical are to be understood similarly, mutatis mutandis, as specified exemplarily and representatively for the foregoing expressions.

The term (R5)-methyl stand for methyl which is substituted by R5. The term 2-(R5)-ethyl stands for ethyl which is substituted in 2-position by R5. The term 3-(R5)-propyl stands for propyl which is substituted in 3-position by R5.

Har stands for a fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, a 3-7C-cycloalkane group as defined herein, an additional heteroaryl ring A as defined herein, or a heterocyclic ring B as defined herein, whereby said Har ring or ring system is attached to the parent molecular group via a substitutable ring carbon or ring nitrogen atom of any of said constituents.

Examples for Har may include, but are not limited to, 5-membered heteroaryl radicals, such as e.g. furanyl, thiophenyl, pyrrolyl, oxazolyl, isoxazolyl, thiazolyl, isothiazolyl, imidazolyl, pyrazolyl, triazolyl, thiadiazolyl, oxadiazolyl, and 6-membered heteroaryl radicals, such as e.g. pyridinyl, pyrimidinyl, pyrazinyl or pyridazinyl, and the benzo-fused derivatives thereof such as e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl, benzimidazolyl, benzotriazolyl, benzoxadiazolyl or benzothiadiazolyl, as well as naphthyridinyl, indolizinyl or purinyl.

Het stands for a fully saturated or partially unsaturated mono- or fused bicyclic ring or ring system made up of a first constituent being a 3- to 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, a 3-7C-cycloalkane group as defined herein, or an additional heterocyclic ring B as defined herein, whereby said Het ring or ring system is attached to the parent molecular group via a substitutable ring carbon or ring nitrogen atom of any of said constituents.

Examples for Het may include, but are not limited to, aziridinyl, azetidinyl, pyrrolidinyl, piperidinyl, homopiperidinyl, pyrazolidinyl, imidazolidinyl, piperazinyl, homopiperazinyl, morpholinyl or thiomorpholinyl, and the partially unsaturated derivatives thereof such as e.g. pyrrolinyl, imidazolinyl or pyrazolinyl, and the oxo substituted derivatives of the aforementioned examples such as e.g. 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl or 5-oxo-1,4-diazepanyl, or S-oxo-thiomorpholinyl or S,S-dioxo-thiomorpholinyl, and the benzo-fused derivatives of the aforementioned examples such as e.g. indolinyl, isoindolinyl, 1,2,3,4-tetrahydroquinolinyl or 1,2,3,4-tetrahydroisoquinolinyl, as well as 1,3-benzodioxolyl, 2,3-dihydro-1,4-benzodioxinyl, 2,3-dihydrobenzothiophenyl, chromenyl, chromanyl, or 2,3-dihydrobenzofuranyl.

More detailed exemplary Het radicals include those isomers of the abovementioned examples which are attached via a ring nitrogen atom, such as e.g., without being limited to, aziridin-1-yl, azetidin-1-yl, pyrrolidin-1-yl, piperidin-1-yl, homopiperidin-1-yl, piperazin-1-yl homopiperazin-1-yl, morpholin-4-yl or thiomorpholin-4-yl, or S-oxo-thiomorpholin-4-yl or S,S-dioxo-thiomorpholin-4-yl.

Other more detailed exemplary Het radicals include those isomers of the abovementioned examples which are attached via a ring carbon atom, such as e.g., without being limited to, pyrrolidin-2-yl, pyrrolidin-2-yl, piperidin-2-yl, piperidin-3-yl, piperidin-4-yl or piperazin-2-yl.

As used herein, the term "oxo" forms a carbonyl moiety when attached at a carbon atom, a sulfoxide moiety when attached to a sulfur atom and a sulfonyl moiety when two of said terms are attached to a sulfur atom.

In a first embodiment, Cyc is optionally substituted by halogen on its benzene ring, and is a group of formula A

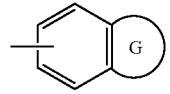

(A)

in which
G is optionally substituted by Rda and/or Rdb, and is a 5- or 6-membered saturated heterocyclic ring comprising one or two heteroatoms independently selected from the group consisting of nitrogen, oxygen and sulfur, in which
Rda is 1-4C-alkyl or halogen,
Rdb is 1-4C-alkyl or halogen, whereby said Cyc ring system is attached to the parent molecular group via a substitutable benzoring carbon atom.

In a second embodiment Cyc is a group of formula A

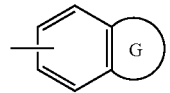

(A)

in which
G is a 5- or 6-membered saturated heterocyclic ring comprising one or two heteroatoms independently selected from the group consisting of nitrogen, oxygen and sulfur, whereby said Cyc ring system is attached to the parent molecular group via any substitutable carbon atom of the benzene ring.

As examples of Cyc may be mentioned indolinyl, isoindolinyl, 1,2,3,4-tetrahydroquinolinyl, 1,2,3,4-tetrahydroisoquinolinyl, 1,3-benzodioxolyl, 2,3-dihydro-1,4-benzodioxinyl, 2,3-dihydrobenzothiophenyl, or 2,3-dihydrobenzofuranyl.

More detailed exemplary Cyc radicals include, without being limited thereto, 1,3-benzodioxolyl, 2,3-dihydro-1,4-benzodioxinyl, chromenyl, chromanyl or 2,3-dihydrobenzofuranyl, as well as 2,2-difluoro-1,3-benzodioxolyl.

Illustratively, as exemplary suitable Cyc radicals may be mentioned, without being limited thereto, 1,3-benzodioxolyl, 2,3-dihydro-1,4-benzodioxinyl, 2,3-dihydrobenzofuranyl, as well as 2,2-difluoro-1,3-benzodioxolyl.

As more specific exemplary suitable Cyc radicals may be mentioned, without being limited thereto, 1,3-benzodioxol-4-yl, 1,3-benzodioxol-5-yl, 2,3-dihydro-1,4-benzodioxin-5-yl, 2,3-dihydro-1,4-benzodioxin-6-yl, 2,3-dihydrobenzofuran-7-yl, as well as 2,2-difluoro-1,3-benzodioxol-4-yl.

It is to be stated that Cyc is an embodiment of Het as defined herein.

In general, unless otherwise mentioned, the terms "Har", "Het" and "Cyc" include all the possible isomeric forms thereof, particularly the positional isomers thereof. Thus, for example, the term pyridyl or pyridinyl includes pyridin-2-yl, pyridin-3-yl and pyridin-4-yl.

Unless otherwise noted, constituents which are optionally substituted as stated herein, may be substituted by their substituents or parent molecular groups at any possible position.

Notably, unless otherwise mentioned, the substituents Rba, Rbb and Rbc may be attached at any possible position of the phenyl or naphthyl radical.

Yet notably, unless otherwise mentioned, Ar may be substituted by its substituents or parent molecular groups at any possible position.

Still yet notably, unless otherwise mentioned, Har and Het may be substituted by their substituents or parent molecular groups as mentioned herein at any possible position, such as e.g. at any substitutable ring carbon or ring nitrogen atom.

Further notable, in Q-2-4C-alkenyl, the Q moiety is substituted by the 2-4C-alkenyl moiety at any possible position of the Q ring.

Thus e.g., in Har-2-4C-alkenyl, the Har moiety is substituted by the 2-4C-alkenyl moiety at any possible position of the Har ring, particularly the Har moiety is substituted by the 2-4C-alkenyl moiety at any one of its ring carbon atoms. Likewise, in Cyc-2-4C-alkenyl, the Cyc moiety is substituted by the 2-4C-alkenyl moiety at any possible position of the benzo-moiety of Cyc.

Rings containing quaternizable imino-type ring nitrogen atoms (—N═) may be preferably not substituted (i.e. quaternized) on these imino-type ring nitrogen atoms by the mentioned substituents or parent molecular groups.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

The person skilled in the art is aware on account of his/her expert knowledge that certain combinations of the variable characteristics mentioned in the description of this invention lead to chemically less stable compounds. This can apply, for example, to certain compounds, in which—in a manner being disadvantageous for chemical stability—two heteroatoms (S, N or O) would directly meet or would only be separated by one carbon atom. This can also apply, for example, to certain free acid derivatives, such as e.g. certain carbamic acid derivatives containing a free carbamic acid function (N—C(O)OH). Those compounds according to this invention, in which the combination of the abovementioned variable substituents does not lead to chemically less stable compounds, are therefore preferred. Suitable salts for compounds according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to this invention on an industrial scale, are converted into pharmacologically tolerable salts by processes known to the person skilled in the art.

According to expert's knowledge the compounds according to this invention as well as their salts may contain, e.g. when isolated in crystalline form, varying amounts of solvents. Included within the scope of the invention are therefore all solvates and in particular all hydrates of the compounds according to this invention as well as all solvates and in particular all hydrates of the salts of the compounds according to this invention.

In the context of this invention, hyperproliferation and analogous terms are used to describe aberrant/ dysregulated cellular growth, a hallmark of diseases like cancer. This hyperproliferation might be caused by single or multiple cellular / molecular alterations in respective cells and can be, in context of a whole organism, of benign or malignant behaviour. Inhibition of cell proliferation and analogous terms is used to denote an ability of the compound to retard the growth of a cell contacted with that compound as compared to cells not contacted with that compound. Most preferable this inhibition of cell proliferation is 100%, meaning that proliferation of all cells is stopped and/or cells undergo programmed cell death. In some preferred embodiments the contacted cell is a neoplastic cell. A neoplastic cell is defined as a cell with aberrant cell proliferation. A benign neoplasia is described by hyperproliferation of cells, incapable of forming an aggressive, metastasizing tumor in-vivo. In contrast, a malignant neoplasia is described by cells with different cellular and biochemical abnormalities, capable of forming tumor metastasis. The acquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and issue invasion and metastasis.

Inducer of apoptosis and analogous terms are used to identify a compound which executes programmed cell death in cells contacted with that compound. Apoptosis is defined by complex biochemical events within the contacted cell, such as the activation of cysteine specific proteinases ("caspases") and the fragmentation of chromatin. Induction of apoptosis in cells contacted with the compound might not necessarily coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic is used in a more general sense to identify compounds which kill cells by various mechanisms, including the induction of apoptosis/ programmed cell death in a cell cycle dependent or cell-cycle independent manner.

Cell cycle specific and analogous terms are used to identify a compound as including apoptosis only in continuously proliferating cells actively passing a specific phase of the cell cycle, but not in resting, non-dividing cells. Continuously proliferating cells are typical for diseases like cancer and characterized by cells in all phases of the cell division cycle, namely in the G ("gap") 1, S ("DNA synthesis"), G2 and M ("mitosis") phase.

Compounds according to aspect 1 of this invention more worthy to be noted are those compounds of formulae Ia or Ib as shown herein, in which
Ra is —C(O)R1, in which either
R1 is 1-7C-alkyl, or imidazolo, or R1 is 1-7C-alkyl which is substituted by one substituent selected from R5, or R1 is 2-4C-alkyl which is substituted by two hydroxyl groups on different carbon atoms, or R1 is 2,2-dimethyl-[1,3]dioxolan-4-yl, or 1-2C-alkyl which is substituted by 2,2-dimethyl-[1,3]dioxolan-4-yl;

or in which
Ra is —C(O)OR2, in which either

R2 is 1-7C-alkyl, 3-7C-cycloalkyl, phenyl, pyridyl, (1-4C-alkoxycarbonyl)-phenyl, or (1-4C-alkoxy)-phenyl, or R2 is 1-7C-alkyl which is substituted by one substituent selected from R5, or R2 is 3-4C-alkyl which is substituted by two hydroxyl groups on different carbon atoms, or R2 is 1-2C-alkyl which is substituted by 2,2-dimethyl-[1,3]dioxolan-4-yl;

or in which
Ra is —C(O)SR2, in which either
R2 is 1-7C-alkyl, or

R2 is 1-7C-alkyl which is substituted by one substituent selected from R5, or

R2 is 3-4C-alkyl which is substituted by two hydroxyl groups on different carbon atoms, or R2 is 1-2C-alkyl which is substituted by 2,2-dimethyl-[1,3]dioxolan-4-yl;

and in which either

Q is Rba- and/or Rbb- and/or Rbc-substituted phenyl, or

Q is unsubstituted phenyl, or

Q is optionally substituted by Rca and/or Rcb, and is Har, or

Q is Cyc;

in which each R5 is independently selected from the group consisting of:

1-4C-alkoxy, 1-4C-alkoxy-2-4C-alkoxy, (1-4C-alkoxy-2-4C-alkoxy)-2-4C-alkoxy, hydroxyl, 1-4C-alkylcarbonyloxy, phenoxy, phenyl-1-4C-alkoxy, 1-4C-alkoxycarbonyl, carboxyl, amino, mono- or di-1-4C-alkylamino, mono- or di-1-4C-alkylaminocarbonyl, carbamoyl, ureido, guanidino, 1-4C-alkylcarbonylamino, Het, Har and phenyl, wherein each of said Har or phenyl radicals alone or part of another group may be unsubstituted or optionally substituted by one or two substituents independently selected from halogen, 1-4C-alkoxy, nitro, trifluoromethyl, 1-4C-alkyl, 1-4C-alkoxycarbonyl and carboxyl, Rba is halogen, 1-4C-alkyl, nitro, trifluoromethyl, 1-4C-alkoxy, mono- or di-1-4C-alkylamino, hydroxyl, 1-4C-alkylcarbonyloxy, cyano, phenyl, morpholino, phenoxy, hydroxy-2-4C-alkoxy, 1-4C-alkoxy-2-4C-alkoxy, 3-7C-cycloalkoxy, 3-7C-cycloalkyl-1-4C-alkoxy, phenyl-1-4C-alkoxy, cyano-1-4C-alkoxy, or completely or predominantly fluorine-substituted 1-4C-alkoxy, Rbb is 1-4C-alkoxy, halogen, trifluoromethyl or 1-4C-alkyl, Rbc is 1-4C-alkoxy, halogen, trifluoromethyl or 1-4C-alkyl, Rca is halogen, 1-4C-alkyl, 1-4C-alkoxy, trifluoromethyl, phenyl, phenoxy or morpholino, Rcb is halogen, 1-4C-alkyl or 1-4C-alkoxy, each Har is independently either a 5-membered monocyclic heteroaryl radical comprising one, two or three heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl, or a 6-membered monocyclic heteroaryl radical comprising one or two nitrogen atoms, such as e.g. any one selected from pyridinyl, pyrazinyl, pyridazinyl and pyrimidinyl, or a 9-membered fused bicyclic heteroaryl radical comprising one, two or three heteroatoms independently selected from nitrogen, oxygen and sulphur, such as e.g. any one selected from indolyl, benzothiophenyl, benzofuranyl, benzoxazoly, benzisoxazolyl, benzothiazolyl, benzoisothiazolyl, benzimidazolyl, indazolyl, benzotriazolyl, benzothiadiazolyl and benzoxadiazolyl, or a 10-membered fused bicyclic heteroaryl radical comprising one, two or three heteroatoms independently selected from nitrogen, oxygen and sulphur, such as e.g. any one selected from quinolinyl, isoquinolinyl, quinoxalinyl, quinazolinyl and cinnolinyl, whereby said Har radical is attached to the parent molecular group via a ring carbon atom or ring nitrogen atom, Het is morpholino, piperidino, pyrrolidino, 4N—H-piperazino, 4N-(1-4C-alkyl)-piperazino, thiomorpholino, S-oxo-thiomorpholino or S,S-dioxo-thiomorpholino, Cyc is optionally substituted by halogen on its benzene ring, and is 1,3-benzodioxolyl, 2,3-dihydro-1,4-benzodioxinyl, 2,2-difluoro-1,3-benzodioxolyl, 2,2-dimethyl-1,3-benzodioxolyl, chromanyl, chromenyl or 2,3-dihydro-benzofuranyl, whereby said Cyc ring system is attached to the parent molecular group via a substitutable benzoring carbon atom;

and the salts, solvates or the solvates of the salts thereof.

Compounds according to aspect 1 of this invention in particular worthy to be noted are those compounds of formula Ia as shown herein, in which
Ra is —C(O)R1, in which either R1 is 1-6C-alkyl, or R1 is 1-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, amino, morpholino, piperidino, pyrrolidino, 4N-(1-4C-alkyl)-piperazino, mono- or di-1-4C-alkylamino, mono- or di-1-4C-alkylaminocarbonyl, carbamoyl, ureido, guanidino, imidazolo, triazolo, pyrazolo, 1-4C-alkylcarbonyloxy or 1-4C-alkylcarbonylamino,
  wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, imidazolo, pyrazolo or phenyl radicals alone or part of another group may be unsubstituted or optionally substituted by one or two substituents independently selected from halogen, 1-4C-alkoxy, nitro and 1-4C-alkyl, or R1 is 3-4C-alkyl which is substituted by two hydroxyl groups on different carbon atoms, or R1 is 1-2C-alkyl which is substituted by 2,2-dimethyl-[1,3]dioxolan-4-yl;

or in which

Ra is —C(O)OR2, in which either

R2 is 1-6C-alkyl, or

R2 is 3-7C-cycloalkyl, phenyl, pyridyl, (1-4C-alkoxycarbonyl)-phenyl, or (1-4C-alkoxy)-phenyl, or R2 is 1-4C-alkyl which is mono-substituted by R5, in which
R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, mono- or di-1-4C-alkylaminocarbonyl or carbamoyl,
  wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or optionally substituted by one or two substituents independently selected from halogen, 1-4C-alkoxy, nitro and 1-4C-alkyl, or R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino,
  wherein each of said imidazolo, pyrazolo or phenyl radicals alone or part of another group can be unsubstituted or optionally substituted by one or two substituents independently selected from halogen, 1-4C-alkoxy, nitro and 1-4C-alkyl, or R2 is 3-4C-alkyl which is substituted by two hydroxyl groups on different carbon atoms, or R2 is 1-2C-alkyl which is substituted by 2,2-dimethyl-[1,3]dioxolan-4-yl;

or in which

Ra is —C(O)SR2, in which either

R2 is 1-6C-alkyl, or

R2 is 1-4C-alkyl which is mono-substituted by R5, in which
R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, mono- or di-1-4C-alkylaminocarbonyl or carbamoyl,
  wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or optionally substituted by one or two substituents independently selected from halogen, 1-4C-alkoxy, nitro and 1-4C-alkyl, or R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino,
  wherein each of said imidazolo, pyrazolo or phenyl radicals alone or part of another group can be unsubstituted or optionally substituted by one or two substituents independently selected from halogen, 1-4C-alkoxy, nitro and 1-4C-alkyl;

and in which either

Q is Rba- and/or Rbb- and/or Rbc-substituted phenyl, or

Q is unsubstituted phenyl, or

Q is substituted by Rca and/or Rcb, and is thiophenyl, furanyl, pyridyl, 1N-methyl-pyrrolyl, 1N-methyl-imidazolyl, 1N-methyl-pyrazolyl, benzothiophenyl or benzofuranyl, or Q is unsubstituted, and is thiophenyl, furanyl, pyridyl, 1N—H-pyrrolyl, 1N—H-pyrazolyl, 1N—H-imidazolyl, 1N-methyl-pyrrolyl, 1N-methyl-imidazolyl, 1N-methyl-pyrazolyl, benzothiophenyl or benzofuranyl, or Q is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3- dihydro-benzofuran-5-yl, 2,3-dihydro-benzofuran-6-yl or 2,3-dihydro-benzofuran-7-yl, or Q is substituted by halogen on its benzene ring, and is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl;

in which

Rba is halogen, 1-4C-alkyl, nitro, trifluoromethyl, 1-4C-alkoxy, mono- or di-1-4C-alkylamino, hydroxyl, 1-4C-alkylcarbonyloxy, cyano, phenyl, morpholino, phenoxy, hydroxy-2-4C-alkoxy, 1-4C-alkoxy-2-4C-alkoxy, or completely or predominantly fluorine-substituted 1-4C-alkoxy, Rbb is 1-4C-alkoxy, halogen or 1-4C-alkyl, Rbc is 1-4C-alkoxy or halogen, Rca is halogen, 1-4C-alkyl, 1-4C-alkoxy, phenyl, phenoxy or morpholino, Rcb is halogen, 1-4C-alkyl or 1-4C-alkoxy, and the salts, solvates or the solvates of the salts thereof.

Compounds according to aspect 1 of this invention in more particular worthy to be noted are those compounds of formula Ia as shown herein, in which Ra is —C(O)R1, in which either R1 is 1-5C-alkyl, or R1 is 1-4C-alkyl which is mono-substituted by R5, in which R5 is 1-4C-alkoxy, 1-4C-alkoxy-2-4C-alkoxy, (1-4C-alkoxy-2-4C-alkoxy)-2-4C-alkoxy, hydroxyl, pyridyl, pyrimidinyl, pyrazinyl, indolyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, morpholino, di-1-4C-alkylaminocarbonyl, carbamoyl, ureido, guanidino, imidazolo, triazolo, pyrazolo or 1-4C-alkylcarbonyloxy, or R1 is 3-4C-alkyl which is substituted by two hydroxyl groups on different carbon atoms, or R1 is 1-2C-alkyl which is substituted by 2,2-dimethyl-[1,3] dioxolan-4-yl;

or in which

Ra is —C(O)OR2, in which either

R2 is 1-5C-alkyl, or

R2 is 3-6C-cycloalkyl, phenyl, pyridyl, (1-4C-alkoxycarbonyl)-phenyl, or (1-4C-alkoxy)-phenyl, or R2 is 1-4C-alkyl which is mono-substituted by R5, in which R5 is pyridyl, pyrimidinyl, pyrazinyl, 1N-(1-4C-alkyl)-imidazolyl, 1N-(1-4C-alkyl)-pyrazolyl, phenyl, (1-4C-alkoxy)-phenyl, 1-4C-alkoxycarbonyl, carboxyl, di-1-4C-alkylaminocarbonyl or carbamoyl, or R2 is 2-4C-alkyl which is mono-substituted by R5, in which R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, morpholino, piperidino, pyrrolidino, 4N-(1-4C-alkyl)-piperazino, di-1-4C-alkylamino, imidazolo, triazolo, pyrazolo, 1-4C-alkylcarbonyloxy or 1-4C-alkylcarbonylamino, or R2 is 3-4C-alkyl which is substituted by two hydroxyl groups on different carbon atoms, or R2 is 1-2C-alkyl which is substituted by 2,2-dimethyl-[1,3] dioxolan-4-yl;

or in which

Ra is —C(O)SR2, in which either

R2 is 1-5C-alkyl, or

R2 is 2-4C-alkyl which is mono-substituted by R5, in which R5 is di-1-4C-alkylamino, hydroxyl or pyridyl;

and in which either

Q is Rba- and/or Rbb- and/or Rbc-substituted phenyl, or

Q is unsubstituted phenyl, or

Q is substituted by Rca, and is thiophenyl, furanyl, pyridyl or 1N-(methyl)-pyrazolyl, or Q is unsubstituted, and is thiophenyl, furanyl, pyridyl, 1N—(H)-pyrrolyl, 1N-(methyl)-pyrrolyl, benzothiophenyl or benzofuranyl, or Q is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl, or Q is substituted by halogen on its benzene ring, and is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl;

in which

Rba is halogen, 1-4C-alkyl, nitro, trifluoromethyl, 1-4C-alkoxy, di-1-4C-alkylamino, hydroxyl, 1-4C-alkylcarbonyloxy, cyano, phenyl, morpholino, phenoxy, hydroxy-2-4C-alkoxy, 1-4C-alkoxy-2-4C-alkoxy, or completely or predominantly fluorine-substituted 1-4C-alkoxy, Rbb is 1-4C-alkoxy, halogen or 1-4C-alkyl, Rbc is 1-4C-alkoxy or halogen, Rca is halogen, 1-4C-alkyl, 1-4C-alkoxy, phenyl, phenoxy or morpholino, and the salts, solvates or the solvates of the salts thereof.

Compounds according to aspect 1 of this invention to be emphasized are those compounds of formula Ia as shown herein, in which
Ra is —C(O)R1, in which either
R1 is methyl, ethyl, propyl or butyl, or
R1 is methyl which is mono-substituted by R5, ethyl which is mono-substituted by R5, or propyl which is mono-substituted by R5, in which
R5 is methoxy, ethoxy, 2-methoxyethoxy, 2-(2-methoxy-ethoxy)-ethoxy, hydroxyl, pyridyl, pyrimidinyl, pyrazinyl, indolyl, thiazolyl, oxazolyl, 1N-methyl-imidazolyl, 1N-methyl-pyrazolyl, phenyl, methoxycarbonyl, ethoxycarbonyl, carboxyl, dimethylaminocarbonyl, morpholino, carbamoyl, ureido, guanidino, imidazolo, triazolo, pyrazolo, ethylcarbonyloxy or methylcarbonyloxy, or
R1 is propyl or butyl, each of which is substituted by two hydroxyl groups on different carbon atoms, or
R1 is methyl or ethyl, each of which is substituted by 2,2-dimethyl-[1,3]dioxolan-4-yl;

or in which
Ra is —C(O)OR2, in which either
R2 is methyl, ethyl, propyl or butyl, or
R2 is cyclohexyl, phenyl, pyridyl, (1-2C-alkoxycarbonyl)-phenyl, or (1-2C-alkoxy)-phenyl, or
R2 is methyl which is mono-substituted by R5, ethyl which is mono-substituted by R5, or propyl which is mono-substituted by R5, in which
R5 is pyridyl, pyrimidinyl, pyrazinyl, 1N-methyl-imidazolyl, 1N-methyl-pyrazolyl, phenyl, (1-2C-alkoxy)-phenyl, methoxycarbonyl, ethoxycarbonyl, carboxyl, di-methylaminocarbonyl or carbamoyl, or
R2 is ethyl which is mono-substituted by R5, or propyl which is mono-substituted by R5, in which
R5 is methoxy, ethoxy, 2-methoxyethoxy, 2-(2-methoxy-ethoxy)-ethoxy, hydroxyl, benzyloxy, phenoxy, morpholino, piperidino, pyrrolidino, 4N-(methyl)-piperazino, dimethylamino, imidazolo, triazolo, pyrazolo, methylcarbonyloxy, ethylcarbonyloxy, methylcarbonylamino or ethylcarbonylamino, or
R2 is propyl or butyl, each of which is substituted by two hydroxyl groups on different carbon atoms, or
R2 is methyl or ethyl, each of which is substituted by 2,2-dimethyl-[1,3]dioxolan-4-yl;

or in which
Ra is —C(O)SR2, in which either
R2 is methyl, ethyl, propyl, butyl or pentyl, or
R2 is ethyl which is mono-substituted by R5, or propyl which is mono-substituted by R5, in which
R5 is dimethylamino, hydroxyl or pyridyl;

and in which either
Q is Rba- and/or Rbb- and/or Rbc-substituted phenyl, or
Q is unsubstituted phenyl, or
Q is substituted by Rca, and is thiophenyl, furanyl, pyridyl or 1N-(methyl)-pyrazolyl, or
Q is unsubstituted, and is thiophenyl, furanyl, pyridyl, 1N—(H)-pyrrolyl, 1N-(methyl)-pyrrolyl, benzothiophenyl or benzofuranyl, or
Q is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl, or
Q is substituted by bromine, chlorine or fluorine on its benzene ring, and is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl;

in which
Rba is chlorine, fluorine, bromine, methy, ethyl, methoxy, ethoxy, isopropyloxy, propoxy, hydroxyl, nitro, trifluoromethyl, dimethylamino, methylcarbonyloxy, cyano, phenyl, morpholino, phenoxy, 2-hydroxyethoxy, difluoromethoxy or trifluoromethoxy,
Rbb is methoxy, ethoxy, fluorine, chlorine, bromine, ethyl or methyl,
Rbc is methoxy, ethoxy, fluorine or chlorine,
Rca is chlorine, fluorine, bromine, methyl, ethyl, methoxy, ethoxy, phenyl, phenoxy or morpholino, and the salts, solvates or the solvates of the salts thereof.

Compounds according to aspect 1 of this invention to be more emphasized are those compounds of formula Ia as shown herein, in which
Ra is —C(O)R1, in which either
R1 is methyl, ethyl or propyl, or
R1 is methyl which is mono-substituted by R5, ethyl which is mono-substituted by R5, or propyl which is mono-substituted by R5, in which
R5 is methoxy, 2-methoxyethoxy, hydroxyl, pyridyl, indolyl, phenyl, methoxycarbonyl, ethoxycarbonyl, dimethylaminocarbonyl, guanidino, imidazolo or methylcarbonyloxy;

or in which
Ra is —C(O)OR2, in which either
R2 is methyl, ethyl, propyl or butyl, or
R2 is cyclohexyl, phenyl, pyridyl, (methoxycarbonyl)-phenyl, or (methoxy)-phenyl, or R2 is methyl which is mono-substituted by R5, ethyl which is mono-substituted by R5, or propyl which is mono-substituted by R5, in which R5 is pyridyl, phenyl, (methoxy)-phenyl, methoxycarbonyl or ethoxycarbonyl, or R2 is ethyl which is mono-substituted by R5, or propyl which is mono-substituted by R5, in which R5 is methoxy, 2-methoxyethoxy, hydroxyl, benzyloxy, morpholino, pyrrolidino, 4N-(methyl)-piperazino, dimethylamino, imidazolo or methylcarbonylamino, or R2 is 2,3-dihydroxypropyl, or R2 is 2,2-dimethyl-[1,3]dioxolan-4-yl-methyl;

or in which

Ra is —C(O)SR2, in which either

R2 is methyl, ethyl, propyl, butyl or pentyl, or

R2 is ethyl which is mono-substituted by R5, or propyl which is mono-substituted by R5, in which R5 is dimethylamino;

and in which either

Q is Rba- and/or Rbb- and/or Rbc-substituted phenyl, or

Q is unsubstituted phenyl, or

Q is substituted by Rca, and is thiophenyl, furanyl or 1N-(methyl)-pyrazolyl, or Q is (morpholino)-pyridyl, or (phenoxy)-thiophenyl, or Q is unsubstituted, and is thiophenyl, furanyl, pyridyl, 1N—(H)-pyrrolyl, benzothiophenyl, 1N-(methyl)-pyrrolyl or benzofuranyl, or Q is 1,3-benzodioxol-5-yl, 1,3-benzodioxol-4-yl, 2,2-difluoro-1,3-benzodioxol-5-yl, 2,2-difluoro-1,3-benzodioxol-4-yl or 2,3-dihydro-benzofuran-4-yl, or Q is substituted by bromine on its benzene ring, and is 1,3-benzodioxol-5-yl or 1,3-benzodioxol-4-yl;

in which

Rba is chlorine, fluorine, bromine, methy, ethyl, methoxy, ethoxy, isopropyloxy, propoxy, hydroxyl, nitro, trifluoromethyl, dimethylamino, methylcarbonyloxy, cyano, phenyl, morpholino, phenoxy, difluoromethoxy or trifluoromethoxy, Rbb is methoxy, ethoxy, fluorine, chlorine or methyl, Rbc is fluorine, Rca is chlorine, methyl, ethyl or phenyl, and the salts, solvates or the solvates of the salts thereof.

Yet compounds according to aspect 1 of this invention to be more emphasized are those compounds of formula Ia as shown herein, in which Ra is —C(O)R1, in which either R1 is methyl, ethyl or propyl, or R1 is methyl which is mono-substituted by R5, ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, pyridyl, pyrimidinyl, pyrazinyl, imidazolo, pyrazolo or methylcarbonyloxy, or R1 is 2,3-dihydroxy-propyl;

or in which

Ra is —C(O)OR2, in which either

R2 is methyl, ethyl or propyl, or

R2 is methyl which is mono-substituted by R5, ethyl which is mono-substituted by R5, or propyl which is mono-substituted by R5, in which R5 is pyridyl, pyrazinyl or pyrimidinyl, or R2 is ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, imidazolo, pyrazolo or methylcarbonyloxy, or R2 is 2,3-dihydroxy-propyl;

or in which

Ra is —C(O)SR2, in which either

R2 is methyl, ethyl or propyl, or

R2 is methyl which is mono-substituted by R5, ethyl which is mono-substituted by R5, or propyl which is mono-substituted by R5, in which R5 is pyridyl or hydroxyl;

and in which either

Q is Rba- and/or Rbb- and/or Rbc-substituted phenyl, or

Q is unsubstituted phenyl, or

Q is substituted by Rca, and is thiophenyl or furanyl, or

Q is unsubstituted, and is thiophenyl, furanyl or pyridyl, or

Q is 1,3-benzodioxol-5-yl, 1,3-benzodioxol-4-yl, 2,2-difluoro-1,3-benzodioxol-5-yl or 2,2-difluoro-1,3-benzodioxol-4-yl;

in which

Rba is chlorine, fluorine, methy, ethyl, methoxy, ethoxy, difluoromethoxy or trifluoromethoxy, Rbb is methoxy, ethoxy, fluorine, chlorine or methyl, Rbc is fluorine,
Rca is chlorine, methyl or ethyl, and the salts, solvates or the solvates of the salts thereof.

Compounds according to aspect 1 of this invention to be in particular emphasized are those compounds of formula Ia as shown herein,
in which
Ra is —C(O)R1, in which either
R1 is methyl, ethyl or propyl, or
R1 is (R5)-methyl, 2-(R5)-ethyl, or 3-(R5)-propyl, in which
R5 is methoxy, ethoxy, 2-methoxyethoxy, hydroxyl, imidazolo, pyridin-2-yl, pyridin-3-yl or pyridin-4-yl, or
R1 is 2,3-dihydroxy-propyl;

or in which
Ra is —C(O)OR2, in which either
R2 is methyl, ethyl or propyl, or
R2 is (R5)-methyl, 2-(R5)-ethyl, or 3-(R5)-propyl, in which
R5 is pyridin-2-yl, pyridin-3-yl or pyridin-4-yl, or
R2 is 2-(R5)-ethyl, or 3-(R5)-propyl, in which
R5 is methoxy, ethoxy, 2-methoxyethoxy, imidazolo or hydroxyl, or
R2 is 2,3-dihydroxy-propyl;

or in which
Ra is —C(O)SR2, in which either
R2 is methyl, ethyl or propyl, or
R2 is (R5)-methyl, 2-(R5)-ethyl, or 3-(R5)-propyl, in which
R5 is pyridin-2-yl, pyridin-3-yl or pyridin-4-yl;

and in which
either
Q is 2-methoxyphenyl, 2-chlorophenyl, 2-ethoxyphenyl or 2-methylphenyl, or
Q is 2-(Rba)-3-(Rbb)-phenyl, in which
Rba is chlorine, methoxy, ethoxy or methyl,
Rbb is methoxy, chlorine, fluorine or methyl, or
Q is 2-(Rba)-5-(Rbb)-phenyl, in which
Rba is chlorine, methoxy, ethoxy or methyl,
Rbb is methoxy, chlorine, fluorine or methyl, or
Q is unsubstituted phenyl, or
Q is unsubstituted, and is furan-2-yl, furan-3-yl or pyridin-3-yl, or
Q is 1,3-benzodioxol-4-yl or 2,2-difluoro-1,3-benzodioxol-4-yl;

and the salts, solvates or the solvates of the salts thereof.

Compounds according to aspect 1 of this invention to be in more particular emphasized are those compounds of formula Ia as shown herein,
in which
Ra is —C(O)R1, in which either
R1 is methyl, ethyl or propyl, or
R1 is methoxy-methyl, 2-methoxy-ethyl, (2-methoxyethoxy)-methyl, 2-(2-methoxyethoxy)-ethyl, hydroxymethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl, or
R1 is 2,3-dihydroxy-propyl;

or in which
Ra is —C(O)OR2, in which either
R2 is methyl, ethyl or propyl, or
R2 is 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl, or
R2 is 2,3-dihydroxy-propyl;

or in which
Ra is —C(O)SR2, in which
R2 is methyl, ethyl or propyl;

and in which
either
Q is 2-methoxyphenyl, or
Q is 2-ethoxyphenyl, or
Q is 2-(Rba)-3-(Rbb)-phenyl, in which
Rba is methoxy or ethoxy,
Rbb is methoxy or methyl, or
Q is 2-(Rba)-5-(Rbb)-phenyl, in which
Rba is methoxy or ethoxy,
Rbb is methoxy or methyl, or
Q is unsubstituted phenyl, or
Q is unsubstituted, and is furan-2-yl, furan-3-yl or pyridin-3-yl, or
Q is 1,3-benzodioxol-4-yl;

and the salts, solvates or the solvates of the salts thereof.

Compounds according to aspect 1 of this invention to be in further more particular emphasized are those compounds of formula Ia as shown herein,
in which
Ra is —C(O)R1, in which
either
R1 is methyl, ethyl or propyl, or R1 is methoxy-methyl, 2-methoxy-ethyl, (2-methoxy-ethoxy)-methyl, 2-(2-methoxyethoxy)-ethyl, hydroxy-methyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl, or R1 is 2,3-dihydroxy-propyl;

or in which

Ra is —C(O)OR2, in which either

R2 is methyl, ethyl or propyl, or

R2 is 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl, or R2 is 2,3-dihydroxy-propyl;

or in which

Ra is —C(O)SR2, in which

R2 is methyl, ethyl or propyl;

and in which either

Q is 2-ethoxyphenyl, or

Q is 2-(Rba)-5-(Rbb)-phenyl, in which

Rba is methoxy,

Rbb is methoxy or methyl, or

Q is 2-(Rba)-5-(Rbb)-phenyl, in which

Rba is ethoxy,

Rbb is methoxy or methyl;

and the salts, solvates or the solvates of the salts thereof.

Compounds according to aspect 2 of this invention worthy to be noted are those compounds of aspect 2, wherein one or where possible more of the following restrictions apply:

a.) Ra is —C(O)R1, —C(O)OR2, —C(O)SR2, —C(O)N(R3)R4, or —S(O)$_2$R1;

b.) Rb is as defined in formulae Ia or Ib as shown below;

c.) Q is optionally substituted by Rba and/or Rbb and/or Rbc, and is phenyl, or optionally substituted by Rca and/or Rcb, and is Har, or Cyc;

d.) R1, R2 and R3 may be the same or different and are independently selected from the group consisting of: 1-7C-alkyl, Ar and Har, wherein each of said 1-7C-alkyl, Ar and Har can be unsubstituted or optionally substituted by at least one substituent independently selected from R5;

e.) R4 is hydrogen;

f.) each R5, Rba, Rbb, Rbc, Rca and Rcb may be the same or different and are independently selected from the group consisting of:
1-7C-alkyl, 3-7C-cycloalkyl, Ar, Har, Het,
halogen, trifluoromethyl,
—C(O)R6, —C(O)OR7, —C(O)N(R8)R9,
—N(R10)C(O)R6, —N(R10)C(O)N(R8)R9,
—OR7 and —N(R8)R9, wherein each of said 1-7C-alkyl, Ar, Har and Het can be unsubstituted or optionally substituted by at least one substituent independently selected from R11;

g.) R6, R7 and R8 may be the same or different and are independently selected from the group consisting of: hydrogen and 1-7C-alkyl, wherein said 1-7C-alkyl can be unsubstituted or optionally substituted by at least one substituent independently selected from R12;

h.) each R9 is independently selected from the group consisting of: hydrogen and 1-7C-alkyl;

i.) each R10 is hydrogen;

j.) R11 is selected from the group consisting of: R5 as defined for restriction f.);

k.) R12 is selected from the group consisting of: R5 as defined for restriction f.);

l.) each Ar is phenyl;

m.) each Har is independently any fully aromatic or partially aromatic mono- or fused bicyclic ring or ring system made up of
a first constituent being a 5- or 6-membered monocyclic unsaturated, aromatic heteroaryl ring A, which heteroaryl ring A comprises one to four heteroatoms independently selected from nitrogen, oxygen and sulfur,
and, optionally, fused to said first constituent,
a second constituent being a benzo group, any 3-7C-cycloalkane group as defined herein, any additional heteroaryl ring A as defined herein, or any heterocyclic ring B as defined herein, whereby said Har ring or ring system is attached to the parent molecular group via a substitutable ring carbon or ring nitrogen atom;

n.) each Het is independently any fully saturated or partially unsaturated mono- or fused bicyclic ring or ring system made up of
a first constituent being a 3- to 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzo group, any 3-7C-cycloalkane group as defined herein, or any additional heterocyclic ring B as defined herein,
whereby said Het ring or ring system is attached to the parent molecular group via a substitutable ring carbon or ring nitrogen atom;

o.) Cyc is as defined in aspect 2 above;

p.) Q is attached to the adjacent 2-4C-alkenyl moiety via any one of its substitutable ring carbon atoms.

Compounds according to aspect 2 of this invention further worthy to be noted are those compounds of formulae la or lb as shown below, in which Ra is —C(O)R1, —C(O)OR2, —C(O)SR2, —C(O)N(R3)R4, or —S(O)$_2$R1;

and either

Q is optionally substituted by Rba and/or Rbb and/or Rbc, and is phenyl, or

Q is bonded to the adjacent unsaturated group via a ring carbon atom, and is optionally substituted by Rca and/or Rcb, and is Har, or Q is Cyc;

in which
R1, R2 and R3 may be the same or different and are independently selected from the group consisting of: 1-7C-alkyl, Ar and Har, wherein each of said 1-7C-alkyl, Ar and Har can be unsubstituted or optionally substituted by at (east one substituent independently selected from R5;
R4 is hydrogen;
each R5, Rba, Rbb, Rbc, Rca and Rcb may be the same or different and are independently selected from the group consisting of:
1-7C-alkyl, 3-7C-cycloalkyl, Ar, Har, Het,
halogen, trifluoromethyl,
—C(O)R6, —C(O)OR7, —C(O)N(R8)R9,
—N(R10)C(O)R6, —N(R10)C(O)N(R8)R9,
—OR7 and —N(R8)R9, wherein each of said 1-7C-alkyl, Ar, Har and Het can be unsubstituted or optionally substituted by at least one substituent independently selected from R11;
R6, R7 and R8 may be the same or different and are independently selected from the group consisting of: hydrogen and 1-7C-alkyl, wherein said 1-7C-alkyl can be unsubstituted or optionally substituted by at least one substituent independently selected from R12;
each R9 is independently selected from the group consisting of: hydrogen and 1-7C-alkyl;
each R10 is hydrogen;
R11 is selected from the group consisting of: R5 as defined afore in this paragraph;
R12 is selected from the group consisting of: R5 as defined afore in this paragraph;
each Ar is phenyl;
each Har is independently any fully aromatic or partially aromatic mono- or fused bicyclic ring or ring system made up of
a first constituent being a 5- or 6-membered monocyclic unsaturated, aromatic heteroaryl ring A, which heteroaryl ring A comprises one to four heteroatoms independently selected from nitrogen, oxygen and sulfur,
and, optionally, fused to said first constituent,
a second constituent being a benzo group, or any additional heteroaryl ring A as defined herein, whereby said Har ring or ring system is attached to the parent molecular group via a substitutable ring carbon or ring nitrogen atom;
each Het is independently any fully saturated or partially unsaturated mono- or fused bicyclic ring or ring system made up of
a first constituent being a 3- to 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzo group, whereby said Het ring or ring system is attached to the parent molecular group via a substitutable ring carbon or ring nitrogen atom;
Cyc is 1,3-benzodioxolyl, 2,3-dihydro-1,4-benzodioxinyl, or 2,3-dihydrobenzofuranyl;

and the salts, solvates or the solvates of the salts thereof.

In the compounds according to the present invention, the significances mentioned in the following details/subdetails and/or variants/subvariants can be considered individually or in any combination thereof:
A first embodimental detail (detail a) of the compounds of aspect 1 or 2 according to this invention includes those compounds of formulae I or, particularly, Ia or Ib as shown below, in which
Ra is —C(O)R1, —C(O)OR2, —C(O)SR2, —C(O)N(R3)R4, or —S(O)$_2$R1;

in which
R1, R2 and R3 may be the same or different and are independently selected from the group consisting of: 1-7C-alkyl, Ar and Har, wherein each of said 1-7C-alkyl, Ar and Har can be unsubstituted or optionally substituted by at least one substituent independently selected from R5;
R4 is hydrogen;
each R5 is independently selected from the group consisting of:
1-7C-alkyl, Ar, Har, Het,
—C(O)R6, —C(O)OR7, —C(O)N(R8)R9,
N(R10)C(O)R6, —N(R10)C(O)N(R8)R9,
—OR7 and —N(R8)R9, wherein each of said 1-7C-alkyl, Ar, Har and Het can be unsubstituted or optionally substituted by at least one substituent independently selected from R11;
R6, R7 and R8 may be the same or different and are independently selected from the group consisting of: hydrogen and 1-7C-alkyl, wherein said 1-7C-alkyl can be unsubstituted or optionally substituted by at least one substituent independently selected from R12;
each R9 is independently selected from the group consisting of: hydrogen and 1-7C-alkyl;
each R10 is hydrogen;
R11 is selected from the group consisting of: R5 as defined in this detail a;
R12 is selected from the group consisting of: R5 as defined in this detail a;
each Ar is phenyl;
each Har is independently any fully aromatic mono- or fused bicyclic ring or ring system made up of a first constituent being a 5- or 6-membered monocyclic unsaturated, aromatic heteroaryl ring A,
which heteroaryl ring A comprises one to four heteroatoms independently selected from nitrogen, oxygen and sulfur,
and, optionally, fused to said first constituent,
a second constituent being a benzo group, whereby said Har ring or ring system is attached to the parent molecular group via a substitutable ring carbon atom;
each Het is independently any fully saturated or partially unsaturated mono- or fused bicyclic ring or ring system made up of
a first constituent being a 3- to 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzo group, whereby said Het ring or ring system is attached to the parent molecular group via a substitutable ring carbon or ring nitrogen atom.

A second embodimental detail (detail b) of the compounds of aspect 1 or 2 according to this invention includes those compounds of formulae I or, particularly, Ia or Ib as shown below, in which
Ra is —C(O)R1, in which
R1 is selected from the group consisting of:
 hydrogen, 1-7C-alkyl, 3-7C-cycloalkyl, Ar and Har,
  wherein 1-7C-alkyl is optionally substituted by at least one substituent independently selected from R5 as defined in aspect 1 or 2, respectively, above, and
  wherein each of said Ar and Har is optionally substituted by one or two substituents independently selected from R5 as defined in aspect 1 or 2, respectively, above.

Compounds according to detail b of this invention more worthy to be mentioned in a subdetail thereof (detail b1a) include those compounds of formulae I or, particularly, Ia or Ib as shown below, in which
Ra is —C(O)R1, in which
R1 is hydrogen, 1-7C-alkyl, 3-7C-cycloalkyl, or 1-7C-alkyl substituted by any one of R5 as defined in aspect 1 or 2 above.

Yet compounds according to detail b of this invention more worthy to be mentioned in a subdetail thereof (detail b1b) include those compounds of formulae I or, particularly, Ia or Ib as shown below, in which
Ra is —C(O)R1, in which
R1 is phenyl, or phenyl substituted by any one of R5 as defined in aspect 1 or 2 above.

Compounds according to detail b of this invention in particular worthy to be mentioned in a subdetail thereof (detail b2a) include those compounds of formulae I or, particularly, Ia or Ib as shown below, in which
Ra is —C(O)R1, in which
R1 is hydrogen, 1-7C-alkyl, 3-7C-cycloalkyl, or 1-7C-alkyl substituted by R5, in which
R5 is 3-7C-cycloalkyl, Ar, Har, Het,
 —C(O)R6, —C(O)OR7, —C(O)N(R8)R9,
 —N(R10)C(O)R6, —N(R10)C(O)OR7, —N(R10)C(O)N(R8)R9, —N(R10)S(O)$_2$R6,
 —N(R10)S(O)$_2$N(R8)R9,
 —OR7, or —N(R8)R9, wherein each of said Ar, Har and Het can be unsubstituted or optionally substituted by one to three substituents independently selected from R11, in which
R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12,
each R9 is independently selected from the group consisting of: hydrogen, 1-7C-alkyl, or 3-7C-cycloalkyl, wherein each of said 1-7C-alkyl and 3-7C-cycloalkyl can be unsubstituted or optionally substituted by at least one substituent independently selected from R12,
each R10 is independently selected from the group consisting of: hydrogen, 1-7C-alkyl, or 3-7C-cycloalkyl,
R11 is as originally defined in aspect 1 or 2 above,
each R12 is independently as originally defined in aspect 1 or 2 above,
each Ar is phenyl,
each Har is independently as originally defined in aspect 1 or 2 above,
each Het is independently as originally defined in aspect 1 or 2 above.

Compounds according to detail b of this invention in more particular worthy to be mentioned in a subdetail thereof (detail b3a) include those compounds of formulae I or, particularly, Ia or Ib as shown below, in which
Ra is —C(O)R1, in which
R1 is hydrogen, 1-7C-alkyl, or 3-7C-cycloalkyl.

Yet compounds according to detail b of this invention in more particular worthy to be mentioned in a subdetail thereof (detail b3b) include those compounds of formulae I or, particularly, Ia or Ib as shown below, in which
Ra is —C(O)R1, in which
R1 is 1-7C-alkyl substituted by R5, in which
R5 is Ar, Har, or Het, wherein each of said Ar, Har and Het can be unsubstituted or optionally substituted by up to three substituents independently selected from R11, in which
R11 is as originally defined in aspect 1 or 2 above,
Ar is phenyl,
Har is as originally defined in aspect 1 or 2 above,
Het is as originally defined in aspect 1 or 2 above.

Still yet compounds according to detail b of this invention in more particular worthy to be mentioned in a subdetail thereof (detail b3c) include those compounds of formulae I or, particularly, Ia or Ib as shown below, in which
Ra is —C(O)R1, in which
R1 is 1-7C-alkyl substituted by R5, in which
R5 is —C(O)R6, —C(O)OR7, —C(O)N(R8)R9, —N(R10)C(O)R6, —N(R10)C(O)OR7, —N(R10)C(O)N(R8)R9, —OR7 and —N(R8)R9, in which
R6, R7 and R8 may be the same or different and are independently selected from the group consisting of: hydrogen, 1-7C-alkyl and 3-7C-cycloalkyl, wherein said 1-7C-alkyl can be unsubstituted or optionally substituted by any one of R12,
each R9 is independently selected from the group consisting of: hydrogen, 1-7C-alkyl and 3-7C-cycloalkyl,
each R10 is independently selected from the group consisting of: hydrogen, 1-7C-alkyl and 3-7C-cycloalkyl,
each R12 is independently as originally defined in aspect 1 or 2 above.

Also still yet compounds according to detail b of this invention in more particular worthy to be mentioned in a subdetail thereof (detail b3d) include those compounds of formulae I or, particularly, Ia or Ib as shown below, in which
Ra is —C(O)R1, in which
R1 is phenyl, or phenyl substituted by R5, in which
R5 is —OR7, in which
R7 is selected from the group consisting of: hydrogen, 1-7C-alkyl, 3-7C-cycloalkyl, and Ar, wherein each of said 1-7C-alkyl, 3-7C-cycloalkyl and Ar can be unsubstituted or optionally substituted by at least one substituent independently selected from R12,
each R12 is independently as originally defined in aspect 1 or 2 above,
each Ar is phenyl.

Further compounds according to detail b of this invention in more particular worthy to be mentioned in a subdetail thereof (detail b3e) include those compounds of formula I or, particularly, formula Ia as shown below, in which
Ra is —C(O)R1, in which
R1 is 1-4C-alkyl which is mono-substituted by R5, in which
R5 is pyridyl, pyrimidinyl, pyrazinyl, indolyl, thiazolyl, oxazolyl, 1N-(1-4C-alkyl)-imidazolyl, 1N-(1-4C-alkyl)-pyrazolyl, morpholino, imidazolo, triazolo or pyrazolo.

Yet further compounds according to detail b of this invention in more particular worthy to be mentioned in a subdetail thereof (detail b3f) include those compounds of formula I or, particularly, formula Ia as shown below, in which
Ra is —C(O)R1, in which
R1 is 1-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, 1-4C-alkoxycarbonyl, carboxyl, di-1-4C-alkylaminocarbonyl, carbamoyl, ureido, guanidino or 1-4C-alkylcarbonyloxy.

Compounds according to detail b of this invention in further more particular worthy to be mentioned in a subdetail thereof (detail b4a) include those compounds of formulae I or, particularly, Ia or Ib as shown below, in which
Ra is —C(O)R1, in which
R1 is 1-7C-alkyl.

Yet compounds according to detail b of this invention in further more particular worthy to be mentioned in a subdetail thereof (detail b4b) include those compounds of formulae I or, particularly, Ia or Ib as shown below, in which
Ra is —C(O)R1, in which
R1 is 1-7C-alkyl substituted by R5, in which
R5 is phenyl, R51-substituted phenyl, Har, R52-substituted Har, Het, or R53-substituted Het, in which
R51 is 1-4C-alkoxy,
Har is attached to the parent molecular group via a ring carbon or ring nitrogen atom,
    and is an unsaturated (aromatic) 5- or 6-membered monocyclic ring comprising one to four heteroatoms independently selected from nitrogen, oxygen and sulfur,
    or an unsaturated (aromatic) 9- or 10-membered fused bicyclic ring comprising one to four heteroatoms independently selected from nitrogen, oxygen and sulfur,
R52 is 1-4C-alkyl,
Het is attached to the parent molecular group via a ring carbon or ring nitrogen atom,
    and is a saturated 3- to 7-membered monocyclic ring comprising one to three heteroatoms independently selected from nitrogen, oxygen and sulfur, and which is optionally substituted by one or two oxo groups,
    or a benzo fused derivative thereof,
R53 is 1-4C-alkyl, or 1-4C-alkylcarbonyl.

Still yet compounds according to detail b of this invention in further more particular worthy to be mentioned in a subdetail thereof (detail b4c) include those compounds of formulae I or, particularly, Ia or Ib as shown below, in which
Ra is —C(O)R1, in which
R1 is 1-7C-alkyl substituted by R5, in which
R5 is 1-4C-alkoxycarbonyl, 1-4C-alkylcarbonyl, carbamoyl, carboxyl, mono- or di-1-4C-alkylaminocarbonyl, mono- or di-1-4C-alkylamino, ureido, 1-4C-alkoxy, or phenyl-1-4C-alkoxy.

Also still yet compounds according to detail b of this invention in further more particular worthy to be mentioned in a subdetail thereof (detail b4d) include those compounds of formulae I or, particularly, Ia or Ib as shown below, in which
Ra is —C(O)R1, in which
R1 is 1-7C-alkyl substituted by R5, in which
R5 is phenyl.

Further still yet compounds according to detail b of this invention in further more particular worthy to be mentioned in a subdetail thereof (detail b4e) include those compounds of formulae I or, particularly, Ia or Ib as shown below, in which
Ra is —C(O)R1, in which
R1 is phenyl, or phenyl substituted by R5, in which
R5 is 1-4C-alkoxy.

Further compounds according to detail b of this invention in further more particular worthy to be mentioned in a subdetail thereof (detail b4f) include those compounds of formula I or, particularly, formula Ia as shown below, in which
Ra is —C(O)R1, in which
R1 is methyl, ethyl, propyl or butyl.

Yet further compounds according to detail b of this invention in further more particular worthy to be mentioned in a subdetail thereof (detail b4g) include those compounds of formula I or, particularly, formula Ia as shown below, in which
Ra is —C(O)R1, in which
R1 is (R5)-methyl, 2-(R5)-ethyl, or 3-(R5)-propyl, in which
R5 is pyridyl, pyrimidinyl, pyrazinyl, imidazolo or pyrazolo.

Still yet further compounds according to detail b of this invention in further more particular worthy to be mentioned in a subdetail thereof (detail b4h) include those compounds of formula I or, particularly, formula Ia as shown below, in which
Ra is —C(O)R1, in which
R1 is (R5)-methyl, 2-(R5)-ethyl, or 3-(R5)-propyl, in which
R5 is methoxy, ethoxy, 2-methoxyethoxy, 2-(2-methoxyethoxy)ethoxy, hydroxyl or methylcarbonyloxy.

Compounds according to detail b of this invention to be emphasized in a subdetail thereof (detail b5a) include those compounds of formula Ia as shown below, in which
Ra is —C(O)R1, in which
R1 is any one selected from methyl, ethyl and propyl.

Yet compounds according to detail b of this invention to be emphasized in a subdetail thereof (detail b5b) include those compounds of formula Ia as shown below, in which
Ra is —C(O)R1, in which
R1 is any one selected from methoxy-methyl, 2-methoxy-ethyl, (2-methoxyethoxy)-methyl, 2-(2-methoxyethoxy)-ethyl, hydroxy-methyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl and 2-(pyridin-4-yl)-ethyl.

Yet compounds according to detail b of this invention to be emphasized in a subdetail thereof (detail b5c) include those compounds of formula Ia as shown below, in which Ra is —C(O)R1, in which R1 is 2,3-dihydroxypropyl.

A third embodimental detail (detail c) of the compounds of aspect 1 or 2 according to this invention includes those compounds of formulae I or, particularly, Ia or Ib as shown below, in which Ra is —S(O)$_2$R1, in which R1 is Ar, Har, or Het, wherein each of said Ar and Har is optionally substituted by one or two substituents independently selected from R5 as defined in aspect 1 or 2, respectively, above.

A fourth embodimental detail (detail d) of the compounds of aspect 1 or 2 according to this invention includes those compounds of formulae I or, particularly, Ia or Ib as shown below, in which Ra is —C(O)OR2, in which R2 is selected from the group consisting of:
   1-7C-alkyl, 3-7C-cycloalkyl and Ar,
      wherein 1-7C-alkyl is optionally substituted by at least one substituent independently selected from R5 as defined in aspect 1 or 2, respectively, above, and
      wherein Ar is optionally substituted by one or two substituents independently selected from R5 as defined in aspect 1 or 2, respectively, above.

Compounds according to detail d of this invention more worthy to be mentioned in a subdetail thereof (detail d1a) include those compounds of formulae I or, particularly, Ia or Ib as shown below, in which Ra is —C(O)OR2, in which R2 is 1-7C-alkyl, 3-7C-cycloalkyl, or 1-7C-alkyl substituted by at least one substituent independently selected from R5 as defined in aspect 1 or 2 above.

Yet compounds according to detail d of this invention more worthy to be mentioned in a subdetail thereof (detail d1b) include those compounds of formulae I or, particularly, Ia or Ib as shown below, in which Ra is —C(O)OR2, in which R2 is phenyl, or phenyl substituted by any one of R5 as defined in aspect 1 or 2 above.

Compounds according to detail d of this invention in particular worthy to be mentioned in a subdetail thereof (detail d2) include those compounds of formulae I or, particularly, Ia or Ib as shown below, in which Ra is —C(O)OR2, in which R2 is 1-7C-alkyl, 3-7C-cycloalkyl, or 1-7C-alkyl substituted by R5, in which R5 is 3-7C-cycloalkyl, Ar, Har, Het,
   —C(O)R6, —C(O)OR7, —C(O)N(R8)R9,
   —N(R10)C(O)R6, —N(R10)C(O)OR7, —N(R10)C(O)N(R8)R9, —N(R10)S(O)$_2$R6,
   —N(R10)S(O)$_2$N(R8)R9,
   —OR7 and —N(R8)R9, wherein each of said Ar, Har and Het can be unsubstituted or optionally substituted by one to three substituents independently selected from R11, in which R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12, each R9 is independently selected from the group consisting of: hydrogen, 1-7C-alkyl and 3-7C-cycloalkyl, wherein each of said 1-7C-alkyl and 3-7C-cycloalkyl can be unsubstituted or optionally substituted by at least one substituent independently selected from R12, each R10 is independently selected from the group consisting of: hydrogen, 1-7C-alkyl and 3-7C-cycloalkyl, R11 is as originally defined in aspect 1 or 2 above, each R12 is independently as originally defined in aspect 1 or 2 above, each Ar is phenyl, each Har is independently as originally defined in aspect 1 or 2 above, each Het is independently as originally defined in aspect 1 or 2 above.

Compounds according to detail d of this invention in more particular worthy to be mentioned in a subdetail thereof (detail d3a) include those compounds of formulae I or, particularly, Ia or Ib as shown below, in which Ra is —C(O)OR2, in which R2 is 1-7C-alkyl, or 3-7C-cycloalkyl.

Yet compounds according to detail d of this invention in more particular worthy to be mentioned in a subdetail thereof (detail d3b) include those compounds of formulae I or, particularly, Ia or Ib as shown below, in which Ra is —C(O)OR2, in which R2 is 1-7C-alkyl substituted by R5, in which R5 is Ar, Har, or Het, wherein each of said Ar, Har and Het can be unsubstituted or optionally substituted by up to three substituents independently selected from R11, in which R11 is as originally defined in aspect 1 or 2 above, Ar is phenyl, Har is as originally defined in aspect 1 or 2 above, Het is as originally defined in aspect 1 or 2 above.

Still yet compounds according to detail d of this invention in more particular worthy to be mentioned in a subdetail thereof (detail d3c) include those compounds of formulae I or, particularly, Ia or Ib as shown below, in which Ra is —C(O)OR2, in which R2 is 2-7C-alkyl substituted by R5, in which R5 is —C(O)R6, —C(O)OR7, —C(O)N(R8)R9,
   —N(R10)C(O)R6, —N(R10)C(O)OR7, —N(R10)C(O)N(R8)R9,
   —OR7, or —N(R8)R(9), in which R6, R7 and R8 may be the same or different and are independently selected from the group consisting of: hydrogen, 1-7C-alkyl and 3-7C-cycloalkyl, wherein said 1-7C-alkyl can be unsubstituted or optionally substituted by any of R12, each R9 is independently selected from the group consisting of: hydrogen, 1-7C-alkyl and 3-7C-cycloalkyl, each R10 is independently selected from the group consisting of: hydrogen, 1-7C-alkyl and 3-7C-cycloalkyl, each R12 is independently as originally defined in aspect 1 or 2 above.

Also still yet compounds according to detail d of this invention in more particular worthy to be mentioned in a subdetail thereof (detail d3d) include those compounds of formulae I or, particularly, Ia or Ib as shown below, in which
Ra is —C(O)OR2, in which
R2 is phenyl, or phenyl substituted by R5, in which
R5 is —OR7, in which
R7 is selected from the group consisting of: hydrogen, 1-7C-alkyl, 3-7C-cycloalkyl, and Ar, wherein each of said 1-7C-alkyl, 3-7C-cycloalkyl and Ar can be unsubstituted or optionally substituted by at least one substituent independently selected from R12, each R12 is independently as originally defined in aspect 1 or 2 above, each Ar is phenyl.

Further compounds according to detail d of this invention in more particular worthy to be mentioned in a subdetail thereof (detail d3e) include those compounds of formula I or, particularly, formula Ia as shown below, in which
Ra is —C(O)OR2, in which
either
R2 is 1-4C-alkyl which is mono-substituted by R5, in which
R5 is pyridyl, pyrimidinyl, pyrazinyl, phenyl, or (1-4C-alkoxy)-phenyl,
or
R2 is 2-4C-alkyl which is mono-substituted by R5, in which
R5 is morpholino, piperidino, pyrrolidino, 4N-(1-4C-alkyl)-piperazino, imidazolo, triazolo or pyrazolo.

Yet further compounds according to detail d of this invention in more particular worthy to be mentioned in a subdetail thereof (detail d3f) include those compounds of formula I or, particularly, formula Ia as shown below, in which
Ra is —C(O)OR2, in which
either
R2 is 1-4C-alkyl which is mono-substituted by R5, in which
R5 is 1-4C-alkoxycarbonyl, carboxyl, di-1-4C-alkylaminocarbonyl or carbamoyl,
or
R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, di-1-4C-alkylamino, 1-4C-alkylcarbonyloxy or 1-4C-alkylcarbonylamino.

Compounds according to detail d of this invention in further more particular worthy to be mentioned in a subdetail thereof (detail d4a) include those compounds of formulae I or, particularly, Ia or Ib as shown below, in which
Ra is —C(O)OR2, in which
R2 is 1-7C-alkyl.

Yet compounds according to detail d of this invention in further more particular worthy to be mentioned in a subdetail thereof (detail d4b) include those compounds of formulae I or, particularly, Ia or Ib as shown below, in which
Ra is —C(O)OR2, in which
R2 is 1-7C-alkyl substituted by R5, in which
R5 is phenyl, R51-substituted phenyl, Har, R52-substituted Har, Het, or R53-substituted Het, in which
R51 is 1-4C-alkoxy,
Har is attached to the parent molecular group via a ring carbon or ring nitrogen atom,
and is an unsaturated (aromatic) 5- or 6-membered monocyclic ring comprising one to four heteroatoms independently selected from nitrogen, oxygen and sulfur,
or an unsaturated (aromatic) 9- or 10-membered fused bicyclic ring comprising one to four heteroatoms independently selected from nitrogen, oxygen and sulfur,
R52 is 1-4C-alkyl,
Het is attached to the parent molecular group via a ring carbon or ring nitrogen atom, and is a saturated 3- to 7-membered monocyclic ring comprising one to three heteroatoms independently selected from nitrogen, oxygen and sulfur, and which is optionally substituted by one or two oxo groups, or a benzo fused derivative thereof,
R53 is 1-4C-alkyl, or 1-4C-alkylcarbonyl.

Still yet compounds according to detail d of this invention in further more particular worthy to be mentioned in a subdetail thereof (detail d4c) include those compounds of formulae I or, particularly, Ia or Ib as shown below, in which
Ra is —C(O)OR2, in which
R2 is 2-7C-alkyl substituted by R5, in which
R5 is 1-4C-alkoxycarbonyl, 1-4C-alkylcarbonyl, carbamoyl, carboxyl, mono- or di-1-4C-alkylaminocarbonyl, mono- or di-1-4C-alkylamino, ureido, 1-4C-alkoxy, or phenyl-1-4C-alkoxy.

Also still yet compounds according to detail d of this invention in further more particular worthy to be mentioned in a subdetail thereof (detail d4d) include those compounds of formulae I or, particularly, Ia or Ib as shown below, in which
Ra is —C(O)OR2, in which
R2 is 1-7C-alkyl substituted by R5, in which
R5 is phenyl.

Further still yet compounds according to detail d of this invention in further more particular worthy to be mentioned in a subdetail thereof (detail d4e) include those compounds of formulae I or, particularly, Ia or Ib as shown below, in which
Ra is —C(O)OR2, in which
R2 is phenyl, or phenyl substituted by R5, in which
R5 is 1-4C-alkoxy.

Further compounds according to detail d of this invention in further more particular worthy to be mentioned in a subdetail thereof (detail d4f) include those compounds of formula I or, particularly, formula Ia as shown below, in which
Ra is —C(O)OR2, in which
R2 is methyl, ethyl, propyl or butyl.

Yet further compounds according to detail d of this invention in further more particular worthy to be mentioned in a subdetail thereof (detail d4g) include those compounds of formula I or, particularly, formula Ia as shown below, in which
Ra is —C(O)OR2, in which
R2 is (R5)-methyl, 2-(R5)-ethyl, or 3-(R5)-propyl, in which
R5 is pyridyl, pyrimidinyl or pyrazinyl.

Still yet further compounds according to detail d of this invention in further more particular worthy to be mentioned in a subdetail thereof (detail d4h) include those compounds of formula I or, particularly, formula Ia as shown below, in which
Ra is —C(O)OR2, in which
R2 is 2-(R5)-ethyl, or 3-(R5)-propyl, in which R5 is methoxy, ethoxy, 2-methoxyethoxy, 2-(2-methoxyethoxy)ethoxy, hydroxyl or methylcarbonyloxy.

Compounds according to detail d of this invention to be emphasized in a subdetail thereof (detail d5a) include those compounds of formula Ia as shown below, in which
Ra is —C(O)OR2, in which
R2 is any one selected from methyl, ethyl and propyl.

Yet compounds according to detail d of this invention to be emphasized in a subdetail thereof (detail d5b) include those compounds of formula Ia as shown below, in which
Ra is —C(O)OR2, in which
R2 is any one selected from 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl and 2-(pyridin-4-yl)-ethyl.

Yet compounds according to detail d of this invention to be emphasized in a subdetail thereof (detail d5c) include those compounds of formula Ia as shown below, in which
Ra is —C(O)OR2, in which
R1 is 2,3-dihydroxypropyl.

A fifth embodimental detail (detail e) of the compounds of aspect 1 or 2 according to this invention includes those compounds of formulae I or, particularly, Ia or Ib as shown below, in which
Ra is —C(O)SR2, in which
R2 is 1-7C-alkyl, 3-7C-cycloalkyl, or 1-7C-alkyl substituted by any one of R5 as defined in aspect 1 or 2, respectively, above.

Compounds according to detail e of this invention in particular worthy to be mentioned in a subdetail thereof (detail e1) include those compounds of formulae I or, particularly, Ia or Ib as shown below, in which
Ra is —C(O)SR2, in which
R2 is 1-7C-alkyl.

Compounds according to detail e of this invention to be emphasized in a subdetail thereof (detail e2) include those compounds of formula Ia as shown below, in which
Ra is —C(O)SR2, in which
R2 is any one selected from methyl, ethyl and propyl.

Yet compounds according to detail e of this invention to be emphasized in a subdetail thereof (detail e3) include those compounds of formula Ia as shown below, in which
Ra is —C(O)SR2, in which
R2 is any one selected from 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl and 2-(pyridin-4-yl)-ethyl.

A sixth embodimental detail (detail f) of the compounds of aspect 1 or 2 according to this invention includes those compounds of formulae I or, particularly, Ia or Ib as shown below, in which
Ra is —C(O)N(R3)R4, in which
R3 is selected from the group consisting of:
 hydrogen, 1-7C-alkyl, or 3-7C-cycloalkyl,
  wherein 1-7C-alkyl is optionally substituted by one substituent selected from R5 as defined in aspect 1 or 2, respectively, above;
R4 is selected from the group consisting of:
 hydrogen, 1-7C-alkyl, or 3-7C-cycloalkyl,
  wherein 1-7C-alkyl is optionally substituted by one substituent selected from R5 as defined in aspect 1 or 2, respectively, above.

Compounds according to detail f of this invention more worthy to be mentioned in a subdetail thereof (detail f1) include those compounds of formulae I or, particularly, Ia or Ib as shown below, in which
Ra is —C(O)N(R3)R4, in which
R3 is 1-7C-alkyl, 3-7C-cycloalkyl, or 1-7C-alkyl substituted by any one of R5 as defined in aspect 1 or 2 above,
R4 is hydrogen, 1-7C-alkyl, or 3-7C-cycloalkyl.

Compounds according to detail f of this invention in particular worthy to be mentioned in a subdetail thereof (detail f2) include those compounds of formulae I or, particularly, Ia or Ib as shown below, in which
Ra is —C(O)N(R3)R4, in which
R3 is 1-7C-alkyl, or 3-7C-cycloalkyl,
R4 is hydrogen, 1-7C-alkyl, or 3-7C-cycloalkyl.

Yet compounds according to detail f of this invention in particular worthy to be mentioned in a subdetail thereof (detail f3) include those compounds of formulae I or, particularly, Ia or Ib as shown below, in which
Ra is —C(O)N(R3)R4, in which
R3 is 1-7C-alkyl substituted by any one of R5 as defined in aspect 2 above,
R4 is hydrogen, 1-7C-alkyl, or 3-7C-cycloalkyl.

Compounds according to detail f of this invention in more particular worthy to be mentioned in a subdetail thereof (detail f4) include those compounds of formulae I or, particularly, Ia or Ib as shown below, in which
Ra is —C(O)N(R3)R4, in which
R3 is 1-7C-alkyl,
R4 is hydrogen.

A seventh embodimental detail (detail g) of the compounds of aspect 1 or 2 according to this invention includes those compounds of formulae I or, particularly, Ia or Ib as shown below, in which
Ra is —S(O)$_2$N(R3)R4, in which
R3 is selected from the group consisting of:
 hydrogen, 1-7C-alkyl, or 3-7C-cycloalkyl,
  wherein 1-7C-alkyl is optionally substituted by one substituent selected from R5 as defined in aspect 1 or 2, respectively, above;
R4 is selected from the group consisting of:
 hydrogen, 1-7C-alkyl, or 3-7C-cycloalkyl,
  wherein 1-7C-alkyl is optionally substituted by one substituent selected from R5 as defined in aspect 1 or 2, respectively, above.

An interesting variant (variant a) of the compounds according to this invention includes those compounds of formula I wherein said compounds are compounds from formula Ia:

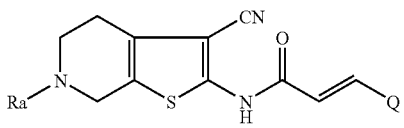

(Ia)

Another variant (variant b) of the compounds according to this invention includes those compounds of formula I wherein said compounds are compounds from formula Ib:

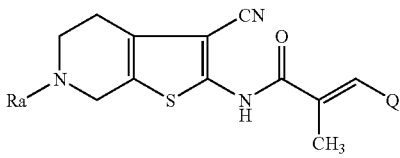

(Ib)

In the view of the foregoing variants and details, it is to be stated that the variant concerning compounds of formula Ia is to be stressed within the meaning of this invention.

Another variant (variant c) of the compounds according to this invention includes those compounds of formula I, particularly of formula Ia or Ib, in which Q is optionally substituted by Rba and/or Rbb and/or Rbc, and is phenyl.

Another variant (variant d) of the compounds according to this invention includes those compounds of formula I, particularly of formula Ia or Ib, in which Q is optionally substituted by Rca and/or Rcb, and is Har.

Another variant (variant e) of the compounds according to this invention includes those compounds of formula I, particularly of formula Ia or Ib, in which Q is Cyc.

A more interesting variant (variant f) of the compounds according to this invention includes those compounds of formula Ia, in which Q is optionally substituted by Rba and/or Rbb and/or Rbc, and is phenyl.

Another more interesting variant (variant g) of the compounds according to this invention includes those compounds of formula Ia, in which Q is optionally substituted by Rca and/or Rcb, and is Har.

Another more interesting variant (variant h) of the compounds according to this invention includes those compounds of formula Ia, in which Q is Cyc.

Compounds according to variant h of this invention to be mentioned in a subvariant thereof (variant h1) include those compounds of formula Ia, in which
Q is Cyc, in which
Cyc is 1,3-benzodioxolyl, or 2,3-dihydro-1,4-benzodioxinyl.

Compounds according to variant h of this invention to be mentioned in a subvariant thereof (variant h2) include those compounds of formula Ia, in which
Q is Cyc, in which
Q is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl, 2,3-dihydro-benzofuran-7-yl, or 4-bromo-1,3-benzodioxol-5-yl.

Compounds according to variant h of this invention to be mentioned in a subvariant thereof (variant h3) include those compounds of formula Ia, in which Q is Cyc, in which
Q is 1,3-benzodioxol-5-yl, 1,3-benzodioxol-4-yl, 2,2-difluoro-1,3-benzodioxol-5-yl, 2,2-difluoro-1,3-benzodioxol-4-yl, or 4-bromo-1,3-benzodioxol-5-yl.

Compounds according to variant h of this invention to be mentioned in a subvariant thereof (variant h4) include those compounds of formula Ia, in which
Q is Cyc, in which
Q is 1,3-benzodioxol-4-yl.

Another more interesting variant (variant i) of the compounds according to this invention includes those compounds of formula Ia, in which Q is Rba- and/or Rbb- and/or Rbc-substituted phenyl.

Compounds according to variant i of this invention to be mentioned in a subvariant thereof (variant i1) include those compounds of formula Ia, in which
Q is Rba- and/or Rbb- and/or Rbc-substituted phenyl, in which
Rba, Rbb and Rbc have the meanings as given in any of the aspects 1 or 2.

Compounds according to variant i of this invention to be mentioned in another subvariant thereof (variant i2) include those compounds of formula Ia, in which
Q is Rba- and/or Rbb- and/or Rbc-substituted phenyl, in which
Rba is 1-4C-alkyl, halogen, trifluoromethyl, 1-4C-alkoxy, nitro, hydroxyl, amino, or mono- or di-1-4C-alkylamino,
Rbb is halogen, or 1-4C-alkoxy,
Rbc is 1-4C-alkoxy.

Compounds according to variant i of this invention to be mentioned in another subvariant thereof (variant i3) include those compounds of formula Ia, in which
Q is Rba- and/or Rbb- and/or Rbc-substituted phenyl, in which
Rba is 1-4C-alkyl, halogen, trifluoromethyl, 1-4C-alkoxy, nitro, or di-1-4C-alkylamino,
Rbb is halogen, or 1-4C-alkoxy,
Rbc is 1-4C-alkoxy.

Compounds according to variant i of this invention to be mentioned in another subvariant thereof (variant i4) include those compounds of formula Ia, in which
Q is Rba- and/or Rbb- and/or Rbc-substituted phenyl, in which
Rba is halogen, 1-4C-alkyl, nitro, trifluoromethyl, 1-4C-alkoxy, di-1-4C-alkylamino, hydroxyl, 1-4C-alkylcarbonyloxy, cyano, phenyl, morpholino, phenoxy, hydroxy-2-4C-alkoxy, 1-4C-alkoxy-2-4C-alkoxy, or completely or predominantly fluorine-substituted 1-4C-alkoxy,
Rbb is 1-4C-alkoxy, halogen or 1-4C-alkyl,
Rbc is 1-4C-alkoxy or halogen.

Compounds according to variant i of this invention to be mentioned in another subvariant thereof (variant i5) include those compounds of formula Ia, in which
Q is Rba- and/or Rbb- and/or Rbc-substituted phenyl, in which
Rba is chlorine, fluorine, bromine, methyl, ethyl, methoxy, ethoxy, isopropyloxy, propoxy, hydroxyl, nitro, trifluoromethyl, dimethylamino, methylcarbonyloxy, cyano, phenyl, morpholino, phenoxy, difluoromethoxy or trifluoromethoxy,
Rbb is methoxy, ethoxy, fluorine, chlorine or methyl,
Rbc is fluorine or chlorine.

Compounds according to variant i of this invention to be mentioned in another subvariant thereof (variant i6) include those compounds of formula Ia, in which
Q is Rba- and/or Rbb- and/or Rbc-substituted phenyl, in which Rba is chlorine, fluorine, bromine, methyl, ethyl, methoxy, ethoxy, difluoromethoxy or trifluoromethoxy,
Rbb is methoxy, ethoxy, fluorine, chlorine or methyl,
Rbc is fluorine.

Compounds according to variant i of this invention to be mentioned in another subvariant thereof (variant i7) include those compounds of formula Ia, in which
Q is 2-(Rba)-phenyl which is optionally substituted by Rbb and/or Rbc.

Compounds according to variant i of this invention to be mentioned in another subvariant thereof (variant i8) include those compounds of formula Ia, in which
Q is phenyl which is substituted by Rba and Rbb.

Compounds according to variant i of this invention to be mentioned in another subvariant thereof (variant i9) include those compounds of formula Ia, in which
Q is Rbb-substituted 2-(Rba)-phenyl.

Compounds according to variant i of this invention to be mentioned in another subvariant thereof (variant i10) include those compounds of formula Ia, in which
Q is 2-(Rba)-5-(Rbb)-phenyl.

Compounds according to variant i of this invention to be mentioned in another subvariant thereof (variant i11) include those compounds of formula Ia, in which
Q is 2-(Rba)-3-(Rbb)-phenyl.

Compounds according to variant i of this invention to be mentioned in another subvariant thereof (variant i12) include those compounds of formula Ia, in which
Q is 5-(Rba)-2-(Rbb)-phenyl.

Compounds according to variant i of this invention to be mentioned in another subvariant thereof (variant i13) include those compounds of formula Ia, in which
Q is 3-(Rba)-2-(Rbb)-phenyl.

Compounds according to variant i of this invention to be mentioned in another subvariant thereof (variant i14) include those compounds of formula Ia, in which
Q is phenyl which is mono-substituted by Rba.

Compounds according to variant i of this invention to be mentioned in another subvariant thereof (variant i15) include those compounds of formula Ia, in which
Q is phenyl which is mono-substituted by Rba, in which
Rba is substituted in the para, or, in particular, meta, or, in more particular, ortho position with respect to the binding position in which the phenyl ring is attached to the ethenyl moiety.

Compounds according to variant i of this invention to be mentioned in another subvariant thereof (variant i16) include those compounds of formula Ia, in which
Q is phenyl which is mono-substituted by Rba on the ortho position with respect to the binding position in which the phenyl ring is attached to the ethenyl moiety, i.e. 2-(Rba)-phenyl.

Compounds according to variant i of this invention to be mentioned in another subvariant thereof (variant i17) include those compounds of formula Ia, in which
Q is phenyl which is mono-substituted by Rba on the meta position with respect to the binding position in which the phenyl ring is attached to the ethenyl moiety, i.e. 3-(Rba)-phenyl.

Compounds according to variant i of this invention to be mentioned in another subvariant thereof (variant i18) include those compounds of formula Ia, in which
Q is 2-(Rba)-phenyl which optionally substituted by Rbb and/or Rbc, in which
Rba is chlorine, fluorine, methyl, ethyl, methoxy, ethoxy, difluoromethoxy or trifluoromethoxy,
Rbb is methoxy, ethoxy, fluorine, chlorine or methyl,
Rbc is fluorine.

Compounds according to variant i of this invention to be mentioned in another subvariant thereof (variant i19) include those compounds of formula Ia, in which
Q is 2-(Rba)-phenyl which optionally substituted by Rbb and/or Rbc, in which
Rba is chlorine, methoxy or, particularly, ethoxy.

Compounds according to variant i of this invention to be mentioned in another subvariant thereof (variant i20) include those compounds of formula Ia, in which
Q is 2-(Rba)-5-(Rbb)-phenyl, in which
Rba is chlorine, fluorine, methyl, ethyl, methoxy, ethoxy, difluoromethoxy or trifluoromethoxy,
Rbb is methoxy, ethoxy, fluorine, chlorine or methyl.

Compounds according to variant i of this invention to be mentioned in another subvariant thereof (variant i21) include those compounds of formula Ia, in which
Q is 2-(Rba)-3-(Rbb)-phenyl, in which
Rba is chlorine, fluorine, methyl, ethyl, methoxy, ethoxy, difluoromethoxy or trifluoromethoxy,
Rbb is methoxy, ethoxy, fluorine, chlorine or methyl.

Compounds according to variant i of this invention to be mentioned in another subvariant thereof (variant i22) include those compounds of formula Ia, in which
Q is phenyl which is mono-substituted by Rba, in which
Rba is chlorine, fluorine, bromine, methyl, ethyl, methoxy, ethoxy, isopropyloxy, propoxy, hydroxyl, nitro, trifluoromethyl, dimethylamino, methylcarbonyloxy, cyano, phenyl, morpholino, phenoxy, difluoromethoxy, trifluoromethoxy or 2-hydroxyethoxy.

Compounds according to variant f of this invention to be mentioned in another subvariant thereof (variant i23) include those compounds of formula Ia, in which
Q is phenyl which is mono-substituted by Rba, in which
Rba is chlorine, methyl, ethyl, methoxy or ethoxy.

Compounds according to variant f of this invention to be mentioned in another subvariant thereof (variant i24) include those compounds of formula Ia, in which
Q is 2-(Rba)-phenyl, in which
Rba is chlorine, fluorine, bromine, methyl, ethyl, methoxy, ethoxy, isopropyloxy, propoxy, hydroxyl, nitro, trifluoromethyl, dimethylamino, methylcarbonyloxy, cyano, phenyl, morpholino, phenoxy, difluoromethoxy, trifluoromethoxy or 2-hydroxyethoxy.

Compounds according to variant f of this invention to be mentioned in another subvariant thereof (variant i25) include those compounds of formula Ia, in which
Q is 2-(Rba)-phenyl, in which
Rba is chlorine, methyl, ethyl, methoxy or ethoxy.

Compounds according to variant i of this invention to be mentioned in another subvariant thereof (variant i26) include those compounds of formula Ia, in which
Q is phenyl which is substituted by Rba and Rbb, in which
Rba is chlorine, methyl, ethyl, methoxy or ethoxy,
Rbb is methoxy, ethoxy, fluorine, chlorine or methyl.

Compounds according to variant i of this invention to be mentioned in another subvariant thereof (variant i27) include those compounds of formula Ia, in which
Q is Rbb-substituted 2-(Rba)-phenyl, in which
Rba is chlorine, methyl, ethyl, methoxy or ethoxy,
Rbb is methoxy, ethoxy, fluorine, chlorine or methyl.

Compounds according to variant i of this invention to be mentioned in another subvariant thereof (variant i28) include those compounds of formula Ia, in which
Q is Rbb-substituted 2-(Rba)-phenyl, in which
Rba is methoxy or ethoxy,
Rbb is methoxy, fluorine, chlorine or methyl.

Compounds according to variant i of this invention to be mentioned in another subvariant thereof (variant i29) include those compounds of formula Ia, in which
Q is Rbb-substituted 2-(Rba)-phenyl, in which
Rba is methyl, ethyl or chlorine,
Rbb is methoxy, fluorine, chlorine or methyl.

Compounds according to variant i of this invention to be mentioned in another subvariant thereof (variant i30) include those compounds of formula Ia, in which
Q is 2-(Rba)-3-(Rbb)-phenyl, in which either
Rba is ethoxy, and
Rbb is methoxy, fluorine, chlorine or methyl.

or
Rba is methoxy, and
Rbb is methoxy, fluorine, chlorine or methyl.

Compounds according to variant i of this invention to be mentioned in another subvariant thereof (variant i31) include those compounds of formula Ia, in which
Q is 2-(Rba)-5-(Rbb)-phenyl, in which either
Rba is ethoxy, and
Rbb is methoxy, fluorine, chlorine or methyl.

or
Rba is methoxy, and
Rbb is methoxy, fluorine, chlorine or methyl.

Compounds according to variant i of this invention to be mentioned in another subvariant thereof (variant i32) include those compounds of formula Ia, in which
Q is any one selected from 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-trifluoromethylphenyl, 2-hydroxyphenyl, 3-hydroxyphenyl, 4-hydroxyphenyl,
2-acetoxyphenyl, 2-bromophenyl, 2-ethylphenyl, 2-cyanophenyl, 2-morpholinophenyl, 2-phenylphenyl, 2-isopropoxyphenyl, 2-propoxyphenyl, 2-phenoxyphenyl, 2-(2-hydroxyethyl)-phenyl, 2-difluoromethoxyphenyl and 2-trifluoromethoxyphenyl.

Compounds according to variant i of this invention to be mentioned in another subvariant thereof (variant i33) include those compounds of formula Ia, in which
Q is 2-methoxyphenyl or 2-ethoxyphenyl.

Compounds according to variant i of this invention to be mentioned in another subvariant thereof (variant i34) include those compounds of formula Ia, in which
Q is any one selected from 2,3-difluorophenyl, 2-fluoro-3-chlorophenyl, 2-fluoro-4-chlorophenyl, 2-chloro-6-fluorophenyl, 2,6-dichlorophenyl, 2,4-dichlorophenyl, 2,6-difluorophenyl, 2-fluoro-4-methoxyphenyl, 2-methyl-5-fluorophenyl, 2-methyl-3-fluorophenyl, 2-methyl-4-fluorophenyl, 2,3-dimethylphenyl, 2,3-dimethoxyphenyl, 2-ethoxy-3-methoxyphenyl, 2,5-dimethoxyphenyl and 2,6-dimethoxyphenyl.

Compounds according to variant i of this invention to be mentioned in another subvariant thereof (variant i35) include those compounds of formula Ia, in which
Q is any one selected from 2,3-dimethoxyphenyl, 2-ethoxy-3-methoxyphenyl, 2-ethoxy-5-methoxyphenyl and 2,5-dimethoxyphenyl.

Compounds according to variant i of this invention to be mentioned in another subvariant thereof (variant i36) include those compounds of formula Ia, in which
Q is any one selected from 2-methoxy-5-chlorophenyl, 2-methoxy-5-methylphenyl, 2-ethoxy-5-chlorophenyl, 2-ethoxy-5-methylphenyl, 2-chloro-5-methoxyphenyl and 2,5-dimethoxyphenyl.

Compounds according to variant i of this invention to be mentioned in another subvariant thereof (variant i37) include those compounds of formula Ia, in which
Q is any one selected from 2-methoxy-3-chlorophenyl, 2-methoxy-3-methylphenyl, 2-ethoxy-3-chlorophenyl, 2-ethoxy-3-methylphenyl, 2-chloro-3-methoxyphenyl and 2,3-dimethoxyphenyl.

Another more interesting variant (variant j) of the compounds according to this invention includes those compounds of formula Ia, in which Q is unsubstituted phenyl.

Another more interesting variant (variant k) of the compounds according to this invention includes those compounds of formula Ia, in which Q is Rca- and/or Rcb-substituted Har.

Compounds according to variant k of this invention to be mentioned in a subvariant thereof (variant k1) include those compounds of formula Ia, in which
Q is Rca- and/or Rcb-substituted Har, in which
Har is pyridyl, furanyl, thiophenyl, or indolyl,
Rca is 1-4C-alkyl, or halogen,
Rcb is halogen.

Compounds according to variant k of this invention to be mentioned in another subvariant thereof (variant k2) include those compounds of formula Ia, in which
Q is Rca-substituted Har, in which
Har is pyridyl, furanyl, thiophenyl or 1N-(methyl)-pyrazolyl,
Rca is chlorine, fluorine, bromine, methyl, ethyl, methoxy, ethoxy, phenyl, phenoxy or morpholino.

Compounds according to variant k of this invention to be mentioned in another subvariant thereof (variant k3) include those compounds of formula Ia, in which
Q is (morpholino)-pyridyl, (phenoxy)-thiophenyl, or Rca-substituted Har, in which
Har is furanyl, thiophenyl or 1N-(methyl)-pyrazolyl,
Rca is chlorine, methyl, ethyl or phenyl.

Compounds according to variant k of this invention to be mentioned in another subvariant thereof (variant k4) include those compounds of formula Ia, in which
Q is any one selected from (chloro)-thiophenyl, such as e.g. 3-chloro-thiophen-2-yl or 5-chloro-thiophen-2-yl; (chloro)-furanyl, such as e.g. 5-chloro-furan-2-yl; (methyl)-furanyl, such as e.g. 5-methyl-furan-2-yl; (ethyl)-furanyl, such as e.g. 5-ethyl-furan-2-yl; (methyl)-thiophenyl, such as e.g. 3-methyl-thiophen-2-yl or 5-methyl-thiophen-2-yl; (phenoxy)-thiophenyl, such as e.g. 3-phenoxy-thiophen-2-yl; (phenyl)-thiophenyl, such as e.g. 5-phenyl-thiophen-2-yl; (phenyl)-furanyl, such as e.g. 5-phenyl-furan-2-yl; (chloro)-1N-(methyl)-pyrazolyl, such as e.g. 4-chloro-1N-(methyl)-pyrazol-3-yl; or (morpholino)-pyridyl, such as e.g. 2-morpholino-pyridin-3-yl.

Another more interesting variant (variant I) of the compounds according to this invention includes those compounds of formula Ia, in which Q is unsubstituted Har.

Compounds according to variant I of this invention to be mentioned in a subvariant thereof (variant I1) include those compounds of formula Ia, in which
Q is unsubstituted Har, in which
Har is pyridyl, thiophenyl or furanyl.

Compounds according to variant I of this invention to be mentioned in a another subvariant thereof (variant I2) include those compounds of formula Ia, in which Q is unsubstituted Har, in which
Har is pyridyl, thiophenyl, furanyl, benzothiophenyl, benzofuranyl, 1N—(H)-pyrrolyl or 1N-(methyl)-pyrrolyl.

Compounds according to variant I of this invention to be mentioned in another subvariant thereof (variant I3) include those compounds of formula Ia, in which Q is any one selected from pyridin-2-yl, pyridin-3-yl, pyridin-4-yl, thiophen-2-yl, thiophen-3-yl, furan-2-yl, furan-3-yl, 1N—(H)-pyrrol-2-yl, 1N—(H)-pyrrol-3-yl, 1N-(methyl)-pyrrol-2-yl and 1N-(methyl)-pyrrol-3-yl.

Compounds according to variant I of this invention to be mentioned in another subvariant thereof (variant I3) include those compounds of formula Ia, in which Q is any one selected from pyridin-3-yl, thiophen-2-yl, thiophen-3-yl, furan-2-yl and furan-3-yl.

Compounds according to aspect 2 of this invention more worthy to be noted are those compounds of formulae Ia or Ib, in which, in a first alternative, Ra is —C(O)R1, in which, R1 is 1-7C-alkyl, or 1-7C-alkyl substituted by R5, in which either R5 is 1-4C-alkoxycarbonyl, 1-4C-alkylcarbonyl, carbamoyl, guanidino, amidino, carboxyl, mono- or di-1-4C-alkylaminocarbonyl, mono- or di-1-4C-alkylamino, ureido, 1-4C-alkoxy, 1-4C-alkoxy-2-4C-alkoxy, or phenyl-1-4C-alkoxy, or R5 is phenyl, R51-substituted phenyl, Har, R52-substituted Har, Het, or R53-substituted Het, in which R51 is 1-4C-alkoxy, Har is attached to the parent molecular group via a ring carbon or ring nitrogen atom, and is an unsaturated (aromatic) 5-membered ring comprising one to four heteroatoms independently selected from nitrogen, oxygen and sulfur, or an unsaturated (aromatic) 6-membered ring comprising one or two nitrogen atoms, or an unsaturated (aromatic) 9-membered fused bicyclic ring system made up of a benzene ring fused to an unsaturated (aromatic) 5-membered ring comprising one to three heteroatoms independently selected from nitrogen, oxygen and sulfur, or an unsaturated (aromatic) 10-membered fused bicyclic ring system made up of a benzene ring fused to an unsaturated (aromatic) 6-membered ring comprising one or two nitrogen atoms, R52 is 1-4C-alkyl, Het is attached to the parent molecular group via a ring nitrogen atom, and is a saturated 3- to 7-membered monocyclic ring comprising one or two heteroatoms independently selected from nitrogen, oxygen and sulfur, and which is optionally substituted by one or two oxo groups, or a benzo-fused derivative thereof, R53 is 1-4C-alkyl, or 1-4C-alkylcarbonyl;

or in which, in a second alternative,

Ra is —C(O)OR2, in which,

R2 is 1-7C-alkyl, or

R2 is 2-7C-alkyl substituted by R5, in which either

R5 is 1-4C-alkoxycarbonyl, 1-4C-alkylcarbonyl, guanidino, amidino, carbamoyl, carboxyl, mono- or di-1-4C-alkylaminocarbonyl, mono- or di-1-4C-alkylamino, ureido, 1-4C-alkoxy, 1-4C-alkoxy-2-4C-alkoxy, or phenyl-1-4C-alkoxy, or R5 is Het, or R53-substituted Het, in which Het is attached to the parent molecular group via a ring nitrogen atom, and is a saturated 3- to 7-membered monocyclic ring comprising one or two heteroatoms independently selected from nitrogen, oxygen and sulfur, and which is optionally substituted by one or two oxo groups, or a benzo-fused derivative thereof, R53 is 1-4C-alkyl, or 1-4C-alkylcarbonyl, or R2 is 1-7C-alkyl substituted by R5, in which R5 is phenyl, R51-substituted phenyl, Har, or R52-substituted Har, in which R51 is 1-4C-alkoxy, Har is attached to the parent molecular group via a ring carbon or ring nitrogen atom, and is an unsaturated (aromatic) 5-membered ring comprising one to four heteroatoms independently selected from nitrogen, oxygen and sulfur, or an unsaturated (aromatic) 6-membered ring comprising one or two nitrogen atoms, or an unsaturated (aromatic) 9-membered fused bicyclic ring system made up of a benzene ring fused to an unsaturated (aromatic) 5-membered ring comprising one to three heteroatoms independently selected from nitrogen, oxygen and sulfur, or an unsaturated (aromatic) 10-membered fused bicyclic ring system made up of a benzene ring fused to an unsaturated (aromatic) 6-membered ring comprising one or two nitrogen atoms, R52 is 1-4C-alkyl;

or in which, in a third alternative,

Ra is —C(O)SR2, in which,

R2 is 1-7C-alkyl;

and in which either

Q is Rba- and/or Rbb- and/or Rbc-substituted phenyl, in which

Rba, Rbb and Rbc are independently as originally defined in aspect 2 above, or, particularly, Q is unsubstituted phenyl, or, yet particularly, Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 4-nitro-phenyl, 2-methyl-phenyl, 3-methyl-phenyl, 4-methyl-phenyl, 2-methoxy-phenyl, 3-methoxy-phenyl, 4-methoxy-phenyl, 2,3-dimethoxy-phenyl, or 2,4-dichloro-phenyl, or, still yet particularly, Q is thiophenyl, furanyl or pyridyl;

and the salts, solvates or the solvates of the salts thereof.

Yet compounds according to aspect 2 of this invention more worthy to be noted are those compounds of formulae Ia or Ib, in which Ra is —C(O)N(R3)R4, in which, R3 is 1-7C-alkyl, or R3 is 2-7C-alkyl substituted by R5, in which either R5 is 1-4C-alkoxycarbonyl, 1-4C-alkylcarbonyl, carbamoyl, carboxyl, mono- or di-1-4C-alkylaminocarbonyl, mono- or di-1-4C-alkylamino, ureido, 1-4C-alkoxy, or phenyl-1-4C-alkoxy, or R5 is Het, or R53-substituted Het, in which Het is attached to the parent molecular group via a ring nitrogen atom,
and is a saturated 3- to 7-membered monocyclic ring comprising one or two heteroatoms independently selected from nitrogen, oxygen and sulfur, and which is optionally substituted by one or two oxo groups,
or a benzo-fused derivative thereof, R53 is 1-4C-alkyl, or 1-4C-alkylcarbonyl, or R2 is 1-7C-alkyl substituted by R5, in which R5 is phenyl, R51-substituted phenyl, Har, or R52-substituted Har, in which R51 is 1-4C-alkoxy, Har is attached to the parent molecular group via a ring carbon atom,
and is an unsaturated (aromatic) 5-membered ring comprising one to four heteroatoms independently selected from nitrogen, oxygen and sulfur,
or an unsaturated (aromatic) 6-membered ring comprising one or two nitrogen atoms,
or an unsaturated (aromatic) 9-membered fused bicyclic ring system made up of a benzene ring fused to an unsaturated (aromatic) 5-membered ring comprising one to three heteroatoms independently selected from nitrogen, oxygen and sulfur,
or an unsaturated (aromatic) 10-membered fused bicyclic ring system made up of a benzene ring fused to an unsaturated (aromatic) 6-membered ring comprising one or two nitrogen atoms, R52 is 1-4C-alkyl;

and in which

R4 is hydrogen;

and in which either

Q is Rba- and/or Rbb- and/or Rbc-substituted phenyl, in which Rba, Rbb and Rbc are independently as originally defined in aspect 2 above, or, particularly, Q is unsubstituted phenyl;

and the salts, solvates or the solvates of the salts thereof.

A special interest within the present invention refers to those compounds according to this invention which are included by one or, when possible, by more of the following special embodiments or subembodiments:

A special embodiment (embodiment 1) of the compounds according to this invention includes those compounds of formula Ia or Ib, in which Ra is —C(O)R1.

A subembodiment (embodiment 1a) of the compounds of embodiment 1 according to this invention includes those compounds of formula Ia, in which Ra is —C(O)R1, in which R1 is methyl, ethyl or propyl.

Another subembodiment (embodiment 1b) of the compounds of embodiment 1 according to this invention includes those compounds of formula Ia, in which Ra is —C(O)R1, in which R1 is methyl which is mono-substituted by R5, ethyl which is mono-substituted by R5, or propyl which is mono-substituted by R5, in which R5 is methoxy, ethoxy, 2-methoxyethoxy, hydroxyl, pyridyl, pyrimidinyl, pyrazinyl, imidazolo or pyrazolo.

Compounds of embodiment 1b more worthy to be mentioned may include those compounds of formula Ia, in which Ra is —C(O)R1, in which R1 is methyl which is mono-substituted by R5, or ethyl which is mono-substituted by R5, in which R5 is methoxy, ethoxy, 2-methoxyethoxy, hydroxyl, pyridyl or imidazolo.

Compounds of embodiment 1b in particular worthy to be mentioned may include those compounds of formula Ia, in which Ra is —C(O)R1, in which R1 is methoxy-methyl, 2-methoxy-ethyl, (2-methoxyethoxy)-methyl, 2-(2-methoxyethoxy)-ethyl, hydroxymethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl or 2-(pyridin-4-yl)-ethyl.

Another subembodiment (embodiment 1c) of the compounds of embodiment 1 according to this invention includes those compounds of formula Ia, in which Ra is —C(O)R1, in which R1 is 2,3-dihydroxypropyl.

Other compounds of embodiment 1 to be mentioned may include those compounds of formula Ia, in which Ra is —C(O)R1, in which R1 is 1-7C-alkyl, such as e.g. methyl, ethyl, propyl or butyl.

Other compounds of embodiment 1 to be mentioned may include those compounds of formula Ia, in which Ra is —C(O)R1, in which R1 is methyl.

Other compounds of embodiment 1 to be mentioned may include those compounds of formula Ia, in which Ra is —C(O)R1, in which R1 is propyl.

Another special embodiment (embodiment 2) of the compounds according to this invention includes those compounds of formula Ia or Ib, in which Ra is —C(O)OR2.

A subembodiment (embodiment 2a) of the compounds of embodiment 1 according to this invention includes those compounds of formula Ia, in which Ra is —C(O)OR2, in which R2 is methyl, ethyl or propyl.

Compounds of embodiment 2a more worthy to be mentioned may include those compounds of formula Ia, in which Ra is —C(O)OR2, in which R2 is ethyl.

Another subembodiment (embodiment 2b) of the compounds of embodiment 1 according to this invention includes those compounds of formula Ia, in which Ra is —C(O)OR2, in which either R2 is methyl which is mono-substituted by R5, ethyl which is mono-substituted by R5, or propyl which is mono-substituted by R5, in which R5 is pyridyl, pyrimidinyl or pyrazinyl.

or

R2 is ethyl which is mono-substituted by R5, or propyl which is mono-substituted by R5, in which R5 is methoxy, ethoxy, 2-methoxyethoxy, hydroxyl, imidazolo or pyrazolo.

Compounds of embodiment 2b more worthy to be mentioned may include those compounds of formula Ia, in which Ra is —C(O)OR2, in which either R2 is methyl which is mono-substituted by R5, or ethyl which is mono-substituted by R5, in which R5 is pyridyl, or R2 is ethyl which is mono-substituted by R5, in which R5 is methoxy, ethoxy, 2-methoxyethoxy, hydroxyl or imidazolo.

Compounds of embodiment 2b in particular worthy to be mentioned may include those compounds of formula Ia, in which Ra is —C(O)OR2, in which R2 is 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl or 2-(pyridin-4-yl)-ethyl.

Another subembodiment (embodiment 2c) of the compounds of embodiment 1 according to this invention includes those compounds of formula Ia, in which Ra is —C(O)OR2, in which R2 is 2,3-dihydroxypropyl.

Other compounds of embodiment 2 to be mentioned may include those compounds of formula Ia, in which Ra is —C(O)OR2, in which R2 is 1-7C-alkyl, such as e.g. methyl, ethyl, tertbutyl, pentyl or hexyl.

Other compounds of embodiment 2 to be mentioned may include those compounds of formula Ia, in which Ra is —C(O)OR2, in which R2 is methyl.

Other compounds of embodiment 2 to be mentioned may include those compounds of formula Ia, in which Ra is —C(O)OR2, in which R2 is butyl.

Other compounds of embodiment 2 to be mentioned may include those compounds of formula Ia, in which Ra is —C(O)OR2, in which R2 is phenyl-1-4C-alkyl, such as e.g. phenethyl or benzyl.

Other compounds of embodiment 2 to be mentioned may include those compounds of formula Ia, in which Ra is —C(O)OR2, in which R2 is phenethyl.

Other compounds of embodiment 2 to be mentioned may include those compounds of formula Ia, in which Ra is —C(O)OR2, in which R2 is phenyl, or R5-substituted phenyl, such as e.g. 3-(R5)-phenyl, in which R5 is 1-4C-alkoxy, such as e.g. methoxy.

Other compounds of embodiment 2 to be mentioned may include those compounds of formula Ia, in which Ra is —C(O)OR2, in which R2 is phenyl.

Other compounds of embodiment 2 to be mentioned may include those compounds of formula Ia, in which Ra is —C(O)OR2, in which R2 is 3-methoxy-phenyl.

Another special embodiment (embodiment 3) of the compounds according to this invention includes those compounds of formula Ia or Ib, in which Ra is —C(O)SR2.

A subembodiment (embodiment 3a) of the compounds of embodiment 1 according to this invention includes those compounds of formula Ia, in which Ra is —C(O)SR2, in which R2 is methyl, ethyl or propyl.

Compounds of embodiment 3a more worthy to be mentioned may include those compounds of formula Ia, in which Ra is —C(O)SR2, in which R2 is ethyl.

Another subembodiment (embodiment 3b) of the compounds of embodiment 1 according to this invention includes those compounds of formula Ia, in which Ra is —C(O)SR2, in which either R2 is methyl which is mono-substituted by R5, ethyl which is mono-substituted by R5, or propyl which is mono-substituted by R5, in which R5 is pyridyl, pyrimidinyl or pyrazinyl.

or

R2 is ethyl which is mono-substituted by R5, or propyl which is mono-substituted by R5, in which R5 is methoxy, ethoxy, 2-methoxyethoxy, hydroxyl, imidazolo or pyrazolo.

Compounds of embodiment 3b more worthy to be mentioned may include those compounds of formula Ia, in which Ra is —C(O)SR2, in which either R2 is methyl which is mono-substituted by R5, or ethyl which is mono-substituted by R5, in which R5 is pyridyl, or R2 is ethyl which is mono-substituted by R5, in which R5 is methoxy, ethoxy, 2-methoxyethoxy, hydroxyl or imidazolo.

Compounds of embodiment 3b in particular worthy to be mentioned may include those compounds of formula Ia, in which Ra is —C(O)SR2, in which R2 is 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl or 2-(pyridin-4-yl)-ethyl.

Other compounds of embodiment 3 to be mentioned may include those compounds of formula Ia, in which Ra is —C(O)SR2, in which R2 is 1-7C-alkyl, such as e.g. ethyl.

Another special embodiment (embodiment 4) of the compounds according to this invention includes those compounds of formula Ia or Ib, in which Ra is —C(O)N(R3)R4;

Other compounds of embodiment 4 to be mentioned may include those compounds of formula Ia, in which Ra is —C(O)N(R3)R4, in which R3 is 1-7C-alkyl, such as e.g. ethyl, R4 is hydrogen.

Another special embodiment (embodiment 5) of the compounds according to this invention includes those compounds of formula Ia or Ib, in which Ra is —S(O)$_2$R1.

Another special embodiment (embodiment 6) of the compounds according to this invention includes those compounds of formula Ia or Ib, in which Ra is —S(O)$_2$N(R3)R4.

Among these aforementioned embodiments, the embodiments 1, 2 and 3 are to be emphasized.

Another special embodiment (embodiment 7) of the compounds according to this invention includes those compounds of formula Ia or Ib, in which Q is unsubstituted phenyl.

Particular compounds of embodiment 7 may include those compounds of formula Ia, in which Q is unsubstituted phenyl.

Another special embodiment (embodiment 8) of the compounds according to this invention includes those compounds of formula Ia or Ib, in which Q is Rba- and/or Rbb- and/or Rbc-substituted phenyl.

Compounds of embodiment 8 worthy to be mentioned may include those compounds of formula Ia, in which Q is Rba- and/or Rbb- and/or Rbc-substituted phenyl, in which Rba is halogen, 1-4C-alkyl, nitro, trifluoromethyl, 1-4C-alkoxy, di-1-4C-alkylamino, hydroxyl, 1-4C-alkylcarbonyloxy, cyano, phenyl, morpholino, phenoxy, or completely or predominantly fluorine-substituted 1-4C-alkoxy, Rbb is 1-4C-alkoxy, halogen or 1-4C-alkyl, Rbc is halogen.

Compounds of embodiment 8 more worthy to be mentioned may include those compounds of formula Ia, in which Q is Rba- and/or Rbb- and/or Rbc-substituted phenyl, in which Rba is chlorine, fluorine, bromine, methyl, ethyl, nitro, methoxy, ethoxy, isopropyloxy, propoxy, hydroxyl, methylcarbonyloxy, cyano, morpholino, difluoromethoxy or trifluoromethoxy, Rbb is methoxy, ethoxy, fluorine, chlorine or methyl, Rbc is fluorine.

Compounds of embodiment 8 further more worthy to be mentioned may include those compounds of formula Ia, in which Q is Rba-substituted phenyl, in which Rba is chlorine, fluorine, bromine, methyl, ethyl, nitro, methoxy, ethoxy, isopropyloxy, propoxy, hydroxyl, methylcarbonyloxy, cyano, morpholino, difluoromethoxy or trifluoromethoxy.

Yet compounds of embodiment 8 further more worthy to be mentioned may include those compounds of formula Ia, in which Q is Rba- and Rbb-substituted phenyl, in which Rba is chlorine, fluorine, bromine, methyl, methoxy or ethoxy, Rbb is methoxy, ethoxy, fluorine, chlorine or methyl.

Yet compounds of embodiment 8 further more worthy to be mentioned may include those compounds of formula Ia, in which Q is Rba- and Rbb- and Rbc-substituted phenyl, in which Rba is chlorine, fluorine, bromine, methyl, methoxy or ethoxy, Rbb is methoxy, ethoxy, fluorine, chlorine or methyl, Rbc is fluorine.

Compounds of embodiment 8 in particular worthy to be mentioned may include those compounds of formula Ia, in which Q is 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-acetoxyphenyl, 2-bromophenyl, 2-ethylphenyl, 2-cyanophenyl, 2-morpholinophenyl, 2-isopropoxyphenyl, 2-propoxyphenyl, 2-difluoromethoxyphenyl or 2-trifluoromethoxyphenyl.

Yet compounds of embodiment 8 in particular worthy to be mentioned may include those compounds of formula Ia, in which Q is substituted by Rbb, and is 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-acetoxyphenyl, 2-bromophenyl, 2-ethylphenyl, 2-cyanophenyl, 2-morpholinophenyl, 2-isopropoxyphenyl, 2-propoxyphenyl, 2-difluoromethoxyphenyl or 2-trifluoromethoxyphenyl, in which Rbb is methoxy, chlorine, fluorine or methyl;

such as e.g.

Q is any one selected from 2,3-difluorophenyl, 2-fluoro-3-chlorophenyl, 2-fluoro-4-chlorophenyl, 2-chloro-6-fluorophenyl, 2,6-dichlorophenyl, 2,4-dichlorophenyl, 2,6-difluorophenyl, 2-fluoro-4-methoxyphenyl, 2-methyl-5-fluorophenyl, 2-methyl-3-fluorophenyl, 2-methyl-4-fluorophenyl, 2,3-dimethylphenyl, 2,3-dimethoxyphenyl, 2-ethoxy-3-methoxyphenyl, 2,5-dimethoxyphenyl and 2,6-dimethoxyphenyl.

Yet compounds of embodiment 8 in particular worthy to be mentioned may include those compounds of formula Ia, in which Q is substituted by Rbb and Rbc, and is 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-acetoxyphenyl, 2-bromophenyl, 2-ethylphenyl, 2-cyanophenyl, 2-morpholinophenyl, 2-isopropoxyphenyl, 2-propoxyphenyl, 2-difluoromethoxyphenyl or 2-trifluoromethoxyphenyl, in which Rbb is methoxy, chlorine, fluorine or methyl, Rbc is fluorine;

such as e.g.

Q is any one selected from 2-chloro-3,6-difluorophenyl and 2,3,6-trifluorophenyl.

Compounds of embodiment 8 in more particular worthy to be mentioned may include those compounds of formula Ia, in which Q is Rba- and/or Rbb- and/or Rbc-substituted phenyl, in which Rba is chlorine, fluorine, methyl, ethyl, methoxy, ethoxy, difluoromethoxy or trifluoromethoxy, Rbb is methoxy, ethoxy, fluorine, chlorine or methyl, Rbc is fluorine.

Compounds of embodiment 8 to be emphasized may include those compounds of formula Ia, in which Q is Rba-substituted phenyl, in which Rba is chlorine, fluorine, methyl, ethyl, methoxy, ethoxy, difluoromethoxy or trifluoromethoxy, especially Rba is chlorine, methyl, methoxy or ethoxy.

Yet compounds of embodiment 8 to be emphasized may include those compounds of formula Ia, in which Q is Rba- and Rbb-substituted phenyl, in which Rba is chlorine, fluorine, methyl, methoxy or ethoxy,
Rbb is methoxy, ethoxy, fluorine, chlorine or methyl, especially
Rba is chlorine, methyl, methoxy or ethoxy,
Rbb is methoxy, chlorine, fluorine or methyl.

Yet compounds of embodiment 8 to be emphasized may include those compounds of formula Ia, in which
Q is Rba- and Rbb- and Rbc-substituted phenyl, in which
Rba is chlorine, fluorine, methyl, methoxy or ethoxy,
Rbb is methoxy, ethoxy, fluorine, chlorine or methyl,
Rbc is fluorine, especially
Rba is chlorine, methyl, methoxy or ethoxy,
Rbb is methoxy, chlorine, fluorine or methyl,
Rbc is fluorine.

Compounds of embodiment 8 to be more emphasized may include those compounds of formula Ia, in which
Q is any one selected from 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-ethylphenyl, 2-difluoromethoxyphenyl and 2-trifluoromethoxyphenyl.

Compounds of embodiment 8 to be more emphasized may include those compounds of formula Ia, in which
Q is any one selected from 2,3-difluorophenyl, 2-fluoro-3-chlorophenyl, 2-fluoro-4-chlorophenyl, 2-chloro-6-fluorophenyl, 2,6-dichlorophenyl, 2,4-dichlorophenyl, 2,6-difluorophenyl, 2-fluoro-4-methoxyphenyl, 2-methyl-5-fluorophenyl, 2-methyl-3-fluorophenyl, 2-methyl-4-fluorophenyl, 2,3-dimethylphenyl, 2,3-dimethoxyphenyl, 2-ethoxy-3-methoxyphenyl, 2,5-dimethoxyphenyl and 2,6-dimethoxyphenyl.

Compounds of embodiment 8 to be in particular emphasized may include those compounds of formula Ia, in which
Q is 2-methoxyphenyl, 2-chlorophenyl, 2-ethoxyphenyl or 2-methylphenyl.

Yet compounds of embodiment 8 to be in particular emphasized may include those compounds of formula Ia, in which
Q is 2-(Rba)-3-(Rbb)-phenyl, in which
Rba is chlorine, methoxy, ethoxy or methyl,
Rbb is methoxy, chlorine or methyl, such as e.g.
Q is 2,3-dimethylphenyl, 2,3-dimethoxyphenyl or 2-ethoxy-3-methoxyphenyl.

Yet compounds of embodiment 8 to be in particular emphasized may include those compounds of formula Ia, in which
Q is 2-(Rba)-5-(Rbb)-phenyl, in which
Rba is chlorine, methoxy, ethoxy or methyl,
Rbb is methoxy, chlorine or methyl, such as e.g.
Q is 2,5-dimethoxyphenyl.

Compounds of embodiment 8 to be in more particular emphasized may include those compounds of formula Ia, in which
Q is 2-methoxyphenyl or 2-ethoxyphenyl.

Yet compounds of embodiment 8 to be in more particular emphasized may include those compounds of formula Ia, in which
Q is 2-(Rba)-3-(Rbb)-phenyl, in which
Rba is methoxy or ethoxy,
Rbb is methoxy or methyl.

Yet compounds of embodiment 8 to be in more particular emphasized may include those compounds of formula Ia, in which
Q is 2-(Rba)-5-(Rbb)-phenyl, in which
Rba is methoxy or ethoxy,
Rbb is methoxy or methyl.

Compounds of embodiment 8 to be in further more particular emphasized may include those compounds of formula Ia, in which
Q is 2-(Rba)-5-(Rbb)-phenyl, in which
Rba is methoxy,
Rbb is methoxy or methyl.

Yet compounds of embodiment 8 to be in further more particular emphasized may include those compounds of formula Ia, in which
Q is 2-(Rba)-5-(Rbb)-phenyl, in which
Rba is ethoxy,
Rbb is methoxy or methyl.

Particular compounds of embodiment 8 may include those compounds of formula Ia, in which
Q is 2-methoxyphenyl.

Yet particular compounds of embodiment 8 may include those compounds of formula Ia, in which
Q is 2,3-dimethoxyphenyl.

Yet particular compounds of embodiment 8 may include those compounds of formula Ia, in which
Q is 2-ethoxy-3-methoxy-phenyl.

Yet particular compounds of embodiment 8 may include those compounds of formula Ia, in which
Q is 2-ethoxy-3-methyl-phenyl.

Yet particular compounds of embodiment 8 may include those compounds of formula Ia, in which
Q is 2,5-dimethoxyphenyl.

Yet particular compounds of embodiment 8 may include those compounds of formula Ia, in which
Q is 2-methoxy-5-methyl-phenyl.

More particular compounds of embodiment 8 may include those compounds of formula Ia, in which
Q is 2-ethoxyphenyl.

Yet more particular compounds of embodiment 8 may include those compounds of formula Ia, in which
Q is 2-ethoxy-5-methoxy-phenyl.

Yet more particular compounds of embodiment 8 may include those compounds of formula Ia, in which
Q is 2-ethoxy-5-methyl-phenyl.

Other compounds of embodiment 8 to be mentioned may include those compounds of formula Ia, in which
Q is Rba- and/or Rbb- and/or Rbc-substituted phenyl, in which
Rba is halogen, 1-4C-alkyl, nitro, trifluoromethyl, or 1-4C-alkoxy,
Rbb is 1-4C-alkoxy, or halogen,
Rbc is 1-4C-alkoxy.

Other compounds of embodiment 8 to be mentioned may include those compounds of formula Ia, in which
Q is Rba- and/or Rbb-substituted phenyl, in which
Rba is halogen, nitro, 1-4C-alkyl, 1-4C-alkoxy, or trifluoromethyl,
Rbb is 1-4C-alkoxy, or halogen.

Other compounds of embodiment 8 to be mentioned may include those compounds of formula Ia, in which
Q is Rba-substituted phenyl, in which
Rba is halogen, nitro, 1-4C-alkyl, 1-4C-alkoxy, or trifluoromethyl;

in particular

Rba is fluorine, chlorine, methyl, nitro, trifluoromethyl, or methoxy.

Other compounds of embodiment 8 to be mentioned may include those compounds of formula Ia, in which Q is Rba- and Rbb-substituted phenyl, in which Rba is 1-4C-alkoxy, or halogen particularly chlorine, Rbb is 1-4C-alkoxy, or halogen particularly chlorine; such as, for example, Q is di-1-4C-alkoxy-phenyl particularly di-methoxy-phenyl, or di-chloro-phenyl.

Other compounds of embodiment 8 to be mentioned may include those compounds of formula Ia, in which Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl.

Other compounds of embodiment 8 to be mentioned may include those compounds of formula Ia, in which Q is 2-chloro-phenyl, 3-chloro-phenyl, 3-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl.

Another special embodiment (embodiment 9) of the compounds according to this invention includes those compounds of formula Ia or Ib, in which Q is optionally substituted by Rca and/or Rcb, and is Har.

Compounds of embodiment 9 worthy to be mentioned may include those compounds of formula Ia, in which Q is optionally substituted by Rca, and is Har, in which Rca is methyl, ethyl or chlorine, Har is furanyl, such as e.g. furan-2-yl or furan-3-yl.

Particular compounds of embodiment 9 may include those compounds of formula Ia, in which Q is unsubstituted Har, in which Har is furanyl, such as e.g. furan-2-yl or furan-3-yl.

Yet particular compounds of embodiment 9 may include those compounds of formula Ia, in which Q is unsubstituted Har, in which Har is thiophenyl, such as e.g. thiophen-2-yl or thiophen-3-yl.

Yet particular compounds of embodiment 9 may include those compounds of formula Ia, in which Q is unsubstituted Har, in which Har is pyridyl, such as e.g. pyridin-2-yl, pyridin-4-yl or, especially, pyridin-3-yl.

More particular compounds of embodiment 9 may include those compounds of formula Ia, in which Q is unsubstituted Har, in which Har is pyridin-3-yl.

Another special embodiment (embodiment 10) of the compounds according to this invention includes those compounds of formula Ia or Ib, in which Q is Cyc.

Compounds of embodiment 10 worthy to be mentioned may include those compounds of formula Ia, in which Q is Cyc, in which Cyc is optionally substituted by halogen on its benzene ring, and is 1,3-benzodioxolyl, 2,3-dihydro-1,4-benzodioxinyl, 2,2-difluoro-1,3-benzodioxolyl or 2,3-dihydro-furanyl, whereby said Cyc ring system is attached to the parent molecular group via a substitutable benzoring carbon atom.

Compounds of embodiment 10 more worthy to be mentioned may include those compounds of formula Ia, in which Q is Cyc, in which Cyc is optionally substituted by bromine on its benzene ring, and is 1,3-benzodioxol-4-yl, 1,3-benzodioxol-5-yl, 2,2-difluoro-1,3-benzodioxol-4-yl or 2,2-difluoro-1,3-benzodioxol-5-yl.

Compounds of embodiment 10 in particular worthy to be mentioned may include those compounds of formula Ia, in which Q is Cyc, in which Cyc is 1,3-benzodioxol-4-yl or 2,2-difluoro-1,3-benzodioxol-4-yl.

Particular compounds of embodiment 10 may include those compounds of formula Ia, in which Q is Cyc, in which Cyc is 1,3-benzodioxol-4-yl.

Other compounds of embodiment 10 to be mentioned may include those compounds of formula Ia, in which Q is 1,3-benzodioxol-5-yl, 2,3-dihydro-1,4-benzodioxin-6-yl, 2,3-dihydro-furan-5-yl, or 2,3-dihydro-furan-6-yl.

Other compounds of embodiment 10 to be mentioned may include those compounds of formula Ia, in which Q is 1,3-benzodioxol-5-yl, or 2,3-dihydro-1,4-benzodioxin-6-yl.

Another special embodiment (embodiment 11) of the compounds according to this invention includes those compounds of formula Ia.

A group of compounds according to special embodiment 1 of the compounds according to this invention may include those compounds of formula Ia or Ib, in which Ra is —C(O)R1, in which R1 is a radical selected from the following List 1.

List 1 consists of the following radicals:

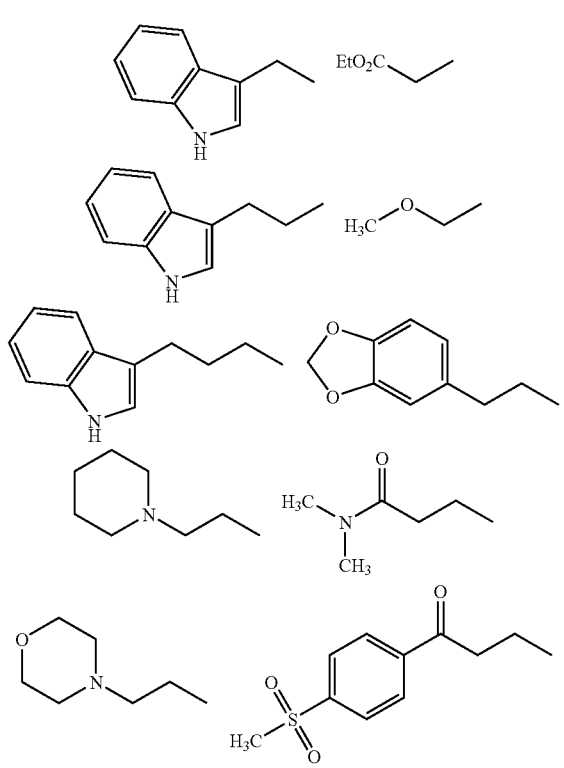

-continued

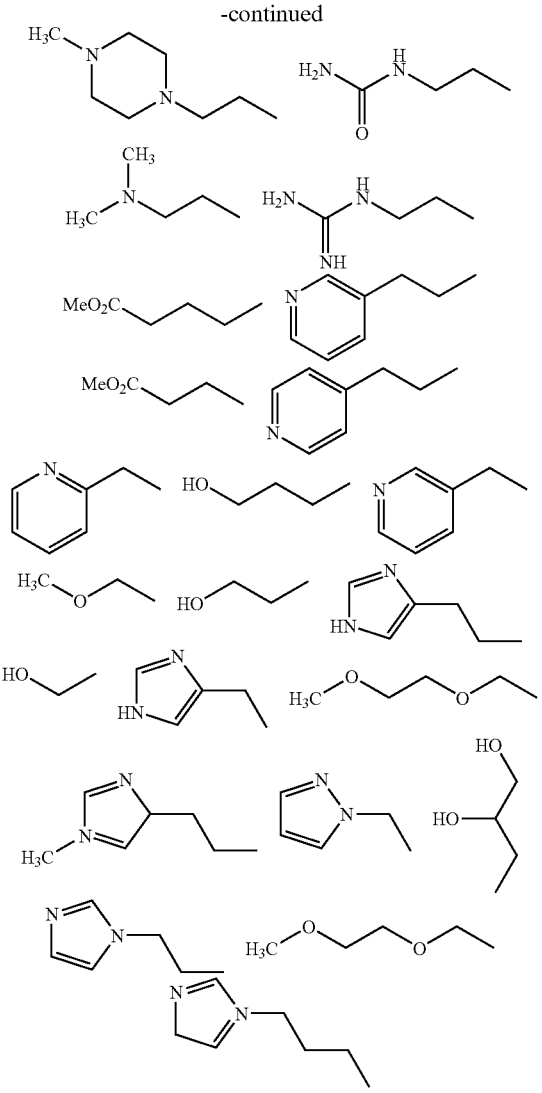

Another group of compounds according to this invention may include those compounds of formula Ia, in which
Q is unsubstituted phenyl, and
Ra is —C(O)R1, in which R1 is a radical selected from the List 1.

Another group of compounds according to this invention may include those compounds of formula Ia, in which
Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl, and
Ra is —C(O)R1, in which R1 is a radical selected from the List 1.

Another group of compounds according to this invention may include those compounds of formula Ia, in which
Q is thiophenyl, furanyl, or pyridyl, and
Ra is —C(O)R1, in which R1 is a radical selected from the List 1.

Another group of compounds according to this invention may include those compounds of formula Ia, in which
Q is any one selected from 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-acetoxyphenyl, 2-bromophenyl, 2-ethylphenyl, 2-cyanophenyl, 2-morpholinophenyl, 2-isopropoxyphenyl, 2-propoxyphenyl, 2-difluoromethoxyphenyl, 2-trifluoromethoxyphenyl, 2,3-difluorophenyl, 2-fluoro-3-chlorophenyl, 2-fluoro-4-chlorophenyl, 2-chloro-6-fluorophenyl, 2,6-dichlorophenyl, 2,4-dichlorophenyl, 2,6-difluorophenyl, 2-fluoro-4-methoxyphenyl, 2-methyl-5-fluorophenyl, 2-methyl-3-fluorophenyl, 2-methyl-4-fluorophenyl, 2,3-dimethylphenyl, 2,3-dimethoxyphenyl, 2-ethoxy-3-methoxyphenyl, 2,5-dimethoxyphenyl and 2,6-dimethoxyphenyl,
Ra is —C(O)R1, in which R1 is a radical selected from the List 1.

A group of compounds according to special embodiment 2 of the compounds according to this invention may include those compounds of formula Ia or Ib, in which
Ra is —C(O)OR2, in which R2 is a radical selected from the following List 2.
List 2 consists of the following radicals:

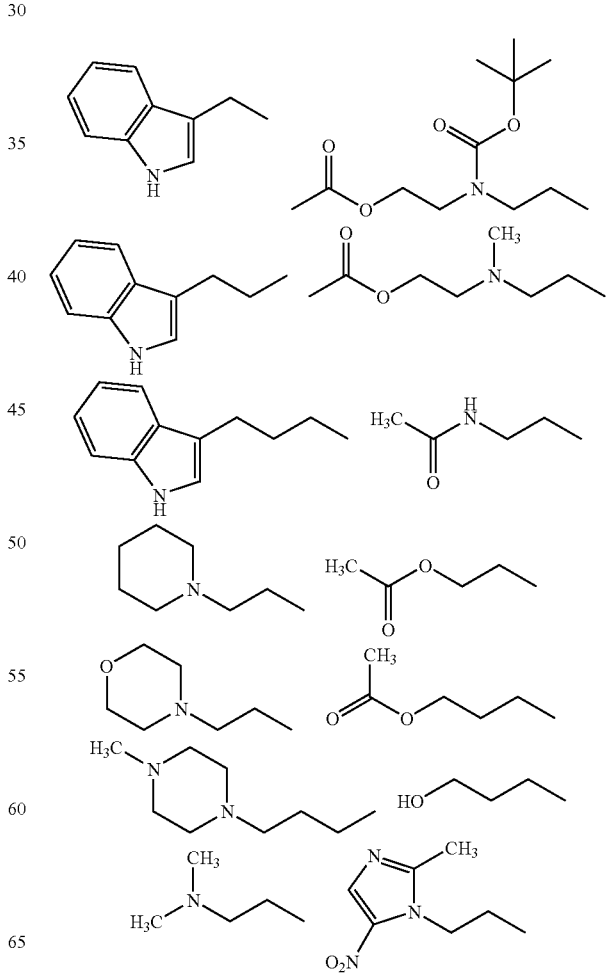

-continued 3-methoxy-phenyl, 4-methoxy-phenyl, 2,3-dimethoxy-phenyl, or 2,4-dichloro-phenyl, and Ra is —C(O)OR2, in which R2 is a radical selected from the List 2.

Another group of compounds according to this invention may include those compounds of formula Ia, in which Q is thiophenyl, furanyl, or pyridyl, and Ra is —C(O)OR2, in which R2 is a radical selected from the List 2.

Another group of compounds according to this invention may include those compounds of formula Ia, in which Q is any one selected from 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-acetoxyphenyl, 2-bromophenyl, 2-ethylphenyl, 2-cyanophenyl, 2-morpholinophenyl, 2-isopropoxyphenyl, 2-propoxyphenyl, 2-difluoromethoxyphenyl, 2-trifluoromethoxyphenyl, 2,3-difluorophenyl, 2-fluoro-3-chlorophenyl, 2-fluoro-4-chlorophenyl, 2-chloro-6-fluorophenyl, 2,6-dichlorophenyl, 2,4-dichlorophenyl, 2,6-difluorophenyl, 2-fluoro-4-methoxyphenyl, 2-methyl-5-fluorophenyl, 2-methyl-3-fluorophenyl, 2-methyl-4-fluorophenyl, 2,3-dimethylphenyl, 2,3-dimethoxyphenyl, 2-ethoxy-3-methoxyphenyl, 2,5-dimethoxyphenyl and 2,6-dimethoxyphenyl, Ra is —C(O)OR2, in which R2 is a radical selected from the List 2.

A group of compounds according to special embodiment 3 of the compounds according to this invention may include those compounds of formula Ia or Ib, in which Ra is —C(O)SR2, in which R2 is a radical selected from the following List 3.

List 3 consists of the following radicals:

Another group of compounds according to this invention may include those compounds of formula Ia, in which Q is unsubstituted phenyl, and Ra is —C(O)OR2, in which R2 is a radical selected from the List 2.

Another group of compounds according to this invention may include those compounds of formula Ia, in which Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 2-methyl-phenyl, 3-methyl-phenyl, 4-methyl-phenyl, Another group of compounds according to this invention may include those compounds of formula Ia, in which Q is unsubstituted phenyl, and Ra is —C(O)SR2, in which R2 is a radical selected from the List 3.

Another group of compounds according to this invention may include those compounds of formula Ia, in which Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl, and Ra is —C(O)SR2, in which R2 is a radical selected from the List 3.

Another group of compounds according to this invention may include those compounds of formula Ia, in which
Q is thiophenyl, furanyl, or pyridyl, and
Ra is —C(O)SR2, in which R2 is a radical selected from the List 3.

Another group of compounds according to this invention may include those compounds of formula Ia, in which Q is any one selected from 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-methylphenyl, 3-methylphenyl, 4-methylphenyl, 2-fluorophenyl, 3-fluorophenyl, 4-fluorophenyl, 2-nitrophenyl, 3-nitrophenyl, 4-nitrophenyl, 2-acetoxyphenyl, 2-bromophenyl, 2-ethylphenyl, 2-cyanophenyl, 2-morpholinophenyl, 2-isopropoxyphenyl, 2-propoxyphenyl, 2-difluoromethoxyphenyl, 2-trifluoromethoxyphenyl, 2,3-difluorophenyl, 2-fluoro-3-chlorophenyl, 2-fluoro-4-chlorophenyl, 2-chloro-6-fluorophenyl, 2,6-dichlorophenyl, 2,4-dichlorophenyl, 2,6-difluorophenyl, 2-fluoro-4-methoxyphenyl, 2-methyl-5-fluorophenyl, 2-methyl-3-fluorophenyl, 2-methyl-4-fluorophenyl, 2,3-dimethylphenyl, 2,3-dimethoxyphenyl, 2-ethoxy-3-methoxyphenyl, 2,5-dimethoxyphenyl and 2,6-dimethoxyphenyl, Ra is —C(O)SR2, in which R2 is a radical selected from the List 3.

In one embodiment, compounds according to aspect 2 of this invention in particular worthy to be noted are those compounds of formulae Ia or Ib as shown herein, in which Ra is —C(O)R1, in which
R1 is 1-5C-alkyl, phenyl, pyridyl, morpholino, indolyl, or 1-5C-alkyl which is substituted by one substituent selected from R5, in which
R5 is 1-4C-alkoxy, phenoxy, 1-4C-alkoxy-2-4C-alkoxy, hydroxyl, benzyloxy, phenyl, pyridyl, indolyl, 1-4C-alkoxycarbonyl, carboxyl, amino, di-1-4C-alkylamino, morpholino, piperidino, pyrrolidino, 4N-(1-4C-alkyl)-piperazin-1-yl, 4N—(H)-piperazin-1-yl, carbamoyl, ureido, guanidino, imidazol-1-yl, 1N—(H)-imidazol-4-yl, or 1N-(1-4C-alkyl)-imidazol-4-yl;

or in which
Ra is —C(O)OR2, in which
either
R2 is 1-5C-alkyl, phenyl, pyridyl, or (1-4C-alkoxy)-phenyl,
or
R2 is 1-5C-alkyl which is substituted by one substituent selected from R5, in which
R5 is phenyl, pyridyl, indolyl, 4-methyl-thiazolyl, 1-4C-alkoxycarbonyl, carboxyl, (1-4C-alkoxy)-phenyl, 1N—(H)-imidazol-4-yl, or 1N-(1-4C-alkyl)-imidazol-4-yl, or
R2 is 2-5C-alkyl which is substituted by one substituent selected from R5, in which
R5 is 1-4C-alkoxy, phenoxy, 1-4C-alkoxy-2-4C-alkoxy, hydroxyl, benzyloxy, 1-4C-alkylcarbonyloxy, amino, di-1-4C-alkylamino, 1-4C-alkylcarbonylamino, morpholino, piperidino, pyrrolidino, 4N-(1-4C-alkyl)-piperazin-1-yl, 4N—(H)-piperazin-1-yl, or imidazol-1-yl;

or in which
Ra is —C(O)SR2, in which
R2 is 1-5C-alkyl, or 2-5C-alkyl which is substituted by one substituent selected from R5, in which
R5 is 1-4C-alkoxycarbonyl, carboxyl, hydroxyl, 1-4C-alkylcarbonyloxy, di-1-4C-alkylamino, 1-4C-alkylcarbonylamino, pyridyl or pyrazinyl;

and in which either
Q is Rba- and/or Rbb- and/or Rbc-substituted phenyl, in which
Rba is halogen, 1-4C-alkyl, nitro, trifluoromethyl, or 1-4C-alkoxy,
Rbb is 1-4C-alkoxy, or halogen,
Rbc is 1-4C-alkoxy,
such as, for example,
Q is Rba-substituted phenyl, in which
Rba is halogen, 1-4C-alkyl, nitro, trifluoromethyl, or 1-4C-alkoxy,
or
Q is Rba- and Rbb-substituted phenyl, in which
Rba is 1-4C-alkoxy, or halogen,
Rbb is 1-4C-alkoxy, or halogen,
such as, for example,
Q is di-(1-4C-alkoxy)-phenyl, or di-(chloro)-phenyl,
or
Q is unsubstituted phenyl,
or
Q is thiophenyl, furanyl, or pyridyl,
or
Q is 1,3-benzodioxol-5-yl, or 2,3-dihydro-1,4-benzodioxin-6-yl;

in particular
either
Q is Rba-substituted phenyl, in which
Rba is fluorine, chlorine, methyl, nitro, trifluoromethyl, or methoxy,
or
Q is di-methoxy-phenyl, or di-chloro-phenyl,
or
Q is unsubstituted phenyl,
or
Q is thiophenyl, furanyl, or pyridyl,
or
Q is 1,3-benzodioxol-5-yl, or 2,3-dihydro-1,4-benzodioxin-6-yl;

and the salts, solvates or the solvates of the salts thereof.

In another embodiment, compounds according to aspect 2 of this invention in particular worthy to be noted are those compounds of formulae Ia or Ib as shown herein, in which
Ra is —C(O)R1, —C(O)OR2, —C(O)SR2, or —C(O)N(R3)R4;

and either

Q is optionally substituted by Rba and/or Rbb and/or Rbc, and is phenyl, or

Q is bonded to the adjacent unsaturated group via a ring carbon atom, and is Har, or Q is Cyc;

in which either

R1, R2 and R3 may be the same or different and are independently selected from: 1-7C-alkyl, and 1-7C-alkyl which is substituted by one substituent selected from R5, in which R5 is 1-4C-alkoxy, phenyl, thiophenyl, furanyl, pyridyl, methylthiazolyl, indolyl, 1-4C-alkoxycarbonyl, 1-4C-alkylcarbonyl, or carbamoyl, or R1, R2 and R3 may be the same or different and are independently selected from: phenyl, and phenyl which is substituted by one substituent selected from R5, in which R5 is 1-4C-alkoxy;

R4 is hydrogen;

each Rba, Rbb and Rbc may be the same or different and are independently selected from the group consisting of:
1-4C-alkyl, nitro,
halogen, trifluoromethyl,
—OR7 and —N(R8)R9;

R7 and R8 may be the same or different and are 1-4C-alkyl;

R9 is 1-4C-alkyl;

Har is pyridyl, thiophenyl, or furanyl;

Cyc is 1,3-benzodioxolyl, 2,3-dihydro-1,4-benzodioxinyl, 2,3-dihydrobenzothiophenyl, or 2,3-dihydrobenzofuranyl;

and the salts, solvates or the solvates of the salts thereof.

Compounds according to aspect 2 of this invention in more particular worthy to be noted are those compounds of formula Ia, in which, in a first alternative, Ra is —C(O)R1, in which, R1 is 1-5C-alkyl, or 1-5C-alkyl substituted by R5, in which R5 is 1-4C-alkoxycarbonyl, 1-4C-alkylcarbonyl, carbamoyl, or 1-4C-alkoxy, or R5 is pyridyl, indol-2-yl, indol-3-yl or thiophenyl, or R5 is phenyl;

or in which, in a second alternative,

Ra is —C(O)OR2, in which, either

R2 is 1-5C-alkyl, or

R2 is 2-5C-alkyl substituted by R5, in which

R5 is 1-4C-alkoxy, or

R2 is 1-5C-alkyl substituted by R5, in which

R5 is 4-methylthiazol-5-yl, or phenyl, or

R2 is phenyl, or phenyl substituted by R5, in which

R5 is 1-4C-alkoxy;

or in which, in a third alternative,

Ra is —C(O)SR2, in which,

R2 is 1-5C-alkyl;

and in which either

Q is Rba- and/or Rbb- and/or Rbc-substituted phenyl, in which

Rba is halogen, 1-4C-alkyl, nitro, trifluoromethyl, or 1-4C-alkoxy,

Rbb is 1-4C-alkoxy, or halogen,

Rbc is 1-4C-alkoxy;

or

Q is unsubstituted phenyl;

or

Q is thiophenyl, furanyl, or pyridyl;

or

Q is 1,3-benzodioxol-5-yl, or 2,3-dihydro-1,4-benzodioxin-6-yl;

and the salts, solvates or the solvates of the salts thereof.

Compounds according to aspect 2 of this invention to be emphasized are those compounds of formula Ia, in which, in a first alternative, Ra is —C(O)R1, in which, R1 is 1-5C-alkyl;

or in which, in a second alternative,

Ra is —C(O)OR2, in which,

R2 is 1-4C-alkyl, phenyl-1-4C-alkyl, phenyl, or R5-substituted phenyl, in which

R5 is 1-4C-alkoxy;

or in which, in a third alternative,

Ra is —C(O)SR2, in which,

R2 is 1-4C-alkyl;

and in which either

Q is Rba- and/or Rbb- and/or Rbc-substituted phenyl, in which

Rba is halogen, 1-4C-alkyl, nitro, trifluoromethyl, or 1-4C-alkoxy,

Rbb is 1-4C-alkoxy, or halogen,

Rbc is 1-4C-alkoxy, such as, for example,

Q is Rba-substituted phenyl, in which

Rba is halogen, 1-4C-alkyl, nitro, trifluoromethyl, or 1-4C-alkoxy, or

Q is Rba- and Rbb-substituted phenyl, in which

Rba is 1-4C-alkoxy, or halogen,

Rbb is 1-4C-alkoxy, or halogen, such as, for example,

Q is di-(1-4C-alkoxy)-phenyl, or di-(chloro)-phenyl;

or

Q is unsubstituted phenyl;

or

Q is thiophenyl, furanyl, or pyridyl;

or

Q is 1,3-benzodioxol-5-yl, or 2,3-dihydro-1,4-benzodioxin-6-yl;

and the salts, solvates or the solvates of the salts thereof.

Compounds according to aspect 2 of this invention to be more emphasized are those compounds of formula Ia, in which, in a first alternative,
Ra is —C(O)R1, in which
R1 is methyl, ethyl, propyl or butyl;

or in which, in a second alternative,
Ra is —C(O)OR2, in which either
R2 is methyl, ethyl, propyl or butyl, or
R2 is benzyl or phenethyl, or
R2 is phenyl or 3-methoxy-phenyl;

or in which, in a third alternative,
Ra is —C(O)SR2, in which
R2 is ethyl;

and in which either
Q is Rba-substituted phenyl, in which
Rba is fluorine, chlorine, methyl, nitro, trifluoromethyl, or methoxy;

or
Q is di-methoxy-phenyl, or di-chloro-phenyl;

or
Q is unsubstituted phenyl;

or
Q is thiophenyl, furanyl, or pyridyl;

or
Q is 1,3-benzodioxol-5-yl, or 2,3-dihydro-1,4-benzodioxin-6-yl;

in particular either
Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl, or
Q is phenyl, or
Q is thiophenyl, furanyl, or pyridyl, or
Q is 1,3-benzodioxol-5-yl;

and the salts, solvates or the solvates of the salts thereof.

Compounds according to aspect 2 of this invention to be in particular emphasized are those compounds of formula Ia, in which, in a first alternative,
Ra is —C(O)R1, in which
R1 is methyl or propyl;

or in which, in a second alternative,
Ra is —C(O)OR2, in which
R2 is methyl, ethyl, butyl, phenethyl or 3-methoxy-phenyl;

or in which, in a third alternative,
Ra is —C(O)SR2, in which
R2 is ethyl;

and in which either
Q is 2-chloro-phenyl, 3-chloro-phenyl, 3-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl, or
Q is phenyl, or
Q is thiophen-2-yl, thiophen-3-yl, furan-2-yl, furan-3-yl or pyridin-3-yl, or
Q is 1,3-benzodioxol-5-yl;

and the salts, solvates or the solvates of the salts thereof.

Compounds according to the present invention can be prepared as described below or as shown in the following reaction scheme, or as disclosed in WO2004/024066 or, particularly, WO2004/024065, the disclosure of which is incorporated herein, or similarly or analogously thereto according to preparation procedures or synthesis strategies known to the person skilled in the art. Accordingly, compounds according to the present invention can be obtained as specified by way of example in the following examples, or similarly or analogously thereto.

Thus, as shown in the reaction scheme below, a compound of formula III, in which Ra has the meanings given above, can be condensed with malonitrile in the presence of sulfur and a suitable base, such as for example an amine (e.g. diethyl amine or morpholine) to give corresponding compounds of formula II in a manner known to the person skilled in the art (e.g. according to a Gewald reaction) or as described in the following examples.

Compounds of formula III are known or can be obtained in an art-known manner.

Compounds of formula II can be reacted with compounds of formula Rb—C(O)—X, in which Rb has the meanings mentioned above and X is a suitable leaving group, preferably a chlorine atom, in an acylation reaction under conditions habitual per se to give the desired compounds of formula I, in which Ra and Rb have the meanings given above.

Alternatively, compounds of the formula I can also be prepared from the corresponding compounds of formula II and corresponding compounds of formula Rb—C(O)—X, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1yl)-N,N,N',N'-tetramethyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride (EDC).

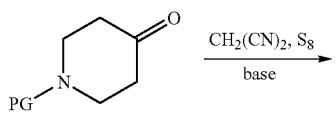

(VI)

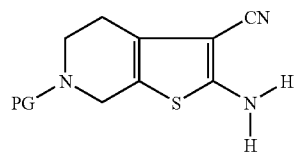

(V)

1. acylation, Rb—C(O)—X
2. deprotection

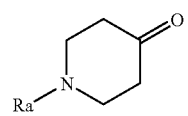

(III)

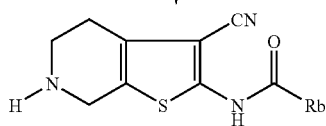

(IV)

CH₂(CN)₂, S₈ | base

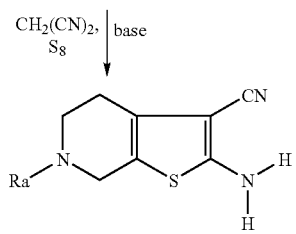

(II)

acylation,
Rb—C(O)—X

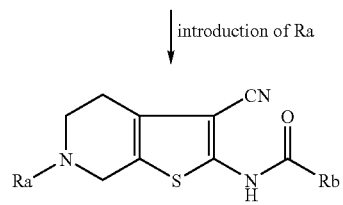

(I)

introduction of Ra

Acid derivatives of formula Rb—C(O)—X are known, commercially available or can be prepared as it is known for the skilled person (e.g. by activation of the corresponding carboxylic acids), or the acrylic acid derivatives are obtained according to art-known procedures, e.g. via CC-bond coupling reactions, like a Knoevenagel or Heck reaction, starting from the appropriate starting compounds.

Optionally, compounds of formula I prepared by the processes described herein can be converted into their salts, or, optionally, salts of the compounds of formula I obtained can be converted into the free compounds. Corresponding processes are known to the person skilled in the art.

In addition, the compounds of formula I can be converted by art-known derivatization into further compounds of formula I.

In an alternative synthesis route, compounds of formula VI, in which PG is a suitable temporary protective group, such as for example tertbutoxycarbonyl (Boc) or one of those mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000), can be condensed with malonitrile in the presence of sulfur and a suitable base as described above to give corresponding compounds of formula V.

Compounds of formula VI are known or can be obtained in an art-known manner.

Compounds of formula V can be acylated with compounds of formula Rb—C(O)—X analogously as mentioned above. Optionally, said amide bond formation can be obtained under microwave assistance. Subsequential deprotection of the protective group PG in a manner customary per se for the skilled person gives compounds of formula IV, in which Rb has the meanings as mentioned above.

Compounds of formula IV can be converted into desired compounds of formula I by introduction of the group Ra via methods known to one of ordinary skill in the art.

More specifically, for example, compounds of the formula I, in which
a) Ra is an acyl group, can be prepared from compounds of formula IV by acylation reaction;
b) Ra is a sulfonyl group, can be obtained from compounds of formula IV by sulfonylation reaction;
c) Ra is an ester group, can be obtained from compounds of formula IV by carbamate formation reaction;
d) Ra is an amide group, can be prepared from compounds of formula IV by urea formation reaction;
e) Ra is a thioester group, can be prepared from compounds of formula IV by thiocarbamate formation reaction;
f.) Ra is a sulfonamide group, can be prepared from compounds of formula IV by sulfamide formation reaction.

The methods mentioned under a) to f) are expediently carried out analogously to the methods known to the person skilled in the art or as described by way of example in the following examples.

The appropriate starting compounds used in the methods mentioned under a) to f) are art-known or can be obtained according to art-known procedures.

Optionally, compounds of formula I can be converted into further compounds of formula I by methods known to one of ordinary skill in the art. More specifically, for example, from compounds of the formula I in which
i) R5 is acyloxy, such as e.g. acetoxy, the corresponding free hydroxyl compounds can be obtained by removal of the acyl group, such as e.g. by saponification reaction;
ii) Het is a cyclic acetal or ketal, such as e.g. the 2,2-dimethyl-[1,3]dioxolan acetal, the corresponding free dihydroxy compounds can be obtained by cleavage of the acetal or ketal, such as e.g. by deacetalization reaction;

iii) R5 is an ester group, such as e.g. methoxycarbonyl, the corresponding free carboxyl compounds can be obtained by deesterification reaction, such as e.g. by saponification reaction.

The methods mentioned under i) to iii) can be expediently carried out analogously to the methods known to the person skilled in the art or as described by way of example in the following examples.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations, alternatives and adaptations to the described invention can be made on the base of art-known knowledge and/or, particularly, on the base of the disclosure (e.g. the explicit, implicit or inherent disclosure) of the present invention without departing from the spirit and scope of this invention as defined by the scope of the appended claims.

The following examples serve to illustrate the invention further without restricting it. Likewise, further compounds of formula I, whose preparation is not explicitly described, can be prepared in an analogous or similar manner or in a manner familiar per se to the person skilled in the art using customary process techniques.

Any or all of the compounds of formula I according to the present invention which are mentioned in the following examples, particularly which are mentioned as final compounds, as well as their salts are a preferred subject of the present invention.

In the examples, MS stands for mass spectrum, calc. for calculated, fnd. for found, Boc for the tertbutoxycarbonyl group, and other abbreviations have their meanings customary per se to the skilled person.

EXAMPLES

Final Compounds:

1. N-(6-Ethoxycarbonyl-3-cyano-4,5,6,7-tetrahydro-thieno[2,3-c]pyridin-2-yl)-3-phenyl-acrylamide

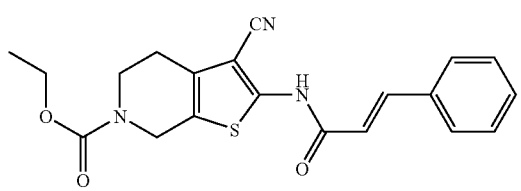

The title compound can be prepared according to general procedure A described below starting from 2-amino-3-cyano-4,7-dihydro-thieno[2,3-c]pyridine-6(5H)-carboxylic acid ethyl ester (compound A1) and 3-phenylacrylyl chloride.

MS: Calc.: $C_{20}H_{19}N_3O_3S$, (381.46). Fnd.: 382.1 [M+H].

2. N-(6-tert-Butoxycarbonyl-3-cyano-4,5,6,7-tetrahydro-thieno[2,3-c]pyridin-2-yl)-3-phenyl-acrylamide

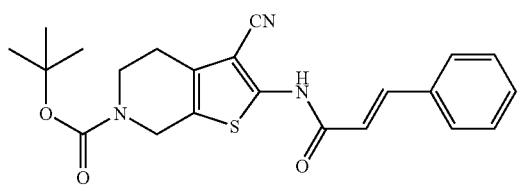

The title compound can be prepared according to general procedure A described below starting from 2-amino-3-cyano-4,7-dihydro-thieno[2,3-c]pyridine-6(5H)-carboxylic acid 1,1-dimethylethyl ester (compound A2) and 3-phenylacrylyl chloride.

MS: Calc.: $C_{22}H_{23}N_3O_3S$, (409.51). Fnd.: 410.0 [M+H].

3. N-(6-Heptanoyl-3-cyano-4,5,6,7-tetrahydro-thieno[2,3-c]pyridin-2-yl)-3-phenyl-acrylamide

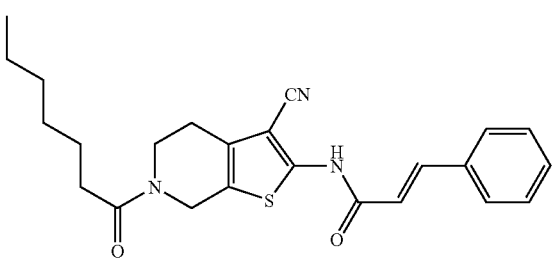

The title compound can be prepared according to general procedure A described below starting from N-(3-cyano-4,5, 6,7-tetrahydro-thieno[2,3-c]pyridin-2-yl)-3-phenyl-acrylamide (compound B1) and heptanoyl chloride.

MS: Calc.: $C_{24}H_{27}N_3O_2S$, (421.57). Fnd.: 422.2 [M+H].

The following compounds 3 to 31 can be prepared according to general procedure A described below starting from 2-amino-3-cyano-4,7-dihydro-thieno[2,3-c]pyridine-6(5H)-carboxylic acid ethyl ester (compound_A1) and the appropriate acrylic acid derivatives, e.g., more precisely, phenyl-acrylic acid, cinnamic acid, furanyl-acrylic acid, thiophenyl-acrylic acid or pyridyl-acrylic acid derivatives.

4. N-(6-Ethoxycarbonyl-3-cyano-4,5,6,7-tetrahydro-thieno[2,3-c]pyridin-2-yl)-3-(2-chlorophenyl)-acrylamide

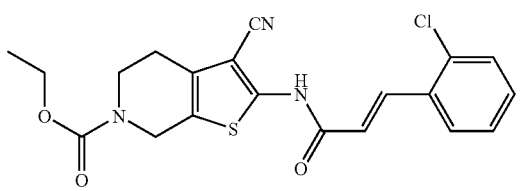

MS: Calc.: $C_{20}H_{18}ClN_3O_3S$, (415.90). Fnd.: 416.0 [M+H].

5. N-(6-Ethoxycarbonyl-3-cyano-4,5,6,7-tetrahydro-thieno[2,3-c]pyridin-2-yl)-3-(3-trifluoromethyl-phenyl)-acrylamide

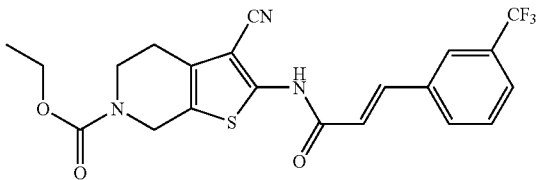

MS: Calc.: $C_{21}H_{18}F_3N_3O_3S$, (449.46). Fnd.: 450.0 [M+H].

6. N-(6-Ethoxycarbonyl-3-cyano-4,5,6,7-tetrahydro-thieno[2,3-c]pyridin-2-yl)-2-methyl-3-phenyl-acrylamide

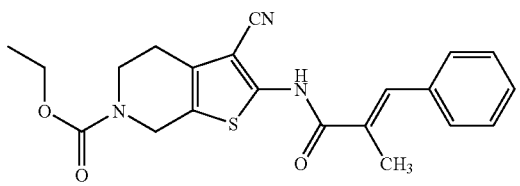

MS: Calc.: $C_{21}H_{21}N_3O_3S$, (395.48). Fnd.: 396.0 [M+H].

7. N-(6-Ethoxycarbonyl-3-cyano-4,5,6,7-tetrahydro-thieno[2,3-c]pyridin-2-yl)-3-pyridyl-acrylamide

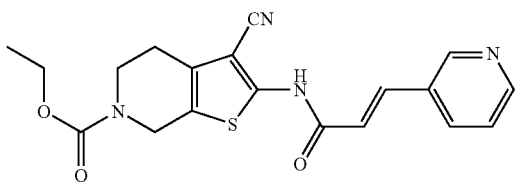

MS: Calc.: $C_{19}H_{18}N_4O_3S$, (382.44). Fnd.: 383.1 [M+H].

8. 3-Cyano-2-((E)-3-thiophen-2-yl-allanoylamino)-4,7-dihydro-5H-thieno[2,3-c]pyridine-6-carboxylic acid ethyl ester

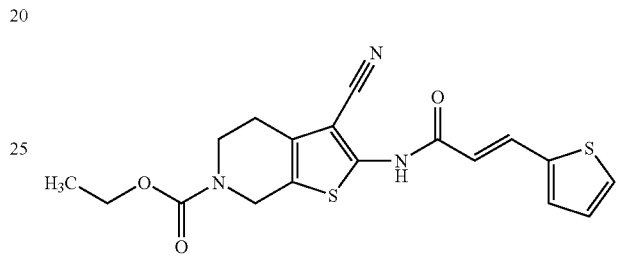

MS: Calc.: C18 H17 N3 O3 S2 (387.48). Fnd.: 388.1 [M+H].

9. 3-Cyano-2-((E)-3-thiophen-3-yl-allanoylamino)-4,7-dihydro-5H-thieno[2,3-c]pyridine-6-carboxylic acid ethyl ester

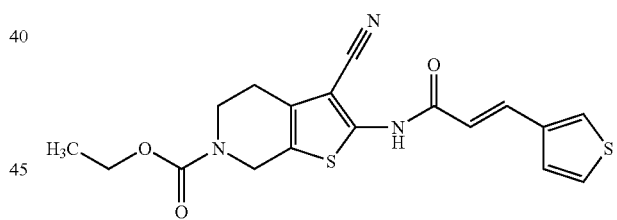

MS: Calc.: C18 H17 N3 O3 S2 (387.48). Fnd.: 388.1 [M+H].

10. 3-Cyano-2-((E)-3-furan-2-yl-allanoylamino)-4,7-dihydro-5H-thieno[2,3-c]pyridine-6-carboxylic acid ethyl ester

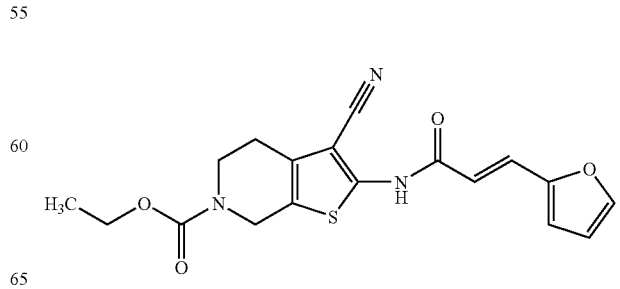

MS: Calc.: C18 H17 N3 O4 S, (371.42). Fnd.: 372 [M+H].

11. 3-Cyano-2-((E)-3-furan-3-yl-allanoylamino)-4,7-dihydro-5H-thieno[2,3-c]pyridine-6-carboxylic acid ethyl ester

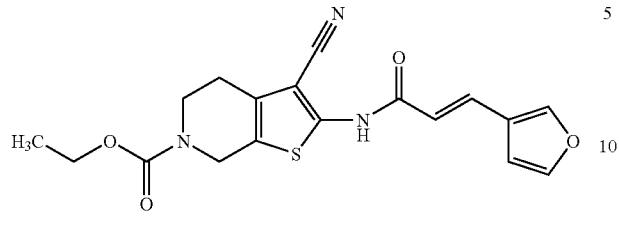

MS: Calc.: C18 H17 N3 O4 S, (371.42). Fnd.: 372.1 [M+H].

12. 3-Cyano-2-((E)-3-o-tolyl-allanoylamino)-4,7-dihydro-5H-thieno[2,3-c]pyridine-6-carboxylic acid ethyl ester

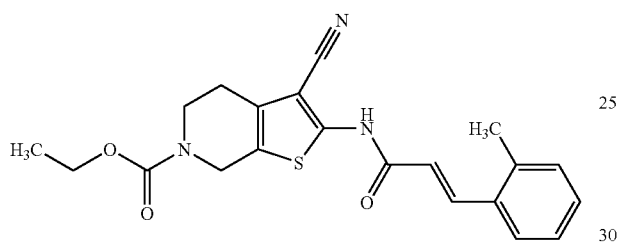

MS: Calc.: C21 H21 N3 O3 S, (395.48). Fnd.: 396 [M+H].

13. 2-[(E)-3-(3-Chloro-phenyl)-allanoylamino]-3-cyano-4,7-dihydro-5H-thieno[2,3-c]pyridine-6-carboxylic acid ethyl ester

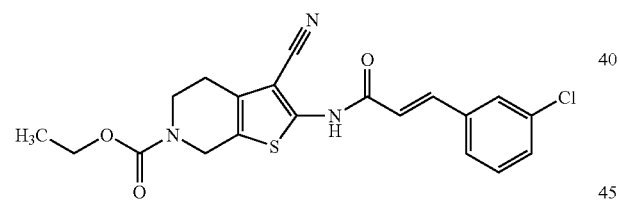

MS: Calc.: C20 H18 Cl N3 O3 S, (415.90). Fnd.: 416.1 [M+H].

14. 3-Cyano-2-((E)-3-thiophen-2-yl-allanoylamino)-4,7-dihydro-5H-thieno[2,3-c]pyridine-6-carboxylic acid ethyl ester

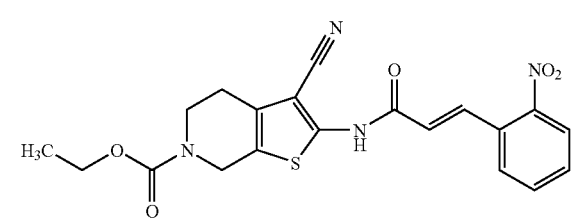

MS: Calc.: C20 H18 N4 O5 S, (426.45). Fnd.: 427.1 [M+H].

15. 3-Cyano-2-[(E)-3-(4-methoxy-phenyl)-allanoylamino]-4,7-dihydro-5H-thieno[2,3-c]pyridine-6-carboxylic acid ethyl ester

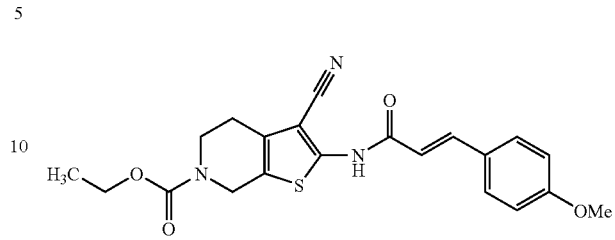

MS: Calc.: C21 H21 N3 O4 S, (411.48). Fnd.: 412.2 [M+H].

16. 3-Cyano-2-((E)-3-m-tolyl-allanoylamino)-4,7-dihydro-5H-thieno[2,3-c]pyridine-6-carboxylic acid ethyl ester

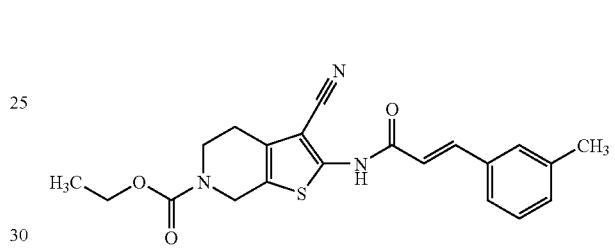

MS: Calc.: C21 H21 N3 O3 S, (395.45). Fnd.: 396 [M+H].

17. 3-Cyano-2-[(E)-3-(2-fluoro-phenyl)-allanoylamino]-4,7-dihydro-5H-thieno[2,3-c]pyridine-6-carboxylic acid ethyl ester

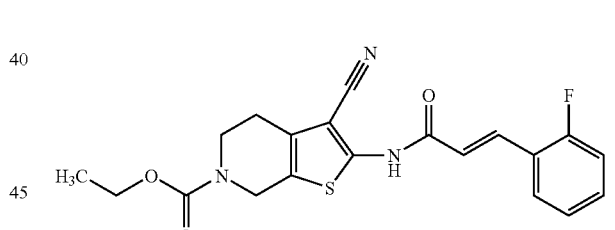

MS: Calc.: C20 H18 F N3 O3 S, (399.45). Fnd.: 400.1 [M+H].

18. 3-Cyano-2-[(E)-3-(4-fluoro-phenyl)-allanoylamino]-4,7-dihydro-5H-thieno[2,3-c]pyridine-6-carboxylic acid ethyl ester

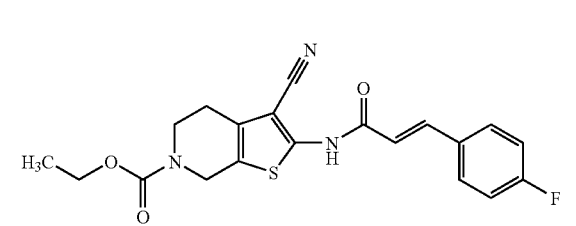

MS: Calc.: C20 H18 F N3 O3 S, (399.45). Fnd.: 400.1 [M+H].

19. 3-Cyano-2-[(E)-3-(3-methoxy-phenyl)-allanoylamino]-4,7-dihydro-5H-thieno[2,3-c]pyridine-6-carboxylic acid ethyl ester

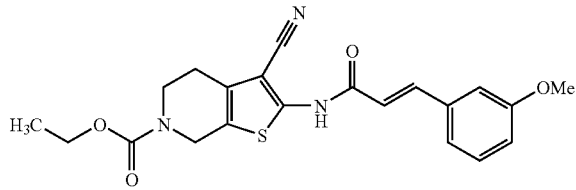

MS: Calc.: C21 H21 N3 O4 S, (411.48). Fnd.: 412.1 [M+H].

20. 3-Cyano-2-[(E)-3-(2,3-dimethoxy-phenyl)-allanoylamino]-4,7-dihydro-5H-thieno[2,3-c]pyridine-6-carboxylic acid ethyl ester

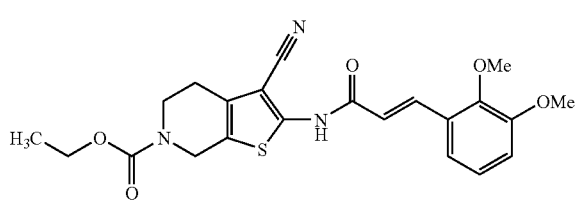

MS: Calc.: C22 H23 N3 O5 S, (441.51). Fnd.: 442.1 [M+H].

21. 3-Cyano-2-[(E)-3-(3-fluoro-phenyl)-allanoylamino]-4,7-dihydro-5H-thieno[2,3-c]pyridine-6-carboxylic acid ethyl ester

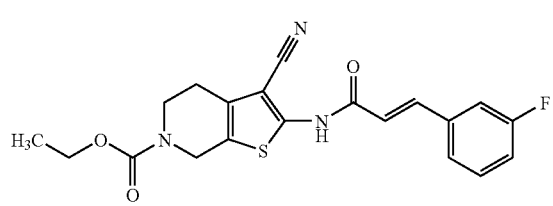

MS: Calc.: C20 H18 FN3 O3 S, (399.45). Fnd.: 400.1 [M+H].

22. 2-[(E)-3-(4-Chloro-phenyl)-allanoylamino]-3-cyano-4,7-dihydro-5H-thieno[2,3-c]pyridine-6-carboxylic acid ethyl ester

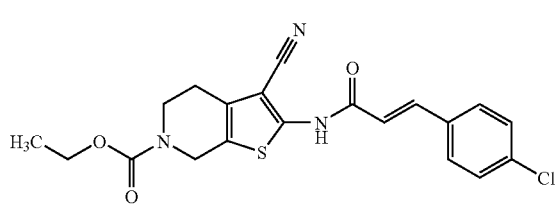

MS: Calc.: C20 H18 Cl N3 O3 S, (415.90). Fnd.: 416.1 [M+H].

23. 3-Cyano-2-[(E)-3-(2-trifluoromethyl-phenyl)-allanoylamino]-4,7-dihydro-5H-thieno[2,3-c]pyridine-6-carboxylic acid ethyl ester

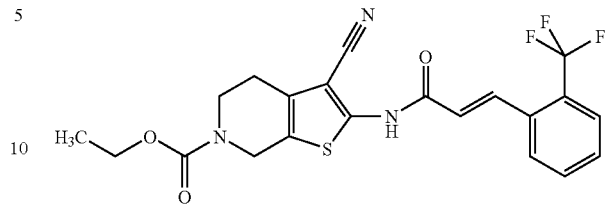

MS: Calc.: C21 H18 F3 N3O3 S, (449.46). Fnd.: 450.1 [M+H].

24. 3-Cyano-2-[(E)-3-(2-methoxy-phenyl)-allanoylamino]-4,7-dihydro-5H-thieno[2,3-c]pyridine-6-carboxylic acid ethyl ester

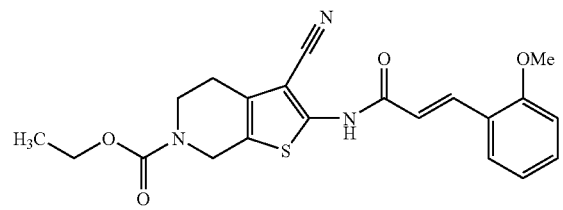

MS: Calc.: C21 H21 N3 O4 S, (411.48). Fnd.: 412.2 [M+H].

25. 3-Cyano-2-[(E)-3-(4-nitro-phenyl)-allanoylamino]-4,7-dihydro-5H-thieno[2,3-c]pyridine-6-carboxylic acid ethyl ester

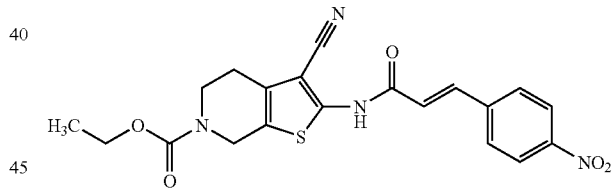

MS: Calc.: C20 H18 N4 O5 S, (426.45). Fnd.: 427.1 [M+H].

26. 3-Cyano-2-[(E)-3-(4-dimethylamino-phenyl)-allanoylamino]-4,7-dihydro-5H-thieno[2,3-c]pyridine-6-carboxylic acid ethyl ester

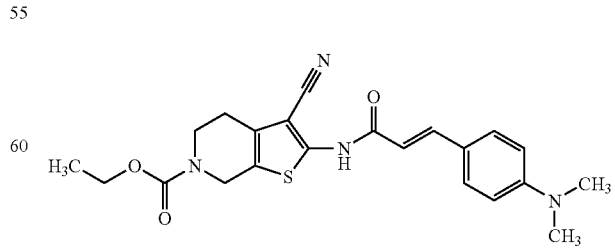

MS: Calc.: C22 H24 N4 O3 S, (424.53). Fnd.: 425.1 [M+H].

27. 3-Cyano-2-((E)-3-p-tolyl-allanoylamino)-4,7-dihydro-5H-thieno[2,3-c]pyridine-6-carboxylic acid ethyl ester

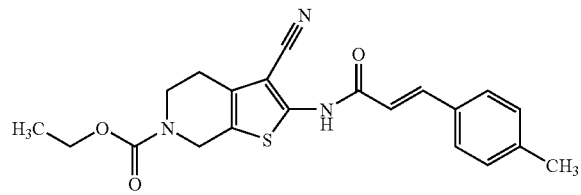

MS: Calc.: C21 H21 N3 O3 S, (395.48). Fnd.: 396.1 [M+H].

28. 3-Cyano-2-[(E)-3-(2,4-dichloro-phenyl)-allanoylamino]-4,7-dihydro-5H-thieno[2,3-c]pyridine-6-carboxylic acid ethyl ester

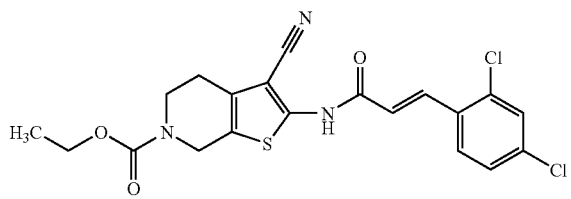

MS: Calc.: C20 H17 Cl2 N3 O3 S, (450.35). Fnd.: 450.1 [M+H].

29. 3-Cyano-2-[(E)-3-(3-nitro-phenyl)-allanoylamino]-4,7-dihydro-5H-thieno[2,3-c]pyridine-6-carboxylic acid ethyl ester

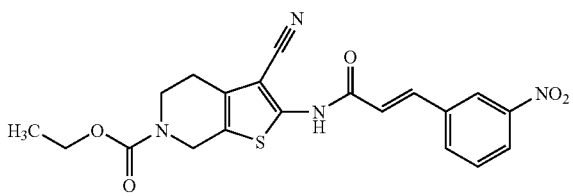

MS: Calc.: C20 H18 N4 O5 S, (426.45). Fnd.: 427.1 [M+H].

30. 2-((E)-3-Benzo[1,3]dioxol-5-yl-allanoylamino)-3-cyano-4,7-dihydro-5H-thieno[2,3-c]pyridine-6-carboxylic acid ethyl ester

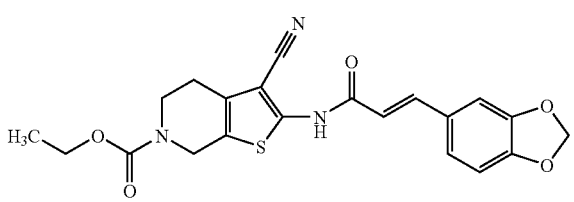

MS: Calc.: C21 H19 N3 O5 S, (425.47). Fnd.: 426.1 [M+H].

31. 3-Cyano-2-[(E) —(2,3,4-trimethoxy-phenyl)-allanoylamino]-4,7-dihydro-5H-thieno[2,3-c]pyridine-6-carboxylic acid ethyl ester

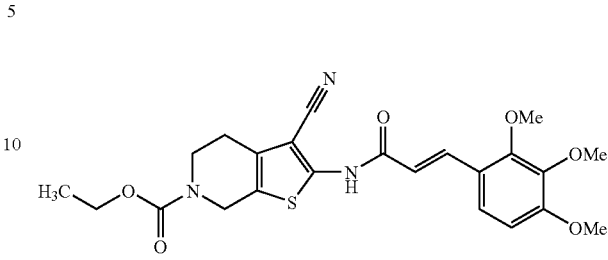

MS: Calc.: C23 H25 N3 O6 S, (471.54). Fnd.: 472 [M+H].

The following compound 32 can be prepared according to general procedure A described below starting from 2-amino-3-cyano-4,7-dihydro-thieno[2,3-c]pyridine-6(5H)-carboxylic acid 1,1-dimethylethyl ester (compound A2) and the pyridyl-acrylic acid chloride.

32. 3-Cyano-2-((E)-3-pyridin-3-yl-allanoylamino)-4,7-dihydro-5H-thieno[2,3-c]pyridine-6-carboxylic acid tert-butyl ester

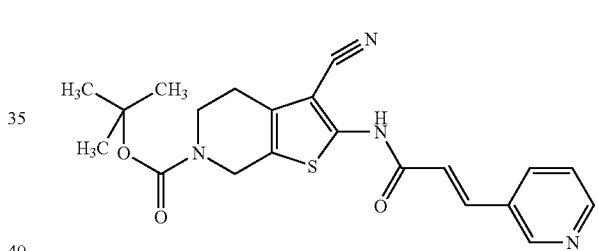

MS: Calc.: C21 H22 N4 O3 S, (410.5). Fnd.: 411 [M+H].

The following compounds 33 and 34 can be prepared according to general procedure A described below starting from N-(3-cyano-4,5,6,7-tetrahydro-thieno[2,3-c]pyridin-2-yl)-3-phenyl-acrylamide (compound B1) and butanoyl chloride, or, respectively, acetyl chloride or acetanhydride.

33. (E)-N-(6-Butyryl-3-cyano-4,5,6,7-tetrahydro-thieno[2,3-c]pyridin-2-yl)-3-phenyl-acrylamide

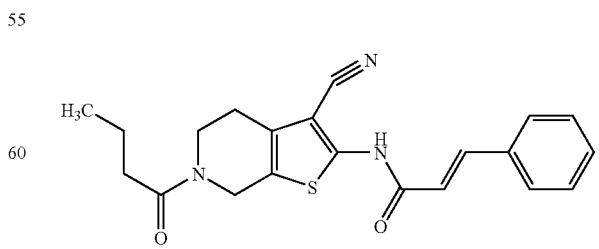

MS: Calc.: C21 H21 N3 O2 S, (379.48). Fnd.: 380.1 [M+H].

34. (E)-N-(6-Acetyl-3-cyano-4,5,6,7-tetrahydro-thieno[2,3-c]pyridin-2-yl)-3-phenyl-acrylamide

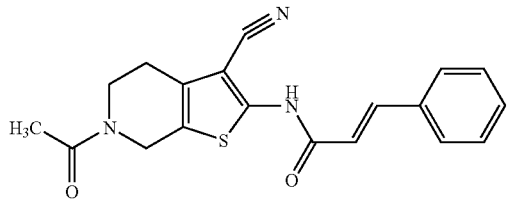

MS: Calc.: C19 H17 N3 O2 S, (351.43). Fnd.: 352.0 [M+H].

The following compounds 35 and 36 can be prepared according to the general procedure F described below starting from N-(3-cyano-4,5,6,7-tetrahydro-thieno[2,3-c]pyridin-2-yl)-3-phenyl-acrylamide (compound B1) or N-(3-cyano-4,5,6,7-tetrahydro-thieno[2,3-c]pyridin-2-yl)-3-(pyridin-3-yl)-acrylamide (compound B2) and ethyl chlorothioformate.

35. 3-Cyano-2-((E)-3-phenyl-allanoylamino)-4,7-dihydro-5H-thieno[2,3-c]pyridine-6-carbothioic acid S-ethyl ester

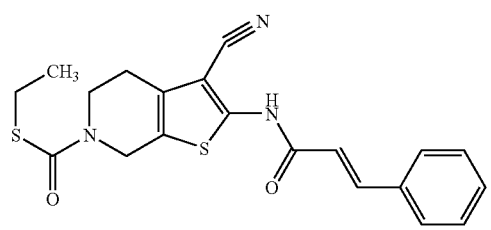

MS: Calc.: C20 H19 N3 O2 S2 (397.52). Fnd.: 397 [M+H].

36. 3-Cyano-2-((E)-3-pyridin-3-yl-allanoylamino)-4,7-dihydro-5H-thieno[2,3-c]pyridine-6-carbothioic acid S-ethyl ester

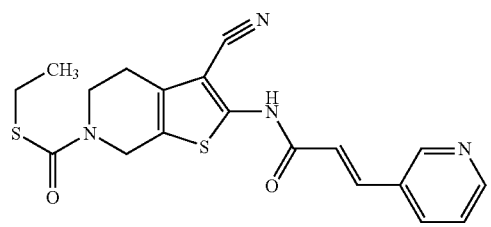

MS: Calc.: C19 H18 N4 O2 S2 (398.52). Fnd.: 398 [M+H].

The following compounds 37 and 38 can be prepared according to the general procedure G described below starting from N-(3-cyano-4,5,6,7-tetrahydro-thieno[2,3-c]pyridin-2-yl)-3-phenyl-acrylamide (compound B1) or N-(3-cyano-4,5,6,7-tetrahydro-thieno[2,3-c]pyridin-2-yl)-3-(pyridin-3-yl)-acrylamide (compound B2) and the appropriate isocyanate or amine/carbonyldiimidazole.

37. 3-Cyano-2-((E)-phenyl-allanoylamino)-4,7-dihydro-5H-thieno[2,3-c]pyridine-6-carboxylic acid ethylamide

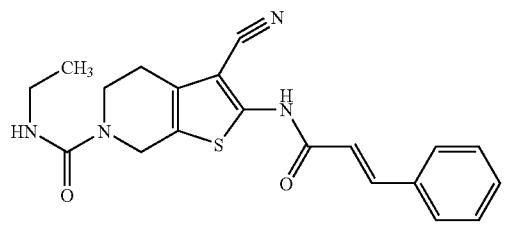

MS: Calc.: C20 H20 N4 O2 S, (380.47). Fnd.: 381 [M+H].

38. 3-Cyano-2-((E)-3-pyridin-3-yl-allanoylamino)-4,7-dihydro-5H-thieno[2,3-c]pyridine-6-carboxylic acid ethylamide

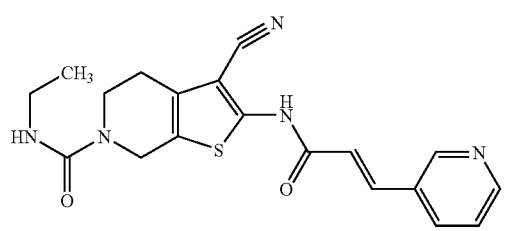

MS: Calc.: C19 H19 N5 O2 S, (381.46). Fnd.: 382.1 [M+H].

The following compound 39 can be prepared according to the general procedure A described below starting from N-(3-cyano-4,5,6,7-tetrahydro-thieno[2,3-c]pyridin-2-yl)-3-(pyridin-3-yl)-acrylamide (compound B2) and butyryl chloride.

39. (E)-N-(6-Butyryl-3-cyano-4,5,6,7-tetrahydro-thieno[2,3-c]pyridin-2-yl)-3-pyridin-3-yl-acrylamide

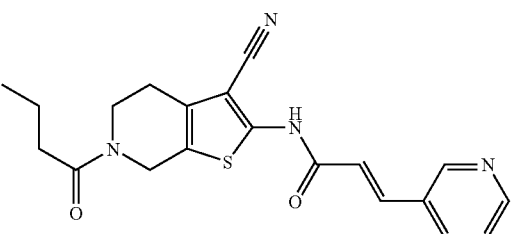

MS: Calc.: C20 H20 N4 O2 S, (380.47). Fnd.: 381 [M+H].

The following compounds 40 to 47 can be prepared according to the general procedure E described below starting from N-(3-cyano-4,5,6,7-tetrahydro-thieno[2,3-c]pyridin-2-yl)-3-(pyridin-3-yl)-acrylamide (compound B2) and the appropriate alcohol.

40. 3-Cyano-2-((E)-3-pyridin-3-yl-allanoylamino)-4,
7-dihydro-5H-thieno[2,3-c]pyridine-6-carboxylic
acid isobutyl ester

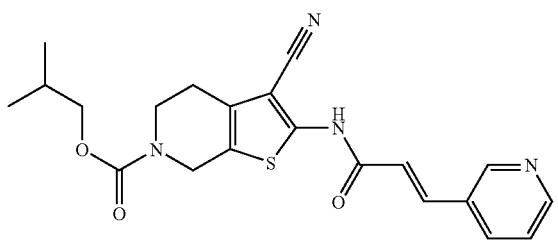

MS: Calc.: C21 H22 N4 O3 S, (410.50). Fnd.: 411 [M+H].

41. 3-Cyano-2-((E)-3-pyridin-3-yl-allanoylamino)-4,
7-dihydro-5H-thieno[2,3-c]pyridine-6-carboxylic
acid 2,2-dimethyl-propyl ester

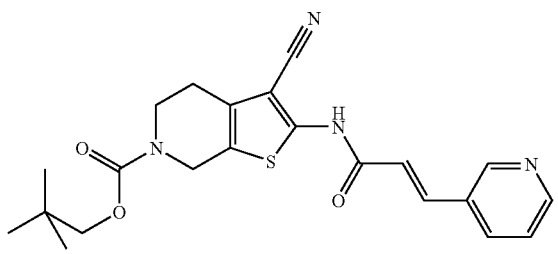

MS: Calc.: C22 H24 N4 O3 S, (424.53). Fnd.: 425 [M+H].

42. 3-Cyano-2-((E)-3-pyridin-3-yl-allanoylamino)-4,
7-dihydro-5H-thieno[2,3-c]pyridine-6-carboxylic
acid hexyl ester

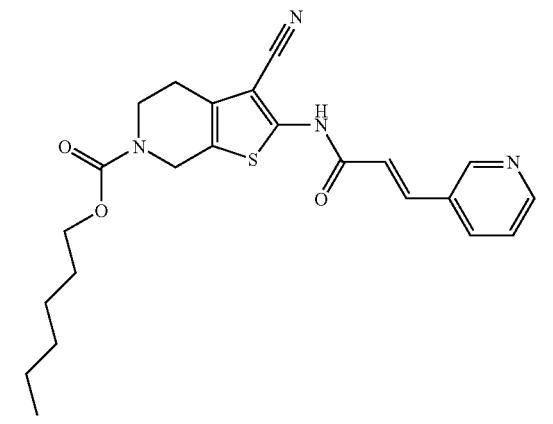

MS: Calc.: C23 H26 N4 O3 S, (438.55). Fnd.: 439 [M+H].

43. 3-Cyano-2-((E)-3-pyridin-3-yl-allanoylamino)-4,
7-dihydro-5H-thieno[2,3-c]pyridine-6-carboxylic
acid butyl ester

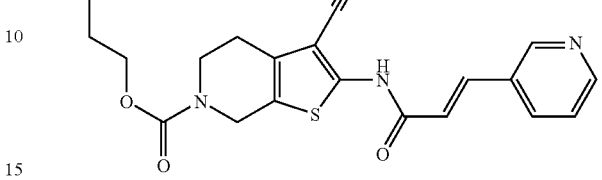

MS: Calc.: C21 H22 N4 O3 S, (410.50). Fnd.: 411 [M+H].

44. 3-Cyano-2-((E)-3-pyridin-3-yl-allanoylamino)-4,
7-dihydro-5H-thieno[2,3-c]pyridine-6-carboxylic
acid methyl ester

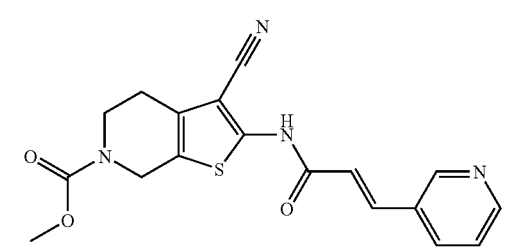

MS: Calc.: C18 H16 N4 O3 S, (468.42). Fnd.: 369 [M+H].

45. 3-Cyano-2-((E)-3-pyridin-3-yl-allanoylamino)-4,
7-dihydro-5H-thieno[2,3-c]pyridine-6-carboxylic
acid 3-methoxy-phenyl ester

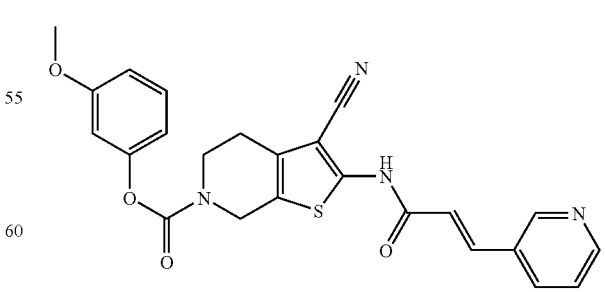

MS: Calc.: C24 H20 N4 O4 S, (460.52). Fnd.: 461 [M+H].

46. 3-Cyano-2-((E)-3-pyridin-3-yl-allanoylamino)-4,7-dihydro-5H-thieno[2,3-c]pyridine-6-carboxylic acid phenyl ester

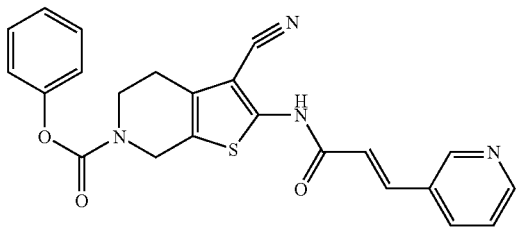

MS: Calc.: C23 H18 N4 O3 S, (430.49). Fnd.: 431 [M+H].

47. 3-Cyano-2-((E)-3-pyridin-3-yl-allanoylamino)-4,7-dihydro-5H-thieno[2,3-c]pyridine-6-carboxylic acid phenethyl ester

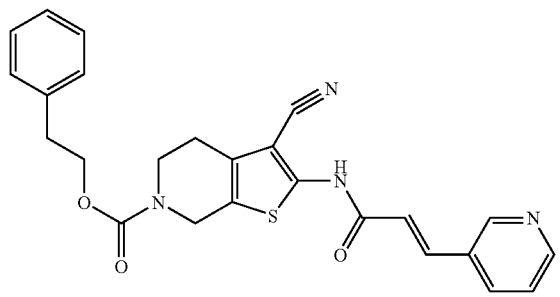

MS: Calc.: C25 H22 N4 O3 S, (458.54).

A. General Procedure for Amide Bond Formation a) 100 mmol of an amine and 120 mmol of an appropriate acid chloride are dissolved either in a minimal amount of pyridine or toluene. In case of toluene as solvent, 125 mmol of a base (e.g. triethylamine) is added. The reaction mixture is stirred for some time at room temperature and, if necessary, is heated for some time either by conventional or microwave assisted heating. Then the solvent is either removed in vacuo or the reaction mixture partitioned between water and an appropriate solvent (e.g. ethyl acetate). In the second case, the aqueous layer is extracted several times with the organic solvent, the combined organic layers are dried (e.g. MgSO$_4$) and concentrated in vacuo. Purification of the crude product is achieved by flash chromatography and/or recristalization from an appropriate solvent (e.g. ethanol).

The corresponding acid chloride can be obtained in an art-known manner, such as e.g. from the free acid with the aid of a suitable chlorination agent, e.g. oxalyl chloride, in a suitable solvent, e.g. dichloromethane with a few drops N,N-dimethylformamide.

In some cases, the amide bond formation reaction is carried out using one of the following methods:

b) 20 mmol of a carboxylic acid and 20 mmol of EDC are dissolved or suspended in an appropriate solvent (e.g. dichloromethane) and 10 mmol of the amine and 0.1 mmol N,N-dimethylaminopyridine (DMAP) are added. After stirring for several hours at room temperature (If necessary, the reaction mixture is heated either by conventional heating or microwave assisted heating.), the reaction mixture is partitioned between water and an appropriate solvent (e.g. ethyl acetate or dichloromethane) and the aqueous layer is extracted several times with the same organic solvent. The combined organic layers are dried (e.g. MgSO$_4$) and concentrated in vacuo. Purification of the crude product is achieved by flash chromatography and/or recristalization from an appropriate solvent (e.g. ethanol).

Starting from the appropriate starting compounds selected from N-(3-cyano-4,5,6,7-tetrahydro-thieno[2,3-c]pyridin-2-yl)-3-(2-methoxy-phenyl)-acrylamide, N-(3-cyano-4,5,6,7-tetrahydro-thieno[2,3-c]pyridin-2-yl)-3-phenyl-acrylamide and N-(3-cyano-4,5,6,7-tetrahydro-thieno[2,3-c]pyridin-2-yl)-3-(2-chloro-phenyl)-acrylamide the following compounds 48 to 51 can be prepared according to the general procedure FF described later herein.

48. 2-[(E)-3-(2-Chloro-phenyl)-allanoylamino]-3-cyano-4,7-dihydro-5H-thieno[2,3-c]pyridine-6-carbothioic acid S-ethyl ester

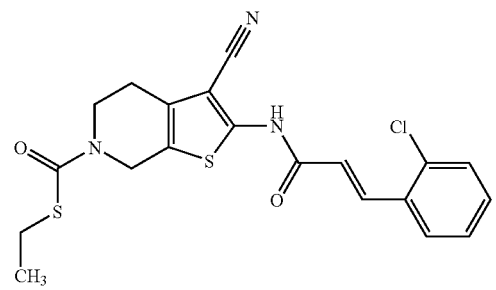

MS: Calc.: C20 H18 Cl N3 O2 S2 (431.97). Fnd.: 432.00 [M+H].

49. 3-Cyano-2-((E)-3-phenyl-allanoylamino)-4,7-dihydro-5H-thieno[2,3-c]pyridine-6-carbothioic acid S-pentyl ester

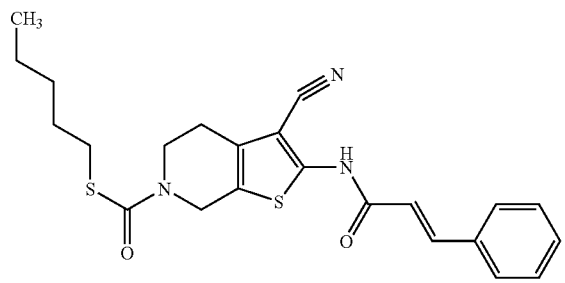

MS: Calc.: C23 H25 N3 O2 S2 (439.60). Fnd.: 440.20 [M+H].

50. 3-Cyano-2-[(E)-3-(2-methoxy-phenyl)-allanoylamino]-4,7-dihydro-5H-thieno[2,3-c]pyridine-6-carbothioic acid S-ethyl ester

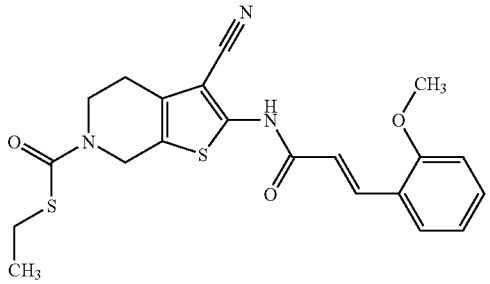

MS: Calc.: C21 H21 N3 O3 S2 (427.55). Fnd.: 428.10 [M+H].

51. 3-Cyano-2-((E)-3-phenyl-allanoylamino)-4,7-dihydro-5H-thieno[2,3-c]pyridine-carbothioic acid S-(2-dimethylamino-ethyl)ester

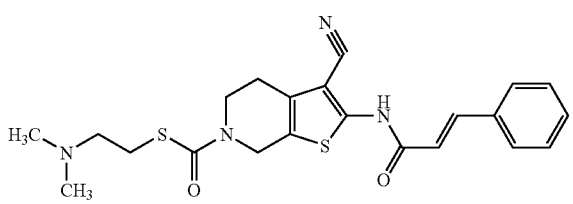

MS: Calc.: C22 H24 N4 O2 S2 (440.59). Fnd.: 441.10 [M+H].

The following compounds 52 and 53 can be generated by treating the appropriate amine with CDI in pyridine. Purification is achieved either by filtration followed by washing (water) and crystallization (ethanol) or removal of solvents in vacuo and subsequent column chromatography on silica gel, using mixtures of dichloromethane, methanol and triethyl amine as eluents. If necessary, the product is recrystallized from an appropriate solvent:

52. (E)-N-[3-Cyano-6-(1-imidazol-1-yl-methanoyl)-4,5,6,7-tetrahydro-thieno[2,3-c]pyridin-2-yl]-3-pyridin-3-yl-acrylamide

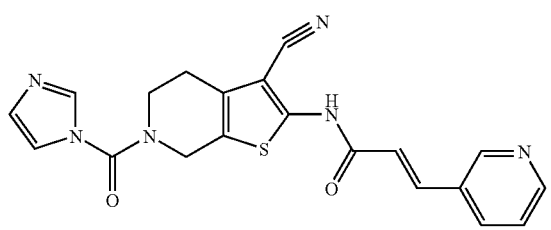

MS: Calc.: C20 H16 N6 O2 S, (404.45). Fnd.: 405.10 [M+H].

53. (E)-N-[3-Cyano-6-(1-imidazol-1-yl-methanoyl)-4,5,6,7-tetrahydro-thieno[2,3-c]pyridin-2-yl]-3-phenyl-acrylamide

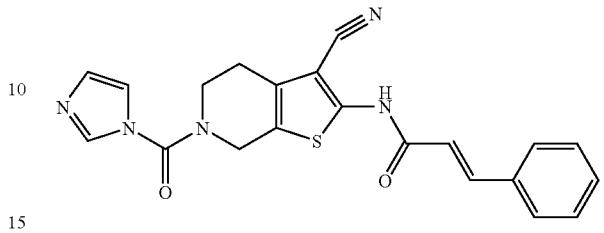

MS: Calc.: C21 H17 N5 O2 S, (403.47). Fnd.: 404.00 [M+H].

AA. Alternative General Procedure for Amide Bond Formation

In a sealable test tube, the corresponding acid (1.5 mmol) is suspended in a mixture of DMF (0.15 mmol) and dichloromethane (7.5 mL). A solution of oxalyl chloride (3.0 mmol) in dichloromethane (7.5 mL) is then added and the mixture stirred for 1 h at room temperature. After that, the solvents and excess of oxalyl chloride are removed in vacuo, the residue is dissolved in toluene (7.5 mL) and added to the corresponding amine (1 mmol) in a vial suitable for microwave technology. Diisopropyl ethyl amine (1.5 mmol) is added, the vial capped and the mixture is heated for 30 min at 150° C. using microwave technology. Purification is achieved either by filtration followed by washing (water) and crystallization (ethanol) or removal of solvents in vacuo and subsequent column chromatography on silica gel, using mixtures of dichloromethane, methanol and triethyl amine as eluents.

The following compounds 54 to 92, and 96 to 99 can be prepared according to general procedure AA mentioned above starting from 2-amino-3-cyano-4,7-dihydro-5H-thieno[2,3-c]pyridine-6-carboxylic acid tert-butyl ester or 2-amino-3-cyano-4,7-dihydro-5H-thieno[2,3-c]pyridine-6-carboxylic acid ethyl ester respectively and the appropriate acrylic acid derivatives which are art-known or which can be prepared according to art-known procedures or according to general procedure H described later herein:

54. 3-Cyano-2-[(E)-3-(2-ethoxy-phenyl)-allanoylamino]-4,7-dihydro-5H-thieno[2,3-c]pyridine-6-carboxylic acid tert-butyl ester

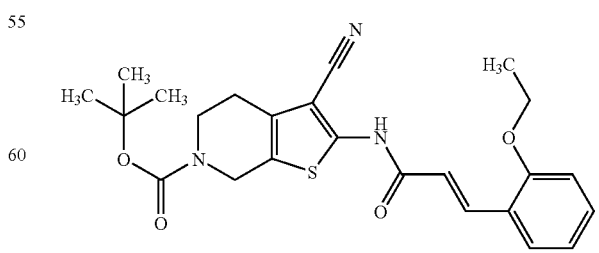

MS: Calc.: C24 H27 N3 O4 S, (453.56). Fnd.: [453.90M+H].

55. 3-Cyano-2-((E)-3-furan-3-yl-allanoylamino)-4,7-dihydro-5H-thieno[2,3-c]pyridine-6-carboxylic acid tert-butyl ester

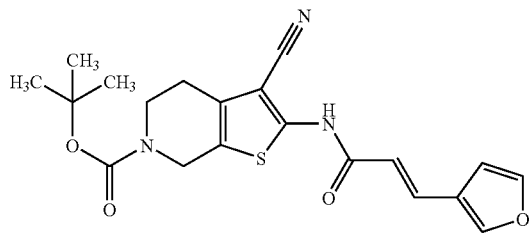

MS: Calc.: C20 H21 N3 O4 S, (399.47). Fnd.: 798.5 [2M+H].

56. 3-Cyano-2-((E)-3-furan-2-yl-allanoylamino)-4,7-dihydro-5H-thieno[2,3-c]pyridine-6-carboxylic acid tert-butyl ester

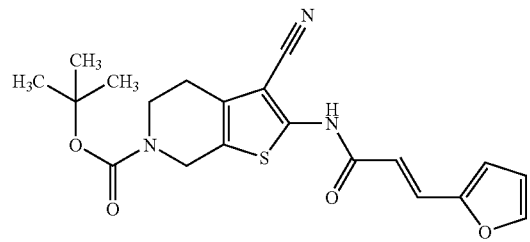

57. 2-[(E)-3-(2-Chloro-3,6-difluoro-phenyl)-allanoylamino]-3-cyano-4,7-dihydro-5H-thieno[2,3-c]pyridine-6-carboxylic acid ethyl ester

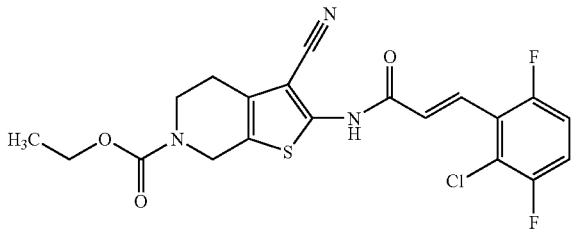

MS: Calc.: C20 H16 Cl F2 N3 O3 S, (451.88). Fnd.: 452.00 [M+H].

58. 3-Cyano-2-[(E)-3-(2,3-difluoro-phenyl)-allanoylamino]-4,7-dihydro-5H-thieno[2,3-c]pyridine-6-carboxylic acid ethyl ester

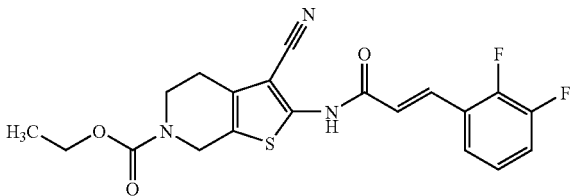

MS: Calc.: C20 H17 F2 N3 O3 S, (417.44). Fnd.: 418.10 [M+H].

59. 2-[(E)-3-(4-Chloro-2-fluoro-phenyl)-allanoylamino]-3-cyano-4,7-dihydro-5H-thieno[2,3-c]pyridine-6-carboxylic acid ethyl ester

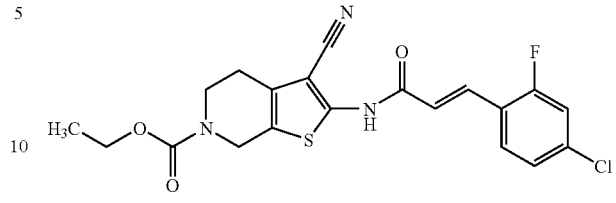

MS: Calc.: C20 H17 Cl F N3 O3 S, (433.89). Fnd.: 434.10 [M+H].

60. 3-Cyano-2-[(E)-3-(4-ethoxy-phenyl)-allanoylamino]-4,7-dihydro-5H-thieno[2,3-c]pyridine-6-carboxylic acid ethyl ester

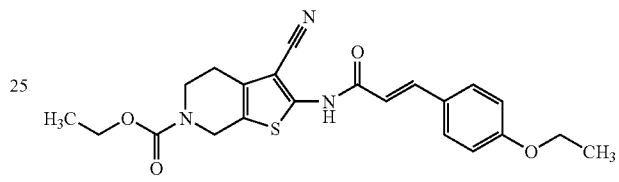

MS: Calc.: C22 H23 N3 O4 S, (425.51). Fnd.: 426.00 [M+H].

61. 3-Cyano-2-[(E)-3-(3-chloro-2-fluoro-phenyl)-allanoylamino]-4,7-dihydro-5H-thieno[2,3-c]pyridine-6-carboxylic acid ethyl ester

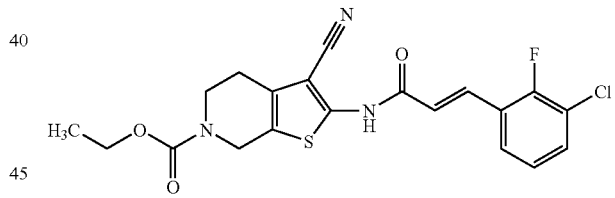

MS: Calc.: C20 H17 Cl F N3 O3 S, (433.89). Fnd.: 434.10 [M+H].

62. 3-Cyano-2-[(E)-3-(2-ethoxy-phenyl)-allanoylamino]-4,7-dihydro-5H-thieno[2,3-c]pyridine-6-carboxylic acid ethyl ester

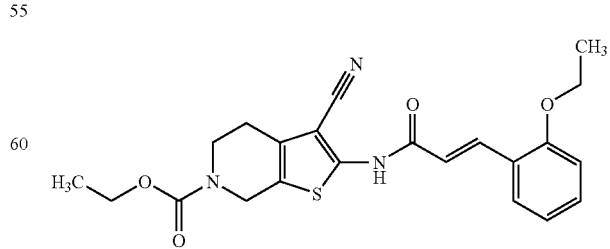

MS: Calc.: C22 H23 N3 O4 S, (425.51). Fnd.: 426.00 [M+H].

63. 3-Cyano-2-[(E)-3-(2,6-dichloro-phenyl)-allanoylamino]-4,7-dihydro-5H-thieno[2,3-c]pyridine-6-carboxylic acid ethyl ester

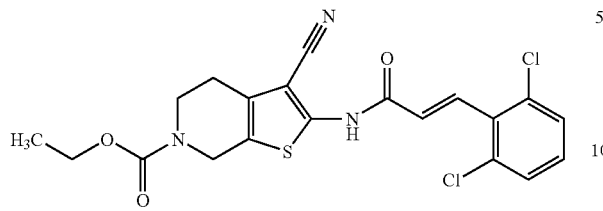

MS: Calc.: C20 H17 Cl2 N3 O3 S, (450.35). Fnd.: 450.00 [M+H].

64. 2-[(E)-3-(3-Chloro-thiophen-2-yl)-allanoylamino]-cyano-4,7-dihydro-5H-thieno[2,3-c]pyridine-6-carboxylic acid ethyl ester

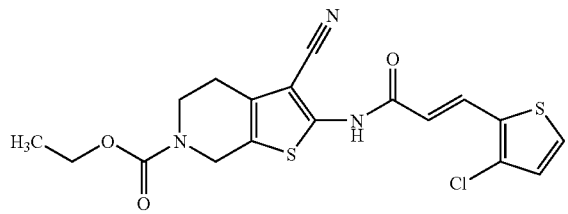

MS: Calc.: C18 H16 Cl N3 O3 S2 (421.93). Fnd.: 422.00 [M+H].

65. 3-Cyano-2-[(E)-3-(2,6-difluoro-phenyl)-allanoylamino]-4,7-dihydro-5H-thieno[2,3-c]pyridine-6-carboxylic acid ethyl ester

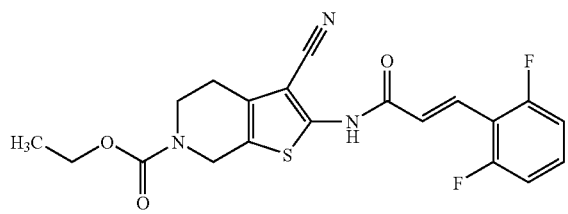

MS: Calc.: C20 H17 F2 N3 O3 S, (417.44). Fnd.: 418.10 [M+H].

66. 2-[(E)-3-(2-Bromo-phenyl)-allanoylamino]-3-cyano-4,7-dihydro-5H-thieno[2,3-c]pyridine-6-carboxylic acid ethyl ester

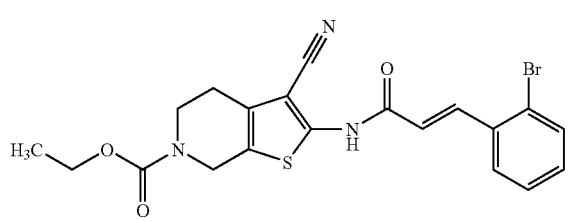

MS: Calc.: C20 H18 Br N3 O3 S, (460.35). Fnd.: 462.00 [M+H].

67. 2-[(E)-3-(2-Chloro-6-fluoro-phenyl)-allanoylamino]-cyano-4,7-dihydro-5H-thieno[2,3-c]pyridine-6-carboxylic acid ethyl ester

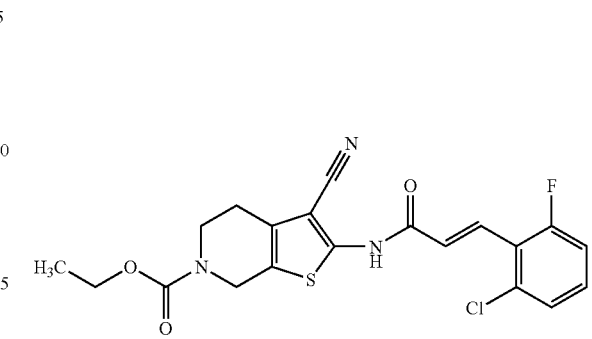

MS: Calc.: C20 H17 Cl F N3 O3 S, (433.89). Fnd.: 434.10 [M+H].

68. 3-Cyano-2-[(E)-3-(2,3,6-trifluoro-phenyl)-allanoylamino]-4,7-dihydro-5H-thieno[2,3-c]pyridine-6-carboxylic acid ethyl ester

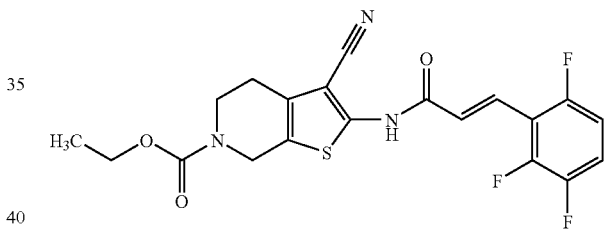

MS: Calc.: C20 H16 F3 N3 O3 S, (435.43). Fnd.: 436.10 [M+H].

69. 2-[(E)-3-(2-Acetoxy-phenyl)-allanoylamino]-3-cyano-4,7-dihydro-5H-thieno[2,3-c]pyridine-6-carboxylic acid ethyl ester

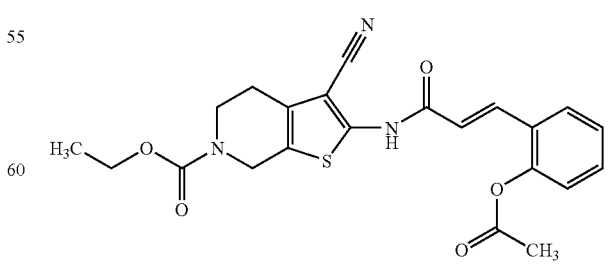

MS: Calc.: C22 H21 N3 O5 S, (439.49). Fnd.: 440.00 [M+H].

70. 3-Cyano-2-[(E)-3-(2-fluoro-4-methoxy-phenyl)-allanoylamino]β4,7-dihydro-5H-thieno[2,3-c]pyridine-6-carboxylic acid ethyl ester

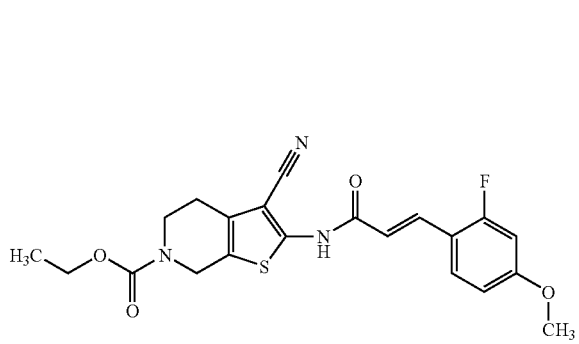

MS: Calc.: C21 H20 F N3 O4 S, (429.47). Fnd.: 430.00 [M+H].

71. 2-((E)-3-Benzo[b]thiophen-3-yl-allanoylamino)-3-cyano-[4,7-d]hydro-5H-thieno[2,3-c]pyridine-6-carboxylic acid ethyl ester

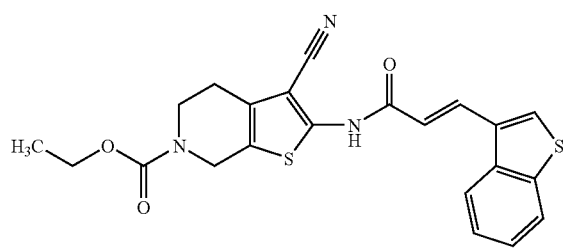

MS: Calc.: C22 H19 N3 O3 S2 (437.54). Fnd.: 438.10 [M+H].

72. 2-[(E)-3-(5-Chloro-thiophen-2-yl)-allanoylamino]-3-cyano-4,7-dihydro-5H-thieno[2,3-c]pyridine-6-carboxylic acid ethyl ester

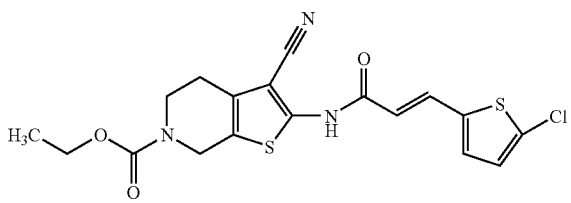

MS: Calc.: C18 H16 Cl N3 O3 S2 (421.93). Fnd.: 422.10 [M+H].

73. 2-((E)-3-Biphenyl-2-yl-allanoylamino)-3-cyano-4,7-dihydro-5H-thieno[2,3-c]pyridine-6-carboxylic acid ethyl ester

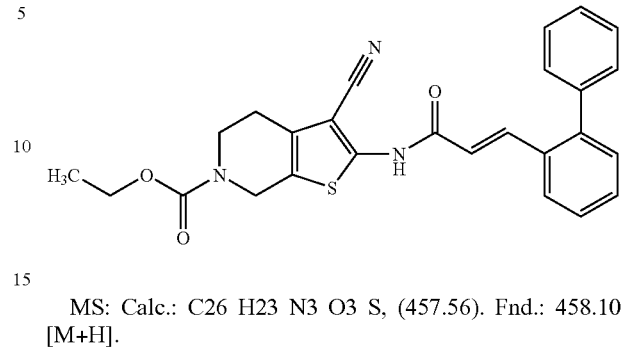

MS: Calc.: C26 H23 N3 O3 S, (457.56). Fnd.: 458.10 [M+H].

74. 3-Cyano-2-[(E)-3-(5-methyl-furan-2-yl)-allanoylamino]-4,7-dihydro-5H-thieno[2,3-c]pyridin-6-carboxylic acid ethyl ester

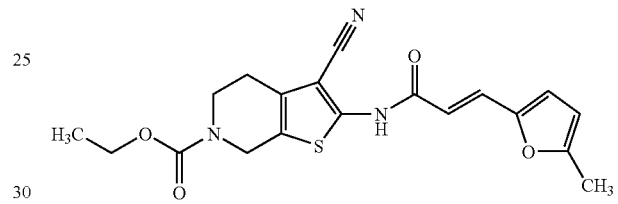

MS: Calc.: C19 H19 N3 O4 S, (385.44). Fnd.: 386.00 [M+H].

75. 3-Cyano-2-[(E)-3-(3-methyl-thiophen-2-yl)-allanoylamino]-4,7-dihydro-5H-thieno[2,3-c]pyridine-6-carboxylic acid ethyl ester

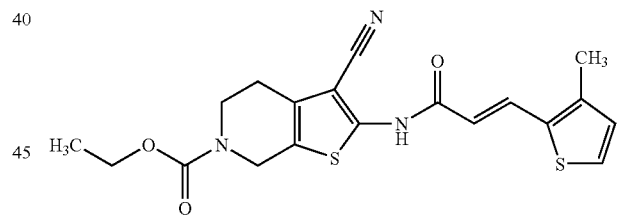

MS: Calc.: C19 H19 N3 O3 S2 (401.51). Fnd.: 402.00 [M+H].

76. 3-Cyano-2-[(E)-3-(5-methyl-thiophen-2-yl)-allanoylamino]-4,7-dihydro-5H-thieno[2,3-c]pyridine-6-carboxylic acid ethyl ester

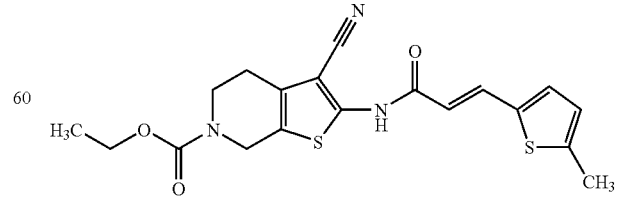

MS: Calc.: C19 H19 N3 O3 S2 (401.51). Fnd.: 402.00 [M+H].

77. 3-Cyano-2-[(E)-3-(5-ethyl-furan-2-yl)-allanoylamino]-4,7-dihydro-5H-thieno[2,3-c]pyridine-6-carboxylic acid ethyl ester

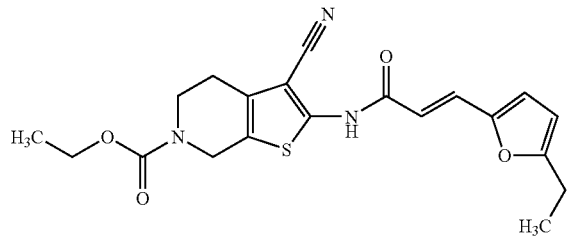

MS: Calc.: C20 H21 N3 O4 S, (399.47). Fnd.: 400.00 [M+H].

78. 2-[(E)-3-(5-Chloro-furan-2-yl)-allanoylamino]-3-cyano-4,7-dihydro-5H-thieno[2,3-c]pyridine-6-carboxylic acid ethyl ester

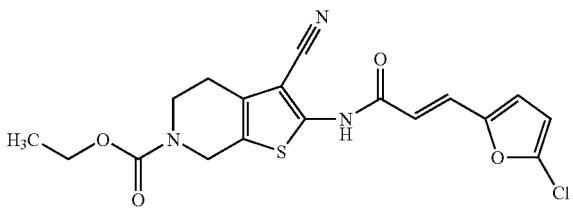

MS: Calc.: C18 H16 Cl N3 O4 S, (405.86). Fnd.: 406.00 [M+H].

79. 3-Cyano-2-[(E)-3-(5-fluoro-2-methyl-phenyl)-allanoylamino]-4,7-dihydro-5H-thieno[2,3-c]pyridine-6-carboxylic acid ethyl ester

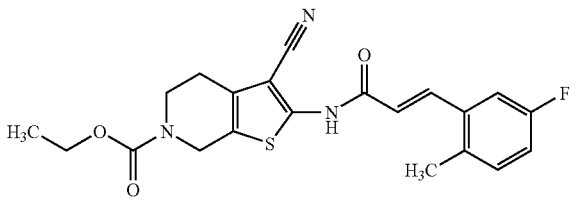

MS: Calc.: C21 H20 F N3 O3 S, (413.47). Fnd.: 414.10 [M+H].

80. 3-Cyano-2-[(E)-3-(3-fluoro-2-methyl-phenyl)-allanoylamino]-4,7-dihydro-5H-thieno[2,3-c]pyridine-6-carboxylic acid ethyl ester

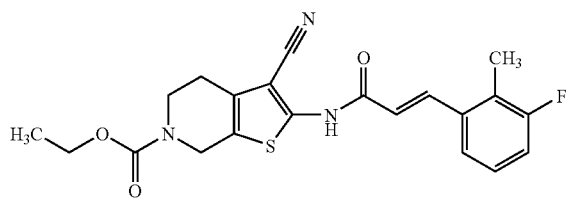

MS: Calc.: C21 H20 F N3 O3 S, (413.47). Fnd.: 414.00 [M+H].

81. 3-Cyano-2-[(E)-3-(3-phenoxy-thiophen-2-yl)-allanoylamino]-4,7-dihydro-5H-thieno[2,3-c]pyridine-6-carboxylic acid ethyl ester

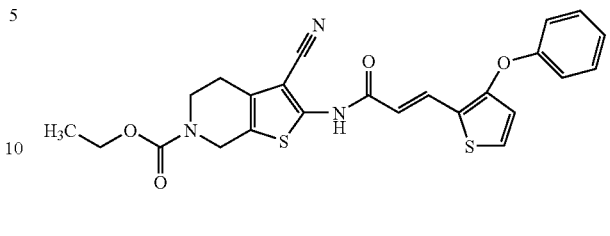

MS: Calc.: C24 H21 N3 O4 S2 (479.58). Fnd.: 479.90 [M+H].

82. 3-Cyano-2-[(E)-3-(2-ethyl-phenyl)-allanoylamino]-4,7-dihydro-5H-thieno[2,3-c]pyridine-6-carboxylic acid ethyl ester

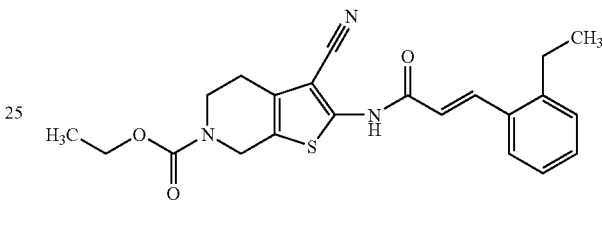

MS: Calc.: C22 H23 N3 O3 S, (409.51). Fnd.: 410.00 [M+H].

83. 3-Cyano-2-[(E)-3-(2-cyano-phenyl)-allanoylamino]-4,7-dihydro-5H-thieno[2,3-c]pyridine-6-carboxylic acid ethyl ester

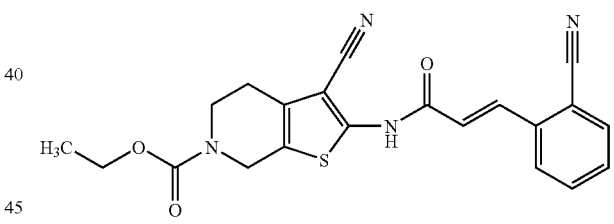

MS: Calc.: C21 H18 N4 O3 S, (406.47). Fnd.: 407.10 [M+H].

84. 2-[(E)-3-Benzofuran-2-yl-allanoylamino]-3-cyano-4,7-dihydro-5H-thieno[2,3-c]pyridine-6-carboxylic acid ethyl ester

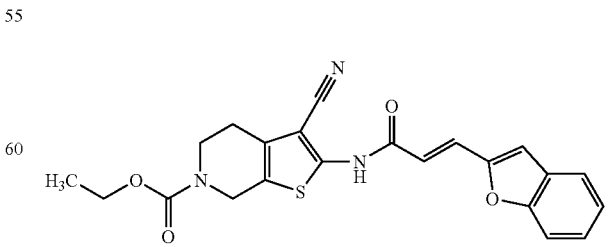

MS: Calc.: C22 H19 N3 O4 S, (421.48). Fnd.: 422.00 [M+H].

85. 3-Cyano-2-[(E)-3-(5-phenyl-thiophen-2-yl)-allanoylamino]-4,7-dihydro-5H-thieno[2,3-c]pyridine-6-carboxylic acid ethyl ester

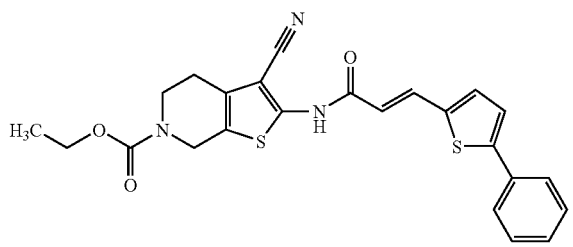

MS: Calc.: C24 H21 N3 O3 S2 (463.58). Fnd.: 464.00 [M+H].

86. 3-Cyano-2-[(E)-3-(2,3-dimethyl-phenyl)-allanoylamino]-4,7-dihydro-5H-thieno[2,3-c]pyridine-6-carboxylic acid ethyl ester

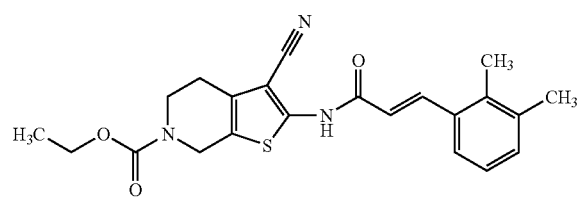

MS: Calc.: C22 H23 N3 O3 S, (409.51). Fnd.: 410.10 [M+H].

87. 3-Cyano-2-[(E)-3-(2,3-dimethoxy-phenyl)-allanoylamino]-4,7-dihydro-5H-thieno[2,3-c]pyridine-6-carboxylic acid ethyl ester

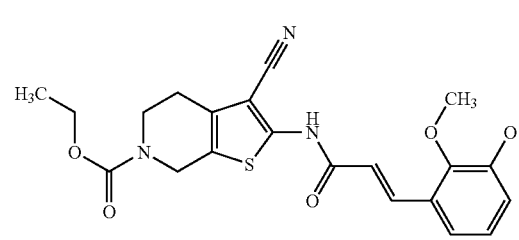

MS: Calc.: C22 H23 N3 O5 S, (441.51). Fnd.: 442.00 [M+H].

88. 3-Cyano-2-[(E)-3-(2-morpholin-4-yl-phenyl)-allanoylamino]-4,7-dihydro-5H-thieno[2,3-c]pyridine-6-carboxylic acid ethyl ester

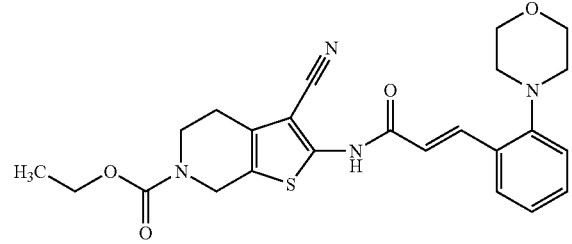

MS: Calc.: C24 H26 N4 O4 S, (466.56). Fnd.: 467.20 [M+H].

89. 3-Cyano-2-[(E)-3-(4-fluoro-2-methyl-phenyl)-allanoylamino]-4,7-dihydro-5H-thieno[2,3-c]pyridine-6-carboxylic acid ethyl ester

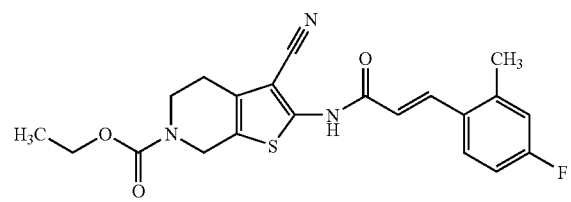

MS: Calc.: C21 H20 F N3 O3 S, (413.47). Fnd.: 414.10 [M+H].

90. 2-[(E)-3-(4-Chloro-1-methyl-1H-pyrazol-3-yl)-allanoylamino]-3-cyano-4,7-dihydro-5H-thieno[2,3-c]pyridine-6-carboxylic acid ethyl ester

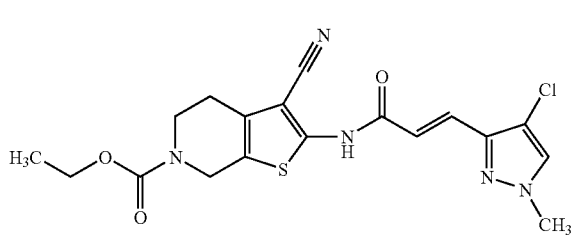

MS: Calc.: C18 H18 Cl N5 O3 S, (419.89). Fnd.: 420.00 [M+H].

91. 3-Cyano-2-[(E)-3-(5-phenyl-furan-2-yl)-allanoylamino]-4,7-dihydro-5H-thieno[2,3-c]pyridine-6-carboxylic acid ethyl ester

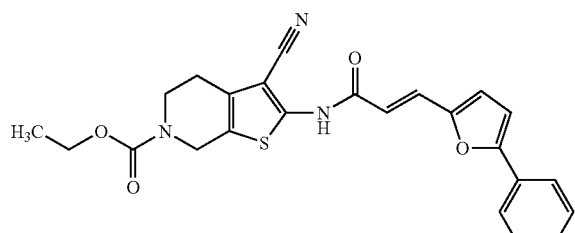

MS: Calc.: C24 H21 N3 O4 S, (447.52). Fnd.: 448.10 [M+H].

92. 3-Cyano-2-[(E)-3-(2-morpholin-3-yl-pyridin-3-yl)-allanoylamino]-4,7-dihydro-5H-thieno-[2,3-c]pyridine-6-carboxylic acid ethyl ester

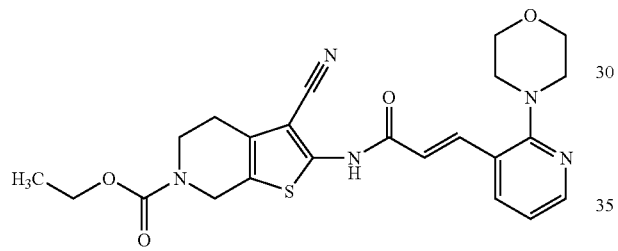

MS: Calc.: C23 H25 N5 O4 S, (467.55). Fnd.: 468.20 [M+H].

93. 3-Cyano-2-[(E)-3-(4-hydroxy-phenyl)-allanoylamino]-4,7-dihydro-5H-thieno[2,3-c]pyridine-6-carboxylic acid ethyl ester

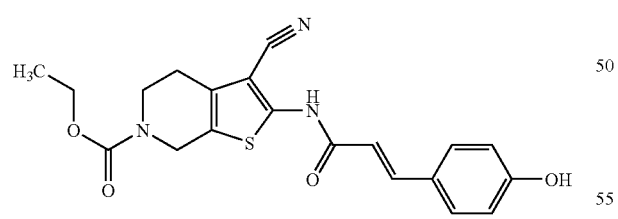

3-Cyano-2-[(E)-3-(4-methoxy-phenyl)-allanoylamino]-4,5,6,7-tetrahydro-benzo[b]thiophene-6-carboxylic acid ethyl ester (0.16 mmol) is dissolved in 2.4 ml dichloromethane. 1.22 ml BBr$_3$ (1M in dichloromethane) is added at −78° C. and the reaction mixture is stirred for 20 hours at room temperature. After aqueous workup and evaporation of the solvent, the crude product is recristallized from ethanol.

MS: Calc.: C20 H19 N3 O4 S, (397.46). Fnd.: 398.00 [M+H].

The following compounds 94 and 95 can be prepared analogously to the preparation of Example 93.

94. 3-Cyano-2-[(E)-3-(3-hydroxy-phenyl)-allanoylamino]-4,7-dihydro-5H-thieno[2,3-c]pyridine-6-carboxylic acid ethyl ester

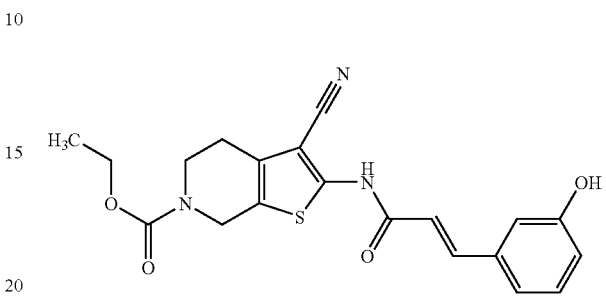

MS: Calc.: C20 H19 N3 O4 S, (397.46). Fnd.: 398.10 [M+H].

95. 3-Cyano-2-[(E)-3-(2-hydroxy-phenyl)-allanoylamino]-4,7-dihydro-5H-thieno[2,3-c]pyridine-6-carboxylic acid ethyl ester

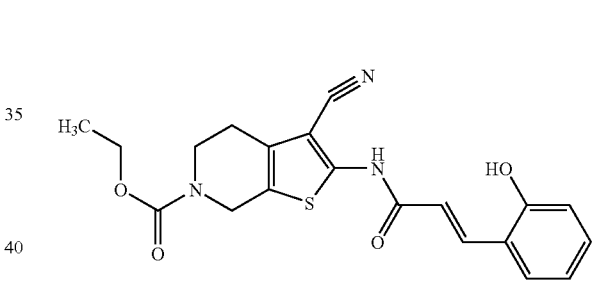

MS: Calc.: C20 H19 N3 O4 S, (397.46). Fnd.: 398.00 [M+H].

96. 3-Cyano-2-[(E)-3-(2-ethoxy-3-methoxy-phenyl)-allanoylamino]-4,7-dihydro-5H-thieno[2,3-c]pyridine-6-carboxylic acid ethyl ester

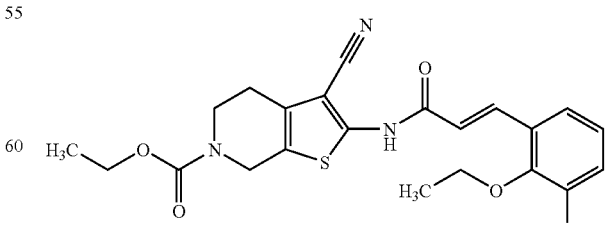

MS: Calc.: C23 H25 N3 O5 S, (455.54). Fnd.: 456.00 [M+H].

97. 3-Cyano-2-[(E)-3-(1-methyl-1H-pyrrol-2-yl)-allanoylamino]-4,7-dihydro-5H-thieno[2,3-c]pyridine-6-carboxylic acid ethyl ester

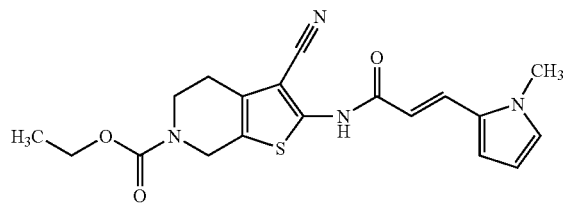

MS: Calc.: C19 H20 N4 O3 S, (384.46). Fnd.: 385.10 [M+H].

98. 3-Cyano-2-[(E)-3-(2-isopropoxy-phenyl)-allanoylamino]-4,7-dihydro-5H-thieno[2,3-c]pyridine-6-carboxylic acid ethyl ester

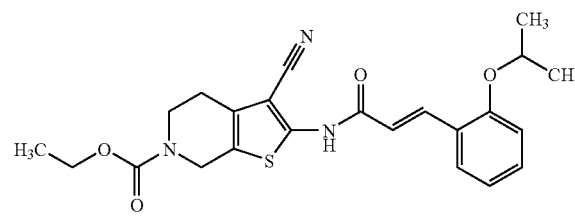

MS: Calc.: C23 H25 N3 O4 S, (439.54). Fnd.: 440.00 [M+H].

99. 3-Cyano-2-[(E)-3-(2-propoxy-phenyl)-allanoylamino]-4,7-dihydro-5H-thieno[2,3-c]pyridine-6-carboxylic acid ethyl ester

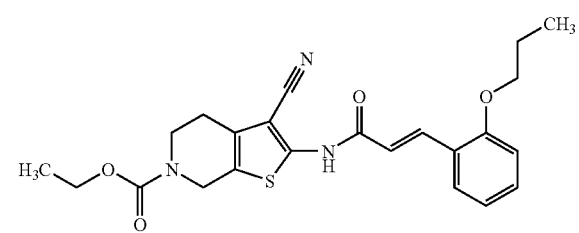

MS: Calc.: C23 H25 N3 O4 S, (439.54). Fnd.: 439.90 [M+H].

The following compounds 100 to 104, 106, and 108 to 111 can be prepared according to general procedure M mentioned above starting from 2-amino-3-cyano-4,7-dihydro-5H-thieno[2,3-c]pyridine-6-carboxylic acid ethyl ester and the appropriate acrylic acid derivatives which can be prepared according to general procedure H described later herein.

100. 3-Cyano-2-((E)-3-pyridin-2-yl-allanoylamino)-4,7-dihydro-5H-thieno[2,3-c]pyridine-6-carboxylic acid ethyl ester

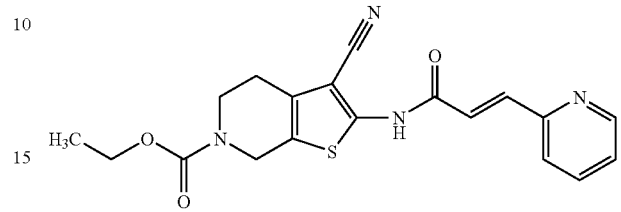

MS: Calc.: C19 H18 N4 O3 S, (382.44). Fnd.: 383.10 [M+H].

101. 3-Cyano-2-((E)-3-pyridin-4-yl-allanoylamino)-4,7-dihydro-5H-thieno[2,3-c]pyridine-6-carboxylic acid ethyl ester

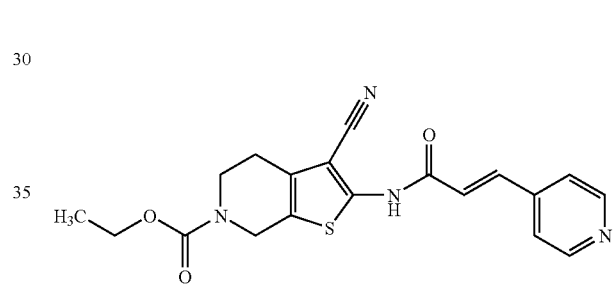

MS: Calc.: C19 H18 N4 O3 S, (382.44). Fnd.: 383.10 [M+H].

102. 3-Cyano-2-[(E)-3-(2,5-dimethoxy-phenyl)-allanoylamino]-4,7-dihydro-5H-thieno[2,3-c]pyridine-6-carboxylic acid ethyl ester

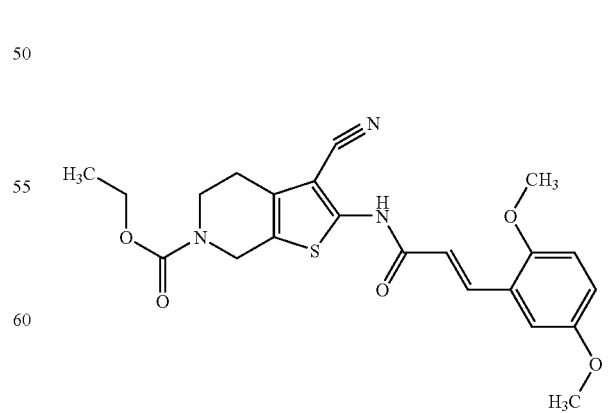

MS: Calc.: C22 H23 N3 O5 S, (441.51). Fnd.: 441.90 [M+H].

103. 3-Cyano-2-((E)-3-1-H-pyrrol-2-yl-allanoy-lamino)-4,7-dihydro-5H-thieno[2,3-c]pyridine-6-carboxylic acid ethylester

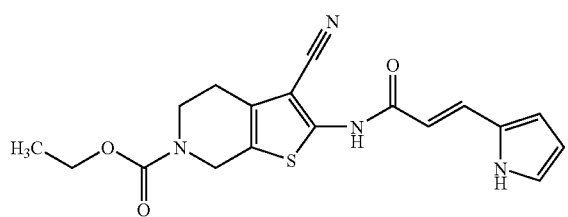

MS: Calc.: C18 H18 N4 O3 S, (370.43). Fnd.: 371.10 [M+H].

104. 3-Cyano-2-[(E)-3-(2-phenoxy-phenyl)-allanoy-lamino]-4,7-dihydro-5H-thieno[2,3-c]pyridine-6-carboxylic acid ethyl ester

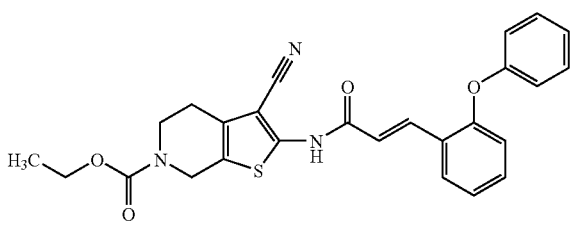

MS: Calc.: C26 H23 N3 O4 S, (473.55). Fnd.: 473.90 [M+H].

105. 3-Cyano-2-{(E)-3-[2-(2-hydroxy-ethoxy)-phenyl]-allanoylamino}-4,7-dihydro-5H-thieno[2,3-c]pyridine-6-carboxylic acid ethyl ester This compound is prepared in analogy to (E)-N-[3-Cyano-6-(2-hydroxy-ethanoyl)-4,5,6,7-tetrahydro-thieno[2,3-c]pyridin-2-yl]-3-phenyl-acrylamide.

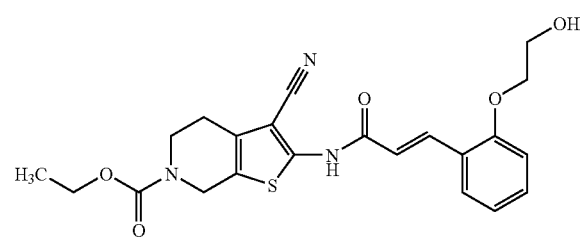

MS: Calc.: C22 H23 N3 O5 S, (441.51). Fnd.: 442.00 [M+H].

106. 5-Cyano-6-[(E)-3-(2,6-dimethoxy-phenyl)-allanoylamino]-1,3,4,7-tetrahydro-[2]pyridine-2-carboxylic acid ethyl ester

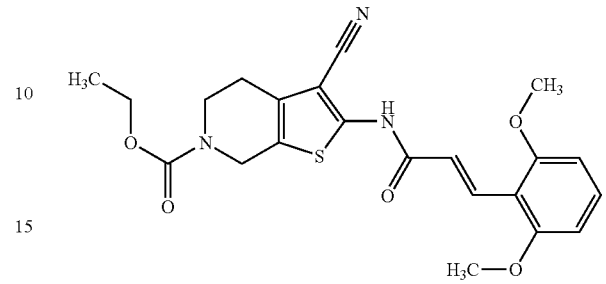

MS: Calc.: C22 H23 N3 O5 S, (441.51). Fnd.: 442.00 [M+H].

107. 3-Cyano-2-{(E)-3-[3-(2-hydroxy-ethoxy)-phenyl]-allanoyl-amino}-4,7-dihydro-5H-thieno[2,3-c]-pyridine-6-carboxylic acid ethyl ester This compound is prepared in analogy to (E)-N-[3-Cyano-6-(2-hydroxy-ethanoyl)-4,5,6,7-tetrahydro-thieno[2,3-c]pyridin-2-yl]-3-phenyl-acrylamide.

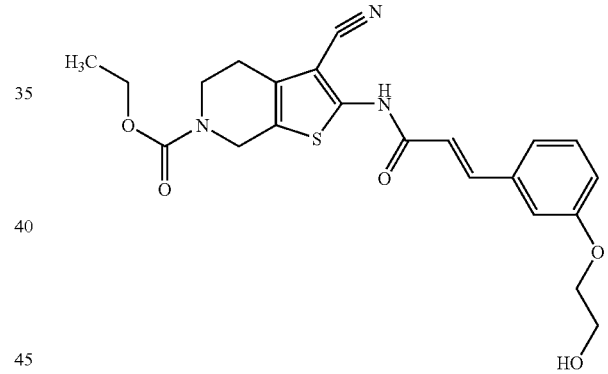

MS: Calc.: C22 H23 N3 O5 S, (441.51). Fnd.: 442.10 [M+H].

108. 3-Cyano-2-[(E)-3-(2,6-dimethoxy-phenyl)-allanoylamino]-4,7-dihydro-5H-thieno[2,3-c]pyridine-6-carboxylic acid ethyl ester

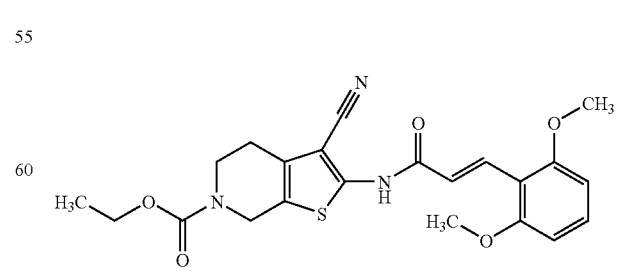

MS: Calc.: C22 H23 N3 O5 S, (441.51). Fnd.: 442.00 [M+H].

109. 2-[(E)-3-(5-Bromo-2-ethoxy-phenyl)-allanoylamino]-3-cyano-4,7-dihydro-5H-thieno[2,3-c]pyridine-6-carboxylic acid ethyl ester

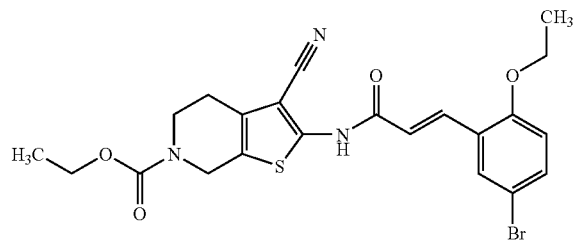

MS: Calc.: C22 H22 Br N3 O4 S, (504.41). Fnd.: 505.10 [M+H].

110. 2-[(E)-3-(5-Bromo-2-methoxy-phenyl)-allanoylamino]-3-cyano-4,7-dihydro-5H-thieno[2,3-c]pyridine-6-carboxylic acid ethyl ester

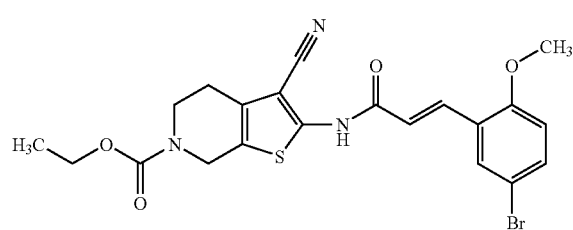

MS: Calc.: C21 H20 Br N3 O4 S, (490.38). Fnd.: 489.9 [M–H].

111. 2-((E)-3-Benzo[1,3]dioxol-4-yl-allanoylamino)-3-cyano-4,7-dihydro-5H-thieno[2,3-c]pyridine-6-carboxylic acid ethyl ester

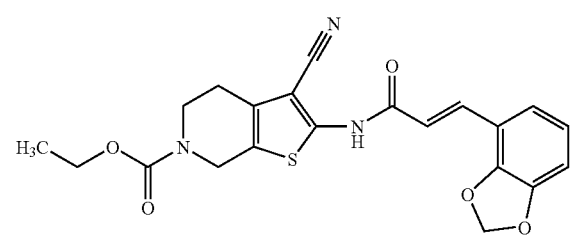

MS: Calc.: C21 H19 N3 O5 S, (425.47). Fnd.: 426.10 [M+H].

The following compounds 112 to 127, 129, 130, 132 to 134, 132 to 134, 135 to 164, and 166 to 168 can be prepared starting from the appropriate starting compound selected from N-(3-cyano-4,5,6,7-tetrahydro-thieno[2,3-c]pyridin-2-yl)-3-phenyl-acrylamide, N-(3-cyano-4,5,6,7-tetrahydro-thieno[2,3-c]pyridin-2-yl)-3-(2-methoxy-phenyl)-acrylamide, N-(3-cyano-4,5,6,7-tetrahydro-thieno[2,3-c]pyridin-2-yl)-3-(2-chloro-phenyl)-acrylamide and N-(3-cyano-4,5,6,7-tetrahydro-thieno[2,3-c]pyridin-2-yl)-3-(pyridin-3-yl)-acrylamide according to general procedure EE as described later herein:

112. 3-Cyano-2-((E)-3-phenyl-allanoylamino)-4,7-dihydro-5H-thieno[2,3-c]pyridine-6-carboxylic acid 2-morpholin-4-yl-ethyl ester

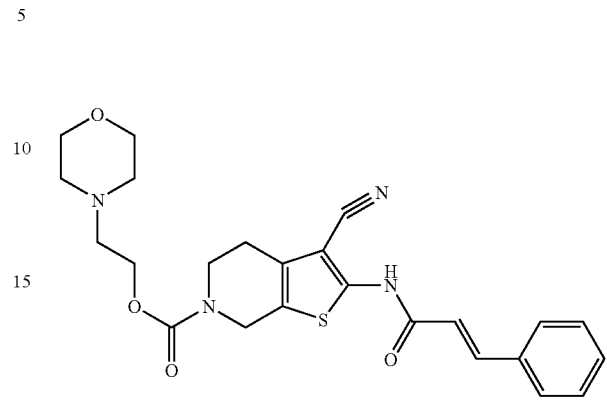

MS: Calc.: C24 H26 N4 O4 S, (466.56). Fnd.: 467.20 [M+H].

113. 3-Cyano-2-((E)-3-phenyl-allanoylamino)-4,7-dihydro-5H-thieno[2,3-c]pyridine-6-carboxylic acid 2-dimethylamino-ethyl ester

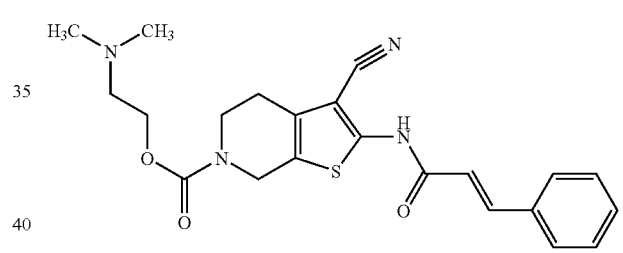

MS: Calc.: C22 H24 N4 O3 S, (424.53). Fnd.: 425.10 [M+H].

114. 3-Cyano-2-((E1-3-phenyl-allanoylamino)-4,7-dihydro-5H-thieno[2,3-c]pyridine-6-carboxylic acid 2-pyrrolidin-1-yl-ethyl ester

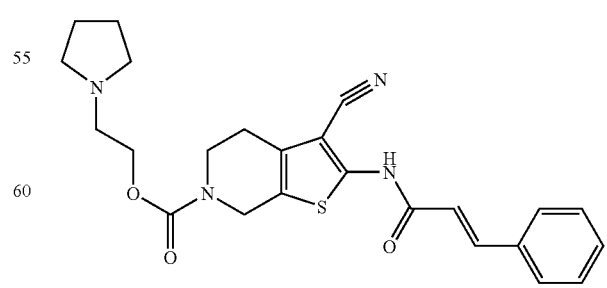

MS: Calc.: C24 H26 N4 O3 S, (450.56). Fnd.: 451.20 [M+H].

115. 3-Cyano-2-((E)-3-phenyl-allanoylamino)-4,7-dihydro-5H-thieno[2,3-c]pyridine-6-carboxylic acid 3-dimethylamino-propyl ester

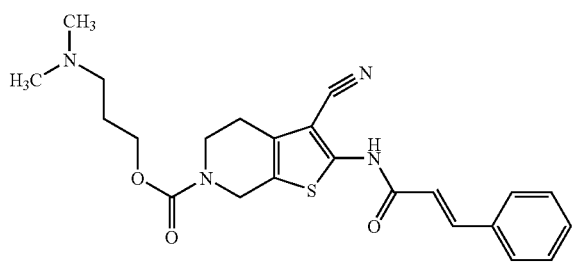

MS: Calc.: C23 H26 N4 O3 S, (438.55). Fnd.: 439.20 [M+H].

116. 3-Cyano-2-((E)-3-phenyl-allanoylamino)-4,7-dihydro-5H-thieno[2,3-c]pyridine-6-carboxylic acid 2-pyridin-2-yl-ethyl ester

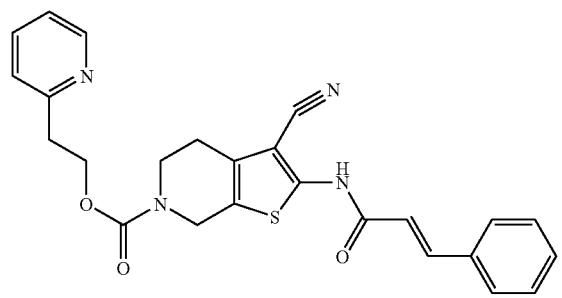

MS: Calc.: C25 H22 N4 O3 S, (458.54). Fnd.: 459.10 [M+H].

117. 3-Cyano-2-((E)-3-phenyl-allanoylamino)-4,7-dihydro-5H-thieno[2,3-c]pyridine-6-carboxylic acid 3-pyridin-4-yl-propyl ester

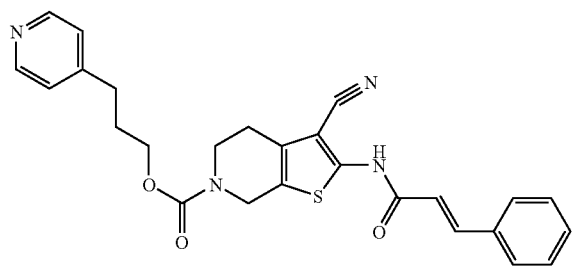

MS: Calc.: C26 H24 N4 O3 S, (472.57). Fnd.: 473.20 [M+H].

118. 3-Cyano-2-((E)-3-phenyl-allanoylamino)-4,7-dihydro-5H-thieno[2,3-c]pyridine-6-carboxylic acid 2-methoxy-ethyl ester

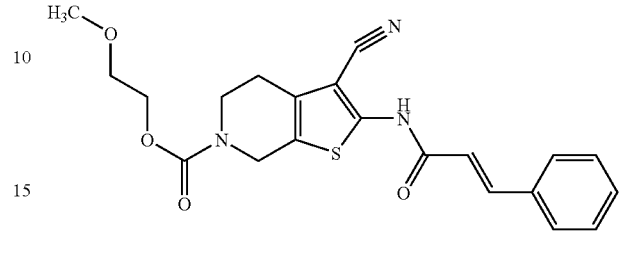

MS: Calc.: C21 H21 N3 O4 S, (411.48). Fnd.: 412.00 [M+H].

119. 3-Cyano-2-((E)-3-phenyl-allanoylamino)-4,7-dihydro-5H-thieno[2,3-c]pyridine-6-carboxylic acid 3-piperidin-1-yl-propyl ester

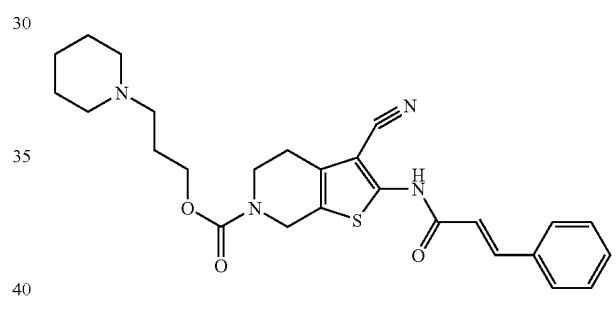

MS: Calc.: C26 H30 N4 O3 S, (478.62). Fnd.: 479.20 [M+H].

120. 3-Cyano-2-((E)-3-phenyl-allanoylamino)-4,7-dihydro-5H-thieno[2,3-c]pyridine-6-carboxylic acid 3-morpholin-4-yl-propyl ester

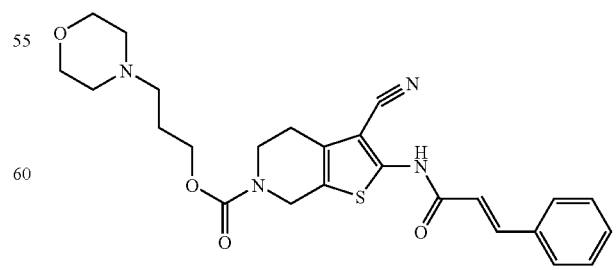

MS: Calc.: C25 H28 N4 O4 S, (480.59). Fnd.: 481.20 [M+H].

121. 3-Cyano-2-((E)-3-phenyl-allanoylamino)-4,7-dihydro-5H-thieno[2,3-c]pyridine-6-carboxylic acid 3-(4-methyl-piperazin-1-yl)-propyl ester

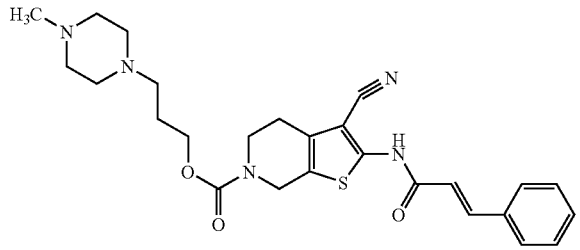

MS: Calc.: C26 H31 N5 O3 S, (493.63). Fnd.: 494.30 [M+H].

122. 3-Cyano-2-((E)-3-phenyl-allanoylamino)-4,7-dihydro-5H-thieno[2,3-c]pyridine-6-carboxylic acid 2-(2-methyl-5-nitro-imidazol-1-yl)-ethyl ester

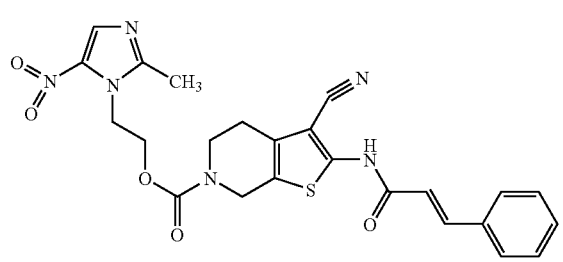

MS: Calc.: C24 H22 N6 O5 S, (506.54). Fnd.: 507.10 [M+H].

123. 3-Cyano-2-((E)-3-phenyl-allanoylamino)-4,7-dihydro-5H-thieno[2,3-c]pyridine-6-carboxylic acid 2-(4-nitro-phenoxy)-ethyl ester

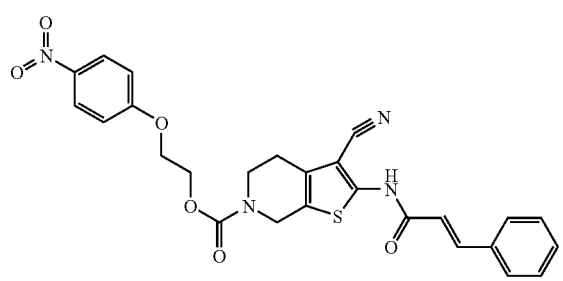

MS: Calc.: C26 H22 N4 O6 S, (518.55). Fnd.: 519.10 [M+H].

124. 3-Cyano-2-((E)-3-phenyl-allanoylamino)-4,7-dihydro-5H-thieno[2,3-c]pyridin-6-carboxylic acid 3-pyridin-2-yl-propyl ester

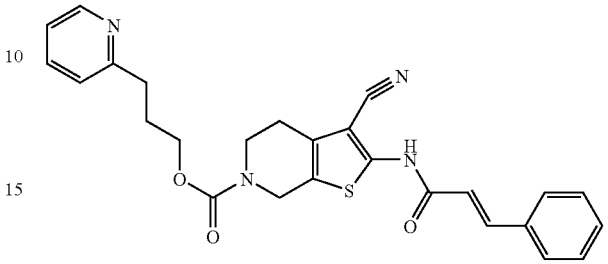

MS: Calc.: C26 H24 N4 O3 S, (472.57). Fnd.: 473.10 [M+H].

125. 3-Cyano-2-((E)-3-phenyl-allanoylamino)-4,7-dihydro-5H-thieno[2,3-c]pyridine-6-carboxylic acid 3-pyridin-3-yl-propyl ester

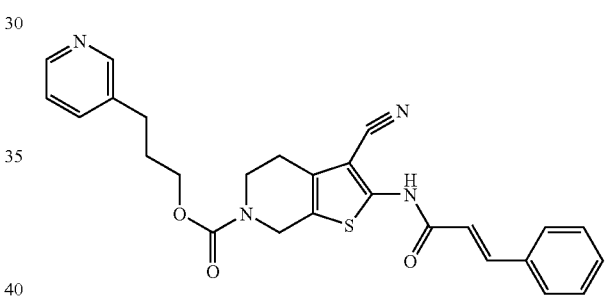

MS: Calc.: C26 H24 N4 O3 S, (472.57). Fnd.: 473.20 [M+H].

126. 3-Cyano-2-((E)-3-phenyl-allanoylamino)-4,7-dihydro-5H-thieno[2,3-c]pyridine-6-carboxylic acid 2-pyridin-4-yl-ethyl ester

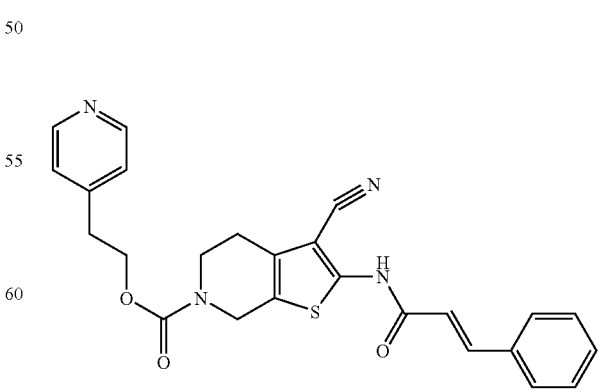

MS: Calc.: C25 H22 N4 O3 S, (458.54). Fnd.: 459.10 [M+H].

127. 3-Cyano-2-((E)-3-phenyl-allanoylamino)-4,7-dihydro-5H-thieno[2,3-c]pyridine-6-carboxylic acid 2,2-dimethyl-[1,3]dioxolan-4-ylmethyl ester

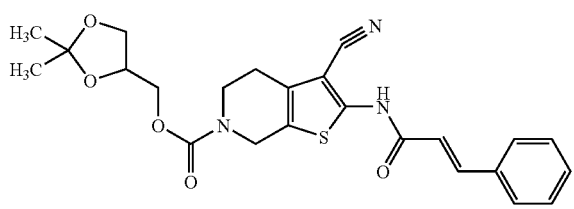

MS: Calc.: C24 H25 N3 O5 S, (467.55). Fnd.: 468.10 [M+H].

128. 3-Cyano-2-((E)-3-phenyl-allanoylamino)-4,7-dihydro-5H-thieno[2,3-c]pyridine-6-carboxylic acid 2,3-dihydroxy-propyl ester

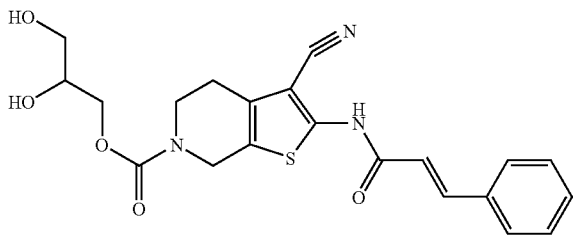

This compound is prepared in analogy to 3-cyano-2-((E)-3-pyridin-3-yl-allanoylamino)-4,7-dihydro-5H-thieno[2,3-c]pyridine-6-carboxylic acid 2,3-dihydroxy-propyl ester.

MS: Calc.: C21 H21 N3 O5 S, (427.48). Fnd.: 428.10 [M+H].

129. 3-Cyano-2-((E)-3-phenyl-allanoylamino)-4,7-dihydro-5H-thieno[2,3-c]pyridine-6-carboxylic acid 2-(2-methoxy-ethoxy)-ethyl ester

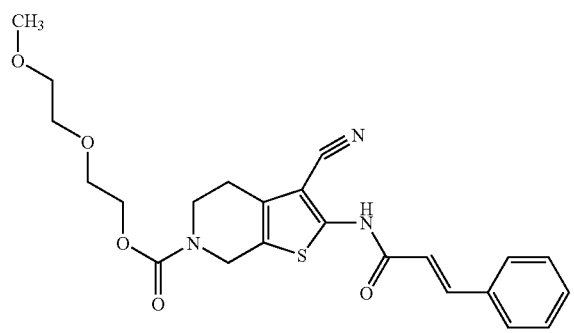

MS: Calc.: C23 H25 N3 O5 S, (455.54). Fnd.: 456.00 [M+H].

130. 3-Cyano-2-((E)-3-phenyl-allanoylamino)-4,7-dihydro-5H-thieno[2,3-c]pyridine-6-carboxylic acid 2-piperidin-1-yl-ethyl ester

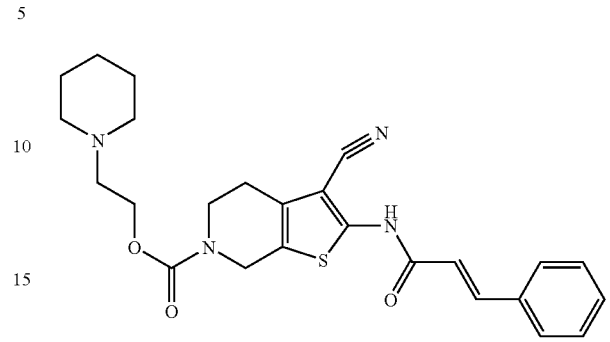

MS: Calc.: C25 H28 N4 O3 S, (464.59). Fnd.: 465.20 [M+H].

131. 3-Cyano-2-((E)-3-phenyl-allanoylamino)-4,7-dihydro-5H-thieno[2,3-c]pyridine-6-carboxylic acid carboxymethyl ester

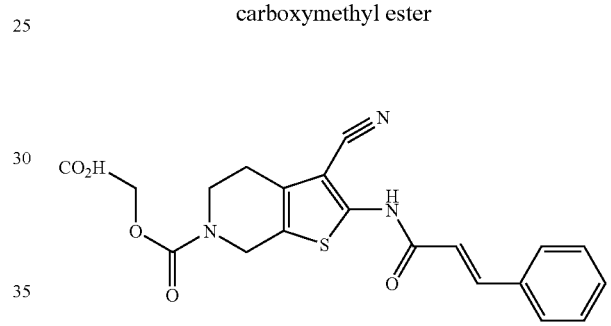

This compound is prepared by standard saponification of the ester function of 3-Cyano-2-((E)-3-phenyl-allanoylamino)-4,7-dihydro-5H-thieno[2,3-c]pyridine-6-carboxylic acid methoxycarbonylmethyl ester.

MS: Calc.: C20 H17 N3 O5 S, (411.44). Fnd.: 412.00 [M+H].

132. 3-Cyano-2-((E)-3-phenyl-allanoylamino)-4,7-dihydro-5H-thieno[2,3-c]pyridine-6-carboxylic acid 2-(4-methyl-piperazin-1-yl)-ethyl ester

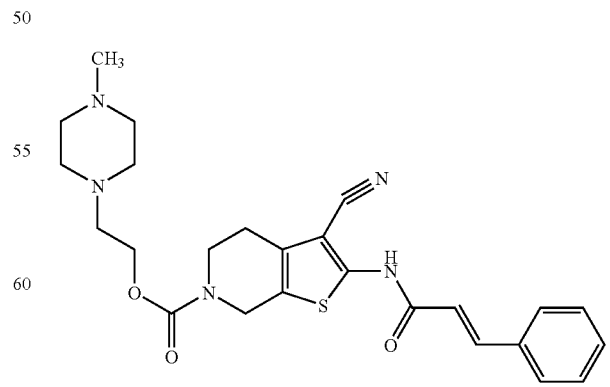

MS: Calc.: C25 H29 N5 O3 S, (479.61). Fnd.: 480.20 [M+H].

133. 3-Cyano-2-((E)-3-phenyl-allanoylamino)-4,7-dihydro-5H-thieno[2,3-c]pyridine-6-carboxylic acid methoxycarbonylmethyl ester

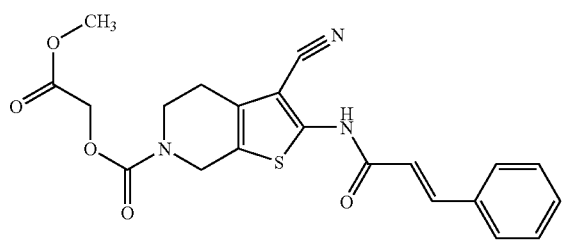

MS: Calc.: C21 H19 N3 O5 S, (425.47). Fnd.: 426.10 [M+H].

134. 3-Cyano-2-((E)-3-phenyl-allanoylamino)-4,7-dihydro-5H-thieno[2,3-c]pyridine-6-carboxylic acid 2-acetylamino-ethyl ester

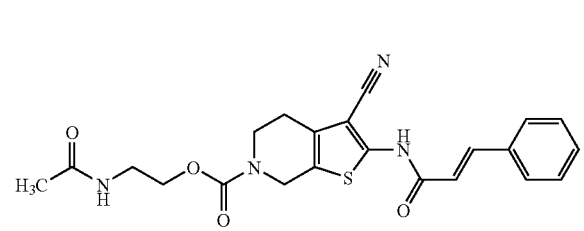

MS: Calc.: C22 H22 N4 O4 S, (438.51). Fnd.: 439.10 [M+H].

135. 3-Cyano-2-((E)-3-phenyl-allanoylamino)-4,7-dihydro-5H-thieno[2,3-c]pyridine-6-carboxylic acid 2-hydroxy-ethyl ester

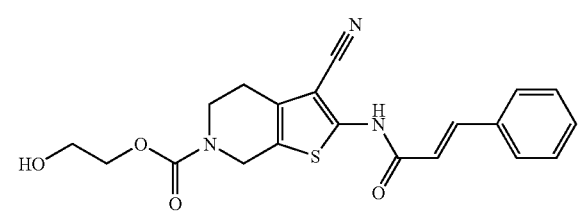

This compound is prepared according to (E)-N-[3-cyano-6-(2-hydroxy-ethanoyl)-4,5,6,7-tetrahydro-thieno[2,3-c]pyridin-2-yl]-3-phenyl-acrylamide.
MS: Calc.: C20 H19 N3 O4 S, (397.46). Fnd.: 398.10 [M+H].

136. 3-Cyano-2-((E)-3-phenyl-allanoylamino)-4,7-dihydro-5H-thieno[2,3-c]pyridine-6-carboxylic acid 2-imidazol-1-yl-ethyl ester

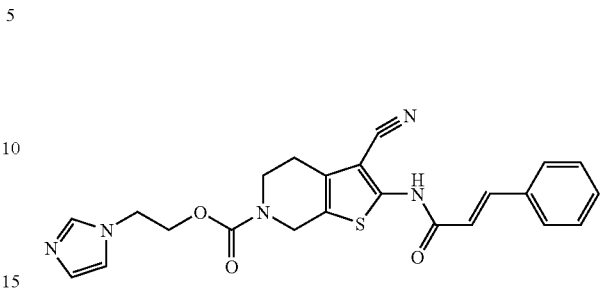

MS: Calc.: C23 H21 N5 O3 S, (447.52). Fnd.: 448.20 [M+H].

137. 3-Cyano-2-[(E)-3-(2-methoxy-phenyl)-allanoylamino]-4,7-dihydro-5H-thieno[2,3-c]pyridine-6-carboxylic acid 2-methoxy-ethyl ester

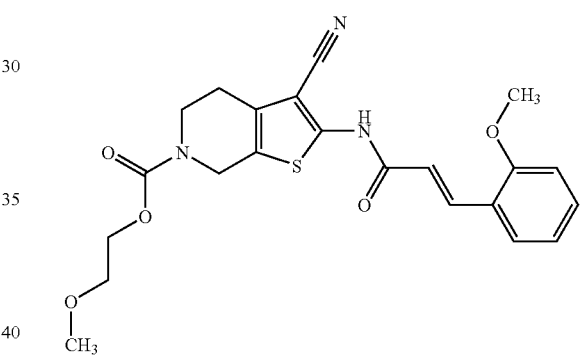

MS: Calc.: C22 H23 N3 O5 S, (441.51). Fnd.: 442.10 [M+H].

138. 3-Cyano-2-[(E)-3-(2-methoxy-phenyl)-allanoylamino]-4,7-dihydro-5H-thieno[2,3-c]pyridine-6-carboxylic acid pyridin-2-ylmethyl ester

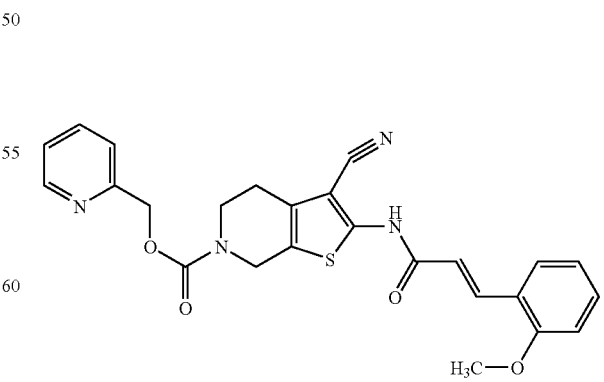

MS: Calc.: C25 H22 N4 O4 S, (474.54). Fnd.: 475.10 [M+H].

139. 3-Cyano-2-[(E)-3-(2-methoxy-phenyl)-allanoylamino]-4,7-dihydro-5H-thieno[2,3-c]pyridine-6-carboxylic acid 2-pyridin-2-yl-ethyl ester

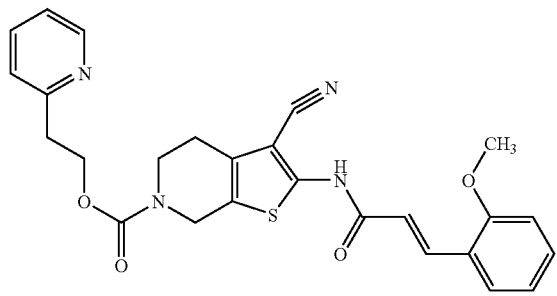

MS: Calc.: C26 H24 N4 O4 S, (488.57). Fnd.: 489.10 [M+H].

140. 3-Cyano-2-[(E)-3-(2-methoxy-phenyl)-allanoylamino]-4,7-dihydro-5H-thieno[2,3-c]pyridine-6-carboxylic acid pyridin-3-ylmethyl ester

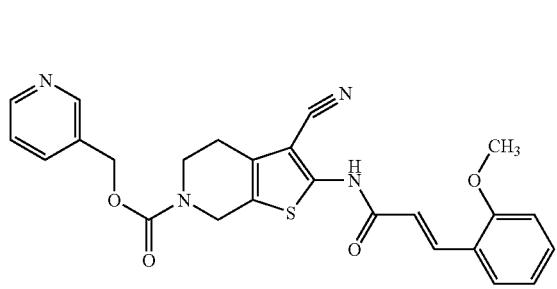

MS: Calc.: C25 H22 N4 O4 S, (474.54). Fnd.: 475.20 [M+H].

141. 3-Cyano-2-[(E)-3-(2-methoxy-phenyl)-allanoylamino]-4,7-dihydro-5H-thieno[2,3-c]pyridine-6-carboxylic acid pyridin-4-ylmethyl ester

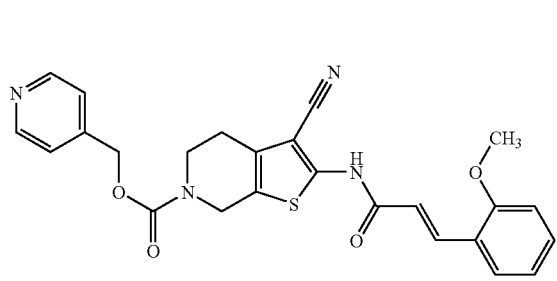

MS: Calc.: C25 H22 N4 O4 S, (474.54). Fnd.: 475.20 [M+H].

142. 2-[(E)-3-(2-Chloro-phenyl)-allanoylamino]-3-cyano-4,7-dihydro-5H-thieno[2,3-c]pyridine-6-carboxylic acid 2-methoxy-ethyl ester

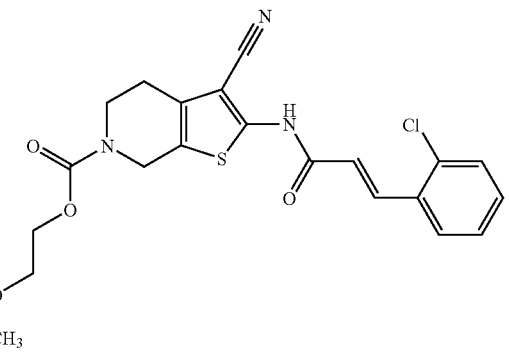

MS: Calc.: C21 H20 Cl N3 O4 S, (445.93). Fnd.: 446.00 [M+H].

143. 3-Cyano-2-((E)-3-pyridin-3-yl-allanoylamino)-4,7-dihydro-5H-thieno[2,3-c]pyridine-6-carboxylic acid 4-methoxy-phenyl ester

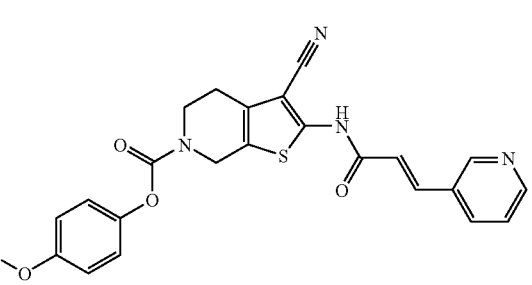

MS: Calc.: C24 H20 N4 O4 S, (460.52). Fnd.: 461.20 [M+H].

144. 3-Cyano-2-((E)-3-pyridin-3-yl-allanoylamino)-4,7-dihydro-5H-thieno[2,3-c]pyridine-6-carboxylic acid benzyl ester

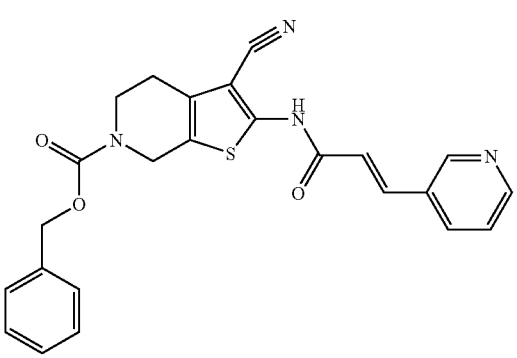

MS: Calc.: C24 H20 N4 O3 S, (444.52). Fnd.: 445.10 [M+H].

145. 3-Cyano-2-((E)-3-pyridin-3-yl-allanoylamino)-4,7-dihydro-5H-thieno[2,3-c]pyridine-6-carboxylic acid propyl ester

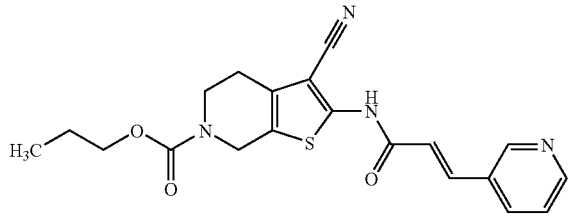

MS: Calc.: C20 H20 N4 O3 S, (396.47). Fnd.: 397.10 [M+H].

146. 3-Cyano-2-((E)-3-pyridin-3-yl-allanoylamino)-4,7-dihydro-5H-thieno[2,3-c]pyridine-6-carboxylic acid 2-(4-methoxy-phenyl)-ethyl ester

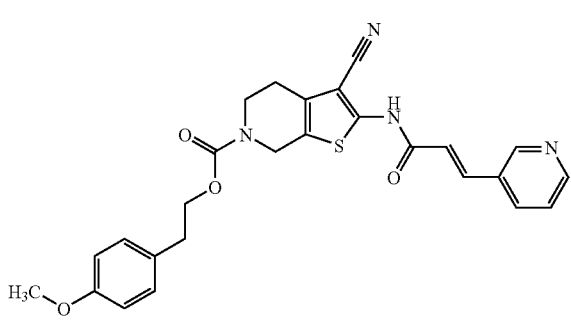

MS: Calc.: C26 H24 N4 O4 S, (488.57). Fnd.: 489.10 [M+H].

147. 3-Cyano-2-((E)-3-pyridin-3-yl-allanoylamino)-4,7-dihydro-5H-thieno[2,3-c]pyridine-6-carboxylic acid 3-methoxy-benzyl ester

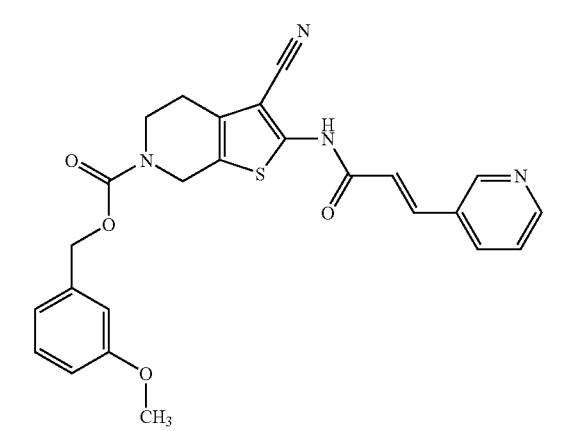

MS: Calc.: C25 H22 N4 O4 S, (474.54). Fnd.: 475.10 [M+H].

148. 3-Cyano-2-((E)-3-pyridin-3-yl-allanoylamino)-4,7-dihydro-5H-thieno[2,3-c]pyridine-6-carboxylic acid 3-phenyl-propyl ester

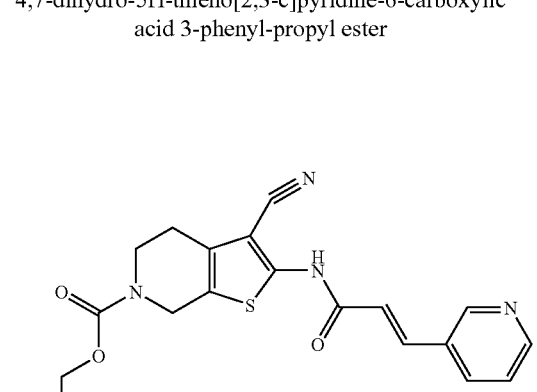

MS: Calc.: C26 H24 N4 O3 S, (472.57). Fnd.: 473.20 [M+H].

149. 3-Cyano-2-((E)-3-pyridin-3-yl-allanoylamino)-4,7-dihydro-5H-thieno[2,3-c]pyridine-6-carboxylic acid pyridin-2-ylmethyl ester

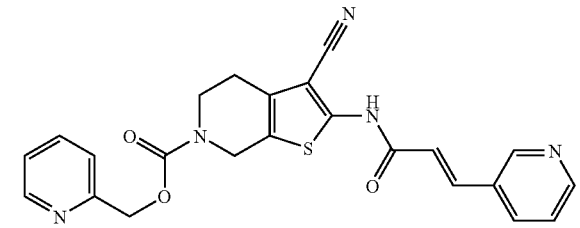

MS: Calc.: C23 H19 N5 O3 S, (445.50). Fnd.: 446.20 [M+H].

150. 3-Cyano-2-((E)-3-pyridin-3-yl-allanoylamino)-4,7-dihydro-5H-thieno[2,3-c]pyridine-6-carboxylic acid pyridin-3-ylmethyl ester

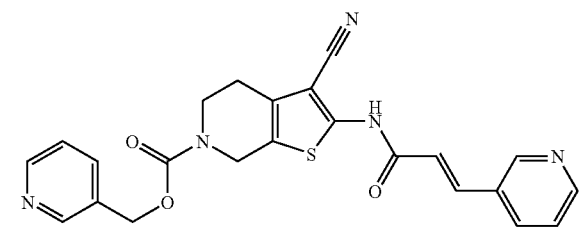

MS: Calc.: C23 H19 N5 O3 S, (445.50). Fnd.: 446.20 [M+H].

151. 3-Cyano-2-((E)-3-pyridin-3-yl-allanoylamino)-
4,7-dihydro-5H-thieno[2,3-c]pyridine-6-carboxylic
acid 4-methoxycarbonyl-phenyl ester

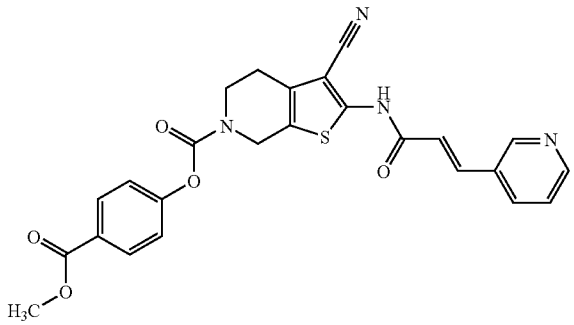

MS: Calc.: C25 H20 N4 O5 S, (488.53). Fnd.: 489.20 [M+H].

152. 3-Cyano-2-((E)-3-pyridin-3-yl-allanoylamino)-
4,7-dihydro-5H-thieno[2,3-c]pyridine-6-carboxylic
acid 2-(3-methoxy-phenyl)-ethyl ester

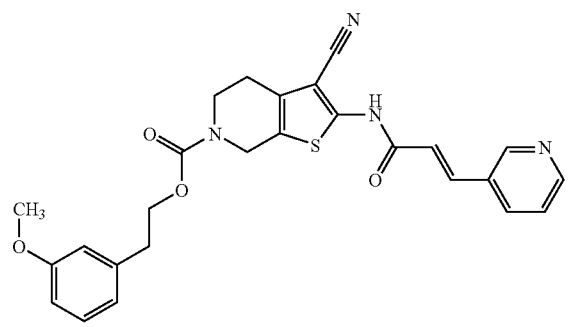

MS: Calc.: C26 H24 N4 O4 S, (488.57). Fnd.: 489.20 [M+H].

153. 3-Cyano-2-((E)-3-pyridin-3-yl-allanoylamino)-
4,7-dihydro-5H-thieno[2,3-c]pyridine-6-carboxylic
acid 2-(2-methoxy-phenyl)-ethyl ester

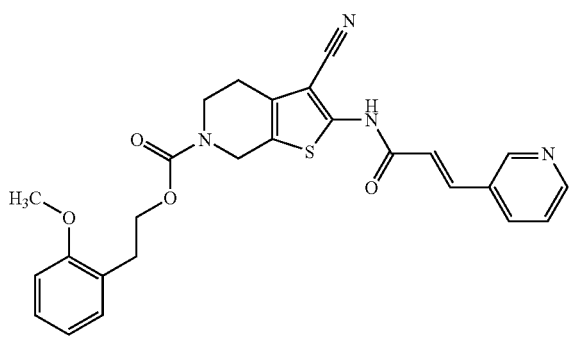

MS: Calc.: C26 H24 N4 O4 S, (488.57). Fnd.: 489.10 [M+H].

154. 3-Cyano-2-((E)-3-pyridin-3-yl-allanoylamino)-
4,7-dihydro-5H-thieno[2,3-c]pyridine-6-carboxylic
acid pyridin-2-yl ester

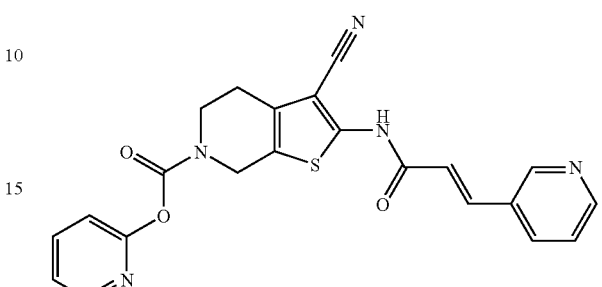

MS: Calc.: C22 H17 N5 O3 S, (431.48). Fnd.: 432.00 [M+H].

155. 3-Cyano-2-((E)-3-pyridin-3-yl-allanoylamino)-
4,7-dihydro-5H-thieno[2,3-c]pyridine-6-carboxylic
acid methyl ester

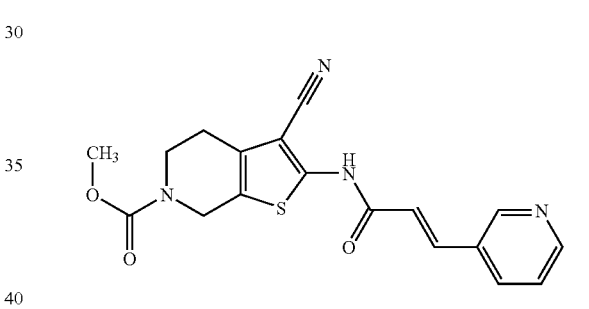

MS: Calc.: C18 H16 N4 O3 S, (368.42). Fnd.: 469.10 [M+H].

156. 3-Cyano-2-((E)-3-pyridin-3-yl-allanoylamino)
4,7-dihydro-5H-thieno[2,3-c]pyridine-6-carboxylic
acid 2-morpholin-4-yl-ethyl ester

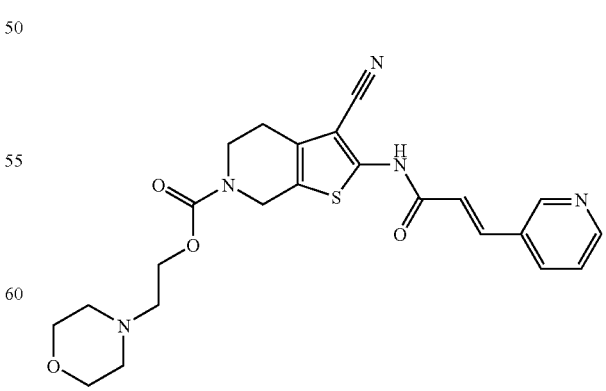

MS: Calc.: C23 H25 N5 O4 S, (467.55). Fnd.: 468.10 [M+H].

157. 3-Cyano-2-((E)-3-pyridin-3-yl-allanoylamino)-4,7-dihydro-5H-thieno[2,3-c]pyridine-6-carboxylic acid 3-pyridin-3-yl-propyl ester

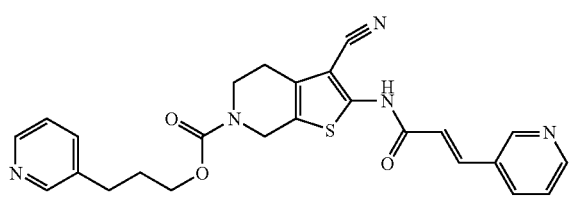

MS: Calc.: C25 H23 N5 O3 S, (473.56). Fnd.: 474.20 [M+H].

158. 3-Cyano-2-((E)-3-pyridin-3-yl-allanoylamino)-4,7-dihydro-5H-thieno[2,3-c]pyridine-6-carboxylic acid 2-pyridin-2-ylethyl ester

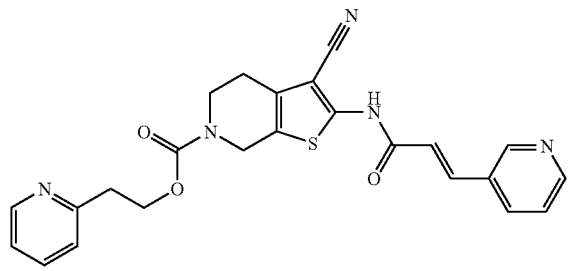

MS: Calc.: C24 H21 N5 O3 S, (459.53). Fnd.: 460.20 [M+H].

159. 3-Cyano-2-((E)-3-pyridin-3-yl-allanoylamino)-4,7-dihydro-5H-thieno[2,3-c]pyridine-6-carboxylic acid 2-pyridin-3-yl-ethyl ester

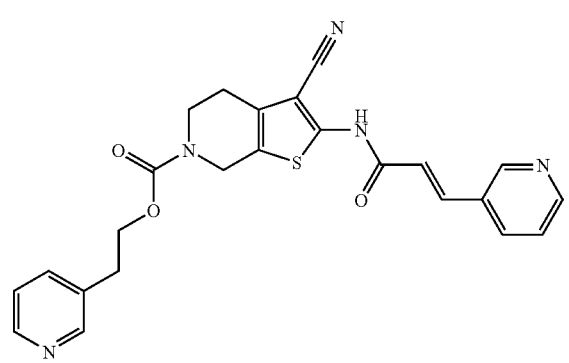

MS: Calc.: C24 H21 N5 O3 S, (459.53). Fnd.: 460.20 [M+H].

160. 3-Cyano-2-((E)-3-pyridin-3-yl-allanoylamino)-4,7-dihydro-5H-thieno[2,3-c]pyridine-6-carboxylic acid pyridin-4-ylmethyl ester

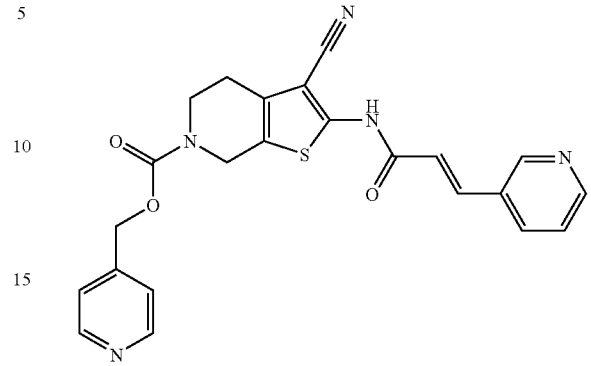

MS: Calc.: C23 H19 N5 O3 S, (445.50). Fnd.: 446.20 [M+H].

161. 3-Cyano-2-((E)-3-pyridin-3-yl-allanoylamino)-4,7-dihydro-5H-thieno[2,3-c]pyridine-6-carboxylic acid ethoxycarbonylmethyl ester

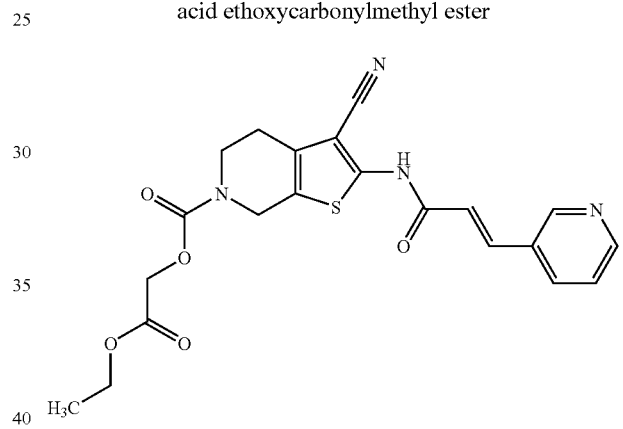

MS: Calc.: C21 H20 N4 O S, (440.48). Fnd.: 441.10 [M+H].

162. 3-Cyano-2-((E)-3-pyridin-3-yl-allanoylamino)-4,7-dihydro-5H-thieno[2,3-c]pyridine-6-carboxylic acid 2-methoxycarbonyl-ethyl ester

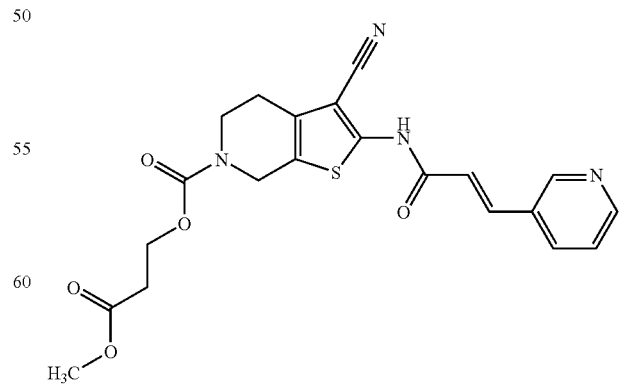

MS: Calc.: C21 H20 N4 O5 S, (440.48). Fnd.: 441.10 [M+H].

163. 3-Cyano-2-((E)-3-pyridin-3-yl-allanoylamino)-
4,7-dihydro-5H-thieno[2,3-c]pyridine-carboxylic
acid 3-dimethylamino-propyl ester

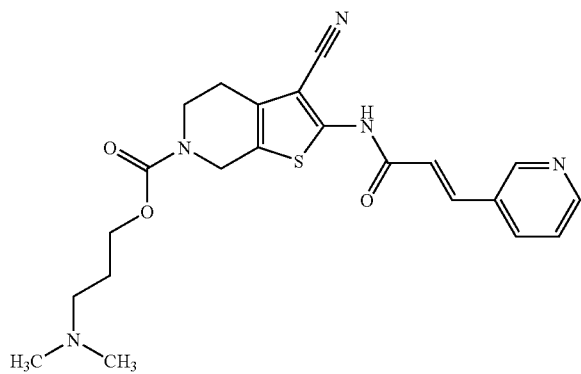

MS: Calc.: C22 H25 N5 O3 S, (439.54). Fnd.: 440.20 [M+H].

164. 3-Cyano-2-((E)-3-pyridin-3-yl-allanoylamino)-
4,7-dihydro-5H-thieno[2,3-c]pyridine-6-carboxylic
acid 2,2-dimethyl-[1,3]dioxolan-4-ylmethyl ester

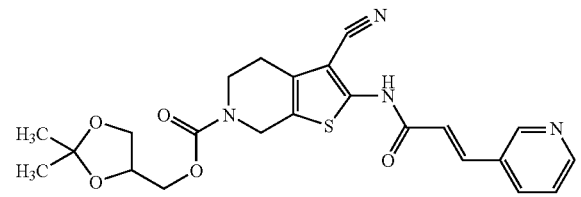

MS: Calc.: C23 H24 N4 O5 S, (468.54). Fnd.: 469.00 [M+H].

165. 3-Cyano-2-((E)-3-pyridin-3-yl-allanoylamino)-
4,7-dihydro-5H-thieno[2,3-c]pyridine-6-carboxylic
acid 2,3-dihydroxy-propyl ester

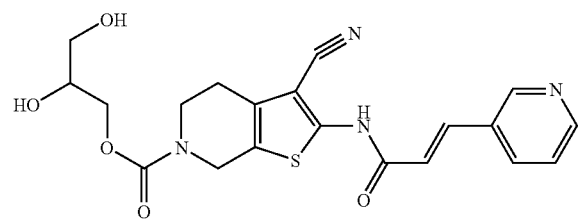

0.26 mmol of 3-Cyano-2-((E)-3-phenyl-allanoylamino)-4,7-dihydro-5H-thieno[2,3-c]pyridine-6-carboxylic acid 2,2-dimethyl-[1,3]dioxolan-4-ylmethyl ester are dissolved in 10 ml AcCN/H2O (2/1) and 0.1 eq PTSA is added. After stirring over night, some triethylamine is added and the solvent removed. Recrystallization from ethanol gives the desired product in 80% yield.

MS: Calc.: C20 H20 N4 O5 S, (428.47). Fnd.: 429.00 [M+H].

166. 3-Cyano-2-((E)-3-pyridin-3-yl-allanoylamino)-
4,7-dihydro-5H-thieno[2,3-c]pyridine-6-carboxylic
acid 2-benzyloxy-ethyl ester

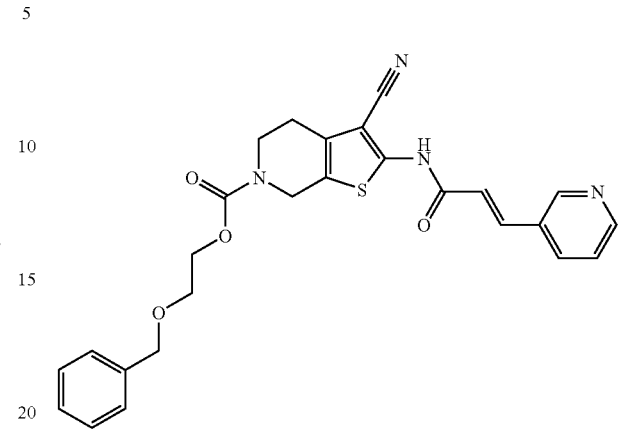

MS: Calc.: C26 H24 N4 O4 S, (488.57). Fnd.: 489.20 [M+H].

167. 3-Cyano-2-((E)-3-pyridin-3-yl-allanoylamino)-
4,7-dihydro-5H-thieno[2,3-c]pyridine-6-carboxylic
acid 2-methoxy-ethyl ester

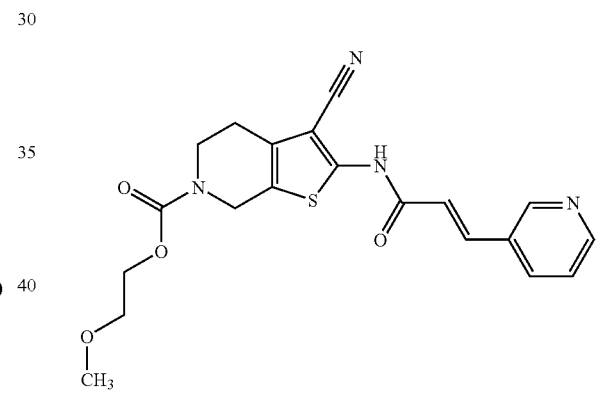

MS: Calc.: C20 H20 N4 O4 S, (412.47). Fnd.: 413.10 [M+H].

168. 3-Cyano-2-((E)-3-pyridin-3-yl-allanoylamino)-
4,7-dihydro-5H-thieno[2,3-c]pyridine-6-carboxylic
acid cyclohexyl ester

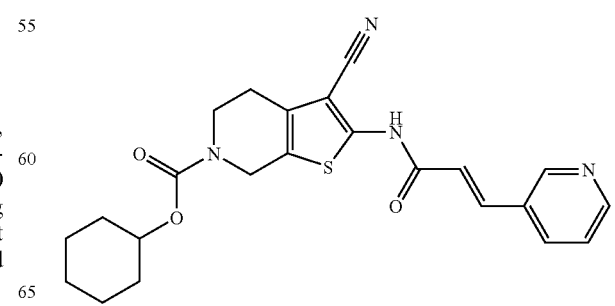

MS: Calc.: C23 H24 N4 O3 S, (436.54). Fnd.: 437.10 [M+H].

AAA. Further Alternative General Procedure for the Formation of Amide Bonds a) Starting from the Trifluoroacetate Salt:

To a solution of the appropriate acid (1.5 mmol) in dichloromethane (5 ml), carbonyldiimidazole (CDI, 1.78 mmol) is added. The reaction vessel is equipped with a bubbler, the mixture is stirred until the gas evolution is completed (30 min, approximately). Then, a mixture of the suspension of the appropriate starting trifluoroacetate salt in dichloromethane (10 ml) and triethylamine (0.2 g, 2 mmole) is added to the reaction mixture. Stirring is continued for 18 to 24 hours at room temperature, the reaction is monitored by TLC.

Work up A: if the reaction mixture is a solution, it is extracted by three portions of 5% sodium hydrogencarbonate (10 ml each) and once by water (10 ml), the organic layer is evaporated and the residue subjected to purification.

Work up B: if the reaction mixture is a suspension, the solid product is filtered off. If the amount of this solid product is not sufficient, the mother liquor is further worked up as procedure A.

Purification: The majority of the products can be recrystallized from acetonitrile, in some cases by simple trituration of the organic residue with acetonitrile. After filtration, the crystals are washed with diethyl ether.

b) Starting from the Free Amine Using EDCL

A mixture of the appropriate starting base (1 mmol), the appropriate acid (1.5 mmol), ethyl-dimethylaminopropylcarbodiimide (EDCl, 0.29 g, 1.5 mmol), 4-dimethylaminopyridine (DMAP, 0.25 g, 0.2 mmol) and water-free dichloromethane (10 ml) are stirred at room temperature for 18 to 24 hours. The reaction mixture is monitored by TLC. The reaction mixture is worked up as in the reactions carried out with CDI.

c) Using Acid Chlorides

To a suspension of the appropriate starting trifluoroacetate salt (1 mmol) in dichloromethane (10 ml) triethylamine (0.4 g, 4 mmol) is added. The formed solution is added to a solution of the appropriate acid chloride (1.2 mmol) in dichloromethane (10 ml) dropwise at 0° C. with stirring and, then, stirring is continued for 24 h at room temperature. The mixture is evaporated and the residue dissolved in dichloromethane. This solution is extracted twice by water (15 ml) and once by saturated sodium chloride solution (15 ml). Purification is carried out as described in procedures a) and b).

The following compounds 169 to 186, 188 to 191, 193 to 198, 200 to 203, and 205 to 229 can be prepared starting from the appropriate starting compound selected from N-(3-cyano-4,5,6,7-tetrahydro-thieno[2,3-c]pyridin-2-yl)-3-phenyl-acrylamide, N-(3-cyano-4,5,6,7-tetrahydro-thieno[2,3-c]pyridin-2-yl)-3-(2-methoxy-phenyl)-acrylamide, N-(3-cyano-4,5,6,7-tetrahydro-thieno[2,3-c]pyridin-2-yl)-3-(2-ethoxy-phenyl)-acrylamide, N-(3-cyano-4,5,6,7-tetrahydro-thieno[2,3-c]pyridin-2-yl)-3-(2-chloro-phenyl)-acrylamide, N-(3-cyano-4,5,6,7-tetrahydro-thieno[2,3-c]pyridin-2-yl)-3-(furan-2-yl)-acrylamide and N-(3-cyano-4,5,6,7-tetrahydro-thieno[2,3-c]pyridin-2-yl)-3-(pyridin-3-yl)-acrylamide according to general procedure AAA mentioned above.

169. (E)-N-(6-Acetyl-3-cyano-4,5,6,7-tetrahydro-thieno[2,3-c]pyridin-2-yl)-3-phenyl-acrylamide

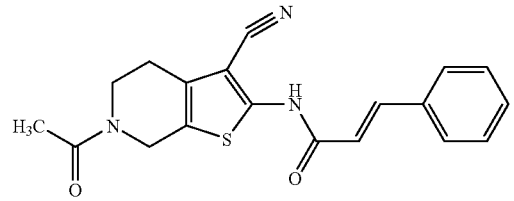

MS: Calc.: C19 H17 N3 O2 S, (351.43). Fnd.: 352.00 [M+H].

170. (E)-N-(6-Butyryl-3-cyano-4,5,6,7-tetrahydro-thieno[2,3-c]pyridin-2-yl)-3-phenyl-acrylamide

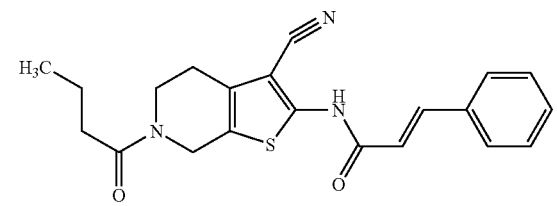

MS: Calc.: C21 H21 N3 O2 S, (379.48). Fnd.: 380.10 [M+H].

171. (E)-N-[3-Cyano-6-(3-1H-indol-3-yl-propanoyl)-4,5,6,7-tetrahydro-thieno[2,3-c]pyridin-2-yl]-3-phenyl-acrylamide

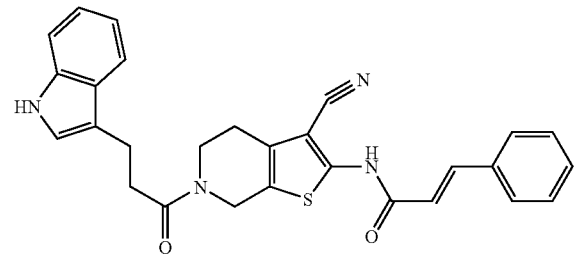

MS: Calc.: C28 H24 N4 O2 S, (480.59). Fnd.: 481.10 [M+H].

172. (E)-N-[3-Cyano-6-(4-1H-indol-3-yl-butanoyl)-4,5,6,7-tetrahydro-thieno[2,3-c]pyridin-2-yl]-3-phenyl-acrylamide

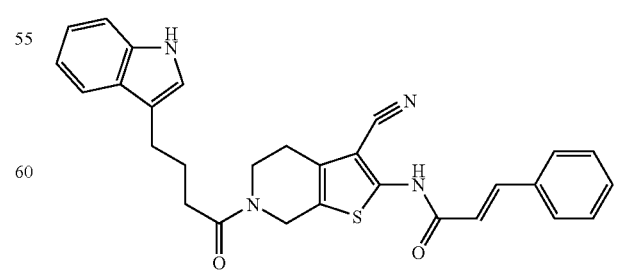

MS: Calc.: C29 H26 N4 O2 S, (494.62). Fnd.: 495.20 [M+H].

173. 4-[3-Cyano-2-((E)-3-phenyl-allanoylamino)-4,7-dihydro-5H-thieno[2,3-c]pyridin-6-yl]-4-oxo-butyric acid methyl ester

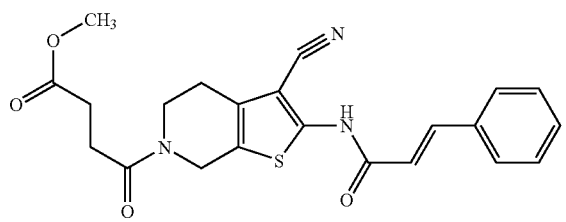

MS: Calc.: C22 H21 N3 O4 S, (423.49). Fnd.: 424.00 [M+H].

174. (E)-N-[3-Cyano-6-(2-pyridin-2-yl-ethanoyl)-4,5,6,7-tetrahydro-thieno[2,3-c]pyridin-2-yl]-3-phenyl-acrylamide

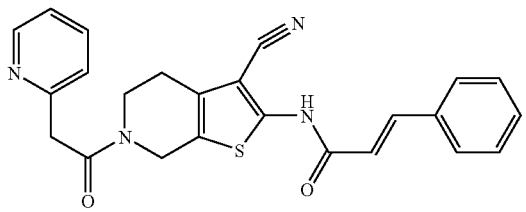

MS: Calc.: C24 H20 N4 O2 S, (428.52). Fnd.: 429.20 [M+H].

175. (E)-N-{3-Cyano-6-[2-(2-methoxy-ethoxy)-ethanoyl]-4,5,6,7-tetrahydro-thieno[2,3-c]pyridin-2-yl}-3-phenyl-acrylamide

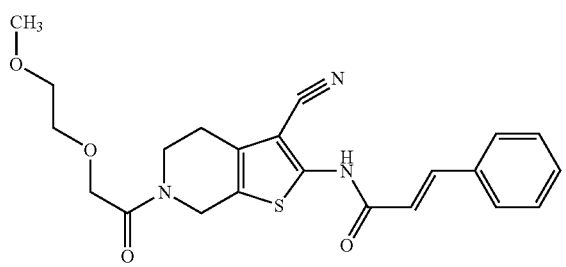

MS: Calc.: C22 H23 N3 O4 S, (425.51). Fnd.: 426.10 [M+H].

176. 3-[3-Cyano-2-((E)-3-phenyl-allanoylamino)-4,7-dihydro-5H-thieno[2,3-c]pyridin-6-yl]-3-oxo-propionic acid ethyl ester

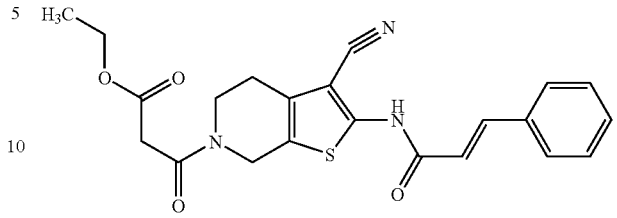

MS: Calc.: C22 H21 N3 O4 S, (423.49). Fnd.: 424.10 [M+H].

177. (E)-N-[3-Cyano-6-(3-methoxy-propanoyl)-4,5,6,7-tetrahydro-thieno[2,3-c]pyridin-2-yl]-3-phenyl-acrylamide

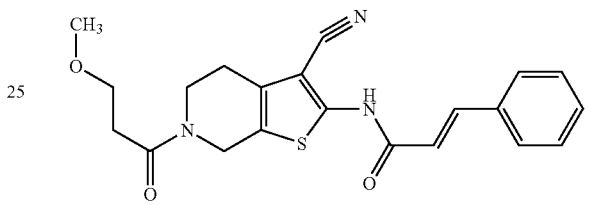

MS: Calc.: C21 H21 N3 O3 S, (395.48). Fnd.: 396.10 [M+H].

178. 4-[3-Cyano-2-((E)-3-phenyl-allanoylamino)-4,7-dihydro-5H-thieno[2,3-c]pyridin-6-yl]-N,N-dimethyl-4-oxo-butyramide

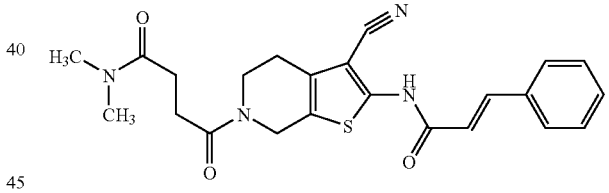

MS: Calc.: C23 H24 N4 O3 S, (436.54). Fnd.: 437.00 [M+H].

179. (E)-N-[3-Cyano-6-(3-ureido-propanoyl)-4,5,6,7-tetrahydro-thieno[2,3-c]pyridin-2-yl]-3-phenyl-acrylamide

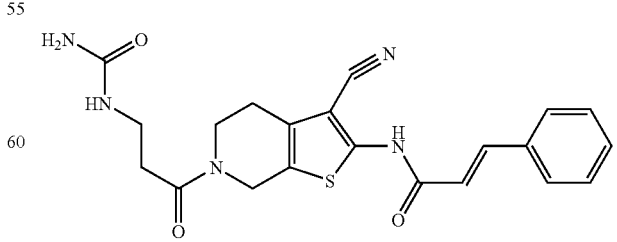

MS: Calc.: C21 H21 N5 O3 S, (423.50). Fnd.: 424.10 [M+H].

180. (E)-N-[3-Cyano-6-(3-guanidino-propanoyl)-4,5,6,7-tetrahydro-thieno[2,3-c]pyridin-2-yl]-3-phenyl-acrylamide

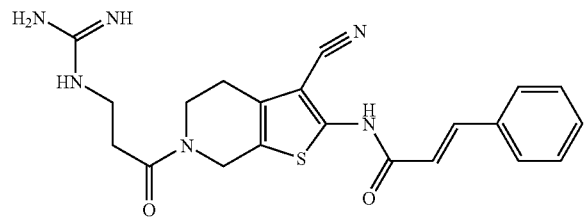

MS: Calc.: C21 H22 N6 O2 S, (422.51). Fnd.: 423.10 [M+H].

181. (E)-N-[3-Cyano-6-(2-methoxy-ethanoyl)-4,5,6,7-tetrahydro-thieno[2,3-c]pyridin-2-yl]-3-phenyl-acrylamide

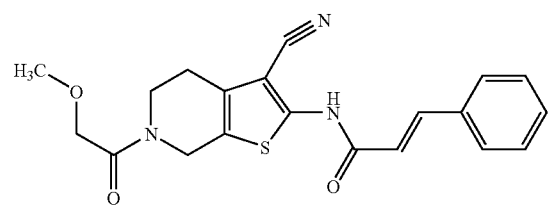

MS: Calc.: C20 H19 N3 O3 S, (381.46). Fnd.: 382.10 [M+H].

182. (E)-N-[3-Cyano-6-(2-1H-indol-3-yl-ethanoyl)-4,5,6,7-tetrahydro-thieno[2,3-c]pyridin-2-yl]-3-phenyl-acrylamide

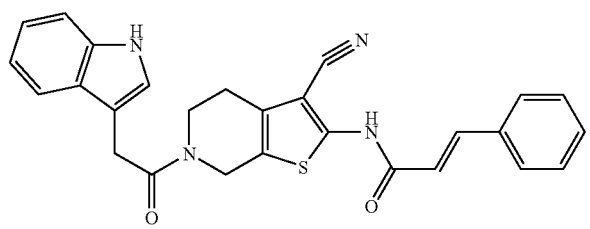

MS: Calc.: C27 H22 N4 O2 S, (466.57). Fnd.: 467.10 [M+H].

183. (E)-N-[3-Cyano-6-(2-pyridin-3-yl-ethanoyl)-4,5,6,7-tetrahydro-thieno[2,3-c]pyridin-2-yl]-3-phenyl-acrylamide

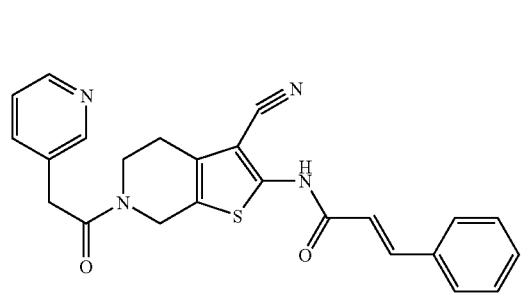

MS: Calc.: C24 H20 N4 O2 S, (428.52). Fnd.: 429.20 [M+H].

184. (E)-N-{3-Cyano-6-[4-(4-methanesulfonyl-phenyl)-4-oxo-butanoyl]-4,5,6,7-tetrahydro-thieno[2,3-c]pyridin-2-yl}-3-phenyl-acrylamide

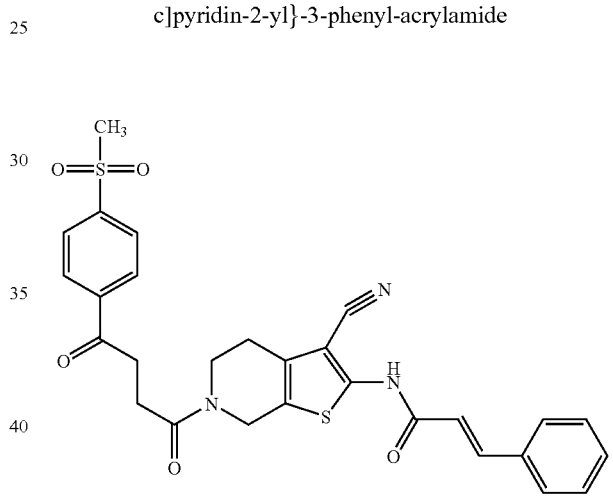

MS: Calc.: C28 H25 N3 O5 S2 (547.66). Fnd.: 548.00 [M+H].

185. (E)-N-[3-Cyano-6-(3-pyridin-3-yl-propanoyl)-4,5,6,7-tetrahydro-thieno[2,3-c]pyridin-2-yl]-3-phenyl-acrylamide

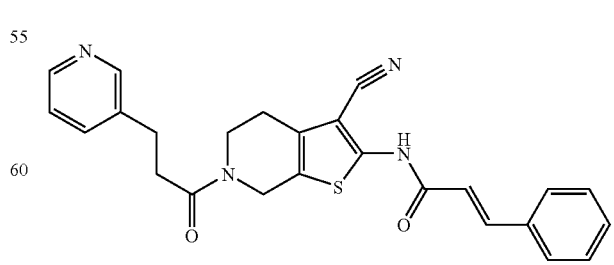

MS: Calc.: C25 H22 N4 O2 S, (442.54). Fnd.: 443.20 [M+H].

186. 5-[3-Cyano-2-((E)-3-phenyl-allanoylamino)-4,7-dihydro-5H-thieno[2,3-c]pyridin-6-yl]-5-oxo-pentanoic acid methyl ester

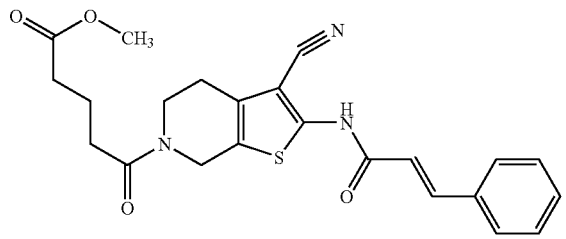

MS: Calc.: C23 H23 N3 O4 S, (437.52). Fnd.: 438.00 [M+H].

187. (E)-N-[3-Cyano-6-(2-hydroxy-ethanoyl)-4,5,6,7-tetrahydro-thieno[2,3-c]pyridin-2-yl]-3-phenyl-acrylamide

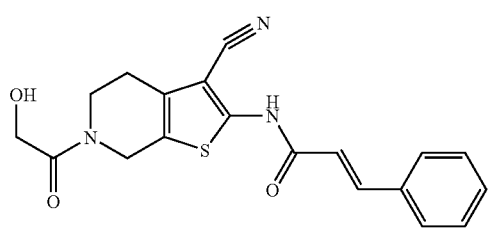

1 mmol of acetic acid 2-[3-cyano-2-((E)-3-phenyl-allanoylamino)-4,7-dihydro-5H-thieno[2,3-c]pyridin-6-yl]-2-oxo-ethyl ester are stirred in 5 ml methanol and 1 ml 45% aqueous NaOH until the reaction is completed. Purification according to the previous preparation affords the desired compound.

MS: Calc.: C19 H17 N3 O3 S, (367.43). Fnd.: 368.00 [M+H].

188. (E)-N-[3-Cyano-6-(2-imidazol-1-yl-ethanoyl)-4,5,6,7-tetrahydro-thieno[2,3-c]pyridin-2-yl]-3-phenyl-acrylamide

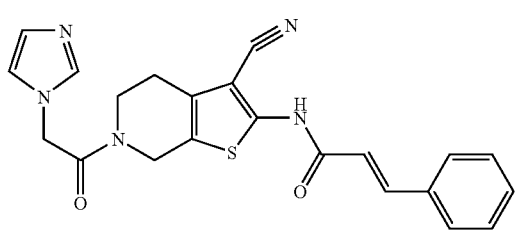

MS: Calc.: C22 H19 N5 O2 S, (417.49). Fnd.: 418.20 [M+H].

189. Acetic acid 2-[3-cyano-2-((E)-3-phenyl-allanoylamino)-4,7-dihydro-5H-thieno[2,3-c]pyridin-6-yl]-2-oxo-ethyl ester

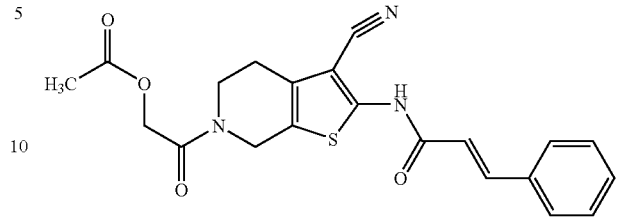

190. (E)-N-[3-Cyano-6-(4-imidazol-1-yl-butanoyl)-4,5,6,7-tetrahydro-thieno[2,3-c]pyridin-2-yl]-3-phenyl-acrylamide

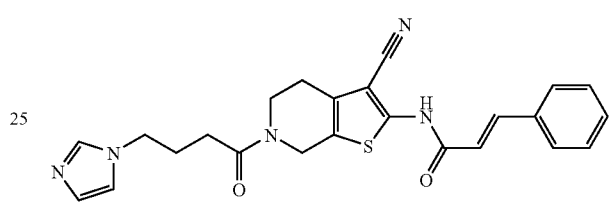

MS: Calc.: C24 H23 N5 O2 S, (445.55). Fnd.: 446.10 [M+H].

191. Acetic acid 4-[3-cyano-2-((E)-3-phenyl-allanoylamino)-4,7-dihydro-5H-thieno[2,3-c]pyridin-6-yl]-4-oxo-butyl ester

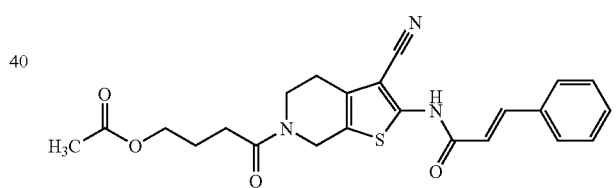

MS: Calc.: C23 H23 N3 O4 S, (437.52). Fnd.: 438.00 [M+H].

192. (E)-N-[3-Cyano-6-(4-hydroxy-butanoyl)-4,5,6,7-tetrahydro-thieno[2,3-c]pyridin-2-yl]-3-phenyl-acrylamide

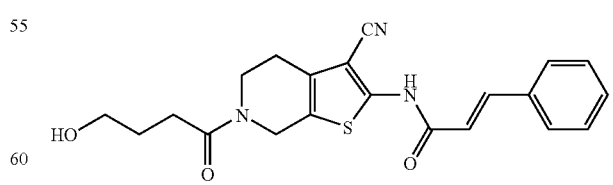

This compound is prepared in analogy to (E)-N-[3-cyano-6-(2-hydroxy-ethanoyl)-4,5,6,7-tetrahydro-thieno[2,3-c]pyridin-2-yl]-3-phenyl-acrylamide.

MS: Calc.: C21 H21 N3 O3 S, (395.48). Fnd.: 396.00 [M+H].

193. (E)-N-[3-Cyano-6-(3-pyridin-3-yl-propanoyl)-4,5,6,7-tetrahydro-thieno[2,3-c]pyridin-2-yl]-3-pyridin-3-yl-acrylamide

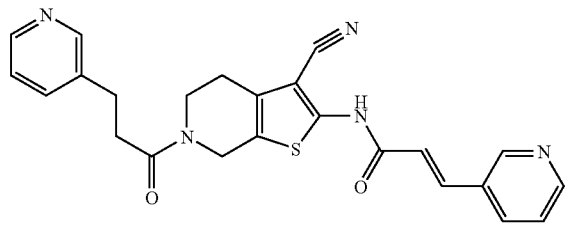

MS: Calc.: C24 H21 N5 O2 S, (443.53). Fnd.: 444.20 [M+H].

194. (E)-N-[3-Cyano-6-(2-methoxy-ethanoyl)-4,5,6,7-tetrahydro-thieno[2,3-c]pyridin-2-yl]-3-pyridin-3-yl-acrylamide

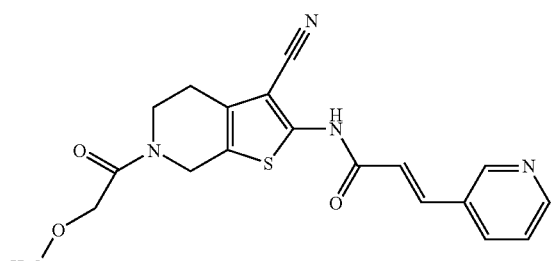

MS: Calc.: C19 H18 N4 O3 S, (382.44). Fnd.: 383.10 [M+H].

195. (E)-N-[3-Cyano-6-(3-methoxy-propanoyl)-4,5,6,7-tetrahydro-thieno[2,3-c]pyridin-2-yl]-3-pyridin-3-yl-acrylamide

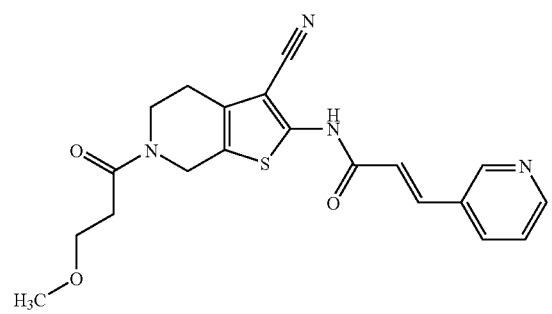

MS: Calc.: C20 H20 N4 O3 S, (396.47). Fnd.: 397.10 [M+H].

196. (E)-N-[3-Cyano-6-(2-pyridin-2-yl-ethanoyl)-4,5,6,7-tetrahydro-thieno[2,3-c]pyridin-2-yl]-3-pyridin-3-yl-acrylamide

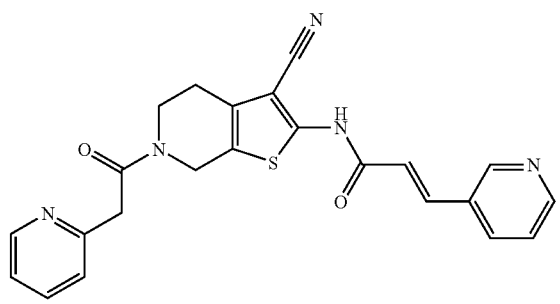

MS: Calc.: C23 H19 N5 O2 S, (429.50). Fnd.: 430.10 [M+H].

197. (E)-N-[3-Cyano-6-(3-[1,2,4]triazol-4-yl-propanoyl)-4,5,6,7-tetrahydro-thieno[2,3-c]pyridin-2-yl]-3-pyridin-3-yl-acrylamide

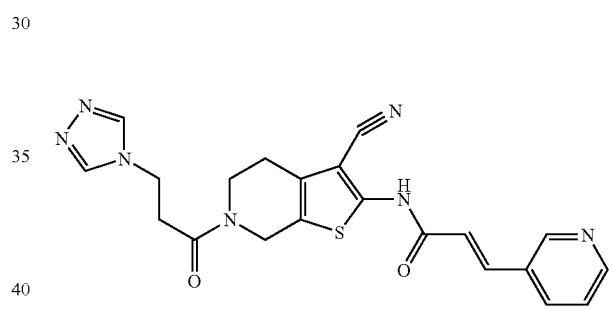

MS: Calc.: C21 H19 N7 O2 S, (433.50). Fnd.: 434.10 [M+H].

198. (E)-N-[3-Cyano-6-(3-thiazol-2-yl-propanoyl)-4,5,6,7-tetrahydro-thieno[2,3-c]pyridin-2-yl]-3-pyridin-3-yl-acrylamide

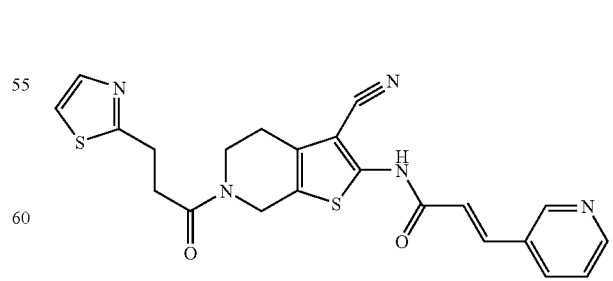

MS: Calc.: C22 H19 N5 O2 S2 (449.56). Fnd.: 450.10 [M+H].

199. 4-[3-Cyano-2-((E)-3-pyridin-3-yl-allanoy-lamino)-4,7-dihydro-5H-thieno[2,3-c]pyridin-6-yl]-4-oxo-butyric acid This compound is prepared by standard saponification of the ester function of the appropriate methyl ester.

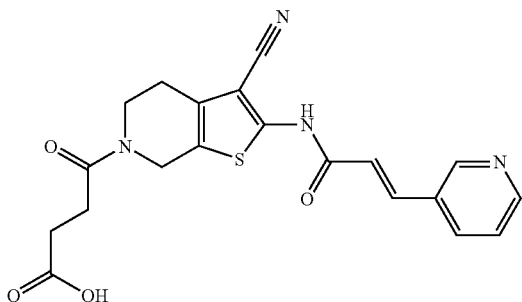

MS: Calc.: C20 H18 N4 O4 S, (410.45). Fnd.: 411.10 [M+H].

200. (E)-N-{3-Cyano-6-[2-(2-methoxy-ethoxy)-ethanoyl]-4,5,6,7-tetrahydro-thieno[2,3-c]pyridin-2-yl}-3-pyridin-3-yl-acrylamide

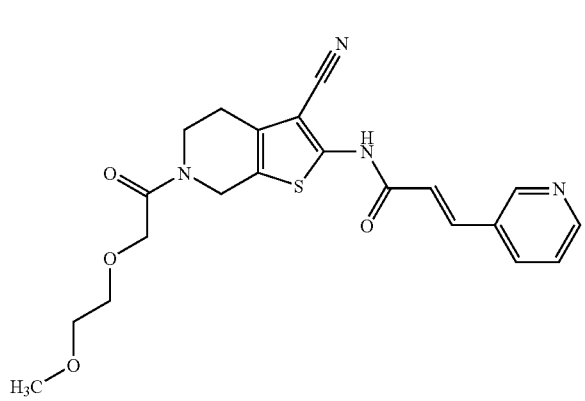

MS: Calc.: C21 H22 N4 O4 S, (426.50). Fnd.: 427.10 [M+H].

201. {3-[3-Cyano-2-((E)-3-pyridin-3-yl-allanoy-lamino-4,7-dihydro-5H-thieno[2,3-c]pyridin-6-yl]-3-oxo-propyl}-carbamic acid tert-butyl ester

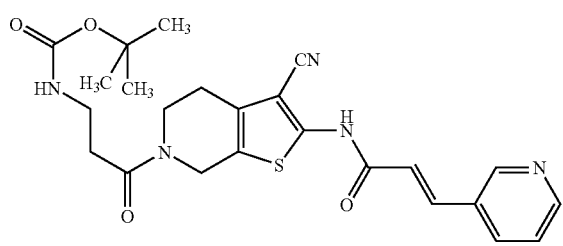

MS: Calc.: C24 H27 N5 O4 S, (481.58). Fnd.: 481.90 [M+H].

202. {4-[3-Cyano-2-((E)-3-pyridin-3-yl-allanoy-lamino)-4,7-dihydro-5H-thieno[2,3-c]pyridin-6-yl]-4-oxo-butyl}-carbamic acid tert-butyl ester

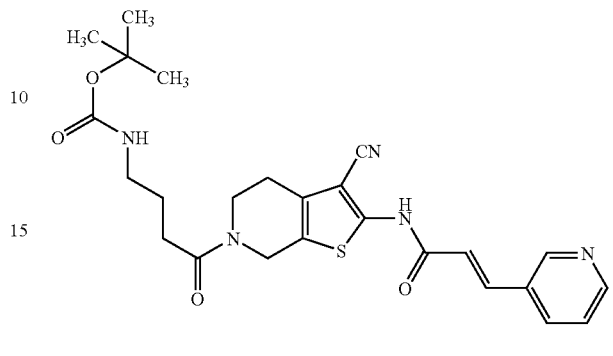

MS: Calc.: C25 H29 N5 O4 S, (495.60). Fnd.: 495.90 [M+H].

203. {2-[3-Cyano-2-((E)-3-pyridin-3-yl-allanoy-lamino)-4,7-dihydro-5H-thieno[2,3-c]pyridin-6-yl]-2-oxoethyl}-carbamic acid tert-butyl ester

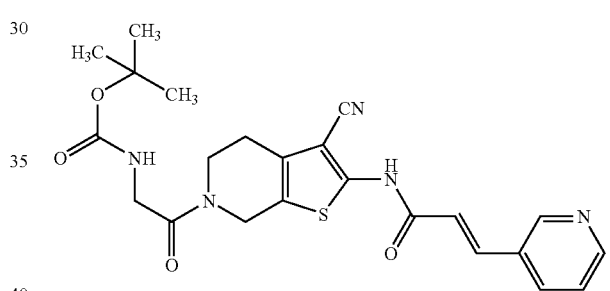

MS: Calc.: C23 H25 N5 O4 S, (467.55). Fnd.: 467.90 [M+H].

204. (E)-N-[6-(4-Amino-butanoyl)-3-cyano-4,5,6,7-tetrahydro-thieno[2,3-c]pyridin-2-yl]-3-pyridin-3-yl-acrylamide This compound is prepared by standard Boc-deprotection starting from {4-[3-cyano-2-((E)-3-pyridin-3-yl-allanoy-lamino)-4,7-dihydro-5H-thieno[2,3-c]pyridin-6-yl]-4-oxo-butyl}-carbamic acid tert-butyl ester.

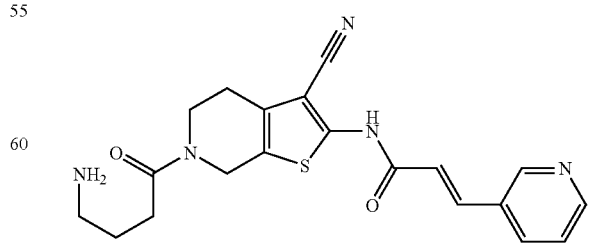

MS: Calc.: C20 H21 N5 O2 S, (395.49). Fnd.: 396.00 [M+H].

205. (E)-N-[3-Cyano-6-(2-pyridin-3-yl-ethanoyl)-4,5,6,7-tetrahydro-thieno[2,3-c]pyridin-2-yl]-3-pyridin-3-yl-acrylamide

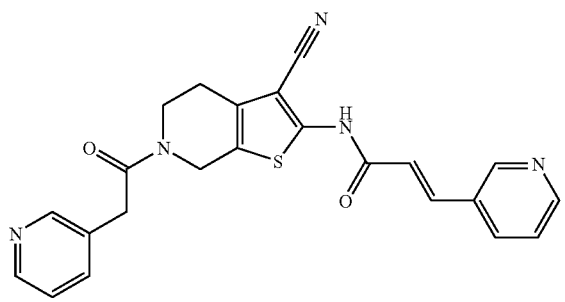

MS: Calc.: C23 H19 N5 O2 S, (429.50). Fnd.: 430.20 [M+H].

206. (E)-N-[3-Cyano-6-(3-pyridin-3-yl-propanoyl)-4,5,6,7-tetrahydro-thieno[2,3-c]pyridin-2-yl]-3-(2-methoxy-phenyl)-acrylamide

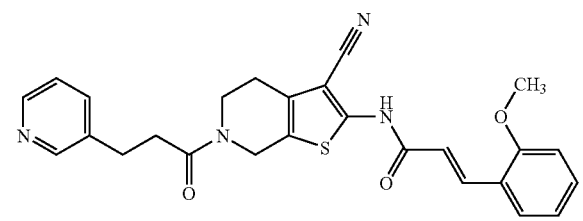

MS: Calc.: C26 H24 N4 O3 S, (472.57). Fnd.: 473.20 [M+H].

207. (E)-N-[3-Cyano-6-(2-pyridin-2-yl-ethanoyl)-4,5,6,7-tetrahydro-thieno[2,3-c]pyridin-2-yl]-3-(2-methoxy-phenyl)-acrylamide

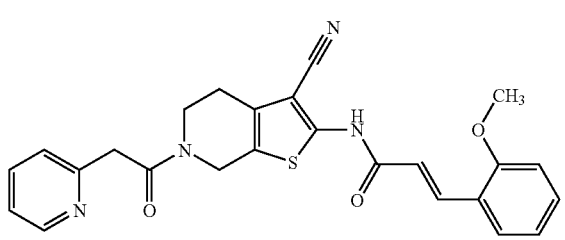

MS: Calc.: C25 H22 N4 O3 S, (458.54). Fnd.: 459.10 [M+H].

208. (E)-N-[3-Cyano-6-(2-pyridin-3-yl-ethanoyl)-4,5,6,7-tetrahydro-thieno[2,3-c]pyridin-2-yl]-3-(2-methoxy-phenyl)-acrylamide

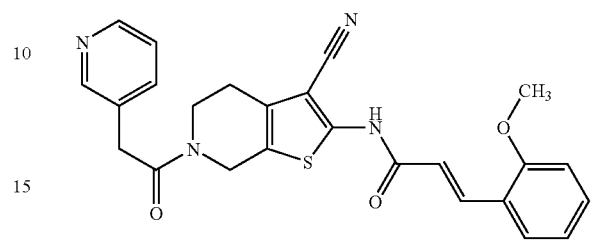

MS: Calc.: C25 H22 N4 O3 S, (458.54). Fnd.: 459.20 [M+H].

209. (E)-N-{3-Cyano-6-[2-(2-methoxy-ethoxy)-ethanoyl]-4,5,6,7-tetrahydro-thieno[2,3-c]pyridin-2-yl}-3-(2-methoxy-phenyl)-acrylamide

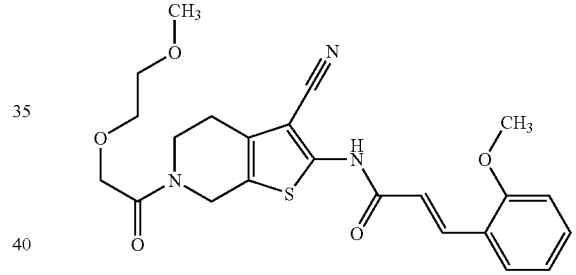

MS: Calc.: C23 H25 N3 O5 S, (455.54). Fnd.: 456.10 [M+H].

210. (E)-N-[3-Cyano-6-(2-methoxy-ethanoyl)-4,5,6,7-tetrahydro-thieno[2,3-c]pyridin-2-yl]-3-(2-methoxy-phenyl)-acrylamide

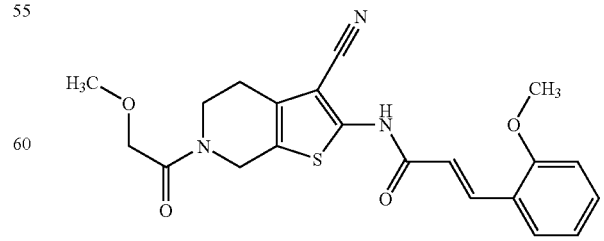

MS: Calc.: C21 H21 N3 O4 S, (411.48). Fnd.: 412.10 [M+H].

211. (E)-N-[3-Cyano-6-(3-methoxy-propanoyl)-4,5,6,7-tetrahydro-thieno[2,3-c]pyridin-2-yl]-3-(2-methoxy-phenyl)-acrylamide

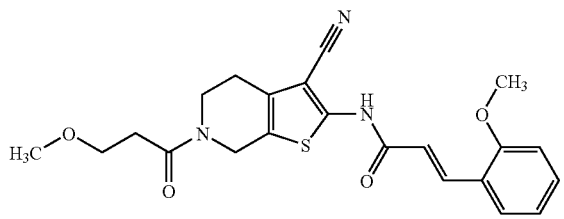

MS: Calc.: C22 H23 N3 O4 S, (425.51). Fnd.: 426.10 [M+H].

212. (E)-3-(2-Chloro-phenyl)-N-[3-cyano-6-(2-pyridin-2-yl-ethanoyl)-4,5,6,7-tetrahydro-thieno[2,3-c]pyridin-2-yl]-acrylamide

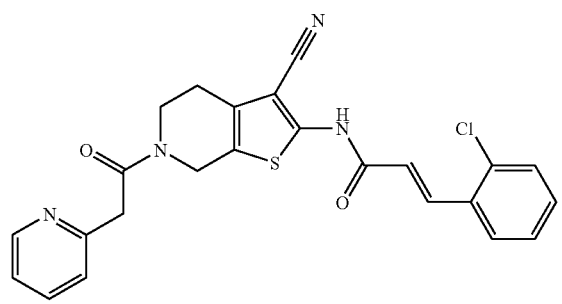

MS: Calc.: C24 H19 Cl N4 O2 S, (462.96). Fnd.: 463.30 [M+H].

213. (E)-3-(2-Chloro-phenyl)-N-[3-cyano-6-(2-pyridin-3-yl-ethanoyl)-4,5,6,7-tetrahydro-thieno[2,3-c]pyridin-2-yl]-acrylamide

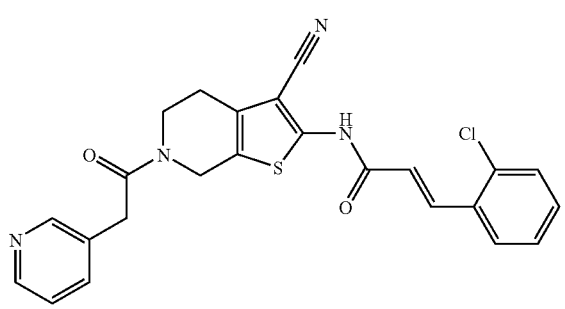

MS: Calc.: C24 H19 Cl N4 O2 S, (462.96). Fnd.: 463.10 [M+H].

214. (E)-3-(2-Chloro-phenyl)-N-[3-cyano-6-(2-pyridin-4-yl-ethanoyl)-4,5,6,7-tetrahydro-thieno[2,3-c]pyridin-2-yl]-acrylamide

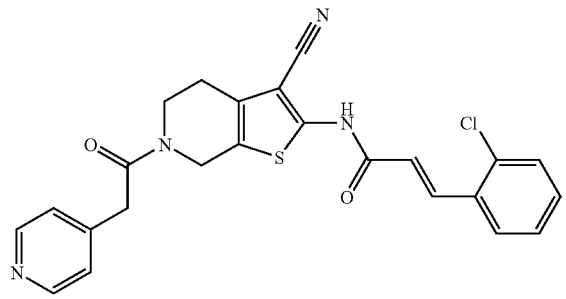

MS: Calc.: C24 H19 Cl N4 O2 S, (462.96). Fnd.: 463.20 [M+H].

215. (E)-3-(2-Chloro-phenyl)-N-[3-cyano-6-(3-pyridin-3-yl-propanoyl)-4,5,6,7-tetrahydro-thieno[2,3-c]pyridin-2-yl]-acrylamide

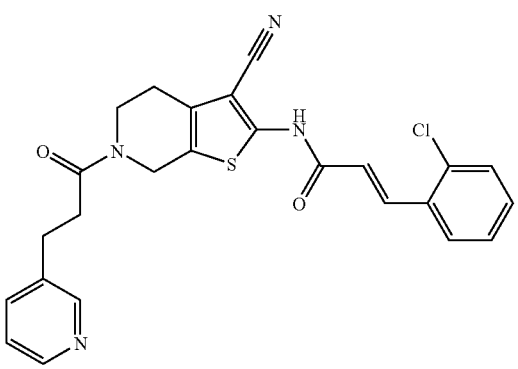

MS: Calc.: C25 H21 Cl N4 O2 S, (476.99). Fnd.: 477.20 [M+H].

216. (E)-N-[3-Cyano-6-(3-methoxy-propanoyl)-4,5,6,7-tetrahydro-thieno[2,3-c]pyridin-2-yl]-3-(2-ethoxy-phenyl)-acrylamide

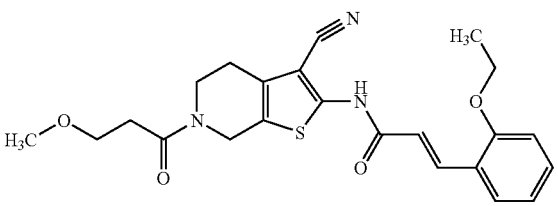

MS: Calc.: C23 H25 N3 O4 S, (439.54). Fnd.: 440.2 [M+H].

217. (E)-N-{3-Cyano-6-[2-(2-methoxy-ethoxy)-ethanoyl]-4,5,6,7-tetrahydro-thieno[2,3-c]pyridin-2-yl}-3-(2-ethoxy-phenyl)-acrylamide

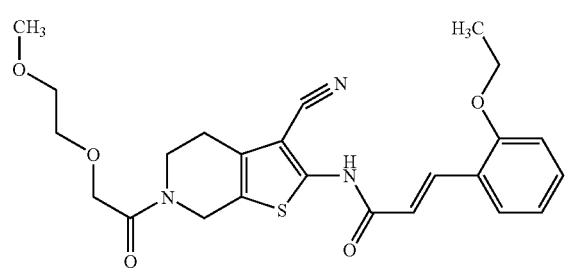

MS: Calc.: C24 H27 N3 O5 S, (469.56). Fnd.: 470.2 [M+H].

218. (E)-N-[3-Cyano-6-(2-pyridin-2-yl-ethanoyl)-4,5,6,7-tetrahydro-thieno[2,3-c]pyridin-2-yl]-3-(2-ethoxy-phenyl)-acrylamide

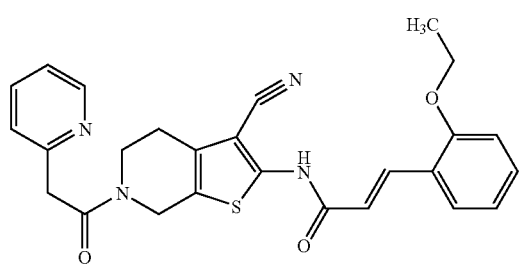

MS: Calc.: C26 H24 N4 O3 S, (472.57). Fnd.: 473.2 [M+H].

219. (E)-N-[3-Cyano-6-(2-pyridin-3-yl-ethanoyl)-4,5,6,7-tetrahydro-thieno[2,3-c]pyridin-2-yl]-3-(2-ethoxy-phenyl)-acrylamide

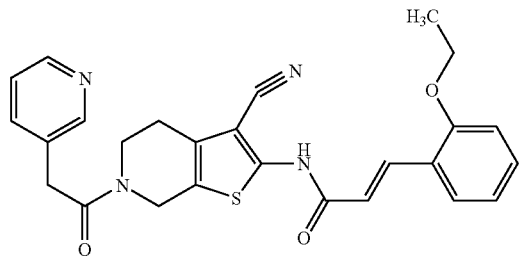

MS: Calc.: C26 H24 N4 O3 S, (472.57). Fnd.: 473.3 [M+H].

220. (E)-N-[3-Cyano-6-(3-pyridin-3-yl-propanoyl)-4,5,6,7-tetrahydro-thieno[2,3-c]pyridin-2-yl]-3-(2-ethoxy-phenyl)-acrylamide

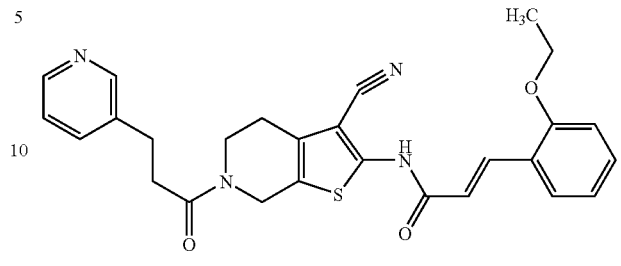

MS: Calc.: C27 H26 N4 O3 S, (486.6). Fnd.: 487.3 [M+H].

221. (E)-N-[3-Cyano-6-(3-phenyl-propanoyl)-4,5,6,7-tetrahydro-thieno[2,3-c]pyridin-2-yl]-3-(2-ethoxy-phenyl)-acrylamide

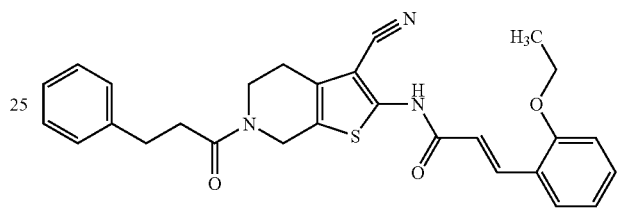

MS: Calc.: C28 H27 N3 O3 S, (485.61). Fnd.: 486.2 [M+H].

222. (E)-N-[3-Cyano-6-(3-pyridin-2-yl-propanoyl)-4,5,6,7-tetrahydro-thieno[2,3-c]pyridin-2-yl]-3-(2-ethoxy-phenyl)-acrylamide

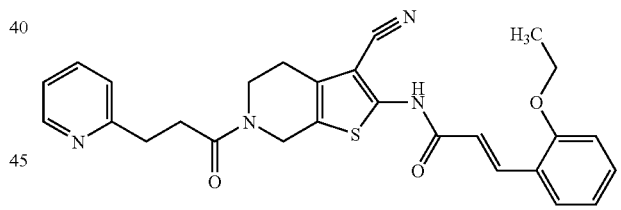

MS: Calc.: C27 H26 N4 O3 S, (486.6). Fnd.: 487.3 [M+H].

223. (E)-N-[3-Cyano-6-(2-methoxy-ethanoyl)-4,5,6,7-tetrahydro-thieno[2,3-c]pyridin-2-yl]-3-(2-ethoxy-phenyl)-acrylamide

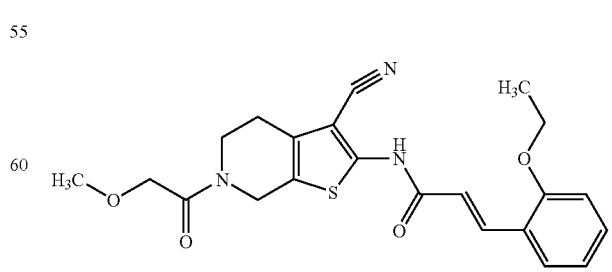

MS: Calc.: C22 H23 N3 O4 S, (425.51). Fnd.: 426.1 [M+H].

224. (E)-N-[3-Cyano-6-(3-imidazol-1-yl-propanoyl)-4,5,6,7-tetrahydro-thieno[2,3-c]pyridin-2-yl]-3-(2-ethoxy-phenyl)-acrylamide

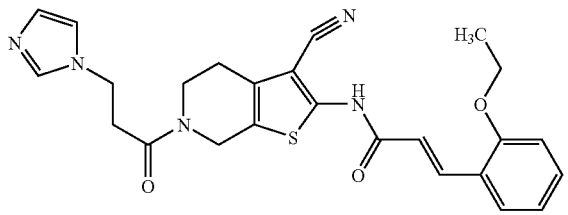

MS: Calc.: C25 H25 N5 O3 S, (475.57). Fnd.: 476.3 [M+H].

225. (E)-N-(6-Butyryl-3-cyano-4,5,6,7-tetrahydro-thieno[2,3-c]pyridin-2-yl)-3-(2-ethoxy-phenyl)-acrylamide

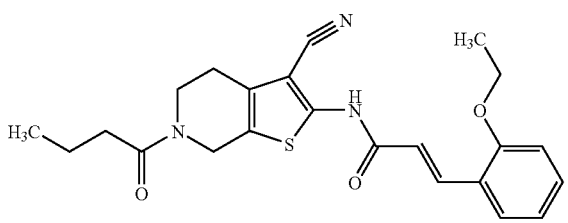

MS: Calc.: C23 H25 N3 O3 S, (423.54). Fnd.: 424.2 [M+H].

226. (E)-N-{3-Cyano-6-[2-(2-methoxy-ethoxy)ethanoyl]-4,5,6,7-tetrahydro-thieno[2,3-c]pyridin-2-yl}-3-furan-2-yl-acrylamide

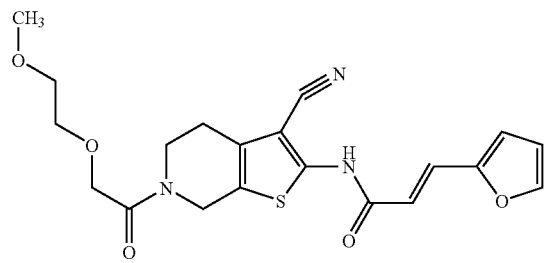

MS: Calc.: C20 H21 N3 O5 S, (415.47). Fnd.: 416.1 [M+H].

227. (E)-N-[3-Cyano-6-(2-pyridin-2-yl-ethanoyl)-4,5,6,7-tetrahydro-thieno[2,3-c]pyridin-2-yl]-3-furan-2-yl-acrylamide

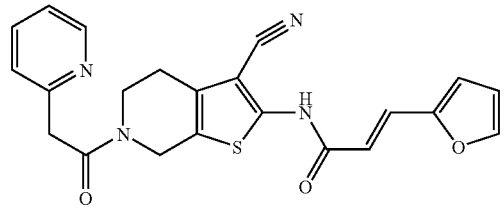

MS: Calc.: C22 H18 N4 O3 S, (418.48). Fnd.: 419.1 [M+H].

228. (E)-N-[3-Cyano-6-(2-pyridin-3-yl-ethanoyl)-4,5,6,7-tetrahydro-thieno[2,3-c]pyridin-2-yl]-3-furan-2-yl-acrylamide

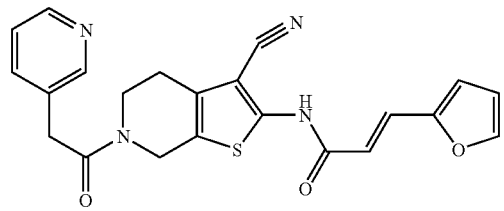

MS: Calc.: C22 H18 N4 O3 S, (418.48). Fnd.: 419.2 [M+H].

229. (E)-N-[3-Cyano-6-(3-pyridin-3-yl-propanoyl)-4,5,6,7-tetrahydro-thieno[2,3-c]pyridin-2-yl]-3-furan-2-yl-acrylamide

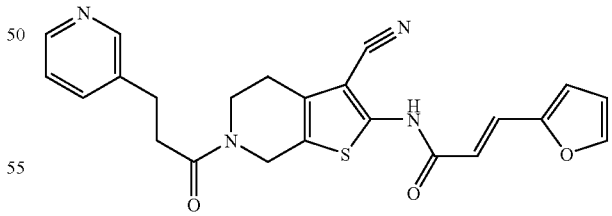

MS: Calc.: C23 H20 N4 O3 S, (432.5). Fnd.: 433.3 [M+H].

The following compounds 230 to 234 can be prepared according to general procedure AA mentioned above starting from 2-amino-3-cyano-4,7-dihydro-5H-thieno[2,3-c]pyridine-6-carboxylic acid ethyl ester and the Appropriate acrylic acid derivatives which are art-known or which can be prepared according to art-known procedures or according to general procedure H described later herein.

230. 3-Cyano-2-[(E)-3-(2,2-difluoro-benzo[1,3]di-oxol-4-yl)-allanoylamino]-4,7-dihydro-5H-thieno[2,3-c]pyridine-6-carboxylic acid ethyl ester

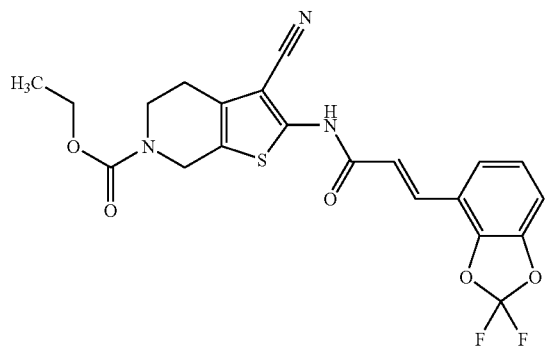

MS: Calc.: C21 H17 F2 N3 O5 S, (461.45). Fnd.: 462 [M+H].

231. 3-Cyano-2{(E), 3-[2-(1,1-difluoro-methoxy)-phenyl]-allanoylamino}-4,7-dihydro-5H-thieno[2,3-c]pyridine-6-carboxylic acid ethyl ester

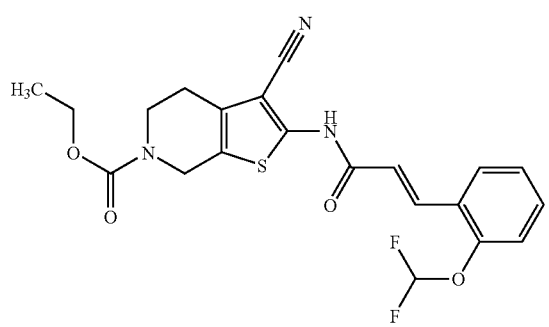

MS: Calc.: C21 H19 F2 N3 O4 S, (447.46). Fnd.: 448.1 [M+H].

232. 2-[(E)-3-(4-Bromo-benzo[1,3]dioxol-5-yl)-allanoylamino]-3-cyano-4,7-dihydro-5H-thieno[2,3-c]pyridine-6-carboxylic acid ethyl ester

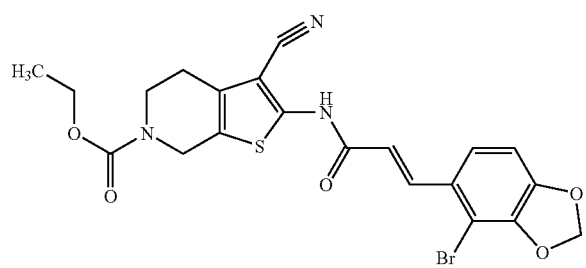

MS: Calc.: C21 H18 Br N3 O5 S, (504.36). Fnd.: 504.0+ 506.0 [M+H].

233. 3-Cyano-2-[(E)-3-(2-trifluoromethoxy-phenyl)-allanoylamino]-4,7-dihydro-5H-thieno[2,3-c]pyridine-6-carboxylic acid ethyl ester

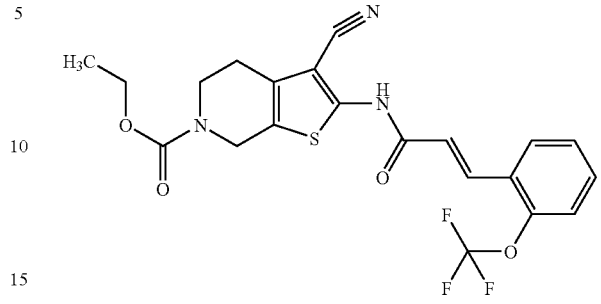

MS: Calc.: C21 H18 F3 N3 O4 S, (465.45). Fnd.: 466.2 [M+H].

234. 3-Cyano-2-((E)-3-2,3-dihydro-benzofuran-7-yl-allanoylamino)-4,7-dihydro-5H-thieno[2,3-c]pyridine-6-carboxylic acid ethyl ester

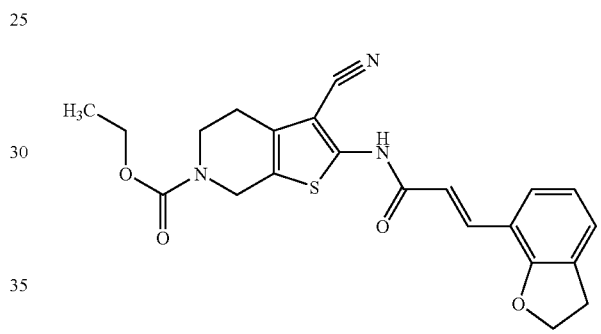

MS: Calc.: C22 H21 N3 O4 S, (423.49). Fnd.: 424.1 [M+H].

The following compounds 235 to 243 can be prepared starting from the appropriate starting compound selected from N-(3-cyano-4,5,6,7-tetrahydro-thieno[2,3-c]pyridin-2-yl)-3-(2-ethoxy-phenyl)-acrylamide and N-(3-cyano-4,5,6,7-tetrahydro-thieno[2,3-c]pyridin-2-yl)-3-(furan-2-yl)-acrylamide according to general procedure EE as described later herein.

235. 3-Cyano-2-[(E)-3-(2-ethoxy-phenyl)-allanoylamino]-4,7-dihydro-5H-thieno[2,3-c]pyridine-6-carboxylic acid 2-methoxy-ethyl ester

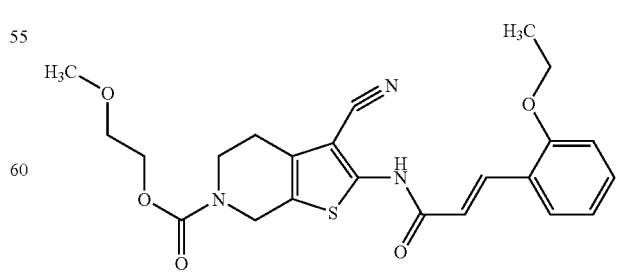

MS: Calc.: C23 H25 N3 O5 S, (455.54). Fnd.: 456.1 [M+H].

236. 3-Cyano-2-[(E)-3-(2-ethoxy-phenyl)-allanoy-lamino]-4,7-dihydro-5H-thieno[2,3-c]pyridin-6-carboxylic acid pyridin-2-ylmethyl ester

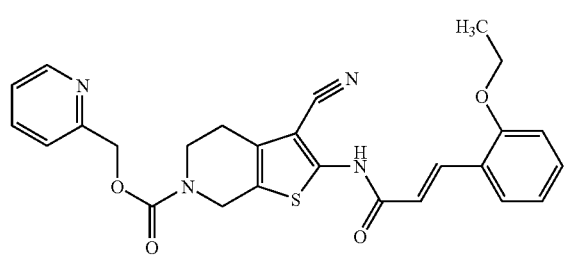

MS: Calc.: C26 H24 N4 O4 S, (488.57). Fnd.: 489.1 [M+H].

237. 3-Cyano-2-[(E)-3-(2-ethoxy-phenyl)-allanoy-lamino]-4,7-dihydro-5H-thieno[2,3-c]pyridine-6-carboxylic acid pyridin-3-ylmethyl ester

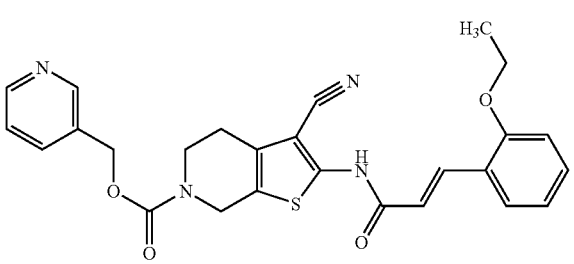

MS: Calc.: C26 H24 N4 O4 S, (488.57). Fnd.: 489.3 [M+H].

238. 3-Cyano-2-[(E)-3-(2-ethoxy-phenyl)-allanoy-lamino]-4,7-dihydro-5H-thieno[2,3-c]pyridine-6-carboxylic acid pyridin-4-ylmethyl ester

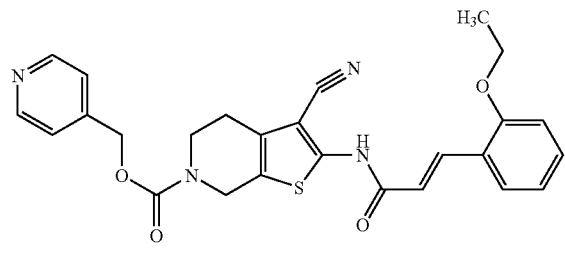

MS: Calc.: C26 H24 N4 O4 S, (488.57). Fnd.: 489.3 [M+H].

239. 3-Cyano-2-[(E)-3-(2-ethoxy-phenyl)-allanoy-lamino]-4,7-dihydro-5H-thieno[2,3-c]pyridine-6-carboxylic acid 2-pyridin-2-yl-ethyl ester

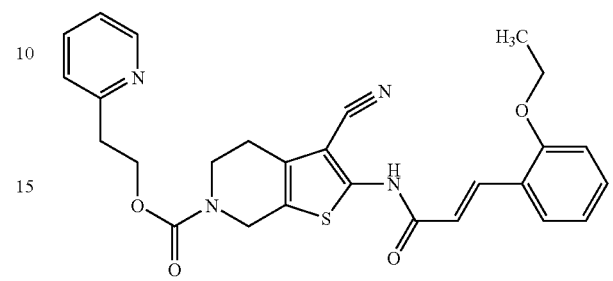

MS: Calc.: C27 H26 N4 O4 S, (502.6). Fnd.: 503.3 [M+H].

240. 3-Cyano-2-((E)-3-furan-2-yl-allanoylamino)-4,7-dihydro-5H-thieno[2,3-c]pyridine-6-carboxylic acid 2-methoxy-ethyl ester

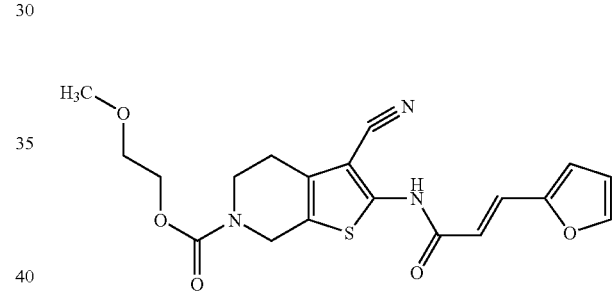

MS: Calc.: C19 H19 N3 O5 S, (401.44). Fnd.: 402.1 [M+H].

241. 3-Cyano-2-((E)-3-furan-2-yl-allanoylamino)-4,7-dihydro-5H-thieno[2,3-c]pyridine-6-carboxylic acid pyridin-2-ylmethyl ester

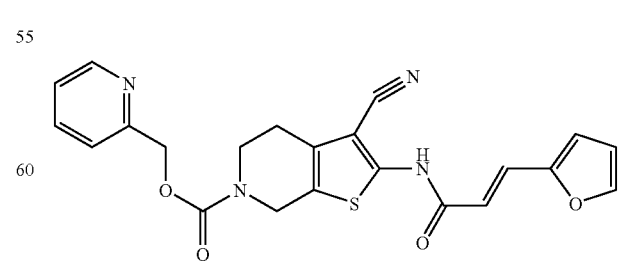

MS: Calc.: C22 H18 N4 O4 S, (434.48). Fnd.: 435.2 [M+H].

242. 3-Cyano-2-((E)-3-furan-2-yl-allanoylamino)-4,7-dihydro-5H-thieno[2,3-c]pyridine-6-carboxylic acid pyridin-3-ylmethyl ester

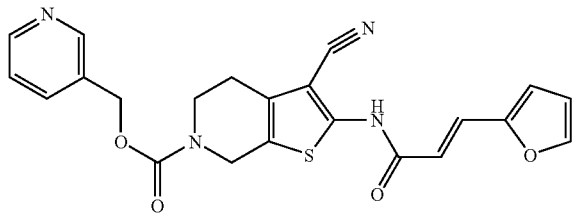

MS: Calc.: C22 H18 N4 O4 S, (434.48). Fnd.: 435.3 [M+H].

243. 3-Cyano-2-((E)-3-furan-2-yl-allanoylamino)-4,7-dihydro-5H-thieno[2,3-c]pyridine-6-carboxylic acid 2-pyridin-2-yl-ethyl ester

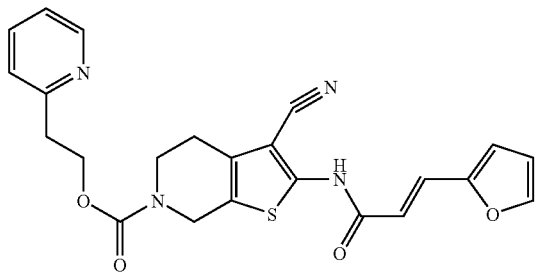

MS: Calc.: C23 H20 N4 O4 S, (448.5). Fnd.: 449.2 [M+H].

244. 3-Cyano-2-((E)-3-furan-2-yl-allanoylamino)-4,7-dihydro-5H-thieno[2,3-c]pyridine-6-carboxylic acid pyridin-4-yl-methyl ester

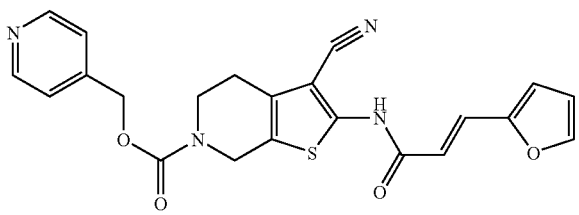

The title compound may be obtained analogously as described for Example 243.

The following compound 245 can be prepared according to general procedure G described below starting from N-(3-cyano-4,5,6,7-tetrahydro-thieno[2,3-c]pyridin-2-yl)-3-(2-ethoxy-phenyl)-acrylamide and the appropriate isocyanate or amine/carbonyldiimidazole.

245. 3-Cyano-2-[(E)-3-(2-ethoxy-phenyl)-allanoylamino]-4,7-dihydro-5H-thieno[2,3-c]pyridine-6-carboxylic acid ethylamide

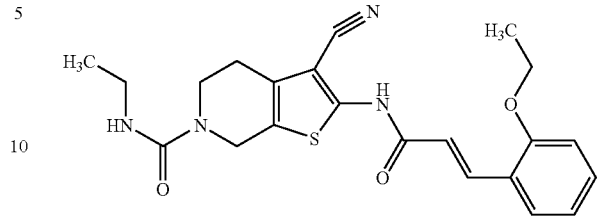

MS: Calc.: C22 H24 N4 O3 S, (424.53). Fnd.: 425.1 [M+H].

The following compounds 246 to 251 may be prepared according to general procedure FF described later herein starting from N-(3-cyano-4,5,6,7-tetrahydro-thieno[2,3-c]pyridin-2-yl)-3-(2-ethoxy-phenyl)-acrylamide or N-(3-cyano-4,5,6,7-tetrahydro-thieno[2,3-c]pyridin-2-yl)-3-(furan-2-yl)-acrylamide respectively.

246. 3-Cyano-2-[(E)-3-(2-ethoxy-phenyl)-allanoylamino]-4,7-dihydro-5H-thieno[2,3-c]pyridine-carbothioic acid S-ethyl ester 247. 3-Cyano-2-[(E)-3-(furan-2-yl)-allanoylamino]-4,7-dihydro-5H-thieno[2,3-c]pyridine-6-carbothioic acid S-ethyl ester 248. 3-Cyano-2-[(E)-3-(2-ethoxy-phenyl)-allanoylamino]-4,7-dihydro-5H-thieno[2,3-c]pyridine-carbothioic acid S-(2-pyridin-4-yl-ethyl)ester 249. 3-Cyano-2-[(E)-3-(furan-2-yl)-allanoylamino]-4,7-dihydro-5H-thieno[2,3-c]pyridine-6-carbothioic acid S-(2-pyridin-4-yl-ethyl)ester 250. 3-Cyano-2-[(E)—(2-ethoxy-phenyl)-allanoylamino]-4,7-dihydro-5H-thieno[2,3-c]pyridine-carbothioic acid S-(2-pyridin-2-yl-ethyl)ester 251. 3-Cyano-2-[(E)-3-furan-2-yl)-allanoylamino]-4,7-dihydro-5H-thieno[2,3-c]pyridine-6-carbothioic acid S-(2-pyridin-2-yl-ethyl)ester Starting Materials:

A1 2-Amino-3-cyano-4,7-dihydro-thieno[2,3-c]pyridine-6(5H)-carboxylic acid ethyl ester

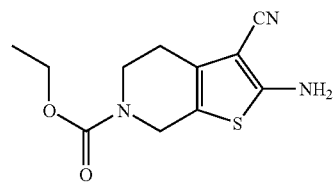

Prepared according to general procedure B described below starting from N-carbethoxy-4-piperidone.

MS: Calc.: $C_{11}H_{13}N_3O_2S$, (251.31). Fnd.: 252.0 [M+H].

B. General Procedure for Condensed 2-Amino-Thiophene-3-Carbonitrile Derivatives 500 mmol of cyclic ketone and 500 mmol of malononitrile are dissolved in a minimal volume of ethanol and 500 mmol elemental sulfur are added. After addition of 500 mmol diethyl amine, the reaction mixture is heated to 60-70° C. for some minutes and then stirred at room temperature for several hours. The reaction mixture is poured on ice/water and the precipitate filtered off. In case there is no or only some precipitate formed, the aqueous layer is extracted several times with dichloromethane or another appropriate organic solvent, the combined organic layers are dried (e.g. MgSO$_4$) and concentrated in vacuo. Purification of the crude product is achieved by flash chromatography and/or recrystallization from an appropriate solvent (e.g. ethanol).

A2. 2-Amino-3-cyano-4,7-dihydro-thieno[2,3-c]pyridine-6(5H)-carboxylic acid 1,1-dimethylethyl ester

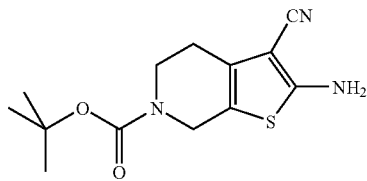

Prepared according to general procedure B starting from Boc-4-piperidone.
MS: Calc.: C$_{13}$H$_{17}$N$_3$O$_2$S, (279.36). Fnd.: 280.0 [M+H].

B1. N-(3-Cyano-4,5,6,7-tetrahydro-thieno[2,3-c]pyridin-2-yl)-3-phenyl-acrylamide

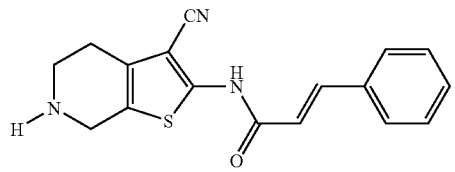

Prepared according to general procedure C described below starting from N-(6-tertbutoxycarbonyl-3-cyano-4,5,6,7-tetrahydro-thieno[2,3-c]pyridin-2-yl)-3-phenyl-acrylamide (compound 2).
MS: Calc.: C$_{17}$H$_{15}$N$_3$OS, (309.39). Fnd.: 310.0 [M+H].

B2. N-(3-Cyano-4,5,6,7-tetrahydro-thieno[2,3-c]pyridin-2-yl)-3-(pyridin-3-yl)acrylamide

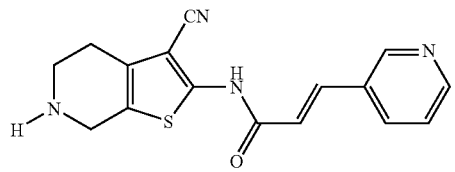

The title compound can be prepared according to general procedure C described below starting from 3-cyano-2-((E)-3-pyridin-3-yl-allanoylamino)-4,7-dihydro-5H-thieno[2,3-c]pyridine-6-carboxylic acid tert-butyl ester (compound 32).

Using similar procedures as described for the compounds B1 or B2, but with suitable choice of starting materials, the following compounds may be prepared:

B3. N-(3-Cyano-4,5,6,7-tetrahydro-thieno[2,3-c]pyridin-2-yl)-3-(2-methoxyphenyl)-acrylamide
B4. N-(3-Cyano-4,5,6,7-tetrahydro-thieno[2,3-c]pyridin-2-yl)-3-(2-ethoxyphenyl)-acrylamide
B5. N-(3-Cyano-4,5,6,7-tetrahydro-thieno[2,3-c]pyridin-2-yl)-3-(2-chlorophenyl)-acrylamide
B6. N-(3-Cyano-4,5,6,7-tetrahydro-thieno[2,3-c]pyridin-2-yl)-3-(2-methylphenyl)-acrylamide
B7. N-(3-Cyano-4,5,6,7-tetrahydro-thieno[2,3-c]pyridin-2-yl)-3-(2-methoxy-3-methyl-phenyl)-acrylamide
B8. N-(3-Cyano-4,5,6,7-tetrahydro-thieno[2,3-c]pyridin-2-yl)-3-(2-ethoxy-3-methyl-phenyl)-acrylamide
B9. N-(3-Cyano-4,5,6,7-tetrahydro-thieno[2,3-c]pyridin-2-yl)-3-(2-methoxy-5-methyl-phenyl)-acrylamide
B10. N-(3-Cyano-4,5,6,7-tetrahydro-thieno[2,3-c]pyridin-2-yl)-3-(2-ethoxy-5-methyl-phenyl)-acrylamide
B11. N-(3-Cyano-4,5,6,7-tetrahydro-thieno[2,3-c]pyridin-2-yl)-3-(2-ethoxy-3-methoxy-phenyl)-acrylamide
B12. N-(3-Cyano-4,5,6,7-tetrahydro-thieno[2,3-c]pyridin-2-yl)-3-(2-ethoxy-5-methoxy-phenyl)-acrylamide
B13. N-(3-Cyano-4,5,6,7-tetrahydro-thieno[2,3-c]pyridin-2-yl)-3-(2,3-dimethoxy-phenyl)-acrylamide
B14. N-(3-Cyano-4,5,6,7-tetrahydro-thieno[2,3-c]pyridin-2-yl)-3-(2,5-dimethoxy-phenyl)-acrylamide
B15. N-(3-Cyano-4,5,6,7-tetrahydro-thieno[2,3-c]pyridin-2-yl)-3-(2-methyl-3-methoxy-phenyl)-acrylamide
B16. N-(3-Cyano-4,5,6,7-tetrahydro-thieno[2,3-c]pyridin-2-yl)-3-(2-methyl-5-methoxy-phenyl)-acrylamide
B17. N-(3-Cyano-4,5,6,7-tetrahydro-thieno[2,3-c]pyridin-2-yl)-3-(2,3-dimethyl-phenyl)-acrylamide
B18. N-(3-Cyano-4,5,6,7-tetrahydro-thieno[2,3-c]pyridin-2-yl)-3-(2,5-dimethyl-phenyl)-acrylamide
B19. N-(3-Cyano-4,5,6,7-tetrahydro-thieno[2,3-c]pyridin-2-yl)-3-(2-chloro-3-methoxy-phenyl)-acrylamide
B20. N-(3-Cyano-4,5,6,7-tetrahydro-thieno[2,3-c]pyridin-2-yl)-3-(2-chloro-5-methoxy-phenyl)-acrylamide
B21. N-(3-Cyano-4,5,6,7-tetrahydro-thieno[2,3-c]pyridin-2-yl)-3-(2-chloro-3-methyl-phenyl)-acrylamide
B22. N-(3-Cyano-4,5,6,7-tetrahydro-thieno[2,3-c]pyridin-2-yl)-3-(2-chloro-5-methyl-phenyl)-acrylamide
B23. N-(3-Cyano-4,5,6,7-tetrahydro-thieno[2,3-c]pyridin-2-yl)-3-(furan-2-yl)-acrylamide
B24. N-(3-Cyano-4,5,6,7-tetrahydro-thieno[2,3-c]pyridin-2-yl)-3-(furan-3-yl)-acrylamide

C. General Procedure for Removal of Boc Protecting Groups

The Boc protected compound is dissolved in dichloromethane/trifluoroacetic acid (TFA) (2/3) and stirred for several hours at room temperature. After evaporation of the solvent and recristalization from an appropriate solvent (e.g. ethanol), the desired product is obtained as TFA salt. The TFA salt may be converted into the free base in a manner customary per se to the skilled person.

D. General Procedure for Sulfonamide Bond Formation 100 mmol of the amine and 150 mmol of the sulfonyl chloride are dissolved in pyridine and stirred for some time at room temperature and, if necessary, is heated for some time either by conventional or microwave assisted heating. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. MgSO$_4$) and concentrated in vacuo. Purification of the crude product is achieved by flash chromatography and/or recristalization from an appropriate solvent (e.g. ethanol).

E. General Procedure for Carbamate Formation 100 mmol pyridine and 65 mmol triphosgene are dissolved in dichloromethane. 65 mmol of the alcohol are added at 0° C. and the reaction is stirred at room temperature for 3 hours. This solution is added to 200 mmol of the amine in dichloromethane at −78° C. and the reaction mixture is allowed to warm to room temperature and stirred for some time. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. $MgSO_4$) and concentrated in vacuo. Purification of the crude product is achieved by flash chromatography and/or recristalization from an appropriate solvent (e.g. ethanol).

EE. Alternative General Procedure for the Preparation of Carbamates

A) Preparation of the imidazole 1-carboxylic ester reagents:

A solution of the appropriate alcohol (10 mmol), 1,1'-carbonyldiimidazole (10 mmol) in dichloromethane (20 ml) is stirred at room temperature for 2 to 3 h while the reaction is monitored by TLC. Then the reaction mixture is extracted by three portions of 10% sodium hydrogencarbonate solution and once by water. The organic layer is dried over sodium sulfate and evaporated to yield a pale yellow oil or colorless solid.

B) Synthesis of carbamates:

To a suspension of the appropriate base (1 mmol) and reagent (1 mmole) in abs. dichloromethane (15 ml), DBU (1.15 mmol) is added and the mixture is stirred for 2 to 7 days, the reaction is monitored by TLC (silica, dichloromethane-methanol 10:1 mixture as an eluent). The reaction mixture is extracted twice by 10% sodium hydrogencarbonate solution, once by water, and the organic layer is dried over sodium sulfate. After evaporation the residue is treated with diethyl ether, the obtained solid is filtered off, washed with a small amount of acetonitrile and finally with diethyl ether. The crude product (51-81%) can be recrystallized from acetonitrile to yield the purified product (34-73%).

C) In case the appropriate chloroformates are commercially available 1 mmol of the chloroformate is reacted with 1 mmol of the amino building block in pyridine. After the reaction is completed, the solvent is removed and the remaining crude product purified as described above.

F. General Procedure for Thiocarbamate Formation 1 equivalent of the amine and 1.3 equivalents of the appropriate chlorothioformate are stirred in pyridine for 3 h at ambient temperature. The mixture is concentrated and the thiocarbamate is crystallized from ethanol and/or purified by flash chromatography on silica gel.

FF. Alternative General Procedure for Thiocarbamate Formation a) Preparation of the imidazole 1-carboxylic thioester reagents: A solution of the appropriate thiol (10 mmol), 1,1'-carbonyldiimidazole (10 mmol) in abs. tetrahydrofurane (20 ml) is stirred at room temperature for 2 to 3 h, the reaction is monitored by TLC. The reaction mixture is extracted by three portions of 10% sodium hydrogencarbonate solution and once by water. The organic layer is dried over sodium sulfate, evaporated to yield a pale yellow oil or colorless solid.

b) Synthesis of thiocarbamates: To a suspension of the appropriate base (1 mmol) and reagent (1 mmole) in abs. dichloromethane (20 ml), DBU (1.2 mmol) is added, the mixture is stirred for 1 to 2 days, the reaction is monitored by TLC (silica, dichloromethane/ethyl acetate 10:1 mixture as an eluent, or, in some cases, ethyl acetate/methanol 1:1). The reaction mixture is extracted twice by 10% sodium hydrogencarbonate solution, once by water, and the organic layer is dried over sodium sulfate. After evaporation the residue is purified by column chromatography.

G. General Procedure for Urea Formation 1 equivalent of the amine and 1 equivalent of the appropriate isocyanate are stirred in dichloromethane over night at ambient temperature. The mixture is concentrated and the residue is subjected to flash chromatography on silica gel (eluent dichloromethane/methanol).

Alternatively, 1 equivalent of the amine, 1 equivalent of N,N-carbonyldiimidazole and 1 equivalent of the second amine are stirred in a suitable solvent, e.g. dichloromethane, over night at ambient temperature. The mixture is concentrated and the residue is subjected to flash chromatography on silica gel.

H. General Procedure for the Formation of Acrylic Acid/Cinnamic Acid Derivatives The appropriate aldehyde and 1.3 eq triethylphosphonoacetate are dissolved in THF and 1 eq DBU is added at 0° C. After stirring until completion of the reaction, 1N HCl (aq) is added and the reaction mixture extracted with dichloromethane. The organic layer is dried over $MgSO_4$ and the solvent removed. The crude ethyl ester is used for the next reaction step.

The crude ethyl ester is suspended in 1N NaOH and the reaction mixture stirred until completion of the reaction (if necessary some THF is added). Then 1N HC (is added until the reaction mixture is slightly acidic and the mixture is extracted with diethylether. The ethereal layer is dried over $MgSO_4$ and the solvent removed. The crude acrylic acid/cinnamic acid derivative is used for the reactions mentioned herein.

It is to be stated, that the person skilled in the art can apply—on the base of his/her expert knowledge, general art and/or analogous or similar art-known procedures—starting from the starting compounds, which are mentioned herein or which can be prepared analogously to the mentioned compounds, the general procedures described herein to the synthesis of those specific examples mentioned herein and further specific examples encompassed from the scope of the present invention.

COMMERCIAL APPLICABILITY

The compounds according to the present invention have miscellaneous valuable pharmacological properties which can make them commercially applicable.

The compounds according to the invention therefore can be employed as therapeutic agents for the treatment and prophylaxis of diseases in human and veterinary medicine.

Thus, for example, in more embodimental detail, the compounds according to this invention are potent and highly efficacious cell-cycle specific inhibitors of cellular (hyper)

proliferation and/or inducers of apoptosis in cancer cells. Therefore, these compounds are expected to be useful for treating (hyper)proliferative diseases and/or disorders responsive to the induction of apoptosis, in particular cancer.

Further on, these compounds can be useful in the treatment of benign or malignant neoplasia. A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by limitless replicative potential and aberrant cell proliferation ("hyperproliferation") as well as evasion from apoptosis. These diseases include benign hypoplasia like that of the prostate ("BPH") or colon epithelium. Most importantly these diseases include malignant neoplasia commonly described as cancer and characterized by tumor cells finally metastasizing into distinct organs or tissues. Malignant neoplasia include solid and hematological tumors. Solid tumors are exemplified by tumors of the breast, bladder, bone, brain, central and peripheral nervous system, colon, endocrine glands (eg thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasia include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

Compounds according to the present invention can be commercially applicable for treatment, prevention or amelioration of the diseases of benign and malignant behavior as described before. Neoplastic cell proliferation might effect normal cell behaviour and organ function. For example the formation of new blood vessels, a process described as neovascularization, is induced by tumors or tumor metastases. Compounds according to this invention can be commercially applicable for treatment of pathophysiological relevant processes caused by benign or neoplastic cell proliferation, such as, but not limited to, neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps or mutation within the cellular target protein. The commercial applicability of compounds according to this invention is not limited to $1^{st}$ line treatment of patients. Patients with resistance to defined cancer chemotherapeutics or target specific anti-cancer drugs ($2^{nd}$ or $3^{rd}$ line treatment) can be also amenable for treatment with compounds according to this invention.

The compounds according to the present invention display a cell cycle dependent cytotoxic activity, more precisely a mitosis confined activity, leading to a mitotic arrest which inevitably results in the onset of apoptosis and/or cell death.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds according to this invention.

The present invention further includes a method useful to modulate apoptosis and/or aberrant cell growth in the therapy of benign or malignant neoplastic diseases, such as e.g. cancer, comprising administering to a subject in need of such therapy a pharmacologically active and therapeutically effective and tolerable amount of one or more of the compounds according to this invention.

The present invention further relates to the use of the compounds according to this invention for the production of pharmaceutical compositions which are employed for the treatment, prophylaxis, inhibition and/or amelioration of the illnesses mentioned.

The present invention further relates to the use of the compounds according to this invention for the production of pharmaceutical compositions which can be used in the treatment, prevention or amelioration of (hyper)proliferative diseases of benign or malignant behaviour and/or disorders responsive to the induction of apoptosis in a mammal, such as, for example, benign or malignant neoplasia, e.g. cancer.

The present invention further relates to the use of the compounds according to this invention for the production of pharmaceutical compositions which can be used use in the treatment, prevention or amelioration of disorders responsive to arresting aberrant cell growth and/or induction of apoptosis.

The present invention further relates to pharmaceutical compositions comprising one or more of the compounds according to this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to combinations comprising one or more of the compounds according to this invention and pharmaceutically acceptable auxiliaries, excipients or vehicles, e.g. for use in the treatment, prevention or amelioration of benign or malignant neoplasia, such as e.g. cancer.

The present invention further relates to a composition consisting essentially of a therapeutically effective and tolerable amount of one or more tetrahydropyridothiophene compounds according to this invention together with the usual pharmaceutically acceptable vehicles, diluents and/or excipients for use in therapy, e.g. for treating, preventing or ameliorating hyperproliferative diseases, such as e.g. cancer, and/or disorders responsive to induction of apoptosis.

The present invention further relates to compounds according to this invention for use in therapy, such as, for example, in the treatment, prevention or amelioration of (hyper)proliferative diseases of benign or malignant behaviour and/or disorders responsive to the induction of apoptosis, such as e.g. those diseases mentioned herein, particularly cancer.

The present invention further relates to compounds according to this invention having anti-proliferative and/or apoptosis inducing activity.

The present invention further relates to pharmaceutical compositions according to this invention having anti-proliferative activity.

The present invention further relates to pharmaceutical compositions according to this invention having apoptosis inducing activity.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Additionally, the invention relates to an article of manufacture, which comprises packaging material and a pharmaceutical agent contained within said packaging material, wherein the pharmaceutical agent is therapeutically effective inhibiting cellular (hyper)proliferation and/or inducing apoptosis, ameliorating the symptoms of a (hyper)proliferative disorder and/or a disease responsive to the induction of apoptosis, and wherein the packaging material comprises a label or package insert which indicates that the pharmaceutical agent is useful for preventing or treating a (hyper)proliferative disorder and/or a diseases responsive to the induction of apoptosis, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention can be prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before.

In one particular embodiment, compounds according to this invention may be combined with one or more art-known anti-cancer agents, such as e.g. with one or more chemotherapeutic and/or target specific anti-cancer agents as described below.

Examples of known chemotherapeutic anti-cancer agents frequently used for combination therapy include, but not are limited to (i) alkylating/carbamoylating agents such as Cyclophosphamide (Endoxan®), Ifosfamid (Holoxan®), Thiotepa (Thiothepa Lederle®), Melphalan (Alkeran®), or chloroethylnitrosourea (BCNU); (ii) platinum derivatives like cis-platin (Platinex® BMS), oxaliplatin or carboplatin (Carboplat® BMS); (iii) antimitotic agents/tubulin inhibitors such as vinca alkaloids (vincristine, vinblastine, vinorelbine), taxanes such as Taxol (Paclitaxel®), Taxotere (Docetaxel®) and analogs as well as new formulations and conjugates thereof; (iv) topoisomerase inhibitors such as anthracyclines such as Doxorubicin (Adriblastin®), epipodophyllotoxines (such as Etoposide (Etopophos®) and camptothecin analogs such as Topotecan (Hycamtin®); (v) pyrimidine antagonists such as 5-fluorouracil (5-FU), Capecitabine (Xeloda®), Ara-binosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) and pernetrexed (Alimta®).

Examples of target specific anti-cancer drug classes used in experimental or standard cancer therapy include but are not limited to (i) kinase inhibitors such as e.g. Glivec (Imatinib®), ZD-1839/Iressa (Gefitinib®), Bay43-9006 (Sorafenib®), SU11248 (Sutent®) or OSI-774/Tarceva (Erlotinib®); (ii) proteasome inhibitors such as PS-341 (Velcade®); (iii) histone deacetylase inhibitors like SAHA, PXD101, MS275, MGCD0103, Depsipeptide/FK228, NVP-LBH589, Valproic acid (VPA) and butyrates; (iv) heat shock protein inhibitors like 17-allylaminogeldanamycin (17-AAG); (v) vascular targeting agents (VAT) and anti-angiogenic drugs like the VEGF antibody Avastin (Bevacizumab®) or the KDR tyrosine kinase inhibitor PTK787/ZK222584 (Vatalanib®); (vi) monoclonal antibodies such as Herceptin (Trastuzumab®) or MabThera/Rituxan (Rituximab®) or C225/Erbitux (Cetuximab®) as well as mutants and conjugates of monoclonal antibodies and antibody fragments; (vii) oligonucleotide based therapeutics like G-3139/Genasense (Oblimersen®); (viii) protease inhibitors (ix) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Other known anti-cancer agents which can be used for combination therapy include bleomycin, retinoids such as all-trans retinoic acid (ATRA), DNA methyltransferase inhibitors such as the 2-deoxycytidine derivative Decitabine (Docagen®), alanosine, cytokines such as interleukin-2 or interferons such as interferon α2 or interferon-γ, TRAIL, DR4/5 agonistic antibodies, FasL- and TNF-R agonists.

As exemplary chemotherapeutic/anti-cancer agents, which can be useful in the combination therapy according to the present invention the following drugs may be mentioned, without being restricted thereto, 5 FU, actinomycin D, ABARELIX, ABCIXIMAB, ACLARUBICIN, ADA-PALENE, ALEMTUZUMAB, ALTRETAMINE, AMINO-GLUTETHIMIDE, AMIPRILOSE, AMRUBICIN, ANAS-TROZOLE, ANCITABINE, ARTEMISININ, AZATHIOPRINE, BASILIXI MAB, BEN DAMUSTINE, BEXXAR, BICALUTAMIDE, BLEOMYCIN, BROXURIDINE, BUSULFAN, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEGFILGRASTIM, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE, VOROZOLE, and ZEVALIN.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents, such as e.g. those mentioned above.

In this context, the present invention further relates to a combination comprising
a first active ingredient, which is at least one tetrahydropyridothiophene compound according to this invention, and
a second active ingredient, which is at least one art-known anti-cancer agent, such as e.g. one or more of those mentioned herein above,
for separate, sequential, simultaneous or chronologically staggered use in therapy, such as e.g. in therapy of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The present invention further relates to a pharmaceutical composition comprising
a first active ingredient, which is at least one tetrahydropyridothiophene compound according to this invention, and
a second active ingredient, which is at least one art-known anti-cancer agent, such as e.g. one or more of those mentioned herein above, and, optionally,
a pharmaceutically acceptable carrier or diluent, for separate, sequential, simultaneous or chronologically staggered use in therapy.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a tetrahydropyridothiophene compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, sequential, separate or chronologically staggered use in therapy. Optionally, said kit comprises instructions for its use in therapy, e.g. to treat hyperproliferative diseases and/or disorders responsive to the induction of apoptosis, such as e.g. cancer.

The present invention further relates to a combined preparation comprising at least one compound according to this invention and at least one art-known anti-cancer agent for simultaneous, sequential or separate administration.

The present invention further relates to pharmaceutical compositions or combinations according to the present invention having anti-proliferative and/or apoptosis inducing properties.

In addition, the present invention further relates to a method for treating in combination therapy (hyper)proliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating (hyper)proliferative diseases of benign or malignant behaviour and/or disorders responsive to the induction of apoptosis, such as e.g. cancer, in a patient comprising administering in combination therapy separately, simultaneously, sequentially or chronologically staggered a pharmaceutically active and therapeutically effective and tolerable amount of a pharmaceutical composition, which comprises a tetrahydropyridothiophene compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In addition, the present invention further relates to the use of a composition, combination, formulation, preparation or kit according to this invention in the manufacture of a pharmaceutical product, such as e.g. a commercial package or a medicament, for treating, preventing or ameliorating (hyper) proliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, sequential or separate use with one or more tetrahydropyridothiophene compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative diseases and/or a disorder responsive to the induction of apoptosis, particularly one of those diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention can be in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions. The pharmaceutical compositions according to the invention can be prepared by processes known per se.

The dosage of the active compounds is carried out in the order of magnitude customary for inhibitors for cellular proliferation or apoptosis inducers. Topical application forms (such as ointments) for the treatment of dermatoses thus contain the active compounds in a concentration of, for example, 0.1-99%. The customary dose in the case of systemic therapy (p.o.) is between 0.3 and 30 mg/kg per day, (i.v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Biological Investigations

The anti-proliferative/cytotoxic activity of the compounds described herein, can be tested on subclones of RKO (RKOp27) human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 20 mM solutions in dimethylsulfoxide (DMSO) and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 4000 cells per well in a volume of 50 µl per well. 24 hours after seeding 50 µl each of the compound dilutions in DMEM are added into each well of the 96 well plate. Each compound dilution is tested as quadruplicates. Wells containing untreated control cells are filled with 50 µl DMEM containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The corresponding $IC_{50}$ values of the compounds for anti-proliferative/cytotoxic activity are determined from the concentration-effect curves.

Representative $IC_{50}$ values for anti-proliferation/cytotoxicity determined in the aforementioned assay are described in the table A ($1^{st}$ column), in which the numbers of the compound correspond to the numbers of the examples.

Any or all of the compounds according to the present invention which are listed in the Table A, as well as their salts, are to be mentioned as a particular interesting subject of the present invention.

TABLE A

Anti-proliferative/cytotoxic activity

| Compound | $IC_{50}$ RKO p27 proliferating [µM] | $IC_{50}$ RKO p27 arrested [µM] |
|---|---|---|
| 1 | <1 | >100 |
| 2, 4, 7 to 14, 16, 19 to 21, 23, 24, 26 to 30, 32 to 39, 43 to 45, and 47 | The $IC_{50}$ values of these listed compounds are all ≦2 | The $IC_{50}$ values of these listed compounds are all >100 |
| 48 to 50, 53, 55, 57, 59 to 62, 64 to 68, 70 to 76, 78 to 80, 82, 83, 85, 86, 89 to 91, 95 to 98, 100, 102 to 104, 106, 108, 111, 112, 114, 116 to 118, 120, 122, 125 to 129, 133 to 140, 142 to 144, 146 to 152, 154 to 156, 158 to 162, 164, 166, 167, 169 to 172, 174 to 178, 181, 183, 185 to 196, 198, 200, 205, 206, 209 to 212, 214 to 219, 221, 223, 224, 226 to 232, and 234 to 243 | The $IC_{50}$ values of these listed compounds are all ≦2 | The $IC_{50}$ values of these listed compounds are all ≧100 |
| 54, 69, 77, 84, 88, 99, 113, 124, 145, 157, 168, 182, 220, 222, and 233 | The $IC_{50}$ values of these listed compounds are all ≦0.5 | The $IC_{50}$ values of these listed compounds are all ≧50 |

To determine the cell cycle specific mode of action, subclones of RKO colon adenocarcinoma cells (RKOp27 or RKOp21 as described by Schmidt et al. in Oncogene 19, 2423-2429; 2000) are seeded into 96 well flat bottom plates at a density of 16000 cells per well in a volume of 50 µl per well in DMEM growth medium with 10% FCS containing 10 µM Ponasterone A. 24 hours after seeding 50 µl each of the compound dilutions in DMEM are added into each well of the 96 well plate. Each compound dilution is tested as quadruplicates. Wells containing untreated control cells are filled with 50 µl DMEM containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. Viability is compared of proliferating cells grown in the absence of the inducer Ponasterone A, versus viability of cells arrested by the expression of ectopic p27Kip1 induced by Ponasterone A. The data of this experimental setting are summarized in table A ($2^{nd}$ column).

To test the anti-proliferative activity/cytotoxicity on cells known to be highly resistant towards distinct classes of chemotherapeutics, HCT15 cells (with P-glycoprotein overexpression) and MCF7 ADR cells, both of them are known to overexpress certain classes of multidrug resistance transporters are used in Alamar Blue assays as described above. Briefly, the compounds are dissolved as 20 mM solutions in dimethylsulfoxide (DMSO) and subsequently diluted in semi-logarithmic steps. DMSO dilutions are further diluted 1:100 into DMEM containing 10% fetal calf serum to a final concentration twice as much as the final concentration in the test. The cells to be tested are seeded into 96 well flat bottom plates at a density of 10000 cells per well in a volume of 50 µl per well. 24 hours after seeding 50 µl each of the compound dilutions in DMEM are added into each well of the 96 well plate. Each compound dilution is tested as quadruplicates. Wells containing untreated control cells are filled with 50 µl DMEM containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The induction of apoptosis can be measured by using a cell death detection ELISA (Roche Biochemicals, Mannheim, Germany). RKO subclones are seeded into 96 well flat bottom plates at a density of 10000 cells per well in a volume of 50 μl per well. 24 hours after seeding 50 μl each of the compound dilutions in DMEM are added into each well of the 96 well plate. Each compound dilution is tested at least as triplicates. Wells containing untreated control cells are filled with 50 μl DMEM containing 1% DMSO. The cells are then incubated with the substances for 24 hours at 37° C. in a humidified atmosphere containing 5% carbon dioxide. As a positive control for the induction of apoptosis, cells are treated with 50 μM Cisplatin (Gry Pharmaceuticals, Kirchzarten, Germany). Medium is then removed and the cells are lysed in 200 μl lysis buffer. After centrifugation as described by the manufacturer, 10 μl of cell lysate is processed as described in the protocol. The degree of apoptosis is calculated as follows: The absorbance at 405 nm obtained with lysates from cells treated with 50 μM cisplatin is set as 100 cpu (cisplatin units), while an absorbance at 405 nm of 0.0 is set as 0.0 cpu. The degree of apoptosis is expressed as cpu in relation to the value of 100 cpu reached with the lysates obtained from cells treated with 50 μM cisplatin.

The mitotis-confined activity can be measured using a methylen blue/eosin staining kit (Merck, Darmstadt, Germany). RKO subclones are seeded into 6 well tissue culture plates at a density of 200000 cells per well in a volume of 2 ml per well. 24 hours after seeding each of the compound dilutions in DMEM containing up to 1% DMSO are added onto each 6 well plate. The cells are then incubated with the substances for 24 hours at 37° C. in a humidified atmosphere containing 5% carbon dioxide. As a positive control for the induction of mitosis, the cells are treated with 20 nM vincristine or paclitaxel. The cells are then harvested by trypsinization and subsequent centrifugation, and washed once with phosphate-buffered saline. Subsequently, the cells are centrifuged on microscope slides for 1 min at 1200 rpm using a cytospin. Cells are then fixed with methanol and stained with methylen blue and eosin according to the manufacturer's recommendations. Mitotic figures can then be visualized by standard microscopy.

Another method to determine the mitosis confined activity can be immunoblotting of cell extracts with an antibody specific for phosphorylated histone H3, which is a generally accepted marker of mitosis. RKO subclones are seeded into 6 well tissue culture plates at a density of 200000 cells per well in a volume of 2 ml per well. 24 hours after seeding each of the compound dilutions in DMEM containing up to 1% DMSO are added onto each 6 well plate. The cells are then incubated with the substances for another 24 hours at 37° C. in a humidified atmosphere containing 5% carbon dioxide. As a positive control for the induction of mitosis, the cells are treated with 20 nM vincristine or paclitaxel. The cells are then harvested by trypsinization and subsequent centrifugation, and washed once with phosphate-buffered saline. Subsequently, the cells are lysed in a lysis buffer containing 50 mM Tris, pH 7A, 150 mM NaCl, 1% NP40, 50 mM NaF, 1 mM $Na_3VO_4$, 1 mM phenylmethylsulfonyl fluoride. The lysates are cleared by centrifugation and the supernatants are collected. Equal amounts of lysate protein are separated in an SDS-polyacrylamide electrophoresis using 12.5% gels and subsequently blotted on immobilon membranes (Millipore, schwalbach, Germany). After blocking unspecific binding sites by incubation of the membrane in 3% bovine serum albumine in tris-buffered saline containing 0.05% tween 20, antibodies specific for phospho-histone H3 (Cell Signaling Technology, Beverly, USA) were added for 1 hour. After intensive washing with tris-buffered saline containing 0.05% tween 20, specific signals were visualized using a horseradish-peroxidase-coupled secondary antibody and the use of the ECL chemoluminescence detection kit (Amersham, Braunschweig, Germany) according to the manufacturer's recommendations.

Figure 1:
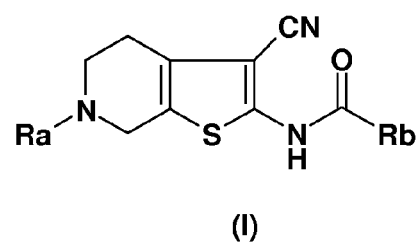
FIG. 1 depicts the compound of formula I.

The invention claimed is:

1. A compound of formula I

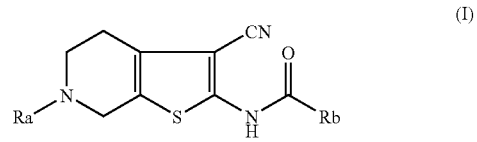

wherein
Ra is —C(O)R1, —C(O)OR2, —C(O)SR2, —C(O)N(R3)R4, —S(O)₂R1, or —S(O)₂N(R3)R4;
Rb is Q-2-4C-alkenyl, in which
Q is optionally substituted by Rba and/or Rbb and/or Rbc, and is phenyl or naphthyl,
or
Q is optionally substituted by Rca and/or Rcb, and is Har,
or
Q is Cyc;
in which
R1, R2 and R3 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R5;
each R4 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R5;
R5, Rba, Rbb, Rbc, Rca and Rcb are the same or different and are independently selected from the group consisting of:
1-7C-alkyl, 3-7C-cycloalkyl, Ar, Har, Het,
halogen, trifluoromethyl, nitro, cyano, guanidino, amidino,
—C(O)R6, —C(O)OR7, —C(O)N(R8)R9, —S(O)₂R6, —S(O)₂N(R8)R9,
—N(R10)C(O)R6, —N(R10)C(O)OR7, —N(R10)C(O)N(R8)R9, —N(R10)S(O)₂R6,
—N(R10)S(O)₂N(R8)R9,
—OC(O)R6, —OC(O)N(R8)R9,
—OR7, —N(R8)R9 and —SR7,
wherein each of said 1-7C-alkyl, 3-7C-cycloalkyl, Ar, Har and Het is unsubstituted or substituted by at least one substituent independently selected from R11;
R6, R7 and R8 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R12;

each R9 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R12;

each R10 is independently selected from the group consisting of: hydrogen, 1-7C-alkyl and 3-7C-cycloalkyl;

R11 is R5;

each R12 is independently selected from R5;

each Ar is independently selected from the group consisting of phenyl and naphthyl;

each Har is the same or different and independently a fully aromatic or partially aromatic mono- or fused bicyclic ring or ring system, which contains at least one heteroatom in the ring or ring system, made up of a first constituent being a 5- or 6-membered monocyclic unsaturated, aromatic heteroaryl ring A, which heteroaryl ring A comprises at least one heteroatom independently selected from the group consisting of nitrogen, oxygen and sulfur, and, optionally, fused to said first constituent, a second constituent being a benzene ring, a 5-6C-cycloalkane ring, an additional heteroaryl ring A, or a heterocyclic ring B, wherein said Har is attached via a substitutable ring carbon or ring nitrogen atom of Har;

each Het is independently a fully saturated or partially unsaturated mono- or fused bicyclic ring or ring system made up of a first constituent being a 3- to 7-membered monocyclic fully saturated or partially unsaturated, non-aromatic heterocyclic ring B, wherein the heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent, a second constituent being a benzo group, a 3-7C-cycloalkane group, or an additional heterocyclic ring B, wherein said Het ring or ring system is attached via a substitutable ring carbon or ring nitrogen atom;

Cyc is optionally substituted by halogen on its benzene ring, and is a group of formula A

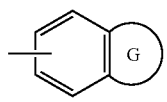

(A)

in which

G is optionally substituted by Rda and/or Rdb, and is a 5- or 6-membered saturated heterocyclic ring comprising one or two heteroatoms independently selected from the group consisting of nitrogen, oxygen and sulfur, in which Rda is 1-4C-alkyl or halogen, Rdb is 1-4C-alkyl or halogen, wherein said Cyc ring system is attached via a substitutable benzoring carbon atom, or a salt thereof.

2. A compound of formula I according to claim 1, wherein

Ra is —C(O)R1, —C(O)OR2, —C(O)SR2, —C(O)N(R3)R4, —S(O)$_2$R1, or —S(O)$_2$N(R3)R4;

Rb is Q-2-4C-alkenyl, in which

Q is optionally substituted by Rba and/or Rbb and/or Rbc, and is phenyl or naphthyl, or Q is optionally substituted by Rca and/or Rcb, and is Har, or Q is Cyc;

in which

R1, R2 and R3 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R5;

each R4 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R5;

R5, Rba, Rbb, Rbc, Rca and Rcb are the same or different and are independently selected from the group consisting of:

1-7C-alkyl, 3-7C-cycloalkyl, Ar, Har, Het, halogen, trifluoromethyl, nitro, cyano, guanidino, amidino,

—C(O)R6, —C(O)OR7, —C(O)N(R8)R9, —S(O)$_2$R6, —S(O)$_2$N(R8)R9,

—N(R10)C(O)R6, —N(R10)C(O)OR7, —N(R10)C(O)N(R8)R9, —N(R10)S(O)$_2$R6,

—N(R10)S(O)$_2$N(R8)R9,

—OC(O)R6, —OC(O)N(R8)R9,

—OR7, —N(R8)R9 and —SR7, wherein each of said 1-7C-alkyl, 3-7C-cycloalkyl, Ar, Har and Het is unsubstituted or substituted by at least one substituent independently selected from R11;

R6, R7 and R8 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R12;

each R9 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R12;

each R10 is independently selected from the group consisting of: hydrogen, 1-7C-alkyl and 3-7C-cycloalkyl;

R11 is R5;

each R12 is independently selected from R5;

each Ar is independently selected from the group consisting of phenyl and naphthyl;

each Har is the same or different and independently a fully aromatic or partially aromatic mono- or fused bicyclic ring or ring system, which contains at least one heteroatom in the ring or ring system, made up of a first constituent being a 5- or 6-membered monocyclic unsaturated, aromatic heteroaryl ring A, which heteroaryl ring A comprises at least one heteroatom independently selected from the group consisting of nitrogen, oxygen and sulfur, and, optionally, fused to said first constituent, a second constituent being a benzene ring, a 5-6C-cycloalkane ring, an additional heteroaryl ring A or a heterocyclic ring B, wherein said Har is attached via a substitutable ring carbon or ring nitrogen atom of Har;

each Het is independently a fully saturated or partially unsaturated mono- or fused bicyclic ring or ring system made up of a first constituent being a 3- to 7-membered monocyclic fully saturated or partially unsaturated, non-aromatic heterocyclic ring B, wherein the heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent, a second constituent being a benzo group, any 3-7C-cycloalkane group or an additional heterocyclic ring B, wherein said Het ring or ring system is attached via a substitutable ring carbon or ring nitrogen atom;

Cyc is a group of formula A

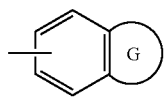

(A)

in which

G is a 5- or 6-membered saturated heterocyclic ring comprising one or two heteroatoms independently selected from the group consisting of nitrogen, oxygen and sulfur, wherein said Cyc ring system is attached via a substitutable benzoring carbon atom;

or a salt thereof.

3. A compound according to claim 1, which is selected from compounds formula Ia or Ib

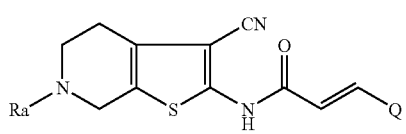

(Ia)

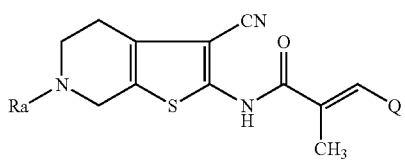

(Ib)

in which

Ra is —C(O)R1, in which

R1 is 1-7C-alkyl, or imidazolo, or

R1 is 1-7C-alkyl which is substituted by one substituent selected from R5, or

R1 is 2-4C-alkyl which is substituted by two hydroxyl groups on different carbon atoms, or R1 is 2,2-dimethyl-[1,3]dioxolan-4-yl, or 1-2C-alkyl which is substituted by 2,2-dimethyl-[1,3]dioxolan-4-yl;

or in which

Ra is —C(O)OR2, in which

R2 is 1-7C-alkyl, 3-7C-cycloalkyl, phenyl, pyridyl, (1-4C-alkoxycarbonyl)-phenyl, or (1-4C-alkoxy)-phenyl, or R2 is 1-7C-alkyl which is substituted by one substituent selected from R5, or R2 is 3-4C-alkyl which is substituted by two hydroxyl groups on different carbon atoms, or R2 is 1-2C-alkyl which is substituted by 2,2-dimethyl-[1,3]dioxolan-4-yl;

or in which

Ra is —C(O)SR2, in which

R2 is 1-7C-alkyl, or

R2 is 1-7C-alkyl which is substituted by one substituent selected from R5, or

R2 is 3-4C-alkyl which is substituted by two hydroxyl groups on different carbon atoms, or R2 is 1-2C-alkyl which is substituted by 2,2-dimethyl-[1,3]dioxolan-4-yl;

and in which

Q is Rba- and/or Rbb- and/or Rbc-substituted phenyl, or

Q is unsubstituted phenyl, or

Q is optionally substituted by Rca and/or Rcb, and is Har, or

Q is Cyc;

in which each R5 is independently selected from the group consisting of:

1-4C-alkoxy, 1-4C-alkoxy-2-4C-alkoxy, (1-4C-alkoxy-2-4C-alkoxy)-2-4C-alkoxy, hydroxyl, 1-4C-alkylcarbonyloxy, phenoxy, phenyl-1-4C-alkoxy; 1-4C-alkoxycarbonyl, carboxyl, amino, mono- or di-1-4C-alkylamino, mono- or di-1-4C-alkylaminocarbonyl, carbamoyl, ureido, guanidino, 1-4C-alkylcarbonylamino, Het, Har and phenyl, wherein each of said Har or phenyl radicals alone or part of another group is unsubstituted or substituted by one or two substituents independently selected from the group consisting of halogen, 1-4C-alkoxy, nitro, trifluoromethyl, 1-4C-alkyl, 1-4C-alkoxycarbonyl and carboxyl, Rba is halogen, 1-4C-alkyl, nitro, trifluoromethyl, 1-4C-alkoxy, mono- or di-1-4C-alkylamino, hydroxyl, 1-4C-alkylcarbonyloxy, cyano, phenyl, morpholino, phenoxy, hydroxy-2-4C-alkoxy, 1-4C-alkoxy-2-4C-alkoxy, 3-7C-cycloalkoxy, 3-7C-cycloalkyl-1-4C-alkoxy, phenyl-1-4C-alkoxy, cyano-1-4C-alkoxy, or completely or predominantly fluorine-substituted 1-4C-alkoxy, Rbb is 1-4C-alkoxy, halogen, trifluoromethyl or 1-4C-alkyl, Rbc is 1-4C-alkoxy, halogen, trifluoromethyl or 1-4C-alkyl, Rca is halogen, 1-4C-alkyl, 1-4C-alkoxy, trifluoromethyl, phenyl, phenoxy or morpholino, Rcb is halogen, 1-4C-alkyl or 1-4C-alkoxy, each Har is independently a 5-membered monocyclic heteroaryl radical comprising one, two or three nitrogen atoms and/or one heteroatom independently selected from the group consisting of oxygen and sulphur, or a 6-membered monocyclic heteroaryl radical comprising one or two nitrogen atoms, or
  a 9-membered fused bicyclic heteroaryl radical comprising one, two or three heteroatoms independently selected from the group consisting of nitrogen, oxygen and sulphur,
or
  a 10-membered fused bicyclic heteroaryl radical comprising one, two or three heteroatoms independently selected from the group consisting of nitrogen, oxygen and sulphur,
wherein said Har is attached via a ring carbon atom or ring nitrogen atom of Har,
Het is morpholino, piperidino, pyrrolidino, 4N—H-piperazino, 4N-(1-4C-alkyl)-piperazino, thiomorpholino, S-oxo-thiomorpholino or S,S-dioxo-thiomorpholino,
Cyc is optionally substituted by halogen on its benzene ring, and is 1,3-benzodioxolyl, 2,3-dihydro-1,4-benzodioxinyl, 2,2-difluoro-1,3-benzodioxolyl, 2,2-dimethyl-1,3-benzodioxolyl, chromanyl, chromenyl or 2,3-dihydro-benzofuranyl,
wherein said Cyc ring system is attached via a substitutable benzoring carbon atom;
or a salt thereof.

4. A compound according to claim 1, which is from formula Ia

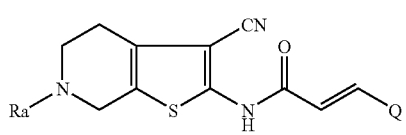

(Ia)

in which
Ra is —C(O)R1, in which
R1 is 1-5C-alkyl,
or
R1 is 1-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, pyridyl, pyrimidinyl, pyrazinyl, indolyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, morpholino, di-1-4C-alkylaminocarbonyl, carbamoyl, ureido, guanidino, imidazolo, triazolo, pyrazolo or 1-4C-alkylcarbonyloxy,
or
R1 is 3-4C-alkyl which is substituted by two hydroxyl groups on different carbon atoms,
or
R1 is 1-2C-alkyl which is substituted by 2,2-dimethyl-[1,3]dioxolan-4-yl;
or in which
Ra is —C(O)OR2, in which
R2 is 1-5C-alkyl,
or
R2 is 3-6C-cycloalkyl, phenyl, pyridyl, (1-4C-alkoxycarbonyl)-phenyl, or (1-4C-alkoxy)-phenyl,
or
R2 is 1-4C-alkyl which is mono-substituted by R5, in which
R5 is pyridyl, pyrimidinyl, pyrazinyl, 1N-(1-4C-alkyl)-imidazolyl, 1N-(1-4C-alkyl)-pyrazolyl, phenyl, (1-4C-alkoxy)-phenyl, 1-4C-alkoxycarbonyl, carboxyl, di-1-4C-alkylaminocarbonyl or carbamoyl, or
R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, morpholino, piperidino, pyrrolidino, 4N-(1-4C-alkyl)-piperazino, di-1-4C-alkylamino, imidazolo, triazolo, pyrazolo, 1-4C-alkylcarbonyloxy or 1-4C-alkylcarbonylamino,
or
R2 is 3-4C-alkyl which is substituted by two hydroxyl groups on different carbon atoms,
or
R2 is 1-2C-alkyl which is substituted by 2,2-dimethyl-[1,3]dioxolan-4-yl;
or in which
Ra is —C(O)SR2, in which
R2 is 1-5C-alkyl,
or
R2 is 2-4C-alkyl which is mono-substituted by R5, in which
R5 is di-1-4C-alkylamino, hydroxyl or pyridyl;
and in which
Q is Rba- and/or Rbb- and/or Rbc-substituted phenyl,
or
Q is unsubstituted phenyl,
or
Q is substituted by Rca, and is thiophenyl, furanyl, pyridyl or 1N-(methyl)-pyrazolyl,
or
Q is unsubstituted, and is thiophenyl, furanyl, pyridyl, 1N—(H)-pyrrolyl, 1N-(methyl)-pyrrolyl, benzothiophenyl or benzofuranyl,
or
Q is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl,
or
Q is substituted by halogen on its benzene ring, and is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl;
in which
Rba is halogen, 1-4C-alkyl, nitro, trifluoromethyl, 1-4C-alkoxy, di-1-4C-alkylamino, hydroxyl, 1-4C-alkylcarbonyloxy, cyano, phenyl, morpholino, phenoxy, hydroxy-2-4C-alkoxy, 1-4C-alkoxy-2-4C-alkoxy, or completely or predominantly fluorine-substituted 1-4C-alkoxy,
Rbb is 1-4C-alkoxy, halogen or 1-4C-alkyl,
Rbc is 1-4C-alkoxy or halogen,
Rca is halogen, 1-4C-alkyl, 1-4C-alkoxy, phenyl, phenoxy or morpholino,
or a salt thereof.

5. A compound according to claim 1, which is from formula Ia

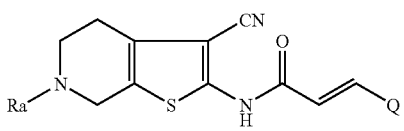

in which
Ra is —C(O)R1, in which
R1 is methyl, ethyl, propyl or butyl,
or
R1 is methyl which is mono-substituted by R5, ethyl which is mono-substituted by R5, or propyl which is mono-substituted by R5, in which
R5 is methoxy, ethoxy, 2-methoxyethoxy, 2-(2-methoxyethoxy)-ethoxy, hydroxyl, pyridyl, pyrimidinyl, pyrazinyl, indolyl, thiazolyl, oxazolyl, 1N-methyl-imidazolyl, 1N-methyl-pyrazolyl, phenyl, methoxycarbonyl, ethoxycarbonyl, carboxyl, dimethylaminocarbonyl, morpholino, carbamoyl, ureido, guanidino, imidazolo, triazolo, pyrazolo, ethylcarbonyloxy or methylcarbonyloxy,
or
R1 is propyl or butyl, each of which is substituted by two hydroxyl groups on different carbon atoms,
or
R1 is methyl or ethyl, each of which is substituted by 2,2-dimethyl-[1,3]dioxolan-4-yl;
or in which
Ra is —C(O)OR2, in which
R2 is methyl, ethyl, propyl or butyl,
or
R2 is cyclohexyl, phenyl, pyridyl, (1-2C-alkoxycarbonyl)-phenyl, or (1-2C-alkoxy)-phenyl,
or
R2 is methyl which is mono-substituted by R5, ethyl which is mono-substituted by R5, or propyl which is mono-substituted by R5, in which
R5 is pyridyl, pyrimidinyl, pyrazinyl, 1N-methyl-imidazolyl, 1N-methyl-pyrazolyl, phenyl, (1-2C-alkoxy)-phenyl, methoxycarbonyl, ethoxycarbonyl, carboxyl, di-methylaminocarbonyl or carbamoyl,
or
R2 is ethyl which is mono-substituted by R5, or propyl which is mono-substituted by R5, in which
R5 is methoxy, ethoxy, 2-methoxyethoxy, 2-(2-methoxyethoxy)-ethoxy, hydroxyl, benzyloxy, phenoxy, morpholino, piperidino, pyrrolidino, 4N-(methyl)-piperazino, dimethylamino, imidazolo, triazolo, pyrazolo, methylcarbonyloxy, ethylcarbonyloxy, methylcarbonylamino or ethylcarbonylamino,
or
R2 is propyl or butyl, each of which is substituted by two hydroxyl groups on different carbon atoms,
or
R2 is methyl or ethyl, each of which is substituted by 2,2-dimethyl-[1,3]dioxolan-4-yl;
or in which
Ra is —C(O)SR2, in which
R2 is methyl, ethyl, propyl, butyl or pentyl,
or
R2 is ethyl which is mono-substituted by R5, or propyl which is mono-substituted by R5, in which R5 is dimethylamino, hydroxyl or pyridyl;
and in which
Q is Rba- and/or Rbb- and/or Rbc-substituted phenyl,
or
Q is unsubstituted phenyl,
or
Q is substituted by Rca, and is thiophenyl, furanyl, pyridyl or 1N-(methyl)-pyrazolyl,
or
Q is unsubstituted, and is thiophenyl, furanyl, pyridyl, 1N—(H)-pyrrolyl, 1N-(methyl)-pyrrolyl, benzothiophenyl or benzofuranyl,
or
Q is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl,
or
Q is substituted by bromine, chlorine or fluorine on its benzene ring, and is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,2-difluoro-1,3-benzodioxol-5-yl, 2,2-difluoro-1,3-benzodioxol-4-yl, 2,3-dihydro-benzofuran-4-yl, 2,3-dihydro-benzofuran-5-yl, 2,3-dihydro-benzofuran-6-yl or 2,3-dihydro-benzofuran-7-yl;
in which
Rba is chlorine, fluorine, bromine, methy, ethyl, methoxy, ethoxy, isopropyloxy, propoxy, hydroxyl, nitro, trifluoromethyl, dimethylamino, methylcarbonyloxy, cyano, phenyl, morpholino, phenoxy, 2-hydroxyethoxy, difluoromethoxy or trifluoromethoxy,
Rbb is methoxy, ethoxy, fluorine, chlorine, bromine, ethyl or methyl,
Rbc is methoxy, ethoxy, fluorine or chlorine,
Rca is chlorine, fluorine, bromine, methyl, ethyl, methoxy, ethoxy, phenyl, phenoxy or morpholino,
or a salt thereof.

6. A compound according to claim 1, which is from formula Ia

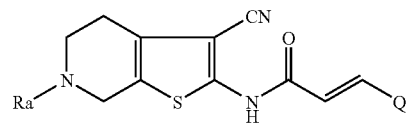

in which
Ra is —C(O)R1, in which
R1 is methyl, ethyl or propyl,
or
R1 is methyl which is mono-substituted by R5, ethyl which is mono-substituted by R5, or propyl which is mono-substituted by R5, in which
R5 is methoxy, 2-methoxyethoxy, hydroxyl, pyridyl, indolyl, phenyl, methoxycarbonyl, ethoxycarbonyl, dimethylaminocarbonyl, guanidino, imidazolo or methylcarbonyloxy;
or in which
Ra is —C(O)OR2, in which
R2 is methyl, ethyl, propyl or butyl, or R2 is cyclohexyl, phenyl, pyridyl, (methoxycarbonyl)-phenyl, or (methoxy)-phenyl, or R2 is methyl which is mono-substituted by R5, ethyl which is mono-substituted by R5, or propyl which is mono-substituted by R5, in which R5 is pyridyl, phenyl, (methoxy)-phenyl, methoxycarbonyl or ethoxycarbonyl, or R2 is ethyl which is mono-substituted by R5, or propyl which is mono-substituted by R5, in which R5 is methoxy, 2-methoxyethoxy, hydroxyl, benzyloxy, morpholino, pyrrolidino, 4N-(methyl)-piperazino, dimethylamino, imidazolo or methylcarbonylamino, or R2 is 2,3-dihydroxypropyl, or R2 is 2,2-dimethyl-[1,3]dioxolan-4-yl-methyl;

or in which

Ra is —C(O)SR2, in which

R2 is methyl, ethyl, propyl, butyl or pentyl, or

R2 is ethyl which is mono-substituted by R5, or propyl which is mono-substituted by R5, in which R5 is dimethylamino;

and in which

Q is Rba- and/or Rbb- and/or Rbc-substituted phenyl, or

Q is unsubstituted phenyl, or

Q is substituted by Rca, and is thiophenyl, furanyl or 1N-(methyl)-pyrazolyl, or Q is (morpholino)-pyridyl, or (phenoxy)-thiophenyl, or Q is unsubstituted, and is thiophenyl, furanyl, pyridyl, 1N—(H)-pyrrolyl, benzothiophenyl, 1N-(methyl)-pyrrolyl or benzofuranyl, or Q is 1,3-benzodioxol-5-yl, 1,3-benzodioxol-4-yl, 2,2-difluoro-1,3-benzodioxol-5-yl, 2,2-difluoro-1,3-benzodioxol-4-yl or 2,3-dihydro-benzofuran-4-yl, or Q is substituted by bromine on its benzene ring, and is 1,3-benzodioxol-5-yl or 1,3-benzodioxol-4-yl;

in which

Rba is chlorine, fluorine, bromine, methy, ethyl, methoxy, ethoxy, isopropyloxy, propoxy, hydroxyl, nitro, trifluoromethyl, dimethylamino, methylcarbonyloxy, cyano, phenyl, morpholino, phenoxy, difluoromethoxy or trifluoromethoxy, Rbb is methoxy, ethoxy, fluorine, chlorine or methyl, Rbc is fluorine, Rca is chlorine, methyl, ethyl or phenyl, or a salt thereof.

7. A compound according to claim 1, which is a compound of formula Ia

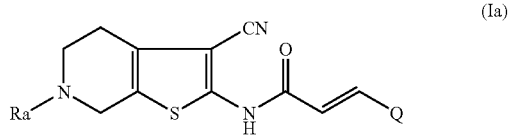

in which

Ra is —C(O)R1, in which

R 1 is methyl, ethyl or propyl, or

R1 is methyl which is mono-substituted by R5, ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, pyridyl, pyrimidinyl, pyrazinyl, imidazolo, pyrazolo or methylcarbonyloxy, or R1 is 2,3-dihydroxy-propyl;

or in which

Ra is —C(O)0R2, in which

R2 is methyl, ethyl or propyl, or

R2 is methyl which is mono-substituted by R5, ethyl which is mono-substituted by R5, or propyl which is mono-substituted by R5, in which R5 is pyridyl, pyrazinyl or pyrimidinyl, or R2 is ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, imidazolo, pyrazolo or methylcarbonyloxy, or R2 is 2,3-dihydroxy-propyl;

or in which

Ra is —C(O)SR2, in which

R2 is methyl, ethyl or propyl, or

R2 is methyl which is mono-substituted by R5, ethyl which is mono-substituted by R5, or propyl which is mono-substituted by R5, in which R5 is pyridyl or hydroxyl;

and in which

Q is Rba- and/or Rbb- and/or Rbc-substituted phenyl, or

Q is unsubstituted phenyl, or

Q is substituted by Rca, and is thiophenyl or furanyl, or

Q is unsubstituted, and is thiophenyl, furanyl or pyridyl, or

Q is 1,3-benzodioxol-5-yl, 1,3-benzodioxol-4-yl, 2,2-difluoro-1,3-benzodioxol-5-yl or 2,2-difluoro-1,3-benzodioxol-4-yl;

in which

Rba is chlorine, fluorine, methy, ethyl, methoxy, ethoxy, difluoromethoxy or trifluoromethoxy, Rbb is methoxy, ethoxy, fluorine, chlorine or methyl, Rbc is fluorine, and Rca is chlorine, methyl or ethyl, or a salt thereof.

8. A compound according to claim 1, which is a compound of formula Ia

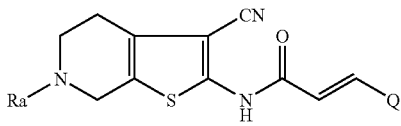

(Ia)

in which
Ra is —C(O)R1, in which
R1 is methyl, ethyl or propyl,
or
R1 is (R5)-methyl, 2-(R5)-ethyl, or 3-(R5)-propyl, in which
R5 is methoxy, ethoxy, 2-methoxyethoxy, hydroxyl, imidazolo, pyridin-2-yl, pyridin-3-yl or pyridin-4-yl,
or
R1 is 2,3-dihydroxy-propyl;
or in which
Ra is —C(O)OR2, in which
R2 is methyl, ethyl or propyl,
or
R2 is (R5)-methyl, 2-(R5)-ethyl, or 3-(R5)-propyl, in which
R5 is pyridin-2-yl, pyridin-3-yl or pyridin-4-yl,
or
R2 is 2-(R5)-ethyl, or 3-(R5)-propyl, in which
R5 is methoxy, ethoxy, 2-methoxyethoxy, imidazolo or hydroxyl,
or
R2 is 2,3-dihydroxy-propyl;
or in which
Ra is —C(O)SR2, in which
R2 is methyl, ethyl or propyl,
or
R2 is (R5)-methyl, 2-(R5)-ethyl, or 3-(R5)-propyl, in which
R5 is pyridin-2-yl, pyridin-3-yl or pyridin-4-yl;
and in which
Q is 2-methoxyphenyl, 2-chlorophenyl, 2-ethoxyphenyl or 2-methylphenyl,
or
Q is 2-(Rba)-3-(Rbb)-phenyl, in which
Rba is chlorine, methoxy, ethoxy or methyl,
Rbb is methoxy, chlorine, fluorine or methyl,
or
Q is 2-(Rba)-5-(Rbb)-phenyl, in which
Rba is chlorine, methoxy, ethoxy or methyl,
Rbb is methoxy, chlorine, fluorine or methyl,
or
Q is unsubstituted phenyl,
or
Q is unsubstituted, and is furan-2-yl, furan-3-yl or pyridin-3-yl,
or
Q is 1,3-benzodioxol-4-yl or 2,2-difluoro-1,3-benzodioxol-4-yl;
or a salt thereof.

9. A compound according to claim 1, which is a compound of formula Ia

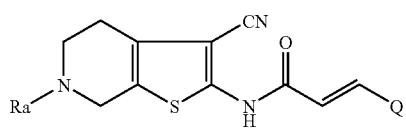

(Ia)

in which
Ra is —C(O)R1, in which
R1 is methyl, ethyl or propyl,
or
R1 is methoxy-methyl, 2-methoxy-ethyl, (2-methoxyethoxy)-methyl, 2-(2-methoxyethoxy)-ethyl, hydroxymethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl,
or
R1 is 2,3-dihydroxy-propyl;
or in which
Ra is —C(O)OR2, in which
R2 is methyl, ethyl or propyl,
or
R2 is 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl,
or
R2 is 2,3-dihydroxy-propyl;
or in which
Ra is —C(O)SR2, in which
R2 is methyl, ethyl or propyl;
and in which
Q is 2-methoxyphenyl,
or
Q is 2-ethoxyphenyl,
or
Q is 2-(Rba)-3-(Rbb)-phenyl, in which
Rba is methoxy or ethoxy,
Rbb is methoxy or methyl,
or
Q is 2-(Rba)-5-(Rbb)-phenyl, in which
Rba is methoxy or ethoxy,
Rbb is methoxy or methyl,
or
Q is unsubstituted phenyl,
or
Q is unsubstituted, and is furan-2-yl, furan-3-yl or pyridin-3-yl,
or
Q is 1,3-benzodioxol-4-yl;
or a salt thereof.

10. A compound according to claim 1, which is a compound of formula Ia

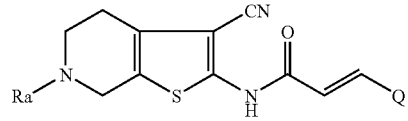

(Ia)

in which
Ra is —C(O)R1, in which
R1 is methyl, ethyl or propyl, or
R1 is methoxy-methyl, 2-methoxy-ethyl, (2-methoxy-ethoxy)-methyl, 2-(2-methoxyethoxy)-ethyl, hydroxy-methyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl,
or
R1 is 2,3-dihydroxy-propyl;
or in which
Ra is —C(O)OR2, in which
R2 is methyl, ethyl or propyl,
or
R2 is 2-methoxy-ethyl, 2-(2-methoxyethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl, or 2-(pyridin-4-yl)-ethyl,
or
R2 is 2,3-dihydroxy-propyl;
or in which
Ra is —C(O)SR2, in which
R2 is methyl, ethyl or propyl;
and in which
Q is 2-ethoxyphenyl,
or
Q is 2-(Rba)-5-(Rbb)-phenyl, in which
Rba is methoxy,
Rbb is methoxy or methyl,
or
Q is 2-(Rba)-5-(Rbb)-phenyl, in which
Rba is ethoxy,
Rbb is methoxy or methyl;
or a salt thereof.

11. A compound according to claim 2, which is a compound of formula Ia

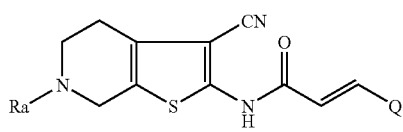

(Ia)

in which
Ra is —C(O)R1, in which
R1 is methyl, ethyl, propyl or butyl,
or
Ra is —C(O)OR2, in which
R2 is methyl, ethyl, propyl or butyl,
or
R2 is benzyl or phenethyl,
or
R2 is phenyl or 3-methoxy-phenyl,
or
Ra is —C(O)SR2, in which
R2 is ethyl; and
Q is 2-chloro-phenyl, 3-chloro-phenyl, 4-chloro-phenyl, 2-fluoro-phenyl, 3-fluoro-phenyl, 4-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl,
or
Q is phenyl,
or
Q is thiophenyl, furanyl, or pyridyl,
or
Q is 1,3-benzodioxolyl, 2,3-dihydro-1,4-benzodioxinyl or 2,3-dihydro-benzofuranyl;
or a salt thereof.

12. A compound according to claim 2, which is a compound of formula Ia

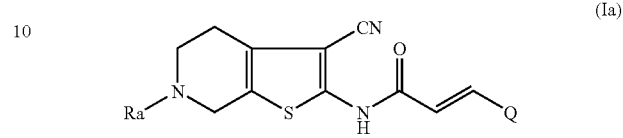

(Ia)

in which
Ra is —C(O)R1, in which
R1 is 1-5C-alkyl, phenyl, pyridyl, morpholino, indolyl, or 1-5C-alkyl which is substituted by one substituent selected from R5, in which
R5 is 1-4C-alkoxy, phenoxy, 1-4C-alkoxy-2-4C-alkoxy, hydroxyl, benzyloxy, phenyl, pyridyl, indolyl, 1-4C-alkoxycarbonyl, carboxyl, amino, di-1-4C-alkylamino, morpholino, piperidino, pyrrolidino, 4N-(1-4C-alkyl)-piperazin-1-yl, 4N—(H)-piperazin-1-yl, carbamoyl, ureido, guanidino, imidazol-1-yl, 1N-(H)-imidazol-4-yl, or 1N-(1-4C-alkyl)-imidazol-4-yl;
or in which
Ra is —C(O)OR2, in which
R2 is 1-5C-alkyl, phenyl, pyridyl, or (1-4C-alkoxy)-phenyl,
or
R2 is 1-5C-alkyl which is substituted by one substituent selected from R5, in which
R5 is phenyl, pyridyl, indolyl, 4-methyl-thiazolyl, 1-4C-alkoxycarbonyl, carboxyl, (1-4C-alkoxy)-phenyl, 1N—(H)-imidazol-4-yl, or 1N-(1-4C-alkyl)-imidazol-4-yl,
or
R2 is 2-5C-alkyl which is substituted by one substituent selected from R5, in which
R5 is 1-4C-alkoxy, phenoxy, 1-4C-alkoxy-2-4C-alkoxy, hydroxyl, benzyloxy, 1-4C-alkylcarbonyloxy, amino, di-1-4C-alkylamino, 1-4C-alkylcarbonylamino, morpholino, piperidino, pyrrolidino, 4N-(1-4C-alkyl)-piperazin-1-yl, 4N—(H)-piperazin-1-yl, or imidazol-1-yl;
or in which
Ra is —C(O)SR2, in which
R2 is 1-5C-alkyl, or 2-5C-alkyl which is substituted by one substituent selected from R5, in which
R5 is 1-4C-alkoxycarbonyl, carboxyl, hydroxyl, 1-4C-alkylcarbonyloxy, di-1-4C-alkylamino, 1-4C-alkylcarbonylamino, pyridyl or pyrazinyl;
and in which
Q is Rba- and/or Rbb- and/or Rbc-substituted phenyl, in which
Rba is halogen, 1-4C-alkyl, nitro, trifluoromethyl, or 1-4C-alkoxy,
Rbb is 1-4C-alkoxy, or halogen,
Rbc is 1-4C-alkoxy,
or
Q is Rba- and Rbb-substituted phenyl, in which
Rba is 1-4C-alkoxy, or halogen,
Rbb is 1-4C-alkoxy, or halogen,
or a salt thereof.

13. A compound according to claim 2, which is a compound of formula Ia

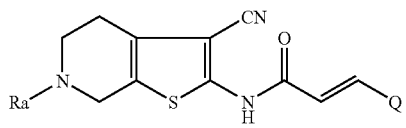

in which,
Ra is —C(O)R1, in which
R1 is methyl or propyl;
or in which
Ra is —C(O)OR2, in which
R2 is methyl, ethyl, butyl, phenethyl or 3-methoxy-phenyl;
or in which,
Ra is —C(O)SR2, in which
R2 is ethyl;
and in which
Q is 2-chloro-phenyl, 3-chloro-phenyl, 3-fluoro-phenyl, 2-trifluoromethyl-phenyl, 2-nitro-phenyl, 3-nitro-phenyl, 2-methyl-phenyl, 3-methyl-phenyl, 4-methyl-phenyl, 3-methoxy-phenyl, 4-methoxy-phenyl, 2,3-dimethoxy-phenyl, or 2,4-dichloro-phenyl,
or
Q is phenyl,
or
Q is thiophen-2-yl, thiophen-3-yl, furan-2-yl, furan-3-yl or pyridin-3-yl,
or
Q is 1,3-benzodioxol-5-yl;
or a salt thereof.

14. A compound according to claim 1, in which
Ra is —C(O)OR2, in which
R2 is ethyl;
or a salt thereof.

15. A compound according to claim 1, which is a compound of formula Ia

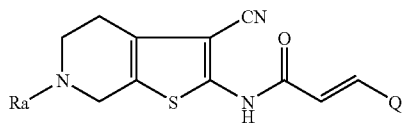

in which
Q is unsubstituted, and is phenyl or furanyl, thiophenyl or pyridyl,
or a salt thereof.

16. A compound according to claim 1, which is a compound of formula Ia

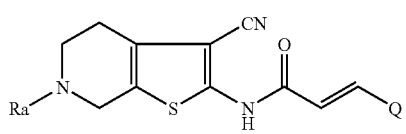

in which
Q is 2-ethoxy-phenyl,
or a salt thereof.

17. A pharmaceutical composition comprising one or more compounds according to claim 1, or a pharmaceutically acceptable salt thereof, together with a pharmaceutically acceptable excipient and/or vehicle.

18. A compound of formula I according to claim 1, wherein Rba, Rbb and Rbc are the same or different and are independently selected from the group consisting of
1-7C-alkyl, 3-7C-cycloalkyl, Ar, Har, Het,
halogen, trifluoromethyl, nitro, cyano, guanidino, amidino,
—C(O)R6, —C(O)OR7, —C(O)N(R8)R9,
—N(R10)C(O)R6, —N(R 10)C(O)OR7, —N(R10)C(O)N(R8)R9, —N(R10)S(O)$_2$R6,
—N(R10)S(O)$_2$N(R8)R9,
—OC(O)R6, —OC(O)N(R8)R9,
—OR7, —N(R8)R9 and —SR7,
wherein each of said 1-7C-alkyl, 3-7C-cycloalkyl, Ar, Har and Het is unsubstituted or substituted by at least one substituent independently selected from R11.

19. A compound of formula I

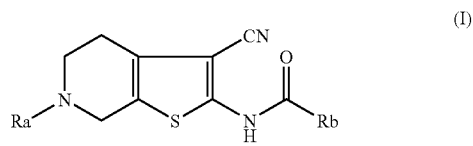

wherein
Ra is —C(O)R1, —C(O)OR2, —C(O)SR2, —C(O)N(R3)R4, —S(O)$_2$R1, or —S(O)$_2$N(R3)R4;
Rb is Q-2-4C-alkenyl, in which
Q is optionally substituted by Rba and/or Rbb and/or Rbc, and is phenyl or naphthyl,
or
Q is optionally substituted by Rca and/or Rcb, and is Har,
or
Q is Cyc;
in which
R1, R2 and R3 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R5;
each R4 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R5;
R5, Rba, Rbb, Rbc, Rca and Rcb are the same or different and are independently selected from the group consisting of:
1-7C-alkyl, 3-7C-cycloalkyl, Ar, Har, Het,
halogen, trifluoromethyl, nitro, cyano, guanidino, amidino,
—C(O)R6, —C(O)OR7, —C(O)N(R8)R9, —S(O)$_2$R6, —S(O)$_2$N(R8)R9,
—N(R10)C(O)R6, —N(R10)C(O)OR7, —N(R10)C(O)N(R8)R9, —N(R10)S(O)$_2$R6,
—N(R10)S(O)$_2$N(R8)R9,
—OC(O)R6, —OC(O)N(R8)R9,
—OR7, —N(R8)R9 and —SR7,
wherein each of said 1-7C-alkyl, 3-7C-cycloalkyl, Ar, Har and Het is unsubstituted or substituted by at least one substituent independently selected from R11;

R6, R7 and R8 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R12;
each R9 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R12;
each R10 is independently selected from the group consisting of: hydrogen, 1-7C-alkyl and 3-7C-cycloalkyl;
R11 is R5;
each R12 is independently selected from R5;
each Ar is independently selected from the group consisting of phenyl and naphthyl;
each Har is the same or different and independently a fully aromatic or partially aromatic mono- or fused bicyclic ring or ring system, which contains at least one heteroatom in the ring or ring system, made up of a first constituent being a 5- or 6-membered monocyclic unsaturated, aromatic heteroaryl ring A,
which heteroaryl ring A comprises at least one heteroatom independently selected from the group consisting of nitrogen, oxygen and sulfur, and, optionally, fused to said first constituent,
a second constituent being a benzene ring, a 5-6C-cycloalkane ring, an additional heteroaryl ring A, or a heterocyclic ring B,
wherein said Har is attached via a substitutable ring carbon or ring nitrogen atom of Har;
each Het is independently a fully saturated or partially unsaturated mono- or fused bicyclic ring or ring system made up of a first constituent being a 3- to 7-membered monocyclic fully saturated or partially unsaturated, non-aromatic heterocyclic ring B,
wherein the heterocyclic ring B comprises one to three heteroatoms independently selected from the group consisting of nitrogen, oxygen and sulfur,
and which heterocyclic ring B is optionally substituted by one or two oxo groups,
and, optionally, fused to said first constituent,
a second constituent being a benzo group, a 3-7C-cycloalkane group, or an additional heterocyclic ring B,
wherein said Het ring or ring system is attached via a substitutable ring carbon or ring nitrogen atom;
Cyc is optionally substituted by halogen on its benzene ring, and is a group of formula A

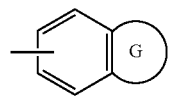

(A)

in which
G is optionally substituted by Rda and/or Rdb, and is a 5- or 6-membered saturated heterocyclic ring comprising one or two heteroatoms independently selected from the group consisting of nitrogen, oxygen and sulfur, in which
Rda is 1-4C-alkyl or halogen,
Rdb is 1-4C-alkyl or halogen,
wherein said Cyc ring system is attached via a substitutable benzoring carbon atom.

20. A salt of a compound of formula I

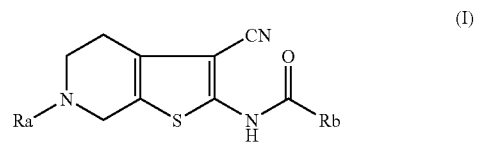

(I)

wherein
Ra is —C(O)R1, —C(O)OR2, —C(O)SR2, —C(O)N(R3)R4, —S(O)₂R1, or —S(O)₂N(R3)R4;
Rb is Q-2-4C-alkenyl, in which
Q is optionally substituted by Rba and/or Rbb and/or Rbc, and is phenyl or naphthyl,
or
Q is optionally substituted by Rca and/or Rcb, and is Har,
or
Q is Cyc;
in which
R1, R2 and R3 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R5;
each R4 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R5;
R5, Rba, Rbb, Rbc, Rca and Rcb are the same or different and are independently selected from the group consisting of:
1-7C-alkyl, 3-7C-cycloalkyl, Ar, Har, Het,
halogen, trifluoromethyl, nitro, cyano, guanidino, amidino,
—C(O)R6, —C(O)OR7, —C(O)N(R8)R9, —S(O)₂R6, —S(O)₂N(R8)R9,
—N(R10)C(O)R6, —N(R10)C(O)OR7, —N(R10)C(O)N(R8)R9, —N(R10)S(O)₂R6,
—N(R10)S(O)₂N(R8)R9,
—OC(O)R6, —OC(O)N(R8)R9,
—OR7, —N(R8)R9 and —SR7,
wherein each of said 1-7C-alkyl, 3-7C-cycloalkyl, Ar, Har and Het is unsubstituted or substituted by at least one substituent independently selected from R11;
R6, R7 and R8 are the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het is unsubstituted or substituted by at least one substituent independently selected from R12;
each R9 is independently selected from the group consisting of: hydrogen, 1-7C-alkyl and 3-7C-cycloalkyl, wherein each of said 1-7C-alkyl and 3-7C-cycloalkyl is unsubstituted or substituted by at least one substituent independently selected from R12;
each R10 is independently selected from the group consisting of: hydrogen, 1-7C-alkyl and 3-7C-cycloalkyl;
R11 is R5;
each R12 is independently selected from R5;
each Ar is independently selected from the group consisting of phenyl and naphthyl;

each Har is the same or different and independently a fully aromatic or partially aromatic mono- or fused bicyclic ring or ring system, which contains at least one heteroatom in the ring or ring system, made up of a first constituent being a 5- or 6-membered monocyclic unsaturated, aromatic heteroaryl ring A, which heteroaryl ring A comprises at least one heteroatom independently selected from the group consisting of nitrogen, oxygen and sulfur, and, optionally, fused to said first constituent, a second constituent being a benzene ring, a 5-6C-cycloalkane ring, an additional heteroaryl ring A, or a heterocyclic ring B, wherein said Har is attached via a substitutable ring carbon or ring nitrogen atom of Har;

each Het is independently a fully saturated or partially unsaturated mono- or fused bicyclic ring or ring system made up of a first constituent being a 3- to 7-membered monocyclic fully saturated or partially unsaturated, non-aromatic heterocyclic ring B, wherein the heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent, a second constituent being a benzo group, a 3-7C-cycloalkane group, or an additional heterocyclic ring B, wherein said Het ring or ring system is attached via a substitutable ring carbon or ring nitrogen atom;

Cyc is optionally substituted by halogen on its benzene ring, and is a group of formula A

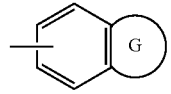

(A)

in which
G is optionally substituted by Rda and/or Rdb, and is a 5- or 6-membered saturated heterocyclic ring comprising one or two heteroatoms independently selected from the group consisting of nitrogen, oxygen and sulfur, in which
Rda is 1-4C-alkyl or halogen,
Rdb is 1-4C-alkyl or halogen,
wherein said Cyc ring system is attached via a substitutable benzoring carbon atom.

21. A pharmaceutical composition comprising one or more compounds according to claim 2, or a pharmaceutically acceptable salt thereof, together with a pharmaceutically acceptable excipient and/or vehicle.

22. A pharmaceutical composition comprising one or more compounds according to claim 3, or a pharmaceutically acceptable salt thereof, together with a pharmaceutically acceptable excipient and/or vehicle.

23. A compound of formula I according to claim 1, wherein Q is optionally substituted by Rba and/or Rbb and/or Rbc, and is phenyl or naphthyl.

24. A compound of formula I according to claim 1, wherein Q is optionally substituted by Rca and/or Rcb, and is Har.

25. A compound of formula I according to claim 1, wherein Q is Cyc.

* * * * *